US008444987B2

(12) United States Patent
Kingsbury et al.

(10) Patent No.: US 8,444,987 B2
(45) Date of Patent: May 21, 2013

(54) COMPOSITIONS AND METHODS FOR THE DIAGNOSIS AND TREATMENT OF IMMUNE DISORDERS

(75) Inventors: Gillian A. Kingsbury, Wayland, MA (US); Kevin R. Leiby, San Fransisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/116,108

(22) Filed: May 26, 2011

(65) Prior Publication Data

US 2012/0148573 A1     Jun. 14, 2012

Related U.S. Application Data

(60) Continuation of application No. 12/284,648, filed on Sep. 24, 2008, now Pat. No. 7,972,797, which is a division of application No. 11/599,098, filed on Nov. 14, 2006, now Pat. No. 7,452,980, which is a continuation of application No. 09/899,980, filed on Jul. 6, 2001, now abandoned, which is a division of application No. 09/560,639, filed on Apr. 28, 2000, now Pat. No. 6,323,334.

(60) Provisional application No. 60/155,862, filed on Sep. 24, 1999.

(51) Int. Cl.
*A61K 39/395*     (2006.01)

(52) U.S. Cl.
USPC ........................................... 424/154.1

(58) Field of Classification Search
None
See application file for complete search history.

(56) References Cited

U.S. PATENT DOCUMENTS

| | | | |
|---|---|---|---|
| 4,281,061 A | 7/1981 | Zuk et al. | 435/7.9 |
| 5,116,964 A | 5/1992 | Capon et al. | |
| 5,262,311 A | 11/1993 | Pardee et al. | |
| 5,591,719 A | 1/1997 | Furcht et al. | |
| 5,721,351 A | 2/1998 | Levinson | |
| 5,840,691 A | 11/1998 | Furcht et al. | |
| 2005/0119209 A1 | 6/2005 | Levinson et al. | |

FOREIGN PATENT DOCUMENTS

| | | |
|---|---|---|
| EP | 239400 | 8/1994 |
| JP | 6-178687 | 6/1994 |
| WO | WO 97/42224 | 11/1997 |
| WO | WO 99/15663 | 4/1999 |
| WO | WO 9934217 A1 | 7/1999 |

OTHER PUBLICATIONS

Eguchi et al., 2005, Gene Therapy, vol. 12: 733-741.*
BD biosciences Technical Resources, Dec. 2010,pp. 1-4.*
Kundu et al., 1997, Immunology, vol. 91: 234-238.*
Santiago et al., 1997, J. Exp. Med. vol. 185: 65-70.*
Altschul et al., 1997, "Gapped BLAST and PSI-BLAST: a new generation of protein database search programs", Nucl Acids Res 25:3389-3402.
Altschul et al., 1990, "Basic Local Alignment Search Tool", J. Mol. Biol. 215:403-410.
Anderson and Coyle, 1994, "TH2 and 'TH2-like'cells in allergy and asthma: pharmacological perspectives", Trends Pharmacol. Sci. 15:324-332.
Aruffo et al., 1990, "CD44 is the principal cell surface receptor for hyaluronate", Cell 61:1303-1313.
Bergers et al., 1994, "Alternative promoter usage of the Fos-responsive gene *Fit-1* generates mRNA isoforms coding for either secreted or membrane-bound proteins related to the IL-1 receptor", EMBO J. 13:1176-1188.
Chen et al., 1993, "RAG-2-deficient blastocyst complementation: an assay of gene function in lymphocyte development", Proc. Natl. Acad. Sci. USA 90:4528-4532.
Clerici et al., 1993, "Restoration of HIV-specific cell-mediated immune responses by interleukin-12 in vitro", Science 262:1721-1724.
Clerici et al., 1993, "Changes in interleukin-2 and interleukin-4 production in asymptomatic, human immunodeficiency virus-seropositive individuals", J. Clin. Invest. 91:759-765.
Cohn et al., 1997, "Induction of airway mucus production by T helper 2 (Th2) cells: a critical role for interleukin 4 in cell recruitment but not mucus production", J. Exp. Med. 186:1737-1747.

(Continued)

*Primary Examiner* — Amy Juedes
(74) *Attorney, Agent, or Firm* — Millennium Pharmaceuticals, Inc.

(57) ABSTRACT

The present invention relates to methods and compositions for the treatment and diagnosis of immune disorders, especially T helper lymphocyte-related disorders. In particular, the invention describes a gene known in the art, alternatively, as ST2, T1 and Fit-1, and referred to herein as the 103 gene. The 103 gene is disclosed herein to be differentially expressed in TH2 cells and not in TH1 cells. Further, the 103 gene product is demonstrated herein to be an important modulator of TH2 and TH2-like immune response both in vitro and in vivo. Thus, the 103 gene, its gene products and antibodies that specifically bind thereto can be used diagnostically or as targets for therapeutic intervention in the treatment of a variety of immune disorders.

In this regard, the invention provides methods for the identification and therapeutic use of compounds for treatments of immune disorders, especially TH cell subpopulation-related disorders and including TH2 and TH2-like disorders (i.e., disorders associated with a TH2 or TH2-like mediated immune response) such as atopic conditions (e.g., allergy and asthma). Additionally, methods are provided for the diagnostic evaluation and prognosis of TH cell subpopulation related disorders, for the identification of subjects exhibiting a predisposition to such conditions, for monitoring patients undergoing clinical evaluation for the treatment of such disorders and for monitoring the efficacy of compounds used in clinical trials.

3 Claims, 33 Drawing Sheets

OTHER PUBLICATIONS

Del Prete et al., 1991, "Purified protein derivative of *Mycobacterium tuberculosis* and excretory-secretory antigen(s) of *Toxocara canis* expand in vitro human T cells with stable and opposite (Type 1 T helper or Type 2 T helper) profile of cytokine production", J. Clin. Invest. 88:346-350.

Fägerstam et al., 1992, "Biospecific interaction analysis using surface plasmon resonance detection applied to kinetic, binding site and concentration analysis", J. Chromatog. 597:397-410.

Firestein et al., 1989, "A new murine $CD4^+$T cell subset with an unrestricted cytokine profile", J. Immunol. 143:518-525.

Frangogiannis et al., 1998, "Resident cardiac mast cells degranulate and release preformed TNF-α initiating the cytokine cascade in experimental canine myocardial ischemia/reperfusion", Circulation 98:699-710.

Gächter et al., 1996, "Transcription of the interleukin-1 receptor-related T1 gene is initiated at different promoters in mast cells and fibroblasts", J. Biol. Chem. 271:124-129.

Gavett et al., 1994, "Depletion of murine $CD4^+$T lymphocytes prevents antigen-induced airway hyperreactivity and pulmonary eosinophilia", Am. J. Respir Cell Mol. Biol. 10:587-593.

George et al., 1994, "Embryonic expression and cloning of the murine GATA-3 gene", Development 120:2673-2686.

Gonazlo et al., 1996, "Mouse eotaxin expression parallels eosinophil accumulation during lung allergic inflammation but it is not restricted to a Th2-type response", Immunity 4:1-14.

Gu et al., 1994, "Deletion of a DNA polymerase β gene segment in T cells using cell type-specific gene targeting", Science 265:103-106.

Hamelmann et al., 1997, "Noninvasive measurement of airway responsiveness in allergic mice using barometric plethysmography", Am. J. Respir. Crit. Care Med. 156:766-775.

Holgate, 1997, "The cellular and mediator basis of asthma in relation to natural history", Lancet 350 (Suppl. 2):5-9.

Kanagawa et al., 1993, "Resistance of mice deficient in IL-4 to retrovirus-induced immunodeficiency syndrome (MAIDS)", Science 262:240-242.

Kaneshima et al., 1994, "Human hematolymphoid cells in SCID mice", Curr. Opin. Immunol. 6:327-333.

Karlin and Altschul, 1993, "Applications and statistics for multiple high-scoring segments in molecular sequences", Proc. Natl. Acad. Sci. USA 90:5873-5877.

Karlin and Altschul, 1990, "Methods for assessing the statistical significance of molecular sequence features by using general scoring schemes", Proc Natl Acad Sci USA 87:2264-2268.

Klemenz et al., 1989, "Serum- and oncoprotein-mediated induction of a gene with sequence similarity to the gene encoding carcinoembryonic antigen", Proc. Natl. Acad. Sci. USA 86:5708-5712.

Ko and Engel, 1993, "DNA binding specificities of the GATA transcription factor family", Mol. Cell. Biol. 13:4011-4022.

Kumar et al., 1997, "Expression of ST2, an interleukin-1 receptor homologue, is induced by proinflammatory stimuli", Biochem. Biophys. Res. Comm. 235:474-478.

Liew, 1994, "Induction and regulation of $CD4^+$T cell subsets", CIBA Foundation Symposium 87:170-178.

Löhning et al., 1998, "T1/ST2 is preferentially expressed on murine Th2 cells, independent of interleukin 4, interleukin 5, and interleukin 10, and important for Th2 effector function", Proc. Natl. Acad. Sci. USA 95:6930-6935.

Lukacs et al., 1994, "Interleukin-4-dependent pulmonary eosinophil infiltration in a murine model of asthma", Am. J. Respir. Cell Mol. Biol. 10:526-532.

Maggi et al., 1994, "Th2-like $CD8^+$T cells showing B cell helper function and reduced cytolytic activity in human immunodeficiency virus type 1 infection", J. Exp. Med. 180:489-495.

Maggi et al., 1994, "Ability of HIV to promote a $T_H1$ to $T_H0$ shift and to replicate preferentially in $T_H2$ to $T_H0$ cells", Science 265:244-248.

Makino et al., 1990, "H-2-associated and background genes influence the development of a murine retrovirus-induced immunodeficiency syndrome", J. Immunol. 144:4347-4355.

Manetti et al., 1994, "CD30 expression by $CD8^+$T cells producing type 2 helper cytokines. Evidence for large numbers of $CD8^+CD30^+$T cell clones in human immunodeficiency virus infection", J. Exp. Med. 180:2407-2411.

McMahan et al., 1991, "A novel IL-1 receptor, cloned from B cells by mammalian expression, is expressed in many cell types", EMBO J. 10:2821-2832.

Metzler and Xu, 1997, "The role of mast cells in atherosclerosis", Int. Arch. Allergy Immunol. 114:10-14.

Moll et al., 1991, "Expression of T-cell-associated serine proteinase 1 during murine *Leishmania major* infection correlates with susceptibility to disease", Infect. Immun. 59:4701-4705.

Mosmann and Moore, 1991, "The role of IL-10 in crossregulation of $T_H1$ and $T_H2$ responses", Immunol Today 12:A49-A53.

Mosmann and Coffman, 1989, "TH1 and TH2 cells: Different patterns of lymphokine secretion lead to different functional properties", Annu. Rev. Immunol. 7:145-173.

Murphy et al., 1990, "Induction by antigen of intrathymic apoptosis of $CD4^+CD8^+TCR^{lo}$ thymocytes in vivo", Science 250:1720-1723.

Myers and Miller, 1988, "Optimal Alignments in Linear Space", Comput. Appl. Biosci. 4:11-17.

Oettgen and Ghea, 1999, "IgE in asthma and atopy: cellular and molecular connections", J. Clin. Invest. 104:829-835.

Ohashi et al., 1992, "Airway hyperresponsiveness, increased intracellular spaces of bronchial epithelium, and increased infiltration of eosinophils and lymphocytes in bronchial mucosa in asthma", Am. Rev Respir. Dis. 145:1469-1476.

Ray and Cohn, 1999, "Th2 cells and GATA-3 in asthma: new insights into the regulation of airway inflammation", J. Clin. Invest. 104:985-993.

Robinson et al., 1993, "Activation of $CD4^+$T cells, increased $T_{H2}$-type cytokine mRNA expression, eosinophil recruitment in bronchoalveolar lavage after allergen inhalation challenge in patients with atopic asthma", J. Allergy Clin. Immunol. 92:313-324.

Romagnani, 1997, "The Th1/Th2 paradigm", Immunol. Today 18:263-266.

Schweitzer and Sharpe, 1998, "Studies using antigen-presenting cells lacking expression of both B7-1 (CD80) and B7-2 (CD86) show distinct requirements for B7 molecules during priming versus restimulation of Th2 but not Th1 cytokine production", J. Immunol. 161:2762-2771.

Seder et al., 1994, "CD28-mediated costimulation of interleukin 2 (IL-2) production plays a critical role in T cell priming for IL-4 and interferon-γ production", J. Exp. Med. 179:299-304.

Seder and Gros, 1995, "The functional role of $CD8^+$T helper type 2 cells", J. Exp. Med. 181:5-7.

Shinkai et al., 1992, "RAG-2-deficient mice lack mature lymphocytes owing to inability to initiate V(D)J rearrangement", Cell 68:855-867.

Tepper et al., 1990, "IL-4 induces allergic-like inflammatory disease and alters T cell development in transgenic mice", Cell 62:457-467.

Tominaga et al., 1999, "Presence and expression of a novel variant form of ST2 gene product in human leukemic cell line UT-7/GM", Biochem. Biophys. Res. Comm. 264:14-18.

Tominaga et al., 1992, "Nucleotide sequence of a complementary DNA for human ST2", Biochim. Biophys. Acta 1171:215-218.

Tominaga et al., 1991, "Molecular cloning of the murine ST2 gene. Characterization and chromosomal mapping", Biochim. Biophys. Acta 1090:1-8.

Tominaga, 1989, "A putative protein of a growth specific cDNA from BALB/c-3T3 cells is highly similar to the extracellular portion of mouse interleukin 1 receptor", FEBS Lett. 258:301-304.

Tsuyuki et al., 1997, "Costimulation through B7-2 (CD86) is required for the induction of a lung mucosal T helper cell 2 (Th2) immune response and altered airway responsiveness", J. Exp. Med. 185:1671-1679.

Volmer et al., 1994, "T lymphocytes derived from skin lesions of patients with *psoriasis vulgaris* express a novel cytokine pattern that is distinct from that of T helper type 2 cells", Eur. J. Immunol. 24:2377-2382.

Wang et al., 1992, "IL-4 activates a distinct signal transduction cascade from IL-3 in factor-dependent myeloid cells", Embo J. 11:4899-4908.

Werenskiold, 1992, "Characterization of a secreted glycoprotein of the immunoglobulin superfamily inducible by mitogen and oncogene", Eur. J. Biochem. 204:1041-1047.

Werenskiold et al., 1989, "Induction of a mitogen-responsive gene after expression of the Ha-*ras* oncogene in NIH 3T3 fibroblasts", Mol. Cell. Biol. 9:5207-5214.

Wierenga et al., 1990, "Evidence for compartmentalization of functional subsets of CD4+T lymphocytes in atopic patients", J. Immunol. 144:4651-4656.

Yamamura et al., 1991, "Defining protective responses to pathogens: Cytokine profiles in leprosy lesions", Science 254:277-279.

Yanagisawa et al., 1993, "Presence of a novel primary response gene ST2L, encoding a product highly similar to the interleukin 1 receptor type 1", FEBS Lett. 318:83-87.

Young et al., 1992, "Expression of cytolytic mediators by synovial fluid lymphocytes in rheumatoid arthritis", Am. J. Path. 140:1261-1268.

Zheng and Flavell, 1997, "The transcription factor GATA-3 is necessary and sufficient for Th2 cytokine gene expression in CD4 T cells", Cell 89:587-596.

GenBank Accession No. E07716, cDNA encoding human ST2, published Jun. 1994.

Tago et al., 2001, Biochem and Biophys. Res. Comm. vol. 285: 1377-1383.

Owens et al., 1994, J. Immunol. Methods, vol. 168: 149-161.

Tominaga, Shinichi, "cDNA encoding mouse ST2 coding," Sep. 1997, (sequence) GenBank [online] Bethesda, MD, USA: National Center for Biotechnology Information. Retrieved from the Internet: URL: http://www.ncbi.nlm.nih.gov/>. GenBank Accession No. E07714.

Tominaga, Shinichi, "RecName: Full=Interleukin-1 receptor-like 1; AltName: Full=Lymphocyte antigen 84; AltName: Full=Protein ST2; AltName: Full=Protein T1; Flags: Precursor," May 2000, (sequence) GenBank [online] Bethesda, MD, USA: National Center for Biotechnology Information. Retrieved from the Internet: URL: http://www.ncbi.nlm.nih.gov/>. GenBank Accession No. P14719.

Yanagisawa, K., et al., "cDNA encoding mouse ST2L which is produced specifically when cell is moving stage G0 to G1," Sep. 1997 (sequence) GenBank [online] Bethesda, MD, USA: National Center for Biotechnology Information. Retrieved from the Internet: URL: http://www.ncbi.nlm.nih.gov/>. GenBank Accession No. E08652.

Yanagisawa, K.,, "ST2L protein—mouse," Nov. 1999 (sequence) GenBank [online] Bethesda, MD, USA: National Center for Biotechnology Information. Retrieved from the Internet: URL: http://www.ncbi.nlm.nih.gov/>. GenBank Accession No. S29498.

Yanagisawa, K., "Homo sapiens mRNA for ST2L, 5' noncoding region including distal exon (exon 1a), complete cds." Jan. 2000, (sequence) GenBank [online] Bethesda, MD, USA: National Center for Biotechnology Information. Retrieved from the Internet: URL: http://www.ncbi.nlm.nih.gov/>. GenBank Accession No. AB012701.

Yanagisawa, K., ST2L [Homo sapien]. Jan. 2000, (sequence) GenBank [online] Bethesda, MD, USA: National Center for Biotechnology Information. Retrieved from the Internet: URL: http://www.ncbi.nlm.nih.gov/>. GenBank Accession No. BAA82405.

Tominaga, Shinichi, "Homo sapiens mRNA for ST2Protein," Feb. 2000, (sequence) GenBank [online] Bethesda, MD, USA: National Center for Biotechnology Information. Retrieved from the Internet: URL: http://www.ncbi.nlm.nih.gov/>. GenBank Accession No. D12763.

Tominaga, Shinichi, "ST2 protein [Homo sapiens]," Feb. 2000, (sequence) GenBank [online] Bethesda, MD, USA: National Center for Biotechnology Information. Retrieved from the Internet: URL: http://www.ncbi.nlm.nih.gov/>. GenBank Accession No. D12763.

Tominaga, Shinichi, "Homo sapiens ST2V mRNA, complete cds," Oct. 1999, (sequence) GenBank [online] Bethesda, MD, USA: National Center for Biotechnology Information. Retrieved from the Internet: URL: http://www.ncbi.nlm.nih.gov/>. GenBank Accession No. AB029084.

Tominaga, Shinichi, "ST2V [Homo sapiens]," Oct. 1999, (sequence) GenBank [online] Bethesda, MD, USA: National Center for Biotechnology Information. Retrieved from the Internet: URL: http://www.ncbi.nlm.nih.gov/>. GenBank Accession No. BAA85894.

Tominaga, Shinichi, "Mouse ST2 Gene," Mar. 1995, (sequence) GenBank [online] Bethesda, MD, USA: National Center for Biotechnology Information. Retrieved from the Internet: URL: http://www.ncbi.nlm.nih.gov/>. GenBank Accession No. Y07519.

Dijkmans, R. et al., "Mouse interferon-gamma (MuIFN-gamma) mRNA sequence," Apr. 1993, (sequence) GenBank [online] Bethesda, MD, USA: National Center for Biotechnology Information. Retrieved from the Internet: URL: http://www.ncbi.nlm.nih.qov/>. GenBank Accession No. M28621.

* cited by examiner

```
          10         20         30         40         50         60
TTAGCGCCAT TGCCATAGAG AGACCTCAGC CATCAATCAC TAGCACATGA TTGACAGACA    60
GAGAATGGGA CTTTGGGCTT TGGCAATTCT GACACTTCCC ATGTATTTGA CAGTTACGGA   120
GGGCAGTAAA TCGTCCTGGG GTCTGGAAAA TGAGGCTTTA ATTGTGAGAT GCCCCCAAAG   180
AGGACGCTCG ACTTATCCTG TGGAATGGTA TTACTCAGAT ACAAATGAAA GTATTCCTAC   240
CCAAAAAAAA AAAAA                                                   250
```

FIG. 1

```
  1 atgattgaca gacagagaat gggactttgg gctttggcaa ttctgacact tcccatgtat
 61 ttgacagtta cggagggcag taaatcgtcc tggggtctgg aaaatgaggc tttaattgtg
121 agatgcccccc aaagaggacg ctcgacttat cctgtggaat ggtattactc agatacaaat
181 gaaagtattc ctactcaaaa aagaaatcgg atctttgtct caagagatcg tctgaagttt
241 ctaccagcca gagtcgaaga ctctgggatt tatgcttgtg ttatcagaag ccccaacttg
301 aataagactg gatacttgaa tgtcaccata cataaaaagc cgccaagctg caatatccct
361 gattatttga tgtactcgac agtacgtgga tcagataaaa atttcaagat aagctgtcca
421 acaattgacc tgtataattg gacagcacct gttcagtggt ttaagaactg caaagctctc
481 caagagccaa ggttcagggc acacaggtcc tacttgttca ttgacaacgt gactcatgat
541 gatgaaggtg actacacttg tcaattcaca cacgcggaga tggaaccaa ctacatcgtg
601 acggccacca gatcattcac agttgaagaa aaaggctttt ctatgtttcc agtaattaca
661 aatcctccat acaaccacac aatggaagtg aaataggaa accagcaag tattgcctgt
721 tcagcttgct ttggcaaagg ctctcacttc ttggctgatg tcctgtggca gattaacaaa
781 acagtagttg gaaattttgg tgaagcaaga attcaagaag aggaaggtcg aaatgaaagt
841 tccagcaatg acatggattg tttaacctca gtgttaagga taactggtgt gacagaaaag
901 gacctgtccc tggaatatga ctgtctggcc ctgaaccttc atggcatgat aaggcacacc
961 ataaggctga aaggaaaca accaagtaag gagtgtccct cacacattgc t
```

FIG. 3A

```
MIDRQRMGLWALAILTLPMYLTVTEGSKSSWGLENEALIVRCPQRGRSTYPVEWYYSD
TNESIPTQKRNRIFVSRDRLKFLPARVEDSGIYACVIRSPNLNKTGYLNVTIHKKPPSCNIP
DYLMYSTVRGSDKNFKITCPTIDLYNWTAPVQWFKNCKALQEPRFAHRSYLFIDNVTH
DDEGDYTCQFTHAENGTNYIVTATRSFTVEEKGFSMPVITNPPYNHTMEVEIGKPASIA
CSACFGKGSHFLADVLWQINKTVVGNFGEARIQEEEGRNESSSNDMDCLTSVLRITGVT
EKDLSLEYDCLALNLHGMIRHTIRLRRKQPSKECPSHIA
```

FIG. 3B

```
   1 tgccattgcc atagagagac ctcagccatc aatcactagc acatgattga cagacagaga
  61 atgggacttt gggctttggc aattctgaca cttcccatgt atttgacagt tacggagggc
 121 agtaaatcgt cctggggtct ggaaaatgag gcttaatlg tgagatgccc ccaaagagga
 181 cgctcgactt atcctgtgga atggtattac tcagatacaa atgaaagtat tcctactcaa
 241 aaaagaaatc ggatctttgt ctcaagagat cgtctgaagt ttctaccagc cagagtggaa
 301 gactctggga tttatgcttg tgttatcaga agccccaact tgaataagac tggatacttg
 361 aatgtcacca tacataaaaa gccgccaagc tgcaatatcc ctgattattt gatgtactcg
 421 acagtacgtg gatcagataa aaatttcaag ataacgtgtc caacaattga cctgtataat
 481 tggacagcac ctgttcagtg gtttaagaac tgcaaagctc tccaagagcc aaggttcagg
 541 gcacacaggt cctacttgtt cattgacaac gtgactcatg atgatgaagg tgactacact
 601 tgtcaattca cacacgcgga gaatggaacc aactacatcg tgacggccac cagatcattc
 661 acagttgaag aaaaaggctt ttctatgttt ccagtaatta caaatcctcc atacaaccac
 721 acaatggaag tggaaatagg aaaaccagca agtattgcct gttcagcttg ctttggcaaa
 781 ggctctcact tcttggctga tgtcctgtgg cagattaaca aaacagtagt tggaaatttt
 841 ggtgaagcaa gaattcaaga agaggaagt cgaaatgaaa gttccagcaa tgacatggat
 901 tgtttaacct cagtgttaag gataactggt gtgacagaaa aggacctgtc cctggaatat
 961 gactgtctgg ccctgaacct tcatggcatg ataaggcaca ccataaggct gagaaggaaa
1021 caaccaattg atcaccgaag catctactac atagttgctg gatgtagttt attgctaatg
1081 tttatcaatg tcttggtgat agtcttaaaa gtgttctgga ttgaggttgc tctgttctgg
1141 agagatatag tgacaccta caaacccgg aacgatggca agctctacga tgcgtacatc
1201 atttaccctc gggtcttccg gggcagcgcg gcgggaaccc actctgtgga gtactttgtt
1261 caccacactc tgcccgacgt tcttgaaaat aaatgtggct acaaattgtg catttatggg
1321 agagacctgt tacctgggca agatgcagcc accgtggtgg aaagcagtat ccagaatagc
1381 agaagacagg tgtttgttct ggccctcac atgatgcaca gcaaggaatt tgcctacgag
1441 caggagattg ctctgcacag cgccctcatc cagaacaact ccaaggtgat tcttattgaa
1501 atggagcctc tgggtgaggc aagccgacta caggttgggg acctgcaaga ttctctccag
1561 catcttgtga aaattcaggg gaccatcaag tggaggggaag atcatgtggc cgacaagcag
1621 tctctaagtt ccaaattctg gaagcatgtg aggtaccaaa tgccagtgcc agaaagagcc
1681 tccaagacgg catctgttgc ggctccgttg agtggcaagg catgcttaga cctgaaacac
1741 ttttgagttg agagctgcgg agtcccagca gtaggcaccg gagtgcaggt gtgcagactt
1801 gaaatgccaa gggtgggggc cccaagtctc agctaaagag caactctagt ttatttttcct
1861 ggttatggta ggagccaccc atcgtttgtt tccggtttcc ttttcctact tcactcttgt
1921 ggcacaagat caaccctgag cttttttcctt ttcttttatt tctctttttg ttccttcttt
1981 taaaagcttt ttaaaattga ttatcttatt tatctacctt tcaaaggtta tccccctcc
2041 cggtgccccc tctacaaatc cccatcctgc ttccctcctc cctgcttcta tgagggtgcc
2101 ccccccacctg cccatccact ccagccttac aggccttgtg ttcccctatg ctggggcatc
2161 gagcctccat aagaccctcc ctctcattca tcaattatct acattctgaa tatcaagccg
2221 acactttgt tttttgtttttt gattttttga gacagggttt ctctgtgtag ccctggctgt
2281 cttgaaactc acattgtaga ccaggctggc ctcgaactca gaatcagcc tgcctctgcc
2341 tccccgagtg ctgggattaa aggcgtgcgc caccacgccg ggctaagcct acactttcag
2401 aataaagttc tgattcacct caaagagcag tctccattccc agaggcagag agccggaaag
2461 agcctccaat gtgcttgtcc aggcagagct gaccttattt gcttaccagt cacaggtaaa
2521 caaagcgttt ctccgtgttg cctcttgtag acatccctgt aatagattag gaagggaatg
2581 agccgtccta ctgaccagtt tgtgaattgt ggtagaaaaa gcgttgacgt ttgttaaata
2641 cttgttagca atgtaaacct cattcctaac acaccagaat ttcttacttt ttattcgtca
2701 attaccgagt tttgtcaagt cagtattaac agatttggtc gaataccttta cccaaattgc
2761 cattacagtc gagcatgttt tcagttctaa atgccttta tatatttttt attcttctta
2821 gaaatacttc ctcactttaa aagtaatgta aagtgtgtt agaaaacata aggtgtaaga
2881 gaaagtatga taaaatataa aaaataatag aaaggaaagg aaatataatg aaaatcataa
2941 ctcttaagat taattttggt aggtctgtat tttaaaatat aattaaattt tataccgata
3001 acttttatag ctgagattgt acactacaga ctaggcagct tttcctattt accaccataa
3061 tgaaaactgg tggctgattt ctttaacatt cacagaagtt ccaaatgtct cattttagac
3121 tgtgctgcag actatggctg aagcagccag aatgagaaac aggtctgcca tgtcacatcg
3181 ggacattttc ctacttactg aaatgtatct gtcactgtgc gacagctaac ttttgtgata
3241 ctcctatgaa atgtgtaggg aatttggaca gaacagaatc aatctatagt cagaggtcct
3301 ctggacagtc ttttccagga gcacacacag accgtgaggt cctaggcacc caggaaacgg
3361 atccagagcc caggcaagtg tcttacaggt accttgaatt ttgccaatag atatgagccc
3421 tgccttagct gagttgctca gtcggtgatg ggactccagg ctgaggtgac aatgaacaca
```

FIG. 4A

```
3481 gaatttggga gactcttgaa aggaggggaa tgttgaactc acggtcaaca tatgaggctg
3541 cagagaagcc gtatgcagaa gtgtgtgtag aggatctaga gtagcccgtt tctctgggga
3601 cagtgtgctc ttagtctgta cccttaggct gggttgccag gtaaacattt gctagtgttc
3661 agttcaaagg ctgaagcttg agctgagggt gatgaggaat tcaaacttcc cctcgcatgc
3721 atccaccctg tggttgcctg gtttgctaag tccacctgct ctgctgtagt agaaggtttt
3781 gatcttctgc agcttcatct acttcttagt gagttgccaa aactgaccac tgaaaagcat
3841 gctgtgtaca taactgtctc atgtcccaga acgtgcaatc aggaggaagt cctcactccc
3901 gataacggaa tccttgctct gtggctgtga ggacgtccct tagcaacctc agatagtaat
3961 ttttcttagg ttggatggaa catagtaacg tgctggattc tttgctaact gaaaatagaa
4021 gtattcggat ttcagaaaga actggataaa tattaatgtt ggtgattatg aaatctcatt
4081 gtgagccgtg tgagtttgag tgtgtattcc atgattgtgc tgaatgaaga cctctaaaaa
4141 tgaaattctc tccaatctca tccctgggaa tagttgcttc ctcatgcctg ctgctccatc
4201 catggaaaat gactaaagag aattattatt tgttcccgag attcttctga taagtctaaa
4261 ctatttgcat gtaattgagc tgggcagcat ggcacacttg ggaggcagag gcaggtggat
4321 ctctgtgagt ttgaggccag cctgctctac agagttagtt ccaggacacc agagctacaa
4381 aaagaaaacc tgtcctaaca acaacagcaa cagctgcagc agcaacaaca acaacaaaga
4441 aaagaagag gaggaggagg aaaggaaaga aggaagaagg aagaagaaag ggaagaaata
4501 atagattttt ctgtaatgaa cacacatatg ctttgatgct tttgctaaac tcaaaatatt
4561 agttttattt tactgttttg aaaggttcaa agcatgatcc atgtaaaaat gtcttctgtg
4621 gggctttctc ccatttctac ttttgttccc ctcatttctt caaagtgctt gtccaggcag
4681 agctgaccct atttgcttac cagttacagg taaacaaagc gtttcctcgt gttgcctctt
4741 gtagccatct ctgtattaga ttaggaaggg aaggagccgt cctactgtcc agtttgtgag
4801 ttctggtaga aagagtgttg aagtttgtta aatgcttgtt ttccatgtat caaaatgtta
4861 tgcctttcct attattatt gtatgacaaa ttatttttca ctgggcaaaa ataattgtgc
4921 cattgactcc ttgtgtgttt tcttcatgtg tgtttgaaga gttctagctt attaaaaaaa
4981 aaaatctag
```

FIG. 4A CONTD

MIDRQRMGLWALAILTLPMYLTVTEGSKSSWGLENEALIVRCPQRGRSTYPVEWYYSD
TNESIPTQKRNRIFVSRDRLKFLPARVEDSGIYACVIRSPNLNKTGYLNVTIHKKPPSCNIP
DYLMYSTVRGSDKNFKJTCPTIDLYNWTAPVQWFKNCKALQEPRFRAHRSYLFIDNVTH
DDEGDYTCQFTHAENGTNYIVTATRSFTVEEKGFSMFPVITNPPYNHTMEVEIGKPASIA
CSACFGKGSHFLADVLWQINKTVVGNFGEARIQEEEGRNESSSNDMDCLTSVLRITGVT
EKDLSLEYDCLALNLHGMIRHTIRLRRKQPIDHRSIYYTVAGCSLLLMFINVLVIVLKVFW
IEVALFWRDIVTPYKTRNDGKLYDAYIIYPRVFRGSAAGTHSVEYFVHHTLPDVLENKC
GYKLCIYGRDLLPGQDAATVVESSIQNSRRQVFVLAPHMMHSKEFAYEQEIALHSALIQ
NNSKVILIEMEPLGEASRLQVGDLQDSLQHLVKIQGTIKWREDHVADKQSLSSKFWKHV
RYQMPVPERASKTASVAAPLSGKACLDLKHF

FIG. 4B

```
   1 aaagagaggc tggctgttgt atttagtaaa gctataaagc tgtaagagaa attggctttc
  61 tgagttgtga aactgtgggc agaaagttga ggaagaaaga actcaagtac aacccaatga
 121 ggttgagata taggctactc ttcccaactc agtcttgaag agtatcacca actgcctcat
 181 gtgtggtgac cttcactgtc gtatgccagt gactcatctg gagtaatctc aacaacgagt
 241 taccaatact tgctcttgat tgataaacag aatggggttt tggatcttag caattctcac
 301 aattctcatg tattccacag cagcaaagtt tagtaaacaa tcatggggcc tggaaaatga
 361 ggctttaatt gtaagatgtc ctagacaagg aaaacctagt tacaccgtgg attggtatta
 421 ctcacaaaca aacaaaagta ttcccactca ggaaagaaat cgtgtgtttg cctcaggcca
 481 acttctgaag tttctaccag ctgaagttgc tgattctggt atttatacct gtattgtcag
 541 aagtcccaca ttcaatagga ctggatatgc gaatgtcacc atatataaaa aacaatcaga
 601 ttgcaatgtt ccagattatt tgatgtatct aacagtatct ggatcagaaa aaaattccaa
 661 aatttattgt cctaccattg acctctacaa ctggacagca cctcttgagt ggtttaagaa
 721 ttgtcaggct cttcaaggat caaggtacag ggcgcacaag tcatttttgg tcattgataa
 781 tgtgatgact gaggacgcag gtgattacac ctgtaaattt atacacaatg aaaatggagc
 841 caattatagt gtgacggcga ccaggtcctt cacggtcaag gatgagcaag gcttttctct
 901 gtttccagta atcggagccc ctgcacaaaa tgaaataaag gaagtggaaa ttggaaaaaa
 961 cgcaaaccta acttgctctg cttgttttgg aaaaggcact cagttcttgg ctgccgtcct
1021 gtggcagctt aatggaacaa aaattacaga ctttggtgaa ccaagaattc aacaagagga
1081 agggcaaaat caaagtttca gcaatgggct ggcttgtcta gacatggttt taagaatagc
1141 tgacgtgaag gaagaggatt tattgctgca gtacgactgt ctggccctga atttgcatgg
1201 cttgagaagg cacaccgtaa gactaagtag gaaaaatcca attgatcatc atagcatcta
1261 ctgcataatt gcagtatgta gtgtattttt aatgctaatc aatgtcctgg ttatcatcct
1321 aaaaatgttc tggattgagg ccactctgct ctggagagac atagctaaac cttacagac
1381 taggaatgat ggaaagctct atgatgctta tgttgtctac ccacggaact acaaatccag
1441 tacagatggg gccagtcgtg tagagcactt tgttcaccag attctgcctg atgttcttga
1501 aaataaatgt ggctatacct tatgcattta tgggagagat atgctacctg gagaagatgt
1561 agtcactgca gtggaaacca acatacgaaa gagcaggcgg cacattttca tcctgacccc
1621 tcagatcact cacaataagg agtttgccta cgagcaggag gttgccctgc actgtgccct
1681 catccagaac gacgccaagg tgatacttat tgagatggag gctctgagcg agctggacat
1741 gctgcaggct gaggcgcttc aggactccct ccagcatctt atgaaagtac aggggaccat
1801 caagtggagg gaggaccaca ttgccaataa aaggtccctg aattccaaat tctggaagca
1861 cgtgaggtac caaatgcctg tgccaagcaa aattcccaga aaggcctcta gtttgactcc
1921 cttggctgcc cagaagcaat agtgcctgct gtgatgtgca aagggatctg ggtttgaagc
1981 tttcctgact tctcctagct ggcttatgcc cctgcactga agtgtgagga gcgggaatat
2041 taaagggatt caggccac
```

FIG.5A

```
  1 mgfwilailt ilmystaakf skqswglene alivrcprqg kpsytvdwyy sqtnksiptq
 61 ernrvfasgq llkflpaeva dsgiytcivr sptfnrtgya nvtiykkqsd cnvpdylmys
121 tvsgseknsk iycptidlyn wtaplewfkn cqalqgsryr ahksflvidn vmtedagdyt
181 ckfihnenga nysvtatrsf tvkdeqgfsl fpvigapaqn eikeveigkn anltcsacfg
241 kgtqflaavl wqlngtkitd fgepriqqee gqnqsfsngl acldmvlria dvkeedlllq
301 ydclalnlhg lrrhtvrlsr knpidhhsiy ciiavcsvfl mlinvlviil kmfwieatll
361 wrdiakpykt rndgklyday vvyprnykss tdgasrvehf vhqilpdvle nkcgytlciy
421 grdmlpgedv vtavetnirk srrhifiltp qithnkefay eqevalhcal iqndakvili
481 emealseldm lqaealqdsl qhlmkvqgti kwredhiank rslnskfwkh vryqmpvpsk
541 iprkassltp laaqkq
```

FIG.5B

```
   1 atctcaacaa cgagttacca atacttgctc ttgattgata aacagaatgg ggttttggat
  61 cttagcaatt ctcacaattc tcatgtattc cacagcagca aagtttagta aacaatcatg
 121 gggcctggaa aatgaggctt taattgtaag atgtcctaga caaggaaaac ctagttacac
 181 cgtggattgg tattactcac aaacaaacaa aagtattccc actcaggaaa gaaatcgtgt
 241 gtttgcctca ggccaacttc tgaagtttct accagctgaa gttgctgatt ctggtattta
 301 tacctgtatt gtcagaagtc ccacattcaa taggactgga tatgcgaatg tcaccatata
 361 taaaaaacaa tcagattgca atgttccaga ttatttgatg tattcaacag tatctggatc
 421 agaaaaaaat tccaaaattt attgtcctac cattgacctc tacaactgga cagcacctct
 481 tgagtggttt aagaattgtc aggctcttca aggatcaagg tacagggcgc acaagtcatt
 541 tttggtcatt gataatgtga tgactgagga cgcaggtgat tacacctgta aatttataca
 601 caatgaaaat ggagccaatt atagtgtgac ggcgaccagg tccttcacgg tcaaggatga
 661 gcaaggcttt tctctgtttc cagtaatcgg agcccctgca caaaatgaaa taaaggaagt
 721 ggaaattgga aaaaacgcaa acctaacttg ctctgcttgt tttggaaaag gcactcagtt
 781 cttggctgcc gtcctgtggc agcttaatgg aacaaaaatt acagactttg gtgaaccaag
 841 aattcaacaa gaggaagggc aaaatcaaag tttcagcaat gggctggctt gtctagacat
 901 ggtttttaaga atagctgacg tgaaggaaga ggatttattg ctgcagtacg actgtctggc
 961 cctgaatttg catggcttga gaaggcacac cgtaagacta agtaggaaaa atccaagtaa
1021 ggagtgtttc tgagactttg atcacctgaa ctttctctag caagtgtaag cagaatggag
1081 tgtggttcca agagatccat caagacaatg ggaatggcct gtgccataaa atgtgcttct
1141 cttcttcggg atgttgtttg ctgtctgatc tttgtagact gttcctgttt gctgggagct
1201 tctctgctgc ttaaattgtt cgtcctcccc cactccctcc tatcgttggt ttgtctagaa
1261 cactcagctg cttctttggt catccttgtt ttctaacttt atgaactccc tctgtgtcac
1321 tgtatgtgaa aggaaatgca ccaacaaccg aaaactg
```

FIG.6A

MGFWILAILTILMYSTAAKFSKQSWGLENEALIVRCPRQGKPSYTVDW
YYSQTNKSIPTQERNRVFASGQLLKFLPAEVADSGIYTCIVRSPTFNRT
GYANVTIYKKQSDCNVPDYLMYSTVSGSEKNSKIYCPTIDLYNWTAPL
EWFKNCQALQGSRYRAHKSFLVIDNVMTEDAGDYTCKFIHNENGAN
YSVTATRSFTVKDEQGFSLFPVIGAPAQNEIKEVEIGKNANLTCSACFG
KGTQFLAAVLWQLNGTKITDFGEPRIQQEEGQNQSFSNGLACLDMVL
RIADVKEEDLLLQYDCLALNLHGLRRHTVRLSRKNPSKECF

FIG.6B

```
   1 cttagctccg tcactgactc caagttcatc ccctctgtct ttcagtttgg ttgagatata
  61 ggctactctt cccaactcag tcttgaagag tatcaccaac tgcctcatgt gtggtgacct
 121 tcactgttgt atgccagtga ctcatctgga gtaatctcaa caacgagtta ccaatacttg
 181 ctcttgattg ataaacagaa tggggttttg gatcttagca attctcacaa ttctcatgta
 241 ttccacagca gcaaagttta gtaaacaatc atggggcctg gaaaatgagg ctttaattgt
 301 aagatgtcct agacaaggaa aacctagtta caccgtggat tggtattact cacaaacaaa
 361 caaaagtatt cccactcagg aaagaaatcg tgtgtttgcc tcaggccgac ttctgaagtt
 421 tctaccagct gaagttgctg attctggtat ttatacctgt attgtcagaa gtcccacatt
 481 caataggact ggatatgcga atgtcaccat atataaaaaa caatcagatt gcaatgttcc
 541 agattatttg atgtattcaa cagtatctgg atcagaaaaa aattccaaaa tttattgtcc
 601 taccattgac ctctacaact ggacagcacc tcttgagtgg tttaagaatt gtcaggctct
 661 tcaaggatca aggtacaggg cgcacaagtc attttggtc attgataatg tgatgactga
 721 ggacgcaggt gattacacct gtaaatttat acacaatgaa aatggagcca attatagtgt
 781 gacggcgacc aggtccttca cggtcaaggt ttggtgtcag agtttctgca aattaaaaaa
 841 gagcttaatc tttagtaata ctcattggat tcaaagtcta atgagaggct tgtgatggt
 901 atactatggt gtacataaat gttgtcgagt ggtttttaat ctttgtttgc aatactttca
 961 acatcatcaa tggccttgaa tgagcaaggc ttttctctgt ttccagtaat cggagcccct
1021 gcacaaaatg aaataaagga agtggaaatt ggaaaaaacg caaacctaac ttgctctgct
1081 tgttttggaa aaggcactca gttcttggct gccgtcctgt ggcagcttaa tggaacaaaa
1141 attacagact ttggtgaacc aagaattcaa caagaggaag gcaaaatca aagtttcagc
1201 aatgggctgg cttgtctaga catggtttta agaatagctg acgtgaagga agaggattta
1261 ttgctgcagt acgactgtct ggccctgaat ttgcatggct tgagaaggca caccgtaaga
1321 ctaagtagga aaaatccaag taaggagtgt ttctgagact ttgatcacct gaactttctc
1381 tagcaagtgt aagcagaatg gagtgtggtt ccaagagatc catcaagaca atgggaatgg
1441 cctgtgccat aaaatgtgct tctcttcttc gggatgttgt ttgctgtctg atctttgtag
1501 actgttcctg tttgctggga gcttctctgc tgcttaaatt gttcgtcctc ccccactccc
1561 tcctatcgtt ggtttgtcta gaacactcag ctgcttcttt ggtcatcctt gttttctaac
1621 tttatgaact ccctctgtgt cactgtatgt gaaaggaaat gcaccaacaa ccgaaaactg
```

FIG.7A

```
   1 mgfwilailt ilmystaakf skqswglene alivrcprqg kpsytvdwyy sqtnksiptq
  61 ernrvfasgr llkflpaeva dsgiytcivr sptfnrtgya nvtiykkqsd cnvpdylmys
 121 tvsgseknsk iycptidlyn wtaplewfkn cqalqgsryr ahksflvidn vmtedagdyt
 181 ckfihnenga nysvtatrsf tvkvwcqsfc klkkslifsn thwiqslmrg fvmvyygvhk
 241 ccrvvfnlcl qyfqhhqwp
```

FIG.7B

```
GTCGACCCACGCGTCCGCCCACGCGTCCGCTGGAGTAATCTCAACAACGAGTTACCAATACTTGCTCTTGATTGATAAA    79

M   G   F   W   I   L   A   I   L   T   I   L   M   Y   S   T   A   A      18
CAGA ATG GGG TTT TGG ATC TTA GCA ATT CTC ACA ATT CTC ATG TAT TCC ACA GCA GCA         137

K   F   S   K   Q   S   W   G   L   E   N   E   A   L   I   V   R   C   P   R      38
AAG TTT AGT AAA CAA TCA TGG GGC CTG GAA AAT GAG GCT TTA ATT GTA AGA TGT CCT AGA     197

Q   G   K   P   S   Y   T   V   D   W   Y   Y   S   Q   T   N   K   S   I   P      58
CAA GGA AAA CCT AGT TAC ACC GTG GAT TGG TAT TAC TCA CAA ACA AAC AAA AGT ATT CCC     257

T   Q   E   R   N   R   V   F   A   S   G   Q   L   L   K   F   L   P   A   A      78
ACT CAG GAA AGA AAT CGT GTG TTT GCC TCA GGC CAA CTT CTG AAG TTT CTA CCA GCT GCA     317

V   A   D   S   G   I   Y   T   C   I   V   R   S   P   T   F   N   R   T   G      98
GTT GCT GAT TCT GGT ATT TAT ACC TGT ATT GTC AGA AGT CCC ACA TTC AAT AGG ACT GGA     377

Y   A   N   V   T   I   Y   K   K   Q   S   D   C   N   V   P   D   Y   L   M     118
TAT GCG AAT GTC ACC ATA TAT AAA AAA CAA TCA GAT TGC AAT GTT CCA GAT TAT TTG ATG     437

Y   S   T   V   S   G   S   E   K   N   S   K   I   Y   C   P   T   I   D   L     138
TAT TCA ACA GTA TCT GGA TCA GAA AAA AAT TCC AAA ATT TAT TGT CCT ACC ATT GAC CTC     497

Y   N   W   T   A   P   L   E   W   F   K   M   S   K   A   F   L   C   F   Q     158
TAC AAC TGG ACA GCA CCT CTT GAG TGG TTT AAG ATG AGC AAG GCT TTT CTC TGT TTC CAG     557

*                                                                                  159
TAA                                                                                  560

TCGGAGCCCCTGCACAAAATGAAATAAAGGAAGTGGAAATTGGCACTCAGTTCTTGGCTGCCGTCCTGTGGCAGCTTAA     639

TGGAACAAAAATTACAGACTTTGGTGAACCAAGAATTCAACAAGAGGAAGGGCAAAATCAAAGTTTCAGCAATGGGCTG    718

GCTTGTCTAGACATGGTTTTAAGAATAGCTGACGTGAAGGAAGAGGATTTATTGCTGCAGTACGACTGTCTGGCCCTGA   797

ATTTGCATGGCTTGAGAAGGCACACCGTAAGACTAAGTAGGAAAAATCCAAGTAAGGAGTGTTTCTGAGACTTTGATCA   876

CCTGAACTTTCTCTAGCAAGTGTAAGCAGAATGGAGTGTGGTTCCAAGAGATCCATCAAGACAATGGGAATGGCCTGTG   955

CCATAAAATGTGCTTCTCTTCTTCGGGATGTTGTTTGCTGTCTGATCTTTCTAGACTGTTCCTGTTTGCTGGGAGCTTC  1034

TCTGCTGCTTAAATTGTTCGTCCTCCCCCACTCCCTCCTATCGTTGGTTTGTCTAGAACACTCAGCTGCTTCTTTGGTC  1113

ATCCTTGTTTTCTAACTTTATGAACTCCCTCTGTGTCACTGTATGTGAAAGGAAATGCACCAACAACCGTAAAAAAAAA  1192

AAAAAAGGGCGGCCGCT                                                                 1210
```

FIG.8

| | |
|---|---|
| P14719 | MIDRQRMGLW ALAILTLPMY LTVTEGSKSS WGLENEALIV RCPQRGRSTY |
| S29498 | MIDRQRMGLW ALAILTLPMY LTVTEGSKSS WGLENEALIV RCPQRGRSTY |
| | |
| P14719 | PVEWYYSDTN ESIPTQKRNR IFVSRDRLKF LPARVEDSGI YACVIRSPNL |
| S29498 | PVEWYYSDTN ESIPTQKRNR IFVSRDRLKF LPARVEDSGI YACVIRSPNL |
| | |
| P14719 | NKTGYLNVTI HKKPPSCNIP DYLMYSTVRG SDKNFKITCP TIDLYNWTAP |
| S29498 | NKTGYLNVTI HKKPPSCNIP DYLMYSTVRG SDKNFKITCP TIDLYNWTAP |
| | |
| P14719 | VQWFKNCKAL QEPRFRAHRS YLFIDNVTHD DEGDYTCQFT HAENGTNYIV |
| S29498 | VQWFKNCKAL QEPRFRAHRS YLFIDNVTHD DEGDYTCQFT HAENGTNYIV |
| | |
| P14719 | TATRSFTVEE KGFSMFPVIT NPPYNHTMEV EIGKPASIAC SACFGKGSHF |
| S29498 | TATRSFTVEE KGFSMFPVIT NPPYNHTMEV EIGKPASIAC SACFGKGSHF |
| | |
| P14719 | LADVLWQINK TVVGNFGEAR IQEEEGRNES SSNDMDCLTS VLRITGVTEK |
| S29498 | LADVLWQINK TVVGNFGEAR IQEEEGRNES SSNDMDCLTS VLRITGVTEK |
| | |
| P14719 | DLSLEYDCLA LNLHGMIRHT IRLRRKQPSK ECPSHIA... .......... |
| S29498 | DLSLEYDCLA LNLHGMIRHT IRLRRKQPID HRSIYYIVAG CSLLLMFINV |
| | |
| P14719 | .......... .......... .......... .......... .......... |
| S29498 | LVIVLKVFWI EVALFWRDIV TPYKTRNDGK LYDAYIIYPR VFRGSAAGTH |
| | |
| P14719 | .......... .......... .......... .......... .......... |
| S29498 | SVEYFVHHTL PDVLENKCGY KLCIYGRDLL PGQDAATVVE SSIQNSRRQV |
| | |
| P14719 | .......... .......... .......... .......... .......... |
| S29498 | FVLAPHMMHS KEFAYEQEIA LHSALIQNNS KVILIEMEPL GEASRLQVGD |
| | |
| P14719 | .......... .......... .......... .......... .......... |
| S29498 | LQDSLQHLVK IQGTIKWRED HVADKQSLSS KFWKHVRYQM PVPERASKTA |
| | |
| P14719 | .......... ........ |
| S29498 | SVAAPLSGKA CLDLKHF |

FIG.9

```
BAA82405    MGFWILAILT  ILMYSTAAKF  SKQSWGLENE  ALIVRCPRQG  KPSYTVDWYY
BAA02233    MGFWILAILT  ILMYSTAAKF  SKQSWGLENE  ALIVRCPRQG  KPSYTVDWYY
Athdc120c9  MGFWILAILT  ILMYSTAAKF  SKQSWGLENE  ALIVRCPRQG  KPSYTVDWYY
BAA85894    MGFWILAILT  ILMYSTAAKF  SKQSWGLENE  ALIVRCPRQG  KPSYTVDWYY BAA82405    SQTNKSIPTQ  ERNRVFASGQ  LLKFLPAEVA  DSGIYTCIVR  SPTFNRTGYA
BAA02233    SQTNKSIPTQ  ERNRVFASGQ  LLKFLPAEVA  DSGIYTCIVR  SPTFNRTGYA
Athdc120c9  SQTNKSIPTQ  ERNRVFASGQ  LLKFLPAAVA  DSGIYTCIVR  SPTFNRTGYA
BAA85894    SQTNKSIPTQ  ERNRVFASGR  LLKFLPAEVA  DSGIYTCIVR  SPTFNRTGYA BAA82405    NVTIYKKQSD  CNVPDYLMYS  TVSGSEKNSK  IYCPTIDLYN  WTAPLEWFKN
BAA02233    NVTIYKKQSD  CNVPDYLMYS  TVSGSEKNSK  IYCPTIDLYN  WTAPLEWFKN
Athdc120c9  NVTIYKKQSD  CNVPDYLMYS  TVSGSEKNSK  IYCPTIDLYN  WTAPLEWFKM
BAA85894    NVTIYKKQSD  CNVPDYLMYS  TVSGSEKNSK  IYCPTIDLYN  WTAPLEWFKN BAA82405    CQALQGSRYR  AHKSFLVIDN  VMTEDAGDYT  CKFIHNENGA  NYSVTATRSF
BAA02233    CQALQGSRYR  AHKSFLVIDN  VMTEDAGDYT  CKFIHNENGA  NYSVTATRSF
Athdc120c9  SKAFLCFQ..  ..........  ..........  ..........  ..........
BAA85894    CQALQGSRYR  AHKSFLVIDN  VMTEDAGDYT  CKFIHNENGA  NYSVTATRSF BAA82405    TVK.......  DEQGFSLFPV  IGAPAQNEIK  EVEIGKNANL  TCSACFGKGT
BAA02233    TVK.......  DEQGFSLFPV  IGAPAQNEIK  EVEIGKNANL  TCSACFGKGT
Athdc120c9  ..........  ..........  ..........  ..........  ..........
BAA85894    TVKVWCQSFC  KLKKSLIFSN  THWIQSLMRG  FVMVYYGVHK  CCRVVFNLCL BAA82405    QFLAAVLWQL  NGTKITDFGE  PRIQQEEGQN  QSFSNGLACL  DMVLRIADVK
BAA02233    QFLAAVLWQL  NGTKITDFGE  PRIQQEEGQN  QSFSNGLACL  DMVLRIADVK
Athdc120c9  ..........  ..........  ..........  ..........  ..........
BAA85894    QYFQHHQWP.  ..........  ..........  ..........  ..........

BAA82405    EEDLLLQYDC  LALNLHGLRR  HTVRLSRKNP  IDHHSIYCII  AVCSVFLMLI
BAA02233    EEDLLLQYDC  LALNLHGLRR  HTVRLSRKNP  SKECF.....  ..........
Athdc120c9  ..........  ..........  ..........  ..........  ..........
BAA85894    ..........  ..........  ..........  ..........  ..........

BAA82405    NVLVIILKMF  WIEATLLWRD  IAKPYKTRND  GKLYDAYVVY  PRNYKSSTDG
BAA02233    ..........  ..........  ..........  ..........  ..........
Athdc120c9  ..........  ..........  ..........  ..........  ..........
BAA85894    ..........  ..........  ..........  ..........  ..........

BAA82405    ASRVEHFVHQ  ILPDVLENKC  GYTLCIYGRD  MLPGEDVVTA  VETNIRKSRR
BAA02233    ..........  ..........  ..........  ..........  ..........
Athdc120c9  ..........  ..........  ..........  ..........  ..........
BAA85894    ..........  ..........  ..........  ..........  ..........

BAA82405    HIFILTPQIT  HNKEFAYEQE  VALHCALIQN  DAKVILIEME  ALSELDMLQA
BAA02233    ..........  ..........  ..........  ..........  ..........
Athdc120c9  ..........  ..........  ..........  ..........  ..........
BAA85894    ..........  ..........  ..........  ..........  ..........

BAA82405    EALQDSLQHL  MKVQGTIKWR  EDHIANKRSL  NSKFWKHVRY  QMPVPSKIPR
BAA02233    ..........  ..........  ..........  ..........  ..........
Athdc120c9  ..........  ..........  ..........  ..........  ..........
BAA85894    ..........  ..........  ..........  ..........  ..........

BAA82405    KASSLTPLAA  QKQ
BAA02233    ..........  ...
Athdc120c9  ..........  ...
BAA85894    ..........  ...
```

FIG. 10

```
P14719      MIDRQRMGLW ALAILTLPMY LTVTEGSKSS WGLENEALIV RCPQRGRSTY
S29498      MIDRQRMGLW ALAILTLPMY LTVTEGSKSS WGLENEALIV RCPQRGRSTY
BAA82405    ......MGFW ILAILTILMY STAAKFSKQS WGLENEALIV RCPRQGKPSY
BAA02233    ......MGFW ILAILTILMY STAAKFSKQS WGLENEALIV RCPRQGKPSY
Athdc120c9  ......MGFW ILAILTILMY STAAKFSKQS WGLENEALIV RCPRQGKPSY
BAA85894    ......MGFW ILAILTILMY STAAKFSKQS WGLENEALIV RCPRQGKPSY P14719      PVEWYYSDTN ESIPTQKRNR IFVSRDRLKF LPARVEDSGI YACVIRSPNL
S29498      PVEWYYSDTN ESIPTQKRNR IFVSRDRLKF LPARVEDSGI YACVIRSPNL
BAA82405    TVDWYYSQTN KSIPTQERNR VFASGQLLKF LPAEVADSGI YTCIVRSPTF
BAA02233    TVDWYYSQTN KSIPTQERNR VFASGQLLKF LPAEVADSGI YTCIVRSPTF
Athdc120c9  TVDWYYSQTN KSIPTQERNR VFASGQLLKF LPAAVADSGI YTCIVRSPTF
BAA85894    TVDWYYSQTN KSIPTQERNR VFASGRLLKF LPAEVADSGI YTCIVRSPTF P14719      NKTGYLNVTI HKKPPSCNIP DYLMYSTVRG SDKNFKITCP TIDLYNWTAP
S29498      NKTGYLNVTI HKKPPSCNIP DYLMYSTVRG SDKNFKITCP TIDLYNWTAP
BAA82405    NRTGYANVTI YKKQSDCNVP DYLMYSTVSG SEKNSKIYCP TIDLYNWTAP
BAA02233    NRTGYANVTI YKKQSDCNVP DYLMYSTVSG SEKNSKIYCP TIDLYNWTAP
Athdc120c9  NRTGYANVTI YKKQSDCNVP DYLMYSTVSG SEKNSKIYCP TIDLYNWTAP
BAA85894    NRTGYANVTI YKKQSDCNVP DYLMYSTVSG SEKNSKIYCP TIDLYNWTAP P14719      VQWFKNCKAL QEPRFRAHRS YLFIDNVTHD DEGDYTCQFT HAENGTNYIV
S29498      VQWFKNCKAL QEPRFRAHRS YLFIDNVTHD DEGDYTCQFT HAENGTNYIV
BAA82405    LEWFKNCQAL QGSRYRAHKS FLVIDNVMTE DAGDYTCKFI HNENGANYSV
BAA02233    LEWFKNCQAL QGSRYRAHKS FLVIDNVMTE DAGDYTCKFI HNENGANYSV
Athdc120c9  LEWFKMSKAF LCFQ...... .......... .......... ..........
BAA85894    LEWFKNCQAL QGSRYRAHKS FLVIDNVMTE DAGDYTCKFI HNENGANYSV P14719      TATRSFTVE. .......EKG FSMFPVITNP PYNHTMEVEI GKPASIACSA
S29498      TATRSFTVE. .......EKG FSMFPVITNP PYNHTMEVEI GKPASIACSA
BAA82405    TATRSFTVK. ......DEQG FSLFPVIGAP AQNEIKEVEI GKNANLTCSA
BAA02233    TATRSFTVK. ......DEQG FSLFPVIGAP AQNEIKEVEI GKNANLTCSA
Athdc120c9  .......... .......... .......... .......... ..........
BAA85894    TATRSFTVKV WCQSFCKLKK SLIFSNTHWI QSLMRGFVMV YYGVHKCCRV P14719      CFGKGSHFLA DVLWQINKTV VGNFGEARIQ EEEGRNESSS NDMDCLTSVL
S29498      CFGKGSHFLA DVLWQINKTV VGNFGEARIQ EEEGRNESSS NDMDCLTSVL
BAA82405    CFGKGTQFLA AVLWQLNGTK ITDFGEPRIQ QEEGQNQSFS NGLACLDMVL
BAA02233    CFGKGTQFLA AVLWQLNGTK ITDFGEPRIQ QEEGQNQSFS NGLACLDMVL
Athdc120c9  .......... .......... .......... .......... ..........
BAA85894    VFNLCLQYFQ HHQWP..... .......... .......... ..........
```

FIG.11A

```
P14719      RITGVTEKDL SLEYDCLALN LHGMIRHTIR LRRKQPSKEC PSHIA.....
S29498      RITGVTEKDL SLEYDCLALN LHGMIRHTIR LRRKQPIDHR SIYYIVAGCS
BAA82405    RIADVKEEDL LLQYDCLALN LHGLRRHTVR LSRKNPIDHH SIYCIIAVCS
BAA02233    RIADVKEEDL LLQYDCLALN LHGLRRHTVR LSRKNPSKEC F.........
Athdc120c9  .......... .......... .......... .......... ..........
BAA85894    .......... .......... .......... .......... ..........

P14719      .......... .......... .......... .......... ..........
S29498      LLLMFINVLV IVLKVFWIEF ALFWRDIVTP YKTRNDGKLY DAYIIYPRVF
BAA82405    VFLMLINVLV IILKMFWIEA TLLWRDIAKP YKTRNDGKLY DAYVVYPRNY
BAA02233    .......... .......... .......... .......... ..........
Athdc120c9  .......... .......... .......... .......... ..........
BAA85894    .......... .......... .......... .......... ..........

P14719      .......... .......... .......... .......... ..........
S29498      RGSAAGTHSV EYFVHHTLPD VLENKCGYKL CIYGRDLLPG QDAATVVESS
BAA82405    KSSTDGASRV EHFVHQILPD VLENKCGYTL CIYGRDMLPG EDVVTAVETN
BAA02233    .......... .......... .......... .......... ..........
Athdc120c9  .......... .......... .......... .......... ..........
BAA85894    .......... .......... .......... .......... ..........

P14719      .......... .......... .......... .......... ..........
S29498      IQNSRRQVFV LAPHMMHSKE FAYEQEIALH SALIQNNSKV ILIEMEPLGE
BAA82405    IRKSRRHIFI LTPQITHNKE FAYEQEVALH CALIQNDAKV ILIEMEALSE
BAA02233    .......... .......... .......... .......... ..........
Athdc120c9  .......... .......... .......... .......... ..........
BAA85894    .......... .......... .......... .......... ..........

P14719      .......... .......... .......... .......... ..........
S29498      ASRLQVGDLQ DSLQHLVKIQ GTIKWREDHV ADKQSLSSKF WKHVRYQMPV
BAA82405    LDMLQAEALQ DSLQHLMKVQ GTIKWREDHI ANKRSLNSKF WKHVRYQMPV
BAA02233    .......... .......... .......... .......... ..........
Athdc120c9  .......... .......... .......... .......... ..........
BAA85894    .......... .......... .......... .......... ..........

P14719      .......... .......... .....
S29498      PERASKTASV AAPLSGKACL DLKHF
BAA82405    PSKIPRKASS LTPLAAQKQ. .....
BAA02233    .......... .......... .....
Athdc120c9  .......... .......... .....
BAA85894    .......... .......... .....
```

FIG. 11B

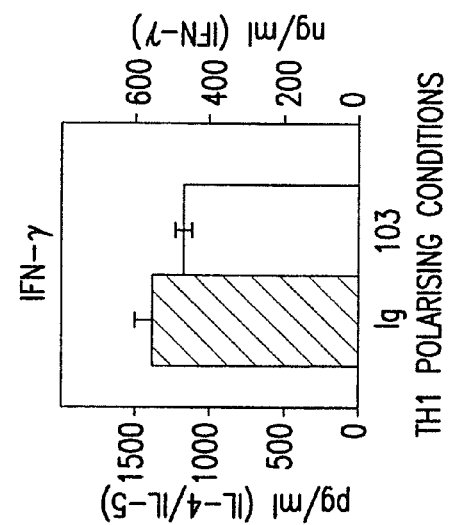
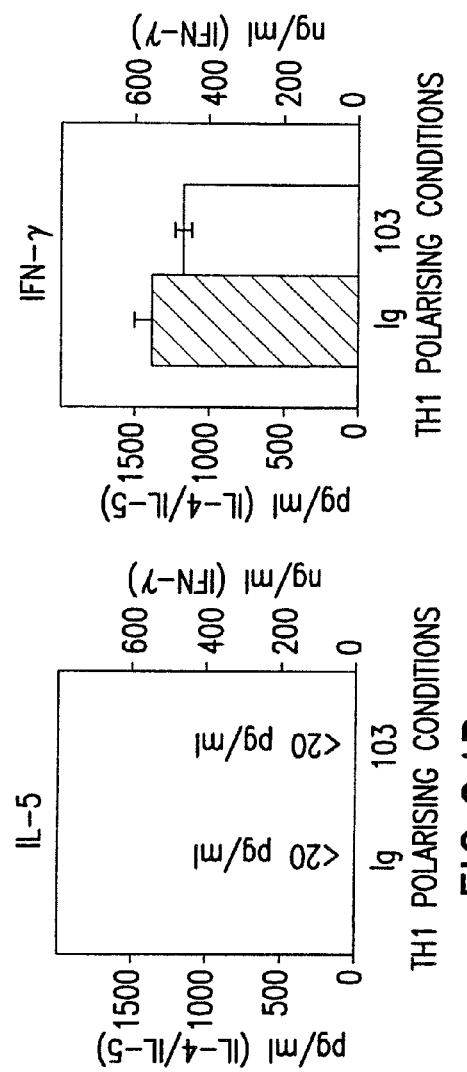
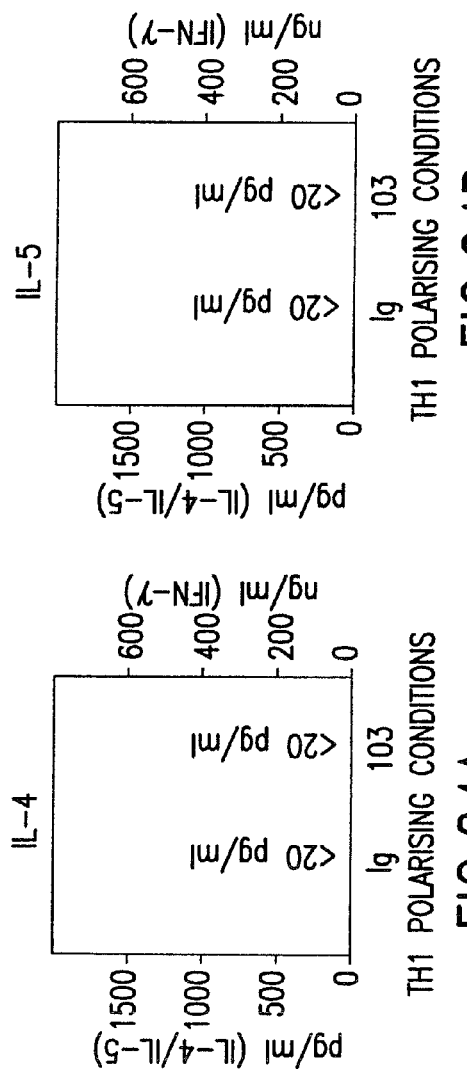
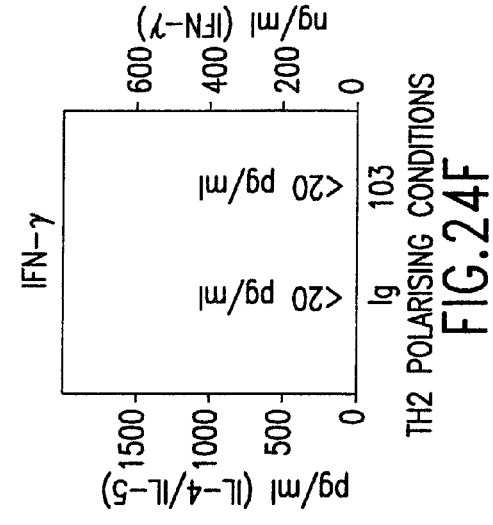
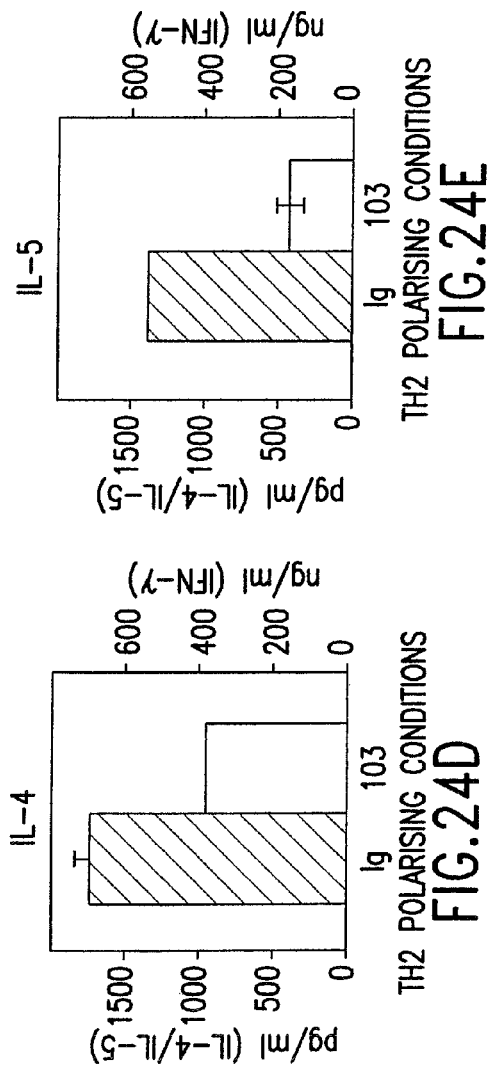

US 8,444,987 B2

COMPOSITIONS AND METHODS FOR THE DIAGNOSIS AND TREATMENT OF IMMUNE DISORDERS

This application claims priority under 35 U.S.C. §119 (e) to U.S. provisional application Ser. No. 60/155,862, filed on Sep. 24, 1999, which is incorporated herein, by reference, in its entirety.

1. FIELD OF THE INVENTION

The present invention relates to methods and compositions for the treatment and diagnosis of immune disorders, especially T lymphocyte-related disorders, including, but not limited to, chronic inflammatory disease and disorders (e.g., Crohn's disease, reactive arthritis, and Lyme disease), insulin-dependent diabetes, organ specific autoimmunity (including, e.g., multiple sclerosis, Hashimoto's thyroiditis and Grave's disease), contact dermatitis, psoriasis, graft rejection, graft versus host disease, sarcoidosis, atopic conditions (e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (e.g., leishmaniasis) and certain viral infections (including HIV and bacterial infections such as tuberculosis and lepromatous leprosy).

In particular, the methods and compositions of the present invention relate to detection and/or modulation of expression and/or activity of a gene product referred to herein as the 103 gene, as well as to detection and/or modulation of expression and/or activity of gene products encoded by the 103 gene (i.e., a "103 gene product").

2. BACKGROUND OF THE INVENTION

The majority of mature T lymphocytes can be divided into two distinct phenotypes: $CD8^+$ cytotoxic T lymphocytes (CTLs), which display the CD8 marker on their cell surface, and $CD4^+$ helper T lymphocytes (T helper or TH cells), which display the CD4 marker on their cell surface. This subdivision is also associated with functional differences between the two cell types CTLs are, in general, involved in cell-mediated, or cellular, immune responses, and are activated by intracellular pathogens such as, for example, microbes and viruses. In particular, foreign antigens (e.g., viral antigens) are synthesized within infected cells and presented on the surfaces of such cells in association with class I major histocompatibility complex (MHC) molecules. CTL precursors display T cell receptors that recognize these antigens, triggering activation, maturation and proliferation of the precursor CTLs and resulting in CTL clones capable of destroying the cells exhibiting the antigens recognized as foreign.

T helper (TH) cells are involved in both humoral (i.e., antibody) and cell-mediated forms of immune response. With respect to the involvement of TH cells in humoral, or antibody, immune response, extracellular antigens are endocytosed by antigen presenting cells (APCs), processed and presented, preferentially in association with class II MHC molecules, to $CD4^+$ class II MHC-restricted TH cells. These TH cells in turn activate B lymphocytes, resulting in antibody production. With respect to the role of TH cells in cell-mediated forms of immune response, some agents, such as mycobacteria which cause tuberculosis and leprosy, are engulfed by macrophages and processed in vacuoles containing proteolytic enzymes and other toxic substances. While these macrophage components are capable of killing and digesting most microbes, agents such as mycobacteria survive and multiply. However, the agents' antigens are processed by the macrophages and presented in association with class II MHC molecules to $CD4^+$ class II MHC-restricted TH cells. These TH cells, in turn, become stimulated to secrete interferon-γ (IFN-γ) which activates macrophages. Such activation results in an increased bacteriocidal ability.

TH cells have been further categorized into two distinct subpopulations, termed TH1 and TH2 cell subpopulations. These two subpopulations of TH cells have been categorized on the basis of their restricted cytokine profiles and different functions. For example, TH1 cells are known to produce IL-2, tumor necrosis factor β (TNF-β) and IFN-γ. TH2 cells are known to produce interleukin 4 (IL-4), interleukin 5 (IL-5), interleukin 10 (IL-10) and interleukin 13 (IL-13). The different subpopulations are derived from a common precursor, or "naive" TH cell population (referred to as THP), and acquire their set pattern of cytokine production during a process referred to as "commitment."

Genetic and environmental factors acting at the level of antigen presentation influence the commitment of a common naive T cell precursor to TH1 or TH2 differentiation. For example, the conditions of antigen stimulation (including both the nature and amount of antigen involved), the type of antigen-presenting cells and the type of hormone and cytokine molecules present all seem to represent determinants of the pattern of TH1 versus TH2 differentiation from a common naive T helper cell precursor. In particular, the decisive role appears to belong to the particular cytokines present in the cells environment. For example, IL-4, which is produced by TH2 and TH2-like cells, also appears to be an important factor in the commitment of naive THP cells to the TH2 subtype. Further, once TH1 and TH2 subpopulations are expanded, the two cell types tend to negatively regulate one another through the actions of cytokines unique to each subpopulation. For example, IFN-γ, which is produced by TH1 cells, negatively regulates TH2 cells, while TH2-produced IL-10 negatively regulates TH1 cells. Moreover, cytokines produced by TH1 and TH2 antagonize the effector functions of one another (Mosmann, T. R. and Moore, 1991, *Immunol. Today* 12:49). Although a full accounting of the exact factors important in driving TH1 and/or TH2 differentiation are, as yet, largely unknown, certain transcription factors activated in response to a given cytokine have been shown to be important in TH1 and/or TH2 differentiation. For example, the activation of signal transducer and activator of transcription (STAT)-6 by IL-4 has been shown to be important in TH2 differentiation, and the activation of STAT-4 has been shown to be important in TH1 differentiation (e.g., Romagnani, S., 1997, *Immunology Today* 18:263-266; Ray, A. and Cohn, L., 1999, *The Journal of Clinical Investigation* 104(8):985-993).

Although the TH1 and TH2 subtypes were originally identified in murine systems (see, for example, Mosmann, T. R. and Coffman, R. L., 1989, *Ann. Rev. Immunol.* 7:145), the existence of TH1-like and TH2-like subpopulations has also been established in humans (see, e.g., Del Prete, A. F. et al., 1991, *J. Cline. Invest.* 88:346; Wiernenga, E. A. et al., 1990, *J. Imm.* 144:4651; Yamamura, M. et al., 1991, *Science* 254: 277; Robinson, D. et al., 1993, *J. Allergy Clin. Imm.* 92:313; Anderson, G. P. and Coyle, A. J., 1994, *Trends in Pharmacological Sciences* 15(9):324-32; Romagnani, S., 1997, *Immunology Today* 18:263-266). Human TH1-like and TH2-like cells have similar cytokine profiles to the TH1 and TH2 cells originally identified in murine systems, and preferentially express activation markers (e.g., CD30 and LAG-1). CD30, a member of the tumor necrosis factor (TNF) receptor family, is primarily expressed by TH2-like cells, and lymphocyte activation gene 3 (LAG-3) is preferentially expressed by TH1-like cells.

TH cells having characteristics (e.g., cytokine production profiles) of both TH1 and TH2 cell subpopulations have been designated TH0 cells (see, e.g., Firestein, G. S. et al., 1989, *J. Imm.* 143:518). CD8+ T cytotoxic (Tc)-cell subpopulations have also been identified based on the cytokines they produce. In general, activated CD8+ CTLs exhibit a TH1-like cytokine profile, but under some conditions CD8+ CTLs exhibit a TH2-like cytokine profile (Seder, R. A. et al., 1995, *J. Exp. Med.* 181:5-7; Manetti, R. et al., 1994, *J. Exp. Med.* 180:2407-2411; Maggi, E. et al., 1994, *J. Exp. Med.* 180:489-495). As noted above, TH1 and TH2 cell subpopulations appear to have great relevance to immune response against infectious agents such as viruses and intracellular parasites.

TH1-like and TH2-like cells appear to function as part of different effector functions of the immune system (see, e.g., Mosmann and Coffmann, supra). For example, TH1-like cells direct the development of cell-mediated immunity, triggering phagocyte mediated host defenses, and are associated with delayed hypersensitivity. Accordingly, infections with intracellular microbes tend to induce TH1-type responses. TH2-like cells drive humoral immune responses, which are associated with, for example, defenses against certain helminthic parasites and are involved in antibody and allergic responses.

Failure to control or resolve an infectious process often results not from an insufficient immune response but, rather, from an inappropriate response. Such inappropriate immune responses underlie a variety of distinct immunological disorders including, for example, mastocytosis (e.g., cutaneous mastocytosis and systemic mastocytosis), interstitial cystitis (IC), and atopic conditions (e.g., IgE-mediated allergic conditions) such as asthma, allergy (in eluding allergic rhinitis), dermatitis (including psoriasis), systemic lupus erythematosus, scleroderma, pathogen susceptibilities, chronic inflammatory disease, organ-specific autoimmunity, graft rejection and graft versus host disease. For example, nonhealing forms of human and murine leishmaniasis result from strong but counterproductive TH2-like-dominated immune responses. Lepromatous leprosy also appears to feature a prevalent but inappropriate, TH2-like response.

Atopic conditions, such as asthma and allergy, are also examples of disorders that arise because of a TH2-like response to allergen (see, e.g., Holgate, S. T., 1997, *Lancet* 350 (suppl. II):5-9; Ray, A. and Cohn, L, supra; Oettgen, H. C. and Geha, R. S., 1999, *The Journal of Clinical Investigation* 104(7):829-835). In particular, such disorders are characterized by the development of IgE antibodies to foreign proteins. IgE antibodies are produced by B cells stimulated with IL-4, a cytokine produced by TH2 and TH2-like cells. Moreover, TH2-like cytokine profiles have been observed, not only in TH cells isolated from patients suffering from asthma and/or allergy, but also in mast cells and CD8+ CTLs isolated from such patients (Anderson and Coyle, supra). Further, animal studies have demonstrated that TH2-like cells play an important role in the induction of inflammation and the chronic pathological changes associated with asthma. For example, the constitutive expression of TH2 cytokines (e.g., IL-4 and IL-5) in mice has been shown to induce an asthma-like syndrome (Ray, A. and Cohn, L, supra).

A bias towards a TH2-like response has also been suggested to contribute to the loss of control of the immune system over HIV infection. In particular, a drop in the ratio of TH1-like cells to other TH cell subpopulations has been suggested to play a critical role in the progression toward disease symptoms. Further, it has been noted that, at least in vitro, TH2-like clones appear to be more efficient supporters of HIV viral replication than TH1-like clones (Romagnani, S., supra).

Further, while TH1-mediated inflammatory responses to many pathogenic microorganisms are beneficial, such responses to self antigens are usually deleterious. It has been suggested that the preferential activation of TH1-like responses is central to the pathogenesis of such human inflammatory autoimmune diseases as multiple sclerosis and insulin-dependent diabetes. For example, TH1-type cytokines predominate in the cerebrospinal fluid of patients with multiple sclerosis, pancreases of insulin-dependent diabetes patients, thyroid glands of Hashimoto's thyroiditis, and gut of Crohn's disease patients, suggesting that such patients mount a TH1-like, not a TH2-like, response to the antigen(s) involved in the etiopathogenesis of such disorders.

A primary goal, for both diagnostic and therapeutic reasons, therefore, would be the ability to identify, isolate and/or target members of a particular TH cell subpopulation. As such, the identification of genes which are differentially expressed within and/or among TH cell subpopulations is desirable. To date, investigations have focused on the expression of a limited number of specific known cytokines and cytokine receptors in the TH cell population. Cytokines, however, exert effects on cell types in addition to specific TH cell subpopulations, i.e., exhibit a variety of pleiotropic effects. It would be beneficial, therefore, to identify reliable markers (e.g., gene sequences) of TH cell subpopulations whose effects are TH cell subpopulation specific, e.g., which, unlike secreted cytokines, are TH cell subpopulation specific.

Discussion or citation of a patent, patent publication or other reference herein shall not be construed as an admission that such patent, patent publication or citation is prior art to the present invention.

3. SUMMARY OF THE INVENTION

The present invention relates to methods and compositions for the diagnosis of immune disorders and for the treatment (e.g., the amelioration or modulation of symptoms associated with) of immune disorders, especially T helper (TH) cell and TH cell-like related disorders such as the TH cell and TH cell-like related disorders described herein below. The invention relates, in particular, to novel methods and compositions which use a gene referred to herein as the 103 gene or a modulator thereof. The gene is also known, alternatively, as T1, ST2 or Fit-1.

The invention is based, in part, on the discovery of a novel nucleotide sequence depicted in FIG. 21 (SEQ ID NO:24) which encodes a previously unknown human 103 gene product, referred to herein as Athdc120c9 (FIG. 21; SEQ ID NO:25). The invention is also based, in part, on the discovery that the 103 gene is expressed, in vivo, in a tightly controlled TH2 or TH2-like specific manner, and that the 103 gene product is an important molecule in signaling TH2-mediated immune responses. In particular, the 103 gene is expressed in a specific subpopulation of T helper cells (i.e., in TH2 or TH2-like cells and not in TH1 or TH1-like cells). For example, results are presented herein which demonstrate that the 103 gene product plays a critical role as a signaling molecule required for the differentiation and function of TH2 and TH2-like cells. In particular, the data presented hereinbelow show that blockage of 103 gene product signaling suppresses both the differentiation and activation of TH2 but not TH1 cell subpopulations. Data are also presented showing that the 103 gene product is a critical regulatory molecule for TH2-mediated immune responses in vivo. In particular, results obtained using animal models for allergy and for asthma are presented herein indicating that the 103 gene product provides a critical signal to TH2-mediated responses in these disorders and that blockage of this signal ameliorates symptoms associated with the disorders. For example, the results presented herein in Section 6.4 demonstrate successful amelioration of asthma symptoms by administration of either an anti-103 antibody (i.e., an antibody that specifically binds to a 103 gene product) or a fusion protein comprising an extracellular or secreted domain of a 103 gene product.

Accordingly, compounds such as natural ligands, derivatives of natural ligands and antibodies that specifically bind to the 103 gene product, can be utilized to modulate (e.g., reduce or increase) the number of TH2 and/or TH2-like cells present in a population or system. For example, TH2 or TH2-like cells can be physically separated away from other cells in a population. Alternatively, the specific destruction of TH2 and/or TH2-like can be targeted. Further, proliferation of TH2 and/or TH2-like cells can be modulated (e.g., induced, increased, inhibited or reduced). Additionally, compounds such as 103 gene sequences or 103 gene products can be utilized to modulate the level of TH2 or TH2-like cell activity and/or to cause modulation in the level of TH2 cell cytokine production (e.g., such methods can bring about a reduction in the level of production of cytokines, such as IL-4, IL-5, IL-10 and IL-13, that are associated with TH2 cell subpopulations and/or with TH2 cell subpopulation activity). For example, IL-4 produced by the TH2 and TH2-like cell subpopulations stimulates B cells which, in turn, produce IgE-type antibodies. Thus conditions that involve an inappropriate IgE immune response, including but not limited to the symptoms which accompany atopic conditions such as allergy and/or asthma, can be treated and/or ameliorated by reducing IL-4 levels, e.g., by using the methods of the present invention to reduce TH2 cell activity.

Given its status as both a TH2 and TH2-like cell subpopulation specific marker and a critical regulatory molecule, the 103 gene, its gene products, and modulators thereof can be used in a variety of novel methods and compositions described herein to diagnose and/or modulate immune system disorders, particularly disorders that are known to be associated with a TH2 or TH2-like cell subpopulation. The 103 gene and its gene products can also be used in a variety of methods and compositions, which are also described herein, to identify and characterize compounds, including, for example, small molecules, that are useful for prognosis, diagnosis, monitoring, rational drug design and/or therapeutic intervention of immune system disorders. Further, molecules, such as certain monoclonal antibodies, that recognize and specifically bind to a ligand binding domain of a 103 gene product can inhibit this binding interaction. Thus, the invention also provides for compounds that inhibit or modulate ligand binding of a 103 gene product. Such compounds can also be used in the methods and compositions of the present invention to modulate 103 gene product activity and thereby modulate immune system disorders, including disorders that are known or believed to be associated with a TH2 or TH2-like cell subpopulation.

In addition, the 103 gene is also expressed in mast cells. Thus, the invention also relates to methods and compositions that can also be utilized to modulate other cell populations, such as mast cells, that specifically express the 103 gene. In particular, the number of mast cells present and/or the amount of mast cell activity or mast cell cytokine production (e.g., from the degranulation of mast cells) can also be modulated using the methods and compositions described herein. Thus conditions, including atopic conditions such as asthma and allergy, mastocytosis (e.g., cutaneous mastocytosis and systemic mastocytosis), and interstitial cystitis (IC) that involve or are mediated by mast cell activity (often in addition to TH2 or TH2-like activity) can be treated by using the methods and compositions of the invention to target mast cells and/or mast cell activity as well as (or instead of) TH2 cells and/or TH2 cell activity.

Thus, the present invention relates to methods for the prognostic and diagnostic evaluation of various TH cell subpopulation-related disorders, and for the identification of subjects who are predisposed to such disorders. Furthermore, the invention provides methods for evaluating and monitoring the efficacy treatments and therapies for various immune disorders, such as for the evaluation of drugs for immune disorders and for monitoring the progress of patients involved in clinical trials for the treatment of immune disorders.

The invention also relates to methods and compositions that can be utilized in the amelioration of symptoms stemming from such immune disorders (e.g., from such TH cell subpopulation disorders) and for modulating TH or TH-like cell responsiveness such as, for example, responsiveness to an antigen. For example, such methods can comprise administering an effective amount of a composition to an individuals exhibiting TH cell subpopulation-related disorders or tendencies so that one or more symptoms of such disorders or tendencies are modulated and/or thereby ameliorated. Additionally, the treatment methods provided by the present invention may result in the stimulation or depletion of one or more of the TH cell subpopulations. "Stimulation," as the term is used herein, can refer to: (a) an effective increase in the number of cells belonging to a TH cell subpopulation via, for example, the proliferation of such TH cell subpopulation cells; or (b) an increase in the activity of cells belonging to a TH cell subpopulation, as would be evidenced, for example, by a per cell increase in the expression of the TH cell subpopulation specific cytokine pattern. "Depletion," as the term is used herein, can refer to: (a) an effective reduction in the number of cells belonging to a TH cell subpopulation via, for example, a reduction in the proliferation of such TH cell subpopulation cells; or (b) a decrease in the activity of cells belonging to a TH cell subpopulation, as would be evidenced, for example, by a per cell decrease in the expression of the TH cell subpopulation-specific cytokine pattern.

Among the compositions that can be utilized as part of such methods are 103 gene sequences; polypeptides comprising 103 gene product amino acid sequences, and antibodies directed against 103 gene products. In addition, such compositions can include compositions, such as small molecule compositions, that modulate 103 gene expression, and/or 103 gene product activity, and can, for example, include compounds identified by the screening methods described herein.

The 103 genes or gene sequences used in the methods and compositions of the present invention encompasses: (a) at least one of the nucleotide sequences and/or fragments thereof that are depicted herein FIGS. 1, 3A, 4A, 5A, 6A, 7A and 8 (SEQ ID NOS:1-5, 10 and 12); (b) any nucleotide sequence or fragment thereof that encodes the amino acid sequence encoded by one of the nucleotide sequences that are depicted in FIGS. 1, 3A, 4A, 5A, 6A, 7A and 8 (SEQ ID NOS:1-5, 10 and 12); (c) any nucleotide sequence that hybridizes to the complement of one of the coding nucleotide sequences depicted herein in FIGS. 1, 3A, 4A, 5A, 6A, 7A and 8 (SEQ ID NOS:1-5, 10 and 12) under stringent conditions, e.g., hybridization to filter-bound DNA in 6× sodium chloride/sodium citrate (SSC) at about 45° C. followed by one or more washes in 0.2×SSC/0.1% SDS at about 50-65° C., or hybridization to filter-bound DNA in 0.5 M sodium pyrophate/7% SDS at about 65° C. followed by one or more washes in 0.2×SSC/1% SDS at about 42-55° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3); (d) any nucleotide sequence that hybridizes to the complement of one of the coding nucleotide sequences depicted herein in FIGS. 1, 3A, 4A, 5A, 6A, 7A and 8 (SEQ ID NOS:1-5, 10 and 12) under highly stringent conditions, e.g., hybridization to filter-bound nucleic acid in 6×SSC at about 45° C. followed by one or more washes in 0.1×SSC/0.2% SDS at about 68° C., or hybridization to filter-bound DNA in 0.5 M sodium pyrophosphate/7% SDS at about 65° C. followed by one or more washes in 0.2×SSC/1% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3), including such other hybridization conditions as those described herein; and (e) the complement of any of the 103 genes or gene sequences recited in (a)-(d) above.

The TH cell subpopulation-related disorders include, for example, TH1 or TH1-like related disorders (i.e., disorders that are associated with a TH1 or TH1-like mediated immune response). Examples of such disorders include chronic inflammatory disease and disorders (e.g., Crohn's disease, reactive arthritis and Lyme disease), insulin-dependent diabetes, organ specific autoimmunity (including multiple sclerosis, Hashimoto's thyroiditis and Grave's disease), contact dermatitis, psoriasis, graft rejection, graft versus host disease and sarcoidosis. The TH cell subpopulation-related disorders further include, for example, TH2 or TH2-like related disorders (i.e., disorders that are associated with a TH2 or TH2-like mediated immune response). Examples of such disorders include atopic conditions such as asthma and allergy (including, e.g., allergic rhinitis, gastrointestinal allergies and food allergies), eosinophilia, conjunctivitis, glomerular nephritis, systemic lupus erythematosus and scleroderma. Other exemplary TH2 and/or TH2-like related disorders include certain pathogen susceptibilities such as helminthic (e.g., leishmaniasis), certain viral infections (including, for example, HIV infection) and bacterial infections (including, for example, tuberculosis and lepromatous leprosy).

The methods and compositions described herein can also be utilized in the prognostic and diagnostic evaluation of disorders involving other immune cells, including CD8+ cytotoxic T lymphocytes ("CTL's"), that exhibit or are capable of exhibiting TH-like cell subpopulation gene expression patterns and/or activities. The methods and compositions described herein can still further be utilized in the amelioration of symptoms stemming from disorders involving such immune cells, especially such CD8+ CTL's, which exhibit TH-like cell subpopulation gene expression patterns and/or activity.

The present invention also relates to methods for the identification of compounds which modulate the expression of genes or the activity (e.g., level) of gene products involved in TH cell subpopulation-related disorders and processes relevant to the differentiation, maintenance and/or effector function of the subpopulations. For example, presented herein are methods for identifying compounds that affect the level of expression of the 103 gene and/or activity of the 103 gene product. Among such methods are, for example, methods for identifying compounds which bind to a 103 gene product.

The present invention encompasses a monoclonal antibody produced by the hybridoma clone M15 3F7.3 (ATCC™ No. PTA-593), the hybridoma clone M15 2O3.1 (ATCC™ No. PTA-591), the hybridoma clone M15 10F7.1 (ATCC™ No. PTA-592), the hybridoma clone M15 1B4.1 (ATCC™ No. PTA-588), the hybridoma clone M15 9F11.1 (ATCC™ No. PTA-590), the hybridoma clone M15 5A16.1 (ATCC™ No. PTA-587), or an antigen binding fragment thereof. An antigen binding fragment of a monoclonal antibody of the invention refers to a fragment of the antibody that binds to a 103 gene product such as a Fab fragment and an F(ab')$_2$ fragment. The present invention further encompasses an isolated antibody that competes with the monoclonal antibody produced by hybridoma clone M15 3F7.3, M15 2O3.1, M15 10F7.1, M15 1B4.1, M15 9F11.1 or M15 5A16.1 for epitope binding. The isolated antibody can be, e.g., a monoclonal antibody, a single chain antibody, a human antibody or a humanized antibody.

The following terms, as they are used in herein, shall have the definitions provided hereinbelow.

The term "aberrant expression," as used herein to describe the expression of a 103 gene product, refers to the overexpression or underexpression of a 103 gene product relative to the level of expression of a 103 gene product by cells obtained from a healthy subject or a subject without an immune disorder state, and/or to a higher or lower level of 103 gene product or transcript in a tissue sample or body fluid obtained from a healthy subject or a subject without an immune disorder state. In particular, a 103 gene product is aberrantly expressed if the level of expression of a 103 gene product is higher or lower by at least 2 fold, at least 5 fold, at least 10 fold, at least 15 fold, at least 25 fold, or at least 50 fold relative to the level of expression of the 103 gene product by cells obtained from a healthy subject or a subject without an immune disorder state, and/or relative to the level of expression of the 103 gene product in a tissue sample or body fluid obtained from a healthy subject or a subject without an immune disorder state.

The term "TH cell subpopulation," as used herein, refers to a population of TH cells exhibiting a gene expression pattern (e.g., a discrete pattern of cytokines and/or receptor or other cell surface molecules) and activity which are distinct from the expression pattern and activity of other TH cells. Such TH cell subpopulations can include, but are not limited to, TH0, TH1 and TH2 cell subpopulations which will, for clarity and example and not by way of limitation, be frequently used herein as representative TH cell subpopulations. In particular and as noted above (Section 2), although TH cell subpopulations such as TH1 and TH2 cell subpopulations were originally discovered in murine systems, the existence of similar TH cell subpopulations (i.e., TH1-"like" and TH2-"like" cell subpopulations) has also been established in other animals, including other mammals such as humans. Thus, it is understood that the particular TH cell subpopulations referred to herein (e.g., TH0, TH1 and TH2 cell subpopulations) refer not only to the CD4+ TH cell subpopulations originally identified in murine systems, but also to equivalent or similar (e.g., functionally equivalent) CD4+ TH cell subpopulations in other animals, including other mammals such as humans.

The term "TH-like cell subpopulation" (e.g., "TH1-like" or "TH2-like"), therefore, as used herein, can refer, not only to a population of CD4+ TH cells having the properties described, above, for a TH cell subpopulation, but also refers to CD4− cells, including CD8+ CTL's, which exhibit TH-like cytokine expression patterns.

"Differential expression," as the term is used herein, is understood to refer to both quantitative as well as qualitative differences in temporal and/or cellular expression patterns, e.g., of a gene or genes.

"Negative modulation", as used herein, refers to a reduction in the level and/or activity of target gene product relative to the level and/or activity of the target gene product in the absence of the modulatory treatment. Alternatively, the term, as used herein, refers to a reduction in the number and/or activity of cells belonging to the TH cell subpopulation relative to the number and/or activity of the TH cell subpopulation in the absence of the modulatory treatment.

"Positive modulation", as used herein, refers to an increase in the level and/or activity of target gene product relative to the level and/or activity of the gene product in the absence of the modulatory treatment. Alternatively, the term, as used herein, refers to an increase in the number and/or activity of cells belonging to the TH cell subpopulation, relative to the number and/or activity of the TH cell subpopulation in the absence of the modulatory treatment.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. In one embodiment, a nucleic acid molecule is cDNA and not genomic DNA. "cDNA", as used herein, refers to a contiguous nucleotide sequence that encodes a polypeptide, and can include, but is not limited to a double-stranded DNA molecule generated via reverse transcription of an mRNA molecule.

"Isolated" or "purified" when used herein to describe a nucleic acid molecule or nucleotide sequence, refers to a nucleic acid molecule or nucleotide sequence which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

"Isolated" or "purified" when used herein to describe a protein or biologically active portion thereof (i.e., a polypeptide, peptide or amino acid fragment), refers to a protein or biologically active portion thereof substantially free of cellular material or other contaminating proteins from the cell or tissue source from which the protein is derived, or substantially free of chemical precursors or other chemicals when chemically synthesized. A protein or biologically active portion thereof (i.e., a polypeptide, peptide or amino acid fragment) that is substantially free of cellular material includes preparations of protein having less than about 30%, 20%, 10%, or 5% (by dry weight) of heterologous protein (also referred to herein as a "contaminating protein").

The following abbreviations are also used herein throughout and have the following meanings:
CTL's cytotoxic T lymphocytes
TH cells T helper cells
APC's antigen presenting cells
MHC major histocompatibility complex
IL-2 interleukin-2
IL-4 interleukin-4
IL-5 interleukin-5
IL-10 interleukin-10
IL-13 interleukin-13
IFN-γ interferon-gamma
TM transmembrane domain
ECD extracellular domain
CD cytoplasmic domain

4. BRIEF DESCRIPTION OF THE FIGURES

FIG. 1. Nucleotide sequence of clone 103.1 of band 103 (SEQ ID NO:1).

FIG. 2. 103 gene products. This diagram illustrates the relationship between the sequence encoded by band 103, 103 gene (also known as ST-2, T1 and Fit-1) products and the IL-1 receptor polypeptide structure. The extracellular, transmembrane and cytoplasmic domains of the proteins are noted, along with the amino acid residues marking the boundaries of these domains. (Adapted from Yanagisawa et al., 1993, FEBS Lett. 318:83-87.)

FIG. 3A-B. A) A nucleotide sequence encoding a secreted form of the murine 103 gene product is depicted (SEQ ID NO:2; GenBank Accession No. E07714). B) An amino acid sequence of a secreted form of murine 103 is depicted (SEQ ID NO:6; GenBank Accession No. P14719).

FIG. 4A-B. A) A nucleotide sequence encoding a transmembrane form of the murine 103 gene product is depicted (SEQ ID NO:3; GenBank Accession No. E08652). B) An amino acid sequence of a transmembrane form of murine 103 is depicted (SEQ ID NO:7; GenBank Accession No. S29498). The signal sequence domain of this transmembrane product extends from about amino acid residue 1 to 23 of SEQ ID NO:7; the extracellular domain of this transmembrane form extends from about amino acid residue 24 to 342 of SEQ ID NO:7; the transmembrane domain of this transmembrane form extends from about amino acids 343 to 366 of SEQ ID NO:7; the cytoplasmic or intracellular domain of this transmembrane form extends from about amino acid residues 367 to 567 of SEQ ID NO:7.

FIG. 5A-B. A) A nucleotide sequence encoding a transmembrane form of the human 103 gene is depicted (SEQ ID NO:4; GenBank Accession No. A13012701). 5B) An amino acid sequence of the transmembrane form of the human 103 gene is depicted (SEQ ID NO:8; GenBank Accession No. BAA82405). The signal sequence of this transmembrane form of the human 103 gene extends from about amino acid residue 1 to 18 of SEQ ID NO:8; the extracellular domain of this transmembrane form extends from about amino acid residues 1 to 323 of SEQ ID NO:8; the transmembrane domain of this transmembrane form extends from about amino acid residues 324 to 350 of SEQ ID NO:8; the cytoplasmic or intracellular domain of this transmembrane form extends from about amino acid residues 351 to 556 of SEQ ID NO:8; and the immunoglobulin (Ig)-like domains of this transmembrane form extends from about amino acid residues 29-89, 126-183 and 228-305.

FIG. 6A-B. A) A nucleotide sequence encoding a secreted form of the human 103 gene is depicted (SEQ ID NO:5; GenBank Accession No. D12763). B) An amino acid sequence of a secreted form of the human 103 gene is depicted (SEQ ID NO:9; GenBank Accession No. BAA02233).

FIG. 7. A) The nucleotide sequence encoding a variant form of the human 103 gene is depicted (SEQ ID NO:10; GenBank Accession No. AB029084). B) The amino acid sequence of a variant form of the human 103 gene is depicted (SEQ ID NO:11; GenBank Accession No. BAA85894).

FIG. 8. The nucleotide sequence (SEQ ID NO:12) and predicted amino acid sequence (SEQ ID NO:13) of the novel human 103 gene referred to herein as Athdc120c9. The signal sequence of the Athdc120c9 gene product extends from about amino acid residues 1 to 18 of the amino acid sequence. The Ig-like domain of the Athdc120c9 gene product extends from about amino acid residues 29 to 89 of the amino acid sequence.

FIG. 9. An alignment of the two forms of the murine 103 gene product (SEQ ID NO:6 and SEQ ID NO:7) using CLUSTAL W (1.74).

FIG. 10. An alignment of the four forms of the human 103 gene product (SEQ ID NO ID:8, SEQ ID NO:9, SEQ ID NO:11 and SEQ ID NO:13) using CLUSTAL W (1.74).

FIG. 11. An alignment of the human and murine forms of the 103 gene product (SEQ ID NO ID:8, SEQ ID NO:9, SEQ ID NO:11, SEQ ID NO:13, SEQ ID NO:6 and SEQ ID NO:7) using CLUSTAL W (1.74).

FIG. 12. Quantitative RT-PCR analysis of 103 gene expression in polarized populations of murine TH cells. RNA samples were harvested from cultured T cell populations 24 hours after tertiary stimulation with antigen. cDNA samples were PCR amplified and the products of those reactions were electrophoresed on a 1% agarose gel and visualized by ethidium bromide staining. 103 gene expression is shown in the upper panel. γ-actin data, bottom panel, was included as a control for differences in sample quality. The numbers above each lane represent the dilution factors of each cDNA. The same cDNA samples were used for both the 103 gene and the γ-actin amplifications.

FIG. 13. Northern blot analysis of 103 gene expression in representative murine TH cell lines (TH2: CDC25, D10.G4, DAX; TH1: AE7.A, Dorris, D1.1). Clones were either unstimulated (−) or stimulated (+) for 6 hours with plate-bound anti-CD3 antibody. Ten micrograms of total RNA were loaded per lane. The positions of 18s and 28s ribosomal RNA are shown as reference markers.

FIG. 14. Northern blot analysis of 103 gene expression in T cell clones and murine tissues. Lane 1: DAX cells, no stimulation; lane 2, AE7 cells, stimulation; lane 3, AE7 cells, no stimulation; lane 4, D10.G4 cells, stimulation; lane 5, D10.G4 cells, no stimulation; lane 6, brain; lane 7, heart; lane 8, lung; lane 9, spleen; lane 10, liver. Clones were stimulated with plate-bound anti-CD3 antibody for 6 hours. 7.5 and 10 micrograms total RNA was used for each cell line and each tissue, respectively. a, b, and c arrows refer to RNA encoding full length (a) and truncated (b,c) forms of the 103 gene. The positions of 18s and 28s ribosomal RNA markers are shown.

FIG. 15. RNAse protection analysis of 103 gene mRNA, illustrating regulation of 103 gene expression in murine TH cell clones. Lanes 2-6: β-actin protection; lanes 9-13: 103 gene protection; lanes 1 and 8: markers; lanes 2 and 9: unstimulated TH1 clones; lanes 3 and 10: stimulated TH1 clones; lanes 4 and 11: unstimulated TH2 clones; lanes 5 and 12: stimulated TH2 clones; lanes 6 and 13: fully RNAse A digested unprotected probe; lanes 7 and 14: probe alone, in absence of added RNAse.

Expected Fragment Sizes:
β-actin protected probe: 250 nucleotides;
β-actin full length probe: 330 nucleotides;
103 gene long form fragment: 257 nucleotides;
103 gene short form fragment: 173 nucleotides;
103 gene full length probe: 329 nucleotides.

FIG. 16. Expression of the soluble and transmembrane forms of the human 103 gene in following hematopoeitic cells was quantitatively determined: resting and phytohemagluti-nin (PHA) activated peripheral blood mononuclear cells (PBMC); resting and PHA activated CD3$^+$ cells; CD4$^+$ and CD8$^+$ T cells; resting Th0, Th1 and Th2 cells; Th0, Th1 and Th2 cells stimulated for 1, 6, 24 or 48 hours with anti-CD3 antibody; resting and lipopolysaccharide (LPS) activated CD19$^+$ B cells; CD 14$^+$ cells; granulocytes; eosinophils; PBMC stimulated with IL-10 and IL-4; and PBMC stimulated with interferon-γ (IFN-γ) and tumor necrosis factor-α (TNF-α).

FIG. 17. Flow cytometry data demonstrates that the 3E10 mAb recognizes and binds to representative clones of the TH2 cell subpopulation (D10.G4; DAX), but not clones of the TH1 subtype (AE7; Dorris). The graphs in this figure present the results of the flow cytometry analyses by depicting the number of cells exhibiting a given level of fluorescence. Staining above background levels represents antigen-specific binding and, therefore, the presence of cell surface 103 gene product. The further to the right the peaks are shifted, the greater the staining intensity, and therefore antibody binding, exhibited by a cell population.

FIG. 18. Analysis of the cytokine profile in mouse BAL. The data presented in this figure reveals high levels of IL-4, IL-5, IL-6, IL-10 and IL-13 in TH2 recipient OVA challenged mice (closed bars). There was no detectable TH2 cytokines in the BAL fluid of mice that received TH2 cells and were not exposed to ovalbumin. Pretreatment with 3E10 mAb resulted in a dramatic reduction in IL-4, IL-5, IL-6 and IL-13, but had no effect on IL-10 levels in the BAL (open bars). OVA challenge of TH1 recipient mice resulted in high levels of IFN-γ in the BAL fluid (closed bars) that was not inhibited by 3E10 mAb (open bars). Data are shown as the mean±sem of 5-6 animals.

FIGS. 19A-B. Anti-103 gene product mAb inhibits TH2 mediated allergic lung inflammation. A) Analysis of the number of eosinophils in the BAL; B) analysis of the number of lymphocytes in the BAL. The number of OVA-specific TH2 cells in dispersed lung tissue as described (Cohn, L. et al., 1997, J. Exp. Med. 186:1737-1747). Lymphocytes were stained with biotinylated clonotypic TCR mAb KJ126 (Cohn, L. et al., 1997 J. Exp. Med. 186:1737-1747) followed by strepavidin-FITC and CD4-PE (Pharmingen, San Diego).

FIG. 20. Inhibition of airway hyperresponsiveness by anti-103 gene product mAb. OVA exposure in TH2 recipient mice resulted in airway hyperresponsiveness (closed squares) compared to mice exposed to PBS (closed circles). Pretreatment with 103 gene product mAb inhibited OVA induced BHR by 80% (open diamonds). The results are shown as the mean Penh±sem of n=5-6 and is representative of 2 separate experiments.

FIGS. 21A-B. Administration of 3E10 mAb or the 103/Ig fusion results in significant decrease in hallmark symptoms of asthma. A) Animals were treated with the anti-103 3E10 antibody (listed in the figure as "3E10 mAB"). As a negative control, a set of animals was treated with a non-specific rat Ig antibody preparation. B) Animals were treated with 103/Ig fusion protein (listed in the figure as "Ig Fus. Prot.") as a negative control, a control set of animals were treated with a non-specific human IgG antibody preparation.

FIG. 22. Crosslinking of 103 gene product augments IL-4 and IL-5 cytokine secretion. TH2 effector cells were activated with plate-bound CD3 (3 µg/ml, 2C11) and CD28 (37.51, 4 µg/ml, Pharmingen San Diego) and 3E10 (20 µg/ml) for 48 hrs. IL-4 and IL-5 levels were measured in the supernatant by ELISA. 3E10 mAb stimulation alone failed to induce TH2 cell activation but augmented both anti-CD3 and anti-CD3+ CD28 induced cytokine production. Soluble 3E10 failed to have any effect on CD3/CD28 mediated cytokine production. These data suggest that activation of 103 gene product provides a stimulatory signal to TH2 cells. There was no effect of the mAb on TH2 cell proliferation as revealed by $^3$H-thymidine incorporation. 3E10 mAb did not modify IFN-γ secretion from TH1 effector cells stimulated under the same conditions.

FIGS. 23A-D. Flow cytometry data demonstrate that the 3E10 mAb recognizes and binds to CD4+ cells cultured in conditions which promoted TH2 development (FIG. 23C), but not in naive CD4+ cells (FIG. 23B) or in CD4+ cells cultured in conditions which promote TH1 development (FIG. 23D); the 3E10 mAb also failed to bind to splenocytes, indicating that the 103 gene product is expressed only on the surface of TH2 or TH2-like cells.

FIG. 24 shows cytokine (IL-4, IL-5 and IFN-γ) levels measured from antigen restimulated CD4+ T cells differentiated with OVA peptide alone, in TH1 polarizing conditions (i.e., with IL-12 and anti-IL-4 mAb) or in TH2 polarizing conditions (i.e., with IL-4 and anti-IL-12 mAb) for five days in the presence of human-Ig (closed bars) or in the presence of the 103-Ig fusion protein (open bars).

Figure 26A:
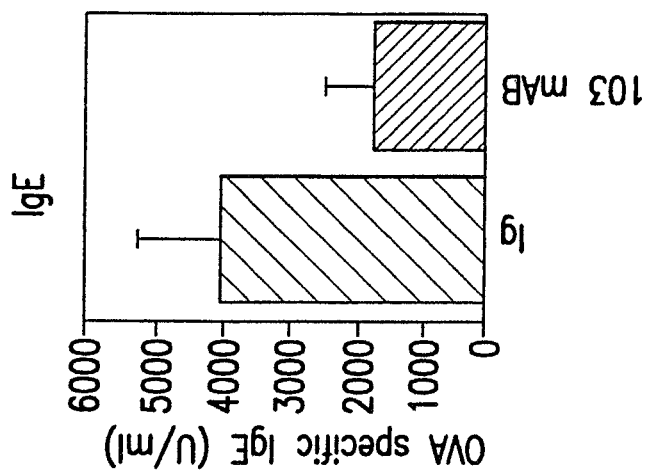
Figure 26B:
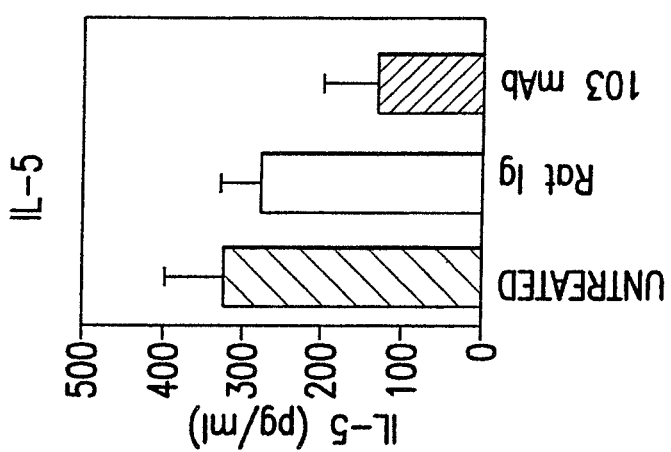
Figure 26C:
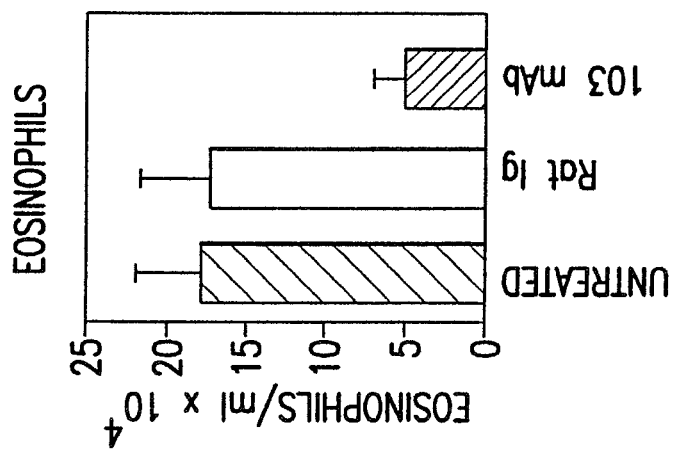

FIGS. 26A-C. Inhibition of cellular and humoral responses in an active immunization model; responses were measured in untreated OVA allergen exposed mice (closed columns), rat IgG1 treated (100 μg) mice (open columns), and 3E10 mAb treated (100 μg) mice (shaded columns); FIG. 26A shows eosinophil counts; FIG. 26B shows measured IL-5 levels; and FIG. 26C shows measured IgE levels in each of the three experiments.

5. DETAILED DESCRIPTION OF THE INVENTION

Methods and compositions for the treatment (e.g., amelioration of symptoms), prognosis and diagnosis of immune disorders, especially TH cell subpopulation-related disorders are described herein. The immune disorders include, but are not limited to, chronic inflammatory disease and disorders (e.g., Crohn's disease, reactive arthritis, and Lyme disease), insulin-dependent diabetes, organ specific autoimmunity (including, e.g., multiple sclerosis, Hashimoto's thyroiditis and Grave's disease), contact dermatitis, psoriasis, graft rejection, graft versus host disease, sarcoidosis, atopic conditions (e.g., asthma and allergy including, but not limited to, allergic rhinitis and gastrointestinal allergies such as food allergies), eosinophilia, conjunctivitis, glomerular nephritis, systemic lupus erythematosus, scleroderma certain pathogen susceptibilities such as helminthic (e.g., leishmaniasis) and certain viral infections (including HIV and bacterial infections such as tuberculosis and lepromatous leprosy).

Specifically, the methods and compositions of the present invention can utilize a gene, referred to herein as the 103 gene or gene sequence, as well as gene products of the 103 gene and/or modulators thereof, e.g., antibodies which specifically bind to such 103 gene products. Certain 103 gene and gene products are alternately referred to in the art as ST2, T1 and Fit-1. See, for example, Klemenz, R. et al., 1989, *Proc. Natl. Acad. Sci. USA* 86:5708-5712; S. Tominaga, 1989, *FEBS Lett.* 258:301-301; A. K. Werenskiold et al., 1989, *Mol. Cell. Biol.* 9:5207-5214; S. Tominaga et al., 1992, *Biochem. Biophys. Acta.* 1171:215-218; A. K. Werenskiold, 1992, *Eur. J. Biochem.* 204:1041-1047; K. Yanagisawa et al., 1993, *FEBS Lett.* 318:83-87; G. Bergers et al., 1994, *EMBO J* 13:1176-1188; S. Kumar, 1997, *Biochem Biophys Res Commun* 235: 474-478; S. Tominaga, 1994, Japanese Patent No. JP 1994178687-A 3) each of which is incorporated herein, by reference, in its entirety.

The present invention encompasses methods and compositions comprising murine 103 gene products and the nucleotide sequences encoding those gene products. The murine 103 gene encodes at least two forms, a 337 amino acid soluble or secreted form, otherwise referred to as murine ST2, and a 567 amino acid transmembrane form, otherwise referred to as murine ST2L (see, e.g., Tominaga et al., 1989, *FEBS Lett.* 258 (2): 301-304; Yanagisawa et al., 1993, *FEBS Lett.* 318 (1): 83-87; Kumar, S., 1997, *Biochem. Biophys. Res. Comm.* 225: 447-478). FIG. 3B depicts the amino acid sequence of a 337 amino acid secreted form of the murine 103 gene product (SEQ ID NO:6) encoded by the nucleic acid sequence in FIG. 3A (SEQ ID NO:2). FIG. 4B depicts the amino acid sequence of a 567 amino acid transmembrane form of the murine 103 gene product (SEQ ID NO:7) encoded by the nucleic acid sequence shown in FIG. 4A (SEQ ID NO:3). FIG. 9 depicts an alignment of the two forms of the murine gene product. The soluble form of the murine 103 gene product (SEQ ID NO:6) consists of the first 328 amino acid residues of the transmembrane form of the murine 103 gene product (SEQ ID NO:7) and 9 different amino acid residues.

The present invention also encompasses methods and compositions comprising human 103 gene products and the nucleotide sequences encoding those gene products. Three forms of human 103 gene products have been described, a 323 amino acid soluble or secreted form, otherwise referred to as human ST2, a 556 transmembrane form, otherwise referred to as human ST2L, and a 259 amino acid form, otherwise referred to as ST2V (see, e.g., Tominaga et al., 1992, *Biochem. Biophys. Res. Comm.* 1171:215-218; Tominaga et al., 1999, *Biochem. Biophys. Res. Comm.* 264:14-18). FIG. 5B depicts the amino acid sequence of a 556 amino acid transmembrane form of the human 103 gene product (SEQ ID NO:8) encoded by the nucleic acid sequence in FIG. 5A (SEQ ID NO:4). FIG. 6B depicts the amino acid sequence of a 323 amino acid secreted form of the human 103 gene product (SEQ ID NO:9) encoded by the nucleic acid sequence shown in FIG. 6A (SEQ ID NO:5). FIG. 7B depicts the amino acid sequence of a 259 amino acid variant form of the human 103 gene product (SEQ ID NO:11) encoded by the nucleic acid sequence shown in FIG. 7A (SEQ ID NO:10). The transmembrane form of the human 103 gene product (SEQ ID NO:8) consists of the first 323 amino acids of the secreted form of the 103 gene product (SEQ ID NO:9). The 259 amino acid form in of the human 103 gene product (SEQ ID NO:11) consists of the first 203 amino acids of the secreted form of the 103 gene product (SEQ ID NO:9). The 259 amino acid form of the human 103 gene product (SEQ ID NO:11) has a hydrophobic tail and lacks the third Ig-like domain found in the secreted form of the human 103 gene product (SEQ ID NO:9).

At least one allelic variant of the secreted form of the human 103 gene exists. The nucleotide sequence of this allelic variant differs from the nucleotide sequence depicted in FIG. 6A (SEQ ID NO:5) in that nucleic acid number 1130 of the allelic variant sequence is a guanine (G) rather than an adenine (A) (see, in particular, the nucleotide sequence disclosed in GenBank Accession No. E07716). However, as will be apparent to one skilled in the art, because this single nucleotide variation (or polymorphism) is located in the non-coding, 3' untranslated region (UTR) of the gene sequence, this allelic variant encodes the same secreted form of a human 103 gene product as does the nucleotide sequence of FIG. 6A (SEQ ID NO:5).

The invention also provides a novel human 103 gene product, disclosed herein for the first time. In particular, FIG. 8 depicts the amino acid sequence (SEQ ID NO:13) of the novel Athdc120c9 gene product, which is encoded by a nucleotide sequence comprising the sequence in the SEQ ID NO:12. In particular, this novel form of a human 103 gene product consists of the first 150 amino acid residues (i.e., amino acid residues 1-150) of the human 103 gene products depicted in FIGS. 5B and 6B (SEQ ID NOS:8 and 9, respectively) and 8 different amino acid residues. The signal sequence of the Athdc120c9 gene product extends from about amino acid residues 1 to 18 of the amino acid sequence. In one embodiment, an isolated polypeptide comprises amino acid residues 19 to 158 in SEQ ID NO:8 (FIG. 8). FIG. 10 depicts an alignment of the four forms of human 103 gene products. FIG. 11 depicts an alignment of the murine and human forms of 103 gene products.

Domains of the 103 gene products (e.g., the domains depicted in FIG. 2) are also among the 103 gene products which can be used in the methods and compositions of the present invention. Likewise, nucleotide sequences which encode any one or more of these domains can also be used in the methods and compositions of this invention.

Figure 2:
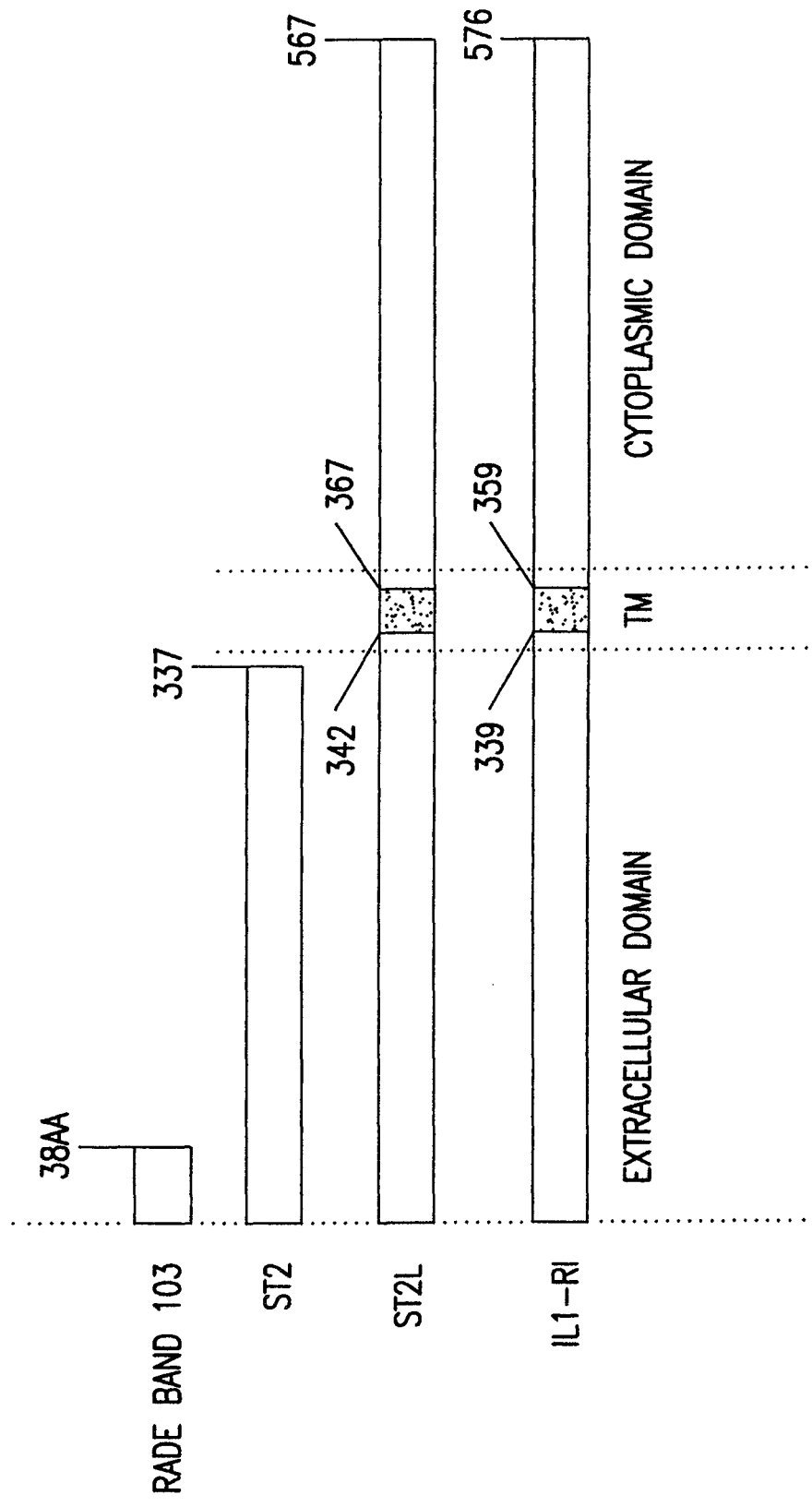

Exemplary domains of the 103 gene products include a signal sequence domain (SS), an extracellular domain (ECD), a transmembrane domain (TM) and a cytoplasmic domain (CD) which is also referred to herein as the intracellular domain. FIG. 2 depicts a schematic alignment of secreted and transmembrane forms of the murine 103 gene product (labeled ST2 and ST2L, respectively) as well as another, related protein: the murine interleukin-1 receptor type 1 protein (IL1-R1). The extracellular, transmembrane and cytoplasmic domains of these proteins are indicated in FIG. 2. In one embodiment, the transmembrane form of the murine 103 gene product has a signal sequence domain corresponding to about amino acid residue 1 to about amino acid residue 23 of the amino acid sequence depicted in FIG. 4B (SEQ ID NO:7), an extracellular domain corresponding to about amino acid residue 24 to about amino acid residue 342 of the amino acid sequence depicted in FIG. 4B (SEQ ID NO:7), a transmembrane domain corresponding to about amino acid residue 343 to about amino acid residue 366 of SEQ ID NO:7, and a cytoplasmic or intracellular domain corresponding to about amino acid residue 367 to about amino acid residue 567 of the amino acid sequence in FIG. 4B (SEQ ID NO:7). In another embodiment, the transmembrane form of the murine 103 gene product has a signal sequence corresponding to about amino acid residues 1 to 23 of SEQ ID NO:7, an extracellular domain corresponding to about amino acids 24 to 333 of SEQ ID NO:7, a transmembrane domain corresponding to about amino acid residues 334 to 355 of SEQ ID NO:7, and a cytoplasmic domain corresponding to amino acid residues 356 to 567 of SEQ ID NO:7.

Similar domains are known to exists in the human 103 gene product. In one embodiment, the transmembrane form of the human 103 gene product has a signal sequence domain corresponding to about amino acid residue 1 to about amino acid residue 18 of the amino acid sequence depicted in FIG. 5B (SEQ ID NO:8), an extracellular domain corresponding to about amino acid residue 19 to about amino acid residue 323 of the amino acid sequence depicted in FIG. 5B (SEQ ID NO:8), a transmembrane domain corresponding to about amino acid residue 324 to about amino acid residue 350, and a cytoplasmic or intracellular domain corresponding to about amino acid residue 351 to 556 of the amino acid sequence in FIG. 5B (SEQ ID NO:8). In another embodiment, the transmembrane form of the human 103 gene product has a signal sequence corresponding to about amino acid residue 1 to about amino acid residue 18 of the amino acid sequence of SEQ ID NO:8, an extracellular domain corresponding to about amino acid residue 19 to about amino acid residue 323 of the amino acid sequence depicted of SEQ ID NO:8, a transmembrane corresponding to about amino acid residue 324 to about amino acid residue 350 of the amino acid sequence of SEQ ID NO:8, and a cytoplasmic domain corresponding to about amino acid residue 351 to amino acid residue 556 of SEQ ID NO:8.

Other domains will also be apparent to those skilled in the art. For example, the 103 gene products of the invention also contain immunoglobulin (Ig)-like domains. An Ig domain typically has the consensus the following consensus sequence, beginning at about 1 to 15 amino acid residues, more preferably about 3 to 10 amino acid residues, and most preferably about 5 amino acid residues from the C-terminal end of the domain: [FY]-Xaa-C-Xaa-[VA]-Xaa-H-COO-, wherein [FY] is either a phenylalanine or a tyrosine residue (preferably tyrosine), where "Xaa" is any amino acid, C is a cysteine residue, [VA] is either valine or an alanine residue (preferably alanine), and COO- is the C-terminus of the domain. The secreted form of human 103 gene product depicted in FIG. 6B (SEQ ID NO:9) has at least three Ig-like domains corresponding to about amino acid residue 29 to about amino acid residue 89, about amino acid residue 126 to about amino acid residue 183, and about amino acid residue 228 to about amino acid residue 305 of the amino acid sequence in FIG. 6B (SEQ ID NO:9). The Ig-like domains corresponding to about amino acid 29 to about amino acid residue 89 and about amino acid residue 228 to about amino acid residue 305 of the amino acid sequence depicted in FIG. 6B (SEQ ID NO:9) have the following consensus sequence, beginning at about 5 amino acid residues from the C-terminal end of the domain: [FY]-Xaa-C-Xaa-[VA]-COO-, wherein [FY] is either a phenylalanine or a tyrosine residue (preferably tyrosine), where "Xaa" is any amino acid, C is a cysteine residue, [VA] is either valine or an alanine residue (preferably alanine), and COO- is the C-terminus of the domain. The Ig-like domain corresponding to about amino acid residue 126 to about amino acid residue 183 the amino acid sequence depicted in FIG. 6B (SEQ ID NO:9) has the following consensus sequence, beginning at about 5 amino acid residues from the C-terminal end of the domain: [FY]-Xaa-C-Xaa-COO-, wherein [FY] is either a phenylalanine or a tyrosine residue (preferably tyrosine), where "Xaa" is any amino acid, C is a cysteine residue, and COO- is the C-terminus of the domain. As noted above, the novel variant of the 103 gene product disclosed herein (i.e., Athdc120c9; FIG. 8, SEQ ID NO:12) consists of the first 150 amino acid residues of the secreted form of human 103 gene product shown in FIG. 8B (SEQ ID NO:13) and 8 different amino acid residues. Thus, as one skilled in the art readily appreciates, the Athdc120c9 gene product also has an Ig-like domain corresponding to about amino acid residue 29 to about amino acid residues 89 of the amino acid sequence depicted in FIG. 8 (SEQ ID NO:13). The Athdc120c9 gene product also has a signal sequence domain corresponding to amino acid residue 1 to about amino acid residue 18 of the amino acid sequence depicted in FIG. 8 (SEQ ID NO:13).

Other exemplary domains of the 103 gene products of the invention include, but are not limited to, ligand binding domains. A skilled artisan can readily identify a ligand binding domain of a 103 gene product, e.g., by preparing antibodies to particular epitopes of the 103 gene product, according to the methods described and demonstrated, e.g., in Section 5.3 and in the Example presented in Section 6.8, below. One skilled in the art will readily appreciate that the amino acid residues corresponding to epitopes that produce antibodies inhibiting the binding of the 103 gene product to a ligand will correspond to ligand binding domains of that 103 gene product.

Functionally equivalent forms of each of these domains will be apparent to those skilled in the art in other forms of the 103 gene products described herein, including human forms of the 103 gene product.

The invention is based, in part, on the discovery that the 103 gene is expressed, in vivo, in a tightly controlled TH2 specific manner, and that the 103 gene product is an important molecule in signaling TH2-mediated immune responses. Thus, compounds such as natural ligands, derivatives of natural ligands and antibodies that specifically bind to the 103 gene product can be utilized to modulate (e.g., reduce) the number of TH2 and/or TH2-like cells present, for example, by physically separating such cells away from other cells in a population or, alternatively, by targeting the specific destruction of TH2 and/or TH2-like cells, or by inhibiting the proliferation of such TH2 and/or TH2-like cells. Additionally, compounds such as 103 gene sequences, 103 gene products or anti-103 antibodies (i.e., antibodies that specifically bind to 103 gene products) can be utilized to reduce the level of TH2 cell activity and/or to cause a reduction in the level of TH2 cell cytokine production (e.g, reduce the level of production of cytokines, such as IL-4, that are associated with TH2 or TH2-like cell subpopulations and/or with TH2 or TH2-like cell subpopulation activity). For example, IL-4 produced by the TH2 cell subpopulation stimulates B cells which, in turn, produce IgE-type antibodies. Thus conditions that involve an inappropriate IgE immune response, including but not limited to the symptoms which accompany atopic conditions such as allergy and/or asthma, can be treated and/or ameliorated by reducing IL-4 levels, e.g., by using the methods of the present invention to reduce TH2 cell activity.

The 103 gene is also expressed in human mast cells, as demonstrated in the Example presented in Section 6.5, below. Thus, the above-described compositions (e.g., natural ligands, derivatives of natural ligands, small molecules and antibodies that specifically bind to the 103 gene product) can also be utilized to modulate the number of mast cells present and/or to modulate the amount of mast cell activity or mast cell cytokine production (e.g., from the degranulation of mast cells). Thus conditions, including atopic conditions such as asthma and allergy, that involve or are mediated by mast cell activity (often in addition to TH2 or TH2-like activity) can be treated by using the methods and compositions of the invention to target mast cells and/or mast cell activity as well as (or instead of) TH2 cells and/or TH2 cell activity.

The 103 gene and nucleotide sequences of the invention are described, in detail, in Section 5.1, below. Further, the gene products of the 103 gene are described herein in Section 5.2, and antibodies to such gene products are described in Section 5.3. Methods for using the 103 genes, their gene products and anti-103 antibodies and/or modulators of 103 gene expression or 103 gene product activity are also described herein.

In particular, methods for the identification of compounds which modulate the expression of genes, such as the 103 gene, involved in (a) TH cell subpopulation-related disorders, and/or (b) the differentiation and effector function of TH cell subpopulations are presented in Section 5.4 The methods include both in vitro assays (described in Section 5.4:1) and in vivo assays (e.g., cell and animal based models of various TH cell subpopulation-related disorders, including the models described in Section 5.4.4). Compositions and methods for the treatment of immune disorders are also described below, in Section 5.5. Pharmaceutical compositions for use, e.g., in the diagnostic and treatment methods of the invention, are described in Section 5.6, as well as methods for administering such compositions. Methods for the prognostic and diagnostic evaluation of various TH cell subpopulation-related disorders, for the identification of subjects exhibiting a predisposition to such disorders, and for monitoring the efficacy of compounds used in clinical trials are described in Section 5.7.

The invention is demonstrated by way of several specific examples presented in Section 6. These examples are presented by way of illustration of the methods described in this section, and are not limiting of that description in any way. Indeed, many modifications and variations of the present invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

5.1. THE 103 GENE

The 103 gene, which is also known as T1, ST2 or Fit-1, is described herein. As used herein, 103 gene or gene sequence refers to: (a) at least one of the nucleotide sequences and/or fragments thereof that are depicted herein FIGS. 1, 3A, 4A, 5A, 6A, 7A and 8 (SEQ ID NOS:1-5, 10 and 12); (b) any nucleotide sequence or fragment thereof that encodes the amino acid sequence encoded by one of the nucleotide sequences that are depicted in FIGS. 1, 3A, 4A, 5A, 6A, 7A and 8 (SEQ ID NOS:1-5, 10 and 12); (c) any nucleotide sequence that hybridizes to the complement of one of the coding nucleotide sequences depicted herein in FIGS. 1, 3A, 4A, 5A, 6A, 7A and 8 (SEQ ID NOS:1-5, 10 and 12) under stringent conditions, e.g., hybridization to filter-bound DNA in 6× sodium chloride/sodium citrate (SSC) at about 45° C. followed by one or more washes in 0.2×SSC/0.1% SDS at about 50-65° C., or hybridization to filter-bound DNA in 0.5 M sodium pyrophosphate/7% SDS at about 65° C. followed by one or more washes in 0.2×SSC/1% SDS at about 42-55° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3); (d) any nucleotide sequence that hybridizes to the complement of one of the coding nucleotide sequences depicted herein in FIGS. 1, 3A, 4A, 5A, 6A, 7A and 8 (SEQ ID NOS:1-5, 10 and 12) under highly stringent conditions, e.g., hybridization to filter-bound nucleic acid in 6×SSC at about 45° C. followed by one or more washes in 0.1×SSC/0.2% SDS at about 68° C., or hybridization to filter-bound DNA in 0.5 M sodium pyrophosphate/7% SDS at about 65° C. followed by one or more washes in 0.2×SSC/1% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3), including such other hybridization conditions as those described herein; and (e) the complement of any of the 103 genes or gene sequences recited in (a)-(d) above.

Preferably, the nucleic acid molecules that hybridize to the complements of the 103 gene sequence disclosed herein are the same length or about the same length as the 103 gene sequence disclosed herein (i.e., about 4989, 1011, 1833, 1357 or 1210 nucleic acids in length) and/or also encode gene products, e.g., gene products that are the same length or about the same length as a 103 gene product encoded by a nucleotide sequence of (a) above (i.e., 567, 556, 337, 328 or 158 amino acid residues in length) and/or are functionally equivalent to a 103 gene product encoded by a nucleotide sequence of (a), above. "Functionally equivalent," as the term is used herein, can refer to, in certain embodiments, a gene product (e.g., a polypeptide) capable of exhibiting a substantially similar in vivo activity as an endogenous 103 gene product encoded by one or more of the above-recited 103 gene sequences. Alternatively, and in certain other embodiments, as when utilized as part of assays such as those described hereinbelow (e.g., in Section 5.4), "functionally equivalent" can refer to peptides or other molecules capable of interacting with other cellular or extracellular molecules in a manner substantially similar to the way in which the corresponding portion of the endogenous 103 gene product would. Functionally equivalent gene products can therefore include naturally occurring 103 gene products present in the same or different species. Functionally equivalent 103 gene products also include gene products that retain at least one of the biological activities of a 103 gene product described above (e.g., which is encoded by the coding sequences depicted herein in FIGS. 1, 3A, 4A, 5A, 6A, 7A and 8; SEQ ID NOS:1-5, 10 and 12). The functionally equivalent 103 gene products of the invention also include gene products which are recognized by and bind to antibodies (polyclonal or monoclonal) directed against one or more of 103 gene products described above (e.g., which are encoded by the coding sequences depicted herein in FIGS. 1, 3A, 4A, 5A, 6A, 7A and 8; SEQ ID NOS:1-5, 10 and 12).

In a preferred embodiment, an isolated nucleic acid molecule encodes a polypeptide comprising amino acid residues 150 to 158 of SEQ ID NO:13 and the nucleic acid molecule hybridizes under stringent conditions (i.e., highly or less stringent conditions defined above) to the complement of a nucleic acid molecule that encodes a polypeptide comprising the amino acid sequence of SEQ ID NO:13. In another preferred embodiment, an isolated nucleic acid molecule encodes a polypeptide comprising amino acid residues 150 to 158 of SEQ ID NO:13 and the nucleic acid molecule hybridizes under stringent conditions (i.e., highly or less stringent conditions defined above) to the complement of the nucleotide sequence of SEQ ID NO:12.

Further, and as those skilled in the art readily appreciate, an amino acid sequence encoded by a given nucleic acid sequence may also be encoded by a number of "degenerate" nucleic acid sequence which are apparent to those skilled in the art. Thus, the 103 gene sequences of the present invention also include degenerate variants of the sequences described in (a) through (d), above.

The 103 gene nucleotide sequences of the invention also encompass: (a) nucleotides that encode a mammalian 103 gene product, including the human and murine 103 gene products depicted herein in FIGS. 3B, 4B, 5B, 6B, 7B and 8 (SEQ ID NOS:6-9, 11 and 13); (b) nucleotides that encode portions of a 103 gene product that corresponds to one or more of its functional domains including, but not limited to, a signal sequence domain, an extracellular domain (ECD), a transmembrane domain (TM), a cytoplasmic domain (CD; also referred to herein as an intracellular domain) an immunoglobulin (Ig) domain and one or more ligand-binding domains; (c) nucleotide sequences that encode one or more splice variants of a 103 gene product including, for example, sequences that encode a splice variant of a 103 gene product; and (d) nucleotide sequences that encode mutants of a 103 gene product in which all or part of one of its domains is deleted or altered including, but not limited to, mutants which encode soluble forms of the 103 gene product in which all or a portion of the TM domain is deleted, and nonfunctional receptors in which all or a portion of a CD is deleted.

The 103 gene nucleotide sequences of the invention still further include nucleotide sequences that encode fusion proteins, such as IgFc fusion proteins, containing any one or more of the 103 gene products described in (a)-(d) supra fused to another polypeptide. A fusion protein comprises all or part (preferably biologically active) of a polypeptide encoded by a 103 nucleotide sequence operably linked to a heterologous polypeptide (i.e., a polypeptide other than the same polypeptide of the invention). Preferably, a fusion protein comprises the polypeptide in SEQ ID NO:13 or a fragment thereof which includes the carboxy-terminus of the polypeptide and a heterologous polypeptide.

The 103 gene nucleotide sequences of the invention still further include nucleotide sequences corresponding to the above described 103 gene nucleotide sequences (i.e., the sequences described in (a)-(d) above and fusion proteins thereof) wherein one or more of the exons or fragments thereof, have been deleted.

Still further, the 103 gene nucleotide sequences of the invention also include nucleotide sequence that have at least 65%, 70%, 75%, 80%, 85%, 90%, 95%, 98% or more nucleotide sequence identity to one or more of the 103 gene nucleotide sequences of (a)-(d) above. The 103 gene nucleotide sequences of the invention also include nucleotide sequences encoding polypeptides that have at least 65%, 70%, 75%, 80%, 85%, 90%, 95%, 98% or more amino acid sequence identity to one or more of the polypeptides encoded by any of the 103 gene nucleotide sequences of (a)-(e) above.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul (1990) Proc. Natl. Acad. Sci. U.S.A. 87:2264-2268, modified as in Karlin and Altschul (1993) Proc. Natl. Acad. Sci. U.S.A. 90:5873-5877. Such an algorithm is incorporated into the NBLAST and XBLAST programs of Altschul et al., 1990, J. Mol. Biol. 215:403-0. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used Another preferred, non-limiting example of a mathematical algorithm utilized for the comparison of sequences is the algorithm of Myers and Miller, (1988) CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The methods and compositions of the invention also encompass nucleic acid molecules, preferably DNA molecules, that hybridize to and are therefore the complements of the 103 gene nucleotide sequences (a) through (e) in the preceding paragraph. Such hybridization conditions can be highly stringent or less highly stringent, as described above. The nucleic acid molecules of the invention that hybridize to the above described DNA sequences include oligodeoxyoligonucleotides ("oligos") which hybridize under highly stringent or stringent conditions to the DNA sequences (a) through (d) in the preceding paragraph. In general, for oligos between 14 and 70 nucleotides in length the melting temperature (Tm) is calculated using the formula: $Tm(°C.)=81.5+16.6(\log[\text{monovalent cations (molar)}])+0.41(\% G+C)-(500/N)$, where N is the length of the probe. If the hybridization is carried out in a solution containing formamide, the melting temperature may be calculated using the equation: $Tm(°C.)=81.5+16.6(\log[\text{monovalent cations (molar)}])+0.41(\% G+C)-(0.61\% \text{formamide})-(500/N)$ where N is the length of the probe. In general, hybridization is carried out at about 20-25 degrees below Tm (for DNA-DNA hybrids) or about 10-15 degrees below Tm (for RNA-DNA hybrids). Other exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos).

These nucleic acid molecules can be used in the methods or compositions of the invention, e.g., as 103 gene antisense molecules which are useful, for example, in 103 gene regulation. The sequences can also be used as antisense primers, e.g., in amplification reactions of 103 gene nucleic acid sequence. Further, such complementary sequences can be used as part of ribozyme and/or triple helix sequence, also useful for 103 gene regulation. Still further, such molecules can be used as components of diagnostic methods whereby the presence of or predisposition to, an immune disorder (e.g., a TH cell subpopulation related disorder) can be detected.

Fragments of the 103 gene and 103 gene nucleotide sequences of the invention can be at least 10 nucleotides in length. In alternative embodiments, the fragments can be about 20, 30, 40, 50, 60, 70, 80, 90, 100, 200, 300, 400, 500, 1000, 1500, 2000, 2500, 3000, 3500, 4000, 4500 or more contiguous nucleotides in length. Alternatively, the fragments can comprise sequences that encode at least 10, 20, 30, 40, 50, 100, 150, 200, 250, 300, 350, 400, 450, 500 or more contiguous amino acid residues of the 103 gene products. Fragments of the 103 gene nucleic acid molecules of the invention can also refer to exons or introns of the above described nucleic acid molecules, as well as portions of the coding regions of such nucleic acid molecules that encode domains such as extracellular domains (ECD), transmembrane domains (TM) and cytoplasmic domains (CD).

In specific embodiments, fragments of the 103 nucleotide sequence comprise at least nucleotides 547 to 557 of SEQ ID NO:12, more preferably at least nucleotides 530 to 557 of SEQ ID NO:12, at least nucleotides 500 to 557 of SEQ ID NO:12, at least nucleotides 450 to 557 of SEQ ID NO:12, at least nucleotides 400 to 557 of SEQ ID NO:12, at least nucleotides 350 to 557 of SEQ ID NO:12, at least nucleotides 300 to 557 of SEQ ED NO:12, at least nucleotides 250 to 557 of SEQ ID NO:12, at least nucleotides 200 to 557 of SEQ ID NO:12, at least nucleotides 150 to 557 of SEQ ID NO:12, at least nucleotides 100 to 557 of SEQ ID NO:12, at least nucleotides 75 to 557 of SEQ ID NO:12, at least nucleotides 50 to 557 of SEQ ID NO:12, or at least nucleotides 25 to 557 of SEQ ID NO:12.

In other embodiments, fragments of the 103 nucleotide sequence comprise at least nucleotides 1200 to 1210 of SEQ ID NO:12, more preferably at least nucleotides 1175 to 1210 of SEQ ID NO:12, at least nucleotides 1150 to 1210 of SEQ ID NO:12, at least nucleotides 1125 to 1210 of SEQ ID NO:12, at least nucleotides 1100 to 1210 of SEQ ID NO:12, at least nucleotides 1075 to 1210 of SEQ ID NO:12, at least nucleotides 1050 to 1210 of SEQ ID NO:12, at least nucleotides 1000 to 1210 of SEQ ID NO:12, at least nucleotides 950 to 1210 of SEQ ID NO:12, at least nucleotides 900 to 1210 of SEQ ID NO:12, at least nucleotides 850 to 1210 of SEQ ID NO:12, at least nucleotides 800 to 1210 of SEQ ID NO:12, at least nucleotides 750 to 1210 of SEQ ID NO:12, at least nucleotides 700 to 1210 of SEQ ID NO:12, at least nucleotides 650 to 1210 of SEQ ID NO:12, at least nucleotides 600 to 1210 of SEQ ID NO:12, at least nucleotides 550 to 1210 of SEQ ID NO:12, at least nucleotides 500 to 1210 of SEQ ID NO:12, at least nucleotides 450 to 1210 of SEQ ID NO:12, at least 400 to 1210 of SEQ ID NO:12, at least nucleotides 350 to 1210 of SEQ ID NO:12, at least nucleotides 300 to 1210 of SEQ ID NO:12, at least nucleotides 250 to 1210 of SEQ ID NO:12, at least nucleotides 200 to 1210 of SEQ ID NO:12, at least nucleotides 150 to 1210 of SEQ ID NO:12, at least nucleotides 100 to 1210 of SEQ ID NO:12, at least nucleotides 50 to 1210 of SEQ ID NO:12, or at least nucleotides 25 to 1210 of SEQ ID NO:12.

In other embodiments, a polypeptide of the invention, e.g., a fragment of a 103 polypeptide, comprises at least amino acid residues 148 to 158 of SEQ ID NO:13, more preferably at least amino acid residues 125 to 158 of SEQ ID NO:13, at least amino acid residues 100 to 158 of SEQ ID NO:13, at least amino acid residues 75 to 158 of SEQ ID NO:13, at least amino acid residues 50 to 158 of SEQ ID NO:13, or at least amino acid residues 25 to 158 of SEQ ID NO:13.

The methods and compositions of the invention also use, and therefore encompass, (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element, such as a heterologous regulatory element, that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

In addition to the gene sequences described above, homologs of these gene sequences and/or full length coding sequences of these genes, as can be present in the same or other species, can be identified and isolated, without undue experimentation, by molecular biological techniques well known in the art. Further, there can exist genes at other genetic loci within the genome of the same species that encode proteins which have extensive homology to one or more domains of such gene products. These genes can also be identified via similar techniques.

For example, the isolated differentially expressed gene sequence can be labeled and used to screen a cDNA library constructed from mRNA obtained from the organism of interest. Hybridization conditions should be of a lower stringency when the cDNA library was derived from an organism different from the type of organism from which the labeled sequence was derived. cDNA screening can also identify clones derived from alternatively spliced transcripts in the same or different species. Alternatively, the labeled fragment can be used to screen a genomic library derived from the organism of interest, again, using appropriately stringent conditions. Low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

Further, a previously unknown 103 gene sequence can be isolated by performing PCR using two degenerate oligonucleotide primer pools designed on the basis of nucleotide sequences within one or more of the above described known 103 gene sequences. The template for the reaction can be cDNA obtained by reverse transcription of mRNA prepared from human or non-human cell lines or tissue known or suspected to express a differentially expressed or pathway gene allele. The PCR product can be subcloned and sequenced to insure that the amplified sequences represent the sequences of a 103 gene nucleic acid sequence.

The PCR fragment can then be used to isolate a full length cDNA clone by a variety of methods. For example, the amplified fragment can be used to screen a bacteriophage cDNA library. Alternatively, the labeled fragment can be used to screen a genomic library.

PCR technology can also be utilized to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of cloning strategies which can be used, see e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

As will be appreciated by those skilled in the art, DNA sequence polymorphisms of a 103 gene identified by the methods of the present invention will typically exist within a population of individual organisms (e.g., within a human population). Such polymorphisms may exist, for example, among individuals within a population due to natural allelic variation. Such polymorphisms include ones that lead to changes in amino acid sequence. An allele is one of a group of genes which occurs alternatively at a given genetic locus. Accordingly, as used herein, an "allelic variant" refers to a nucleotide sequence which occurs at a given locus or to a gene product encoded by the nucleotide sequence. Natural allelic variations can typically result in 1-5% variance in the nucleotide sequence of a given gene.

Alternative alleles or allelic variants can be identified by sequencing the gene of interest in a number of different individuals. This can be readily carried out by using hybridization probes to identify the same genetic locus in a variety of individuals. As used herein, the terms "gene" and "recombinant gene" refer to nucleic acid molecules comprising an open reading frame encoding a polypeptide of the invention. The term can further include nucleic acid molecules comprising upstream and/or exon/intron sequences and structure.

With respect to allelic variants of the 103 genes and gene products of the present invention, any and all nucleotide variations and/or amino acid polymorphisms or variations that are the result of natural allelic variation of the differentially expressed pathway genes and/or gene products are intended to be within the scope of the present invention. Such allelic variants include, but are not limited to, ones that do not alter the functional activity of a differentially expressed or pathway gene product of the invention. Variants also include, but are not limited to "mutant alleles." As used herein, a "mutant allele" of a differentially expressed or pathway gene or gene product of the invention is an allelic variant which does alter the functional activity of the differentially expressed or pathway gene product encoded by that gene.

In cases where the differentially expressed or pathway gene identified is the normal, or wild type, gene, this gene can be used to isolate mutant alleles of the gene. Such an isolation is preferable in processes and disorders which are known or suspected to have a genetic basis. Mutant alleles can be isolated, e.g., from individuals either known or suspected to have a genotype which contributes to TH cell subpopulation-disorder related symptoms. Mutant alleles and mutant allele products can then be utilized in the therapeutic and diagnostic assay systems described below.

A cDNA of a mutant gene can be isolated, for example, by using PCR, a technique which is well known to those of skill in the art. In this case, the first cDNA strand can be synthesized by hybridizing a oligo-dT oligonucleotide to mRNA isolated from tissue known to, or suspected of being expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probed to identify the corresponding mutant allele in the library. The clone containing this gene can then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue can be expressed and screened using standard antibody screening techniques in conjunction with antibodies raised against the normal gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described supra in this Section.

Other allelic variants and/or mutant variants of the 103 genes of the invention include single nucleotide polymorphisms (SNPs), including biallelic SNPs or biallelic markers which have two alleles, both of which are present at a fairly high frequency in a population of organisms. Conventional techniques for detecting SNPs include, e.g., conventional dot blot analysis, single stranded conformational polymorphism (SSCP) analysis (see, e.g., Orita et al., 1989, *Proc. Natl. Acad. Sci. USA* 86:2766-2770), denaturing gradient gel electrophoresis (DGGE), heteroduplex analysis, mismatch cleavage detection, and other routine techniques well known in the art (see, e.g., Sheffield et al., 1989, *Proc. Natl. Acad. Sci.* 86:5855-5892; Grompe, 1993, *Nature Genetics* 5:111-117). Alternative, preferred methods of detecting and mapping SNPs involve microsequencing techniques wherein an SNP site in a target DNA is detected by a single nucleotide primer extension reaction (see, e.g., Goelet et al., PCT Publication No. WO 92/15712; Mundy, U.S. Pat. No. 4,656,127; Vary and Diamond, U.S. Pat. No. 4,851,331; Cohen et al., PCT Publication No. WO 91/02087; Chee et al., PCT Publication No. Wo 95/11995; Landegren et al., 1988, *Science* 241:1077-1080; Nicerson et al., 1990, *Proc. Natl. Acad. Sci.* 87:9823-8927; Pastinen et al., 1997, *Genome Res.* 7:606-614; Pastinen et al., 1996, *Clin. Chem.* 42:1391-1397; Jalanko et al., 1992, *Clin. Chem* 38:39-43; Shumaker et al., 1996, *Hum. Mutation* 7:346-354; Caskey et al., PCT Publication No. 95/00669).

5.2. 103 GENE PRODUCTS

The 103 gene products used and encompassed in the methods and compositions of the present invention include those gene products (e.g., proteins) that are encoded by the 103 gene sequences described in Section 5.1, above, such as, for example, the polypeptides depicted herein in FIGS. 3B, 4B, 5B, 6B, 7B and 8 (SEQ ID NOS:6-9, 11, and 13). In addition, however, the methods and compositions of the invention also use and encompass proteins and polypeptides that represent functionally equivalent gene products. Such functionally equivalent gene products include, but are not limited to, natural variants of the polypeptides depicted herein in FIGS. 3B, 4B, 5B, 6B, 7B and 8 (SEQ ID NOS:6-9, 11, and 13). Such equivalent 103 gene products can contain, e.g., deletions, additions or substitutions of amino acid residues within the amino acid sequences encoded by the 103 gene sequences described above in Section 5.1, but which result in a silent change, thus producing a functionally equivalent 103 gene product. Amino acid substitutions can be made on the basis of similarity in polarity, charge, solubility, hydrophobicity, hydrophilicity and/or the amphipathic nature of the residues involved. For example, nonpolar (i.e., hydrophobic) amino acid residues can include alanine (Ala or A), leucine (Leu or L), isoleucine (Ile or I), valine (Val or V), proline (Pro or P), phenylalanine (Phe or F), tryptophan (Trp or W) and methionine (Met or M); polar neutral amino acid residues can include glycine (Gly or G), serine (Ser or S), threonine (Thr or T), cysteine (Cys or C), tyrosine (Tyr or Y), asparagine (Asn or N) and glutamine (Gln or Q); positively charged (i.e., basic) amino acid residues can include arginine (Arg or R), lysine (Lys or K) and histidine (His or H); and negatively charged (i.e., acidic) amino acid residues can include aspartic acid (Asp or D) and glutamic acid (Glu or E).

"Functionally equivalent," as the term is utilized herein, refers to a polypeptide capable of exhibiting a substantially similar in vivo activity as the endogenous 103 gene product encoded by one or more of the 103 gene sequences described in Section 5.1, above. Alternatively, when utilized as part of assays described hereinbelow (e.g., in Section 5.4), the term "functionally equivalent" can refer to peptides or polypeptides that are capable of interacting with other cellular or extracellular molecules in a manner substantially similar to the way in which the corresponding portion of the endogenous 103 gene product would interact with such other molecules. Preferably, the functionally equivalent 103 gene products of the invention are also the same size or about the same size as an endogenous 103 gene product encoded by one or more of the 103 gene sequences described in Section 5.1, above (i.e., 567, 556, 337, 321, 259 or 158 amino acid residues in length).

Peptides and polypeptides corresponding to one or more domains of the 103 gene products (e.g., TM, ECD, CD, Ig or ligand-binding domains), truncated or deleted 103 gene products (e.g., polypeptides in which one or more domains of a 103 gene product are deleted) and fusion 103 gene proteins (e.g., proteins in which a full length or truncated or deleted 103 gene product, or a peptide or polypeptide corresponding to one or more domains of a 103 gene product is fused to an unrelated protein) are also within the scope of the present invention. Such peptides and polypeptides can be readily designed by those skilled in the art on the basis of the differentially expressed or pathway gene nucleotide and amino acid sequences disclosed above in this Section and in Section 5.1. Exemplary fusion proteins can include, but are not limited to, IgFc fusion proteins which stabilize the 103 gene product and prolong its half-life in vivo. Other exemplary fusion proteins include fusions to any amino acid sequence that allows, e.g., the fusion protein to be anchored to a cell membrane, thereby allowing 103 gene polypeptides to be exhibited on a cell surface; or fusions to an enzyme, to a fluorescent protein or to a luminescent protein which can provide a marker function.

Other modifications of the 103 gene product coding sequences described above can be made to generate polypeptides that are better suited, e.g., for expression, for scale up, etc. and a chosen host cell. For example, cysteine residues can be deleted or substituted with another amino acid in order to eliminate disulfide bridges; N-linked glycosylation sites can be altered or eliminated to achieve, for example, expression of a homogenous product that is more easily recovered and purified from yeast hosts known to hyperglycosylate N-linked sites. To such an end, a variety of amino acid substitutions at one or both of the first or third amino acid residue positions of any one or more of the glycosylation recognition sequences (e.g., N-X-S or N-X-T) and/or an amino acid deletion at the second position of any one or more such recognition sequences will prevent glycosylation of the protein at the modified tripeptide sequence (see, e.g., Miyajima et al., 1986, *EMBO J.* 5:1193-1197).

The differentially expressed or pathway gene products of the invention preferably comprise at least as many contiguous amino acid residues as are necessary to represent an epitope fragment (that is, for the gene products to be recognized by an antibody directed to the 103 gene product). For example, such protein fragments or peptides can comprise at least about 8 contiguous amino acid residues from a full length differentially expressed or pathway gene product. In alternative embodiments, the protein fragments and peptides of the invention can comprise about 10, 20, 30, 40, 50, 60, 70, 80, 90, 100, 150, 200, 250, 300, 350, 400, 450 or more contiguous amino acid residues of a 103 gene product.

The 103 gene products used and encompassed in the methods and compositions of the present invention also encompass amino acid sequences encoded by one or more of the above-described 103 gene sequences of the invention wherein domains encoded by one or more exons of those sequences, or fragments thereof, have been deleted. The 103 gene products of the invention can still further comprise post translational modifications, including, but not limited to, glycosylations, acetylations and myrisalations.

The 103 gene products of the invention can be readily produced, e.g., by synthetic techniques or be methods of recombinant DNA technology using techniques that are well known in the art. Thus, methods for preparing the 103 gene products of the invention are discussed herein. First, the polypeptides and peptides of the invention can be synthesized or prepared by techniques well known in the art. See, for example, Creighton, 1983, *Proteins: Structures and Molecular Principles*, W.H. Freeman and Co., N.Y., which is incorporated herein by reference in its entirety. Peptides can, for example, be synthesized on a solid support or in solution.

Alternatively, recombinant DNA methods which are well known to those skilled in the art can be used to construct expression vectors containing 103 gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, *Molecular Cloning: A Laboratory Manual*, Cold Spring Harbor Press, Cold Spring Harbor, N.Y. which is incorporated by reference herein in their entirety, and Ausubel, 1989, supra. Alternatively, RNA capable of encoding 103 gene protein sequences can be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems can be utilized to express the 103 gene coding sequences of the invention. Such host-expression systems represent vehicles by which the coding sequences of interest can be produced and subsequently purified, but also represent cells which can, when transformed or transfected with the appropriate nucleotide coding sequences, exhibit the 103 gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing 103 gene protein coding sequences; yeast (e.g., *Saccharomyces, Pichia*) transformed with recombinant yeast expression vectors containing the 103 gene protein coding sequences; insect cell systems infected with recombinant virus expression vectors (e.g., baculovirus) containing the 103 gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing 103 gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the 103 gene protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited to, the *E. coli* expression vector pUR278 (Ruther et al., 1983, *EMBO J.* 2:1791), in which the 103 gene protein coding sequence can be ligated individually into the vector in frame with the lacZ coding region so that a fusion protein is produced; pIN vectors (Inouye & Inouye, 1985, *Nucleic Acids Res.* 13:3101-3109; Van Heeke & Schuster, 1989, *J. Biol. Chem.* 264:5503-5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In an insect system, *Autographa californica* nuclear polyhedrosis virus (AcNPV) is used as a vector to express foreign genes. The virus grows in *Spodoptera frugiperda* cells. The 103 gene coding sequence can be cloned individually into non-essential regions (for example the polyhedrin gene) of the virus and placed under control of an AcNPV promoter (for example the polyhedrin promoter). Successful insertion of 103 gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, (e.g., see Smith et al., 1983, *J. Viol.* 46:584; Smith, U.S. Pat. No. 4,215,051).

In mammalian host cells, a number of viral-based expression systems can be utilized. In cases where an adenovirus is used as an expression vector, the 103 gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing 103 gene protein in infected hosts, (e.g., See Logan & Shenk, 1984, *Proc. Natl. Acad. Sci. USA* 81:3655-3659). Specific initiation signals can also be required for efficient translation of inserted 103 gene coding sequences. These signals include the ATG initiation codon and adjacent sequences. In cases where an entire 103 gene, including its own initiation codon and adjacent sequences, is inserted into the appropriate expression vector, no additional translational control signals can be needed. However, in cases where only a portion of the 103 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, *Methods in Enzymol.* 153:516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, WI38, etc.

As used herein, the term "host cell" refers not only to the particular subject cell transfected with a nucleic acid molecule of the invention but to the progeny or potential progeny of such a cell. Because certain modifications may occur in succeeding generations due to either mutation or environmental influences, such progeny may not, in fact, be identical to the parent cell, but are still included within the scope of the term "host cell" as used herein.

For long-term, high-yield production of recombinant proteins, stable expression is preferred. For example, cell lines which stably express the 103 gene protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the 103 gene protein. Such engineered cell lines can be particularly useful in screening and evaluation of compounds that affect the endogenous activity of the 103 gene protein.

A number of selection systems can be used, including but not limited to the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk−, hgprt− or aprt− cells, respectively. Also, antimetabolite resistance can be used as the basis of selection for dhfr, which confers resistance to methotrexate (Wigler et al., 1980, *Proc. Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J Mol. Biol.* 150:1); and hygro, which confers resistance to hygromycin (Santerre et al., 1984, *Gene* 30:147) genes.

Alternatively, any fusion protein may be readily purified by utilizing an antibody specific for the fusion protein being expressed. For example, a system described by Janknecht et al. allows for the ready purification of non-denatured fusion proteins expressed in human cells lines (Janknecht et al., 1991, *Proc. Natl. Acad. Sci. USA* 88: 8972-8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described herein, the 103 gene protein can be labeled, either directly or indirectly, to facilitate detection of a complex formed between the 103 gene protein and a test substance. Any of a variety of suitable labeling systems can be used including but not limited to radioisotopes such as $^{125}I$; enzyme labelling systems that generate a detectable colorimetric signal or light when exposed to substrate; and fluorescent labels.

Indirect labeling involves the use of a protein, such as a labeled antibody, which specifically binds to either a 103 gene product. Such antibodies include but are not limited to polyclonal, monoclonal, chimeric, single chain, Fab fragments and fragments produced by an Fab expression library.

Where recombinant DNA technology is used to produce the 103 gene protein for such assay systems, it can be advantageous to engineer fusion proteins that can facilitate labeling (either direct or indirect), immobilization, solubility and/or detection.

Fusion proteins, which can facilitate solubility and/or expression, and can increase the blood half-life of the protein, can include, but are not limited to soluble Ig-tailed fusion proteins. Methods for engineering such soluble Ig-tailed fusion proteins are well known to those of skill in the art. See, for example U.S. Pat. No. 5,116,964, which is incorporated herein by reference in its entirety. Further, in addition to the Ig-region encoded by the IgG1 vector, the Fc portion of the Ig region utilized can be modified, by amino acid substitutions, to reduce complement activation and Fc binding. (See, e.g., European Patent No. 239400 B1, Aug. 3, 1994). The 103 gene product contained within such Ig-tailed fusion proteins can comprise, for example, the 103 gene extracellular or secreted domain of the 103 gene product or portions (preferably ligand-binding portions) thereof. The example presented in Section 6.2 below describes the construction of an exemplary 103 gene product-Ig fusion protein.

5.3. ANTIBODIES SPECIFIC FOR 103 GENE PRODUCTS

Described herein are methods for the production of antibodies capable of specifically recognizing epitopes of one or more of the 103 gene products described in Section 5.2 above. Such antibodies can include, but are not limited to, polyclonal antibodies, monoclonal antibodies (mAbs), human, humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. The Fc tails of such antibodies can be modified to reduce complement activation and FcR binding. (See, for example, European Patent No. 239400 B1, Aug. 3, 1994).

For the production of antibodies to a 103 gene or gene product, various host animals can be immunized by injection with a 103 gene protein, or a portion thereof. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, can be immunized by injection with differentially expressed or pathway gene product supplemented with adjuvants as also described above. The antibody titer in the immunized animal can be monitored over time by standard techniques, such as with an enzyme linked immunosorbent assay (ELISA) using immobilized polypeptide. If desired, the antibody molecules can be isolated from the animal (e.g., from the blood) and further purified by well-known techniques, such as protein A chromatography to obtain the IgG fraction.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (1975, *Nature* 256:495-497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, *Monoclonal Antibodies And Cancer Therapy*, Alan R. Liss, Inc., pp. 77-96). Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899-903).

Antibody fragments which recognize specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., 1989, *Science* 246:1275-1281) to allow rapid and easy identification of monoclonal Fab fragments with the desired specificity.

Antibodies of the present invention can also be generated using various phage display methods known in the art. In phage display methods, functional antibody domains are displayed on the surface of phage particles which carry the polynucleotide sequences encoding them. Phage expressing an antigen binding domain that binds the antigen of interest (i.e., a 103 gene product) can be selected or identified with antigen, e.g., using labeled antigen or antigen bound or captured to a solid surface or bead. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01 134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Single chain antibodies of the invention can also be generated by known techniques including those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Antibodies to the differentially expressed or pathway gene products can, in turn, be utilized to generate anti-idiotype antibodies that "mimic" such gene products, using techniques well known to those skilled in the art. (See, e.g., Greenspan & Bona, 1993, *FASEB J* 7(5):437-444; and Nissinoff, 1991, *J. Immunol.* 147(8):2429-2438). For example, antibodies which bind to the ECD and competitively inhibit the binding of ligand to the receptor can be used to generate anti-idiotypes that "mimic" the ECD and, therefore, bind and neutralize the ligand. Such neutralizing anti-idiotypes or Fab fragments of such anti-idiotypes can be used in therapeutic regimens of TH cell subpopulation-related disorders.

Antibodies of the present invention may also be described or specified in terms of their binding affinity to a 103 gene product. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M.

The exemplary production of antibodies directed against the 103 gene products of the invention is described in the Examples presented in Section 6, below. Specifically, the Examples presented in Sections 6.4 and 6.5, below, describe the production and characterization of mouse antibodies, including monoclonal antibodies, directed against the extracellular domains of murine and human 103 gene products, respectively. The Example presented in Section 6.7 describes the production of humanized monoclonal antibodies directed against the extracellular domain of a human 103 gene product. In one embodiment, a monoclonal antibody of the invention is produced by the hybridoma clone M15 3F7.3, M15 2O3.1, M15 10F7.1, M15 1B4,1, M15 9F11.1 or M15 5A16.1. The invention also encompasses an antigen binding fragment of a monoclonal antibody produced by the hybridoma clone M15 3F7.3, M15 2O3.1, M15 10F7.1, M15 1B4.1, M15 9F11.1 or M15 5A16.1.

It is understood, therefore, that such antibodies are among the antibodies of the present invention. Likewise, one skilled in the art can readily appreciate and will be able to prepare antibodies that compete with monoclonal antibodies, such as the specific monoclonal antibodies described in the Examples in Sections 6.4, 6.5 and 6.7, for binding to a 103 gene product and which therefore bind to the same epitope of the 103 gene product. Thus, such antibodies which recognize and specifically bind to the same epitope of a 103 gene product, e.g., as the monoclonal antibodies described herein, are also among the antibodies of the present invention. The present invention encompasses an isolated antibody that competes with the monoclonal antibody produced by hybridoma clone M15 3F7.3, M15 2O3.1, M15 10F7.1, M15 1B4.1, M15 9F11.1 or M15 5A16.1 for epitope binding. Antibodies that compete with monoclonal antibodies of the invention can be identified in immunoassays such as a competition ELISA.

In one embodiment, the ability of an antibody to compete with a monoclonal antibody of the invention is determined in an assay comprising: (a) incubating the antibody and the monoclonal antibody with a 103 polypeptide; and (b) measuring the binding of the monoclonal antibody to the 103 polypeptide, so that if less monoclonal antibody binding is measured relative to that measured in the absence of the antibody, the antibody competes with the monoclonal antibody for binding.

In accordance with this embodiment, the monoclonal antibody can be labeled with a detectable substance (e.g., an enzyme, a prosthetic group, a fluorescent material, a luminescent materials, a bioluminescent materials, or a radioisotope) to facilitate measuring the binding of the monoclonal antibody to the 103 polypeptide in an ELISA. Alternatively, a labeled secondary antibody that only recognizes the monoclonal antibody can be incubated with the 103 polypeptide following the incubation with the monoclonal antibody to facilitate measuring the binding of the monoclonal antibody to the 103 polypeptide.

5.3.1. USE OF ANTIBODIES SPECIFIC FOR 103 GENE PRODUCTS

Antibodies directed against a 103 gene product or fragment thereof can be used to detect the a 103 gene product (e.g., in a biological sample) in order to evaluate the abundance and pattern of expression of the polypeptide. Antibodies directed to cell surface epitopes of a 103 gene product can be used to isolate a cell subpopulation of interest (e.g., a TH2 or TH2-like cell subpopulation, for either depletion or augmentation purposes. Antibodies directed against a 103 gene product or fragment thereof can also be used diagnostically to monitor protein levels of a 103 gene product in tissue as part of a clinical testing procedure, e.g., to, for example, determine the efficacy of a given treatment regimen (see, Section 5.7 below). Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, $^{32}$P, $^{3}$H or $^{99}$Tc.

Further, antibodies directed against a 103 gene product or fragment thereof can be used therapeutically to treat, prevent or inhibit an immune disorder described herein (e.g., asthma). Antibodies can also be used to alleviate one or more symptoms associated with an immune disorder described herein. Antibodies can also be used to modify a biological activity of a 103 gene product. For example, antibodies can be used to modulate TH cell subpopulation differentiation, maintenance and/or effector function. To facilitate or enhance its therapeutic effect, an antibody (or fragment thereof) may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

An antibody can also be conjugated to a drug moiety, which is not limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), tumor necrosis factor ("TNF")-α, TNF-β, interferon ("IFN")-γ, granulocyte macrophase colony stimulating factor ("GM-CSF"), granulocyte colony stimulating factor ("G-CSF"), or other growth factors.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with chemotherapeutic agents.

5.4. SCREENING ASSAYS FOR COMPOUNDS THAT INTERACT WITH THE 103 GENE PRODUCT

The following assays are designed to identify compounds that bind to target gene products, bind to other cellular proteins that interact with the 103 gene product, and to compounds that interfere with the interaction of the target gene product with other cellular proteins. For example such techniques can identify ligands for a 103 gene product. A compound which binds a 103 gene product (a 103 gene product ligand, for example) can, e.g., be tested for an ability to ameliorate symptoms of TH2 or TH2-like related disorders such as asthma or allergy. Any such binding compound can also act as a marker for the presence of TH cell subpopulations. Thus, for example, a compound which binds the 103 gene product can act as a marker, for example a diagnostic marker, for TH2 or TH2-like cells, e.g., for TH2 or TH2-like cell differentiation.

Binding compounds can include, but are not limited to, other cellular proteins. Binding compounds can also include, but are not limited to, peptides such as, for example, soluble peptides, including, but not limited to, Ig-tailed fusion peptides, comprising, for example, extracellular portions of 103 gene product transmembrane receptors, and members of random peptide libraries (see, e.g., Lam et al., 1991, *Nature* 354:82-84; Houghten et al., 1991, *Nature* 354:84-86) made of D- and/or L-configuration amino acids, phosphopeptides (including but not limited to members of random or partially degenerate, directed phosphopeptide libraries; see, e.g., Songyang et al., 1993, *Cell* 72:767-778), antibodies (including, but not limited to polyclonal, monoclonal, human, humanized, anti-idiotypic, chimeric or single chain antibodies, and FAb, F(ab')$_2$ and FAb expression library fragments, and epitope-binding fragments thereof), and small organic or inorganic molecules. In the case of receptor-type target molecules, such compounds can include organic molecules (e.g., peptidomimetics) that bind to the ECD and either mimic the activity triggered by the natural ligand (i.e., agonists); as well as peptides, antibodies or fragments thereof, and other organic compounds that mimic the ECD (or a portion thereof) and bind to a "neutralize" natural ligand.

Computer modelling and searching technologies permit identification of compounds, or the improvement of already identified compounds, that can modulate 103 gene expression or activity. Having identified such a compound or composition, the active sites or regions are preferably identified. In the case of compounds affecting receptor molecules, such active sites might typically be ligand binding sites, such as the interaction domains of ligand with receptor itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

The three dimensional geometric structure of the active site is then preferably determined. This can be done by known methods, including X-ray crystallography, which can determine a complete molecular structure. Solid or liquid phase NMR can also be used to determine certain intra-molecular distances within the active site and/or in the ligand binding complex. Any other experimental method of structure determination can be used to obtain partial or complete geometric structures. The geometric structures may be measured with a complexed ligand, natural or artificial, which may increase the accuracy of the active site structure determined.

Methods of computer based numerical modelling can be used to complete the structure (e.g., in embodiments wherein an incomplete or insufficiently accurate structure is determined) or to improve its accuracy. Any art recognized modelling method may be used, including, but not limited to, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. Exemplary forcefields that are known in the art and can be used in such methods include, but are not limited to, the Constant Valence Force Field (CVFF), the AMBER force field and the CHARM force field. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential target or pathway gene product modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of target or pathway gene or gene products and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen et al., 1988, *Acta Pharmaceutical Fennica* 97:159-166; Ripka, (Jun. 16, 1988), *New Scientist* 54-57; McKinaly and Rossmann, 1989, *Annu. Rev. Pharmacol. Toxiciol.* 29:111-122; Perry and Davies, *OSAR: Quantitative Structure-Activity Relationships in Drug Design* pp. 189-193 (Alan R. Liss, Inc. 1989); Lewis and Dean, 1989 *Proc. R. Soc. Lond.* 236:125-140 and 1-162; and, with respect to a model receptor for nucleic acid components, Askew et al., 1989, *J. Am. Chem. Soc.* 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although generally described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein can be useful, for example, for ameliorating the symptoms of immune disorders. For example, in instances in which a TH cell subpopulation-related disorder situation results from a lower overall level of 103 gene expression, 103 gene product, and/or 103 gene product activity in a cell or in tissue involved in such a disorder, compounds that interact with the 103 gene product can include ones which accentuate or amplify the activity of the bound 103 gene protein. Such compounds would bring about an effective increase in the level of 103 gene activity, thus ameliorating symptoms. In instances whereby mutations within the 103 gene cause aberrant 103 gene proteins to be made which have a deleterious effect that leads to a TH cell subpopulation-related disorder, or, alternatively, in instances whereby normal 103 gene activity is necessary for a TH cell subpopulation-related disorder to occur, compounds that bind 103 gene protein can be identified that inhibit the activity of the bound 103 gene protein. Assays for identifying additional compounds as well as for testing the effectiveness of compounds, identified by, for example, techniques, such as those described in Section 5.4.1-5.4.4, are discussed, below, in Section 5.4.5.

5.4.1. IN VITRO SCREENING ASSAYS FOR COMPOUNDS THAT BIND TO A TARGET GENE PRODUCT

In vitro systems can be designed to identify compounds capable of binding the 103 gene products of the invention. Compounds identified can be useful, for example, in modulating the activity of wild type and/or mutant 103 gene products, can be utilized in screens for identifying compounds that disrupt normal 103 gene product interactions, or can in themselves disrupt such interactions.

The principle of the assays used to identify compounds that bind to the 103 gene product involves preparing a reaction mixture of a 103 gene product and a test compound under conditions and for a time sufficient to allow the two components to interact and bind, thus forming a complex which can be removed and/or detected in the reaction mixture. These assays can be conducted in a variety of ways. For example, one method to conduct such an assay involves anchoring 103 gene product or the test substance onto a solid phase and detecting 103 gene product/test compound complexes anchored on the solid phase at the end of the reaction. In one embodiment of such a method, the 103 gene product can be anchored onto a solid surface, and the test compound, which is not anchored, can be labeled, either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the 103 gene product or the test compound to anchor any complexes formed in solution, and a labeled antibody specific for the other component of the possible complex to detect anchored complexes.

As an example, and not by way of limitation, techniques such as those described in this section can be utilized to identify compounds which bind to the 103 gene product. For example, a 103 gene product can be contacted with a compound for a time sufficient to form a 103 gene product/compound complex and then such a complex can be detected.

Alternatively, the compound can be contacted with the 103 gene product in a reaction mixture for a time sufficient to form a 103 gene product/compound complex, and then such a complex can be separated from the reaction mixture.

Among the 103 gene products which can be utilized for such methods are, for example, rat, murine and human 103 gene products, including, but not limited to any of the 103 gene products described above in Section 5.2 or a naturally occurring variant thereof.

The term "naturally occurring variant," as used herein refers to an amino acid sequence homologous to the 103 gene product in the same or a different species, such as, for example, an allelic variant of the 103 gene product which maps to the same chromosomal location as the nucleotide sequences encoding the 103 gene products described above in Section 5.2, or a location syntenic to such a location. Among the allelic variants which can be utilized herein are allelic variant sequences encoded by a nucleotide sequence that hybridizes under stringent conditions described, e.g., in Section 5.1 above, to the complement of a nucleotide sequence encoding the 103 gene products described hereinabove.

5.4.2. ASSAYS FOR PROTEINS THAT INTERACT WITH THE 103 GENE PROTEIN

Any method suitable for detecting protein-protein interactions can be employed for identifying novel 103 protein-cellular or extracellular protein interactions. Among the traditional methods which can be employed are co-immunoprecipitation, crosslinking and co-purification through gradients or chromatographic columns. Utilizing procedures such as these allows for the identification of proteins that interact with a 103 gene product. Once identified, such proteins can be used, for example, to treat or modulate symptoms of an immune disorder, including an immune disorder associated with a TH2 or TH2-like immune response such as an atopic condition (e.g., asthma or allergy). Once identified, such proteins that interact with a 103 gene product can also be used, in conjunction with standard techniques, to identify the corresponding gene that encodes the protein which interacts with the 103 gene product. For example, at least a portion of the amino acid sequence of the gene product can be ascertained using techniques well known to those of skill in the art, such as via the Edman degradation technique (see, e.g., Creighton, 1983, *Proteins: Structures and Molecular Principles*, W.H. Freeman & Co., N.Y., pp. 34-49). The amino acid sequence obtained can be used as a guide for the generation of oligonucleotide mixtures that can be used to screen for gene sequences. Screening can be accomplished, for example, by standard hybridization or PCR techniques. Techniques for the generation of oligonucleotide mixtures and for screening are well-known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of genes which encode proteins interacting with a 103 gene protein. These methods include, for example, probing expression libraries with labeled 103 gene protein, using this protein in a manner similar to the well known technique of antibody probing of λgt11 libraries.

One method which detects protein interactions in vivo, the two-hybrid system, is described in detail for illustration purposes only and not by way of limitation. One version of this system has been described (Chien et al., 1991, *Proc. Natl. Acad. Sci. U.S.A.* 88:9578-9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, in this case, a 103 gene protein known to be involved in TH cell subpopulation differentiation or effector function, or in TH cell subpopulation-related disorders, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with a known "bait" gene product. By way of example, and not by way of limitation, 103 gene products known to be involved in TH cell subpopulation-related disorders and/or differentiation, maintenance, and/or effector function of the subpopulations can be used as the bait gene products. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait (e.g., 103) gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait (e.g., 103) gene product are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait gene product will reconstitute an active GAL4 protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art.

5.4.3. ASSAYS FOR COMPOUNDS THAT INTERFERE WITH 103 GENE PRODUCT/CELLULAR MACROMOLECULE INTERACTION

The 103 gene products of the invention can, in vivo, interact with one or more cellular or extracellular macromolecules, such as proteins. Such macromolecules can include, but are not limited to, nucleic acid molecules and those proteins identified via methods such as those described, above, in Section 5.4.2. For purposes of this discussion, such cellular and extracellular macromolecules are referred to herein as "binding partners". Compounds that disrupt such interactions can be useful in regulating the activity of a 103 gene protein, especially mutant 103 gene proteins. Such compounds can include, but are not limited to molecules such as antibodies, peptides, and the like, as described, for example, in Section 5.4.1 above.

The basic principle of the assay systems used to identify compounds that interfere with the interaction between a 103 gene product and its cellular or extracellular binding partner or partners involves preparing a reaction mixture containing the 103 gene product and the binding partner under conditions and for a time sufficient to allow the two to interact and bind, thus forming a complex. In order to test a compound for inhibitory activity, the reaction mixture is prepared in the presence and absence of the test compound. The test compound can be initially included in the reaction mixture, or can be added at a time subsequent to the addition of 103 gene product and its cellular or extracellular binding Partner. Control reaction mixtures are incubated without the test compound or with a placebo. The formation of any complexes between the 103 gene protein and the cellular or extracellular binding partner is then detected. The formation of a complex in the control reaction, but not in the reaction mixture containing the test compound, indicates that the compound interferes with the interaction of the 103 gene protein and the interactive binding partner. Additionally, complex formation within reaction mixtures containing the test compound and normal 103 gene protein can also be compared to complex formation within reaction mixtures containing the test compound and a mutant 103 gene protein. This comparison can be important in those cases wherein it is desirable to identify compounds that disrupt interactions of mutant but not normal 103 gene proteins.

The assay for compounds that interfere with the interaction of the 103 gene products and binding partners can be conducted in a heterogeneous or homogeneous format. Heterogeneous assays involve anchoring either the 103 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the 103 gene products and the binding partners, e.g., by competition, can be identified by conducting the reaction in the presence of the test substance; i.e., by adding the test substance to the reaction mixture prior to or simultaneously with the 103 gene protein and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the 103 gene protein or the interactive cellular or extracellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of the 103 gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the 103 gene protein and the interactive cellular or extracellular binding partner is prepared in which either the 103 gene product or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt 103 gene protein/cellular or extracellular binding partner interaction can be identified.

In a particular embodiment, the target gene product can be prepared for immobilization using recombinant DNA techniques described in Section 5.2, above. For example, the 103 gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-103 gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the 103 gene protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-103 gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the 103 gene product/binding partner interaction can be detected by adding the labeled antibody and measuring the radioactivity associated with the beads.

In another embodiment of the invention, these same techniques can be employed using peptide fragments that correspond to the binding domains of the 103 gene product and/or the interactive cellular or extracellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner is obtained, short gene segments can be engineered to express peptide fragments of the protein, which can then be tested for binding activity and purified or synthesized.

For example, and not by way of limitation, a 103 gene product can be anchored to a solid material as described, above, in this Section, by making a GST-103 gene fusion protein and allowing it to bind to glutathione agarose beads. The interactive cellular or extracellular binding partner can be labeled with a radioactive isotope, such as $^{35}$S, and cleaved with a proteolytic enzyme such as trypsin. Cleavage products can then be added to the anchored GST-103 gene fusion protein and allowed to bind. After washing away unbound peptides, labeled bound material, representing the cellular or extracellular binding partner binding domain, can be eluted, purified, and analyzed for amino acid sequence by well known methods. Peptides so identified can be produced synthetically or fused to appropriate facilitative proteins using well known recombinant DNA technology.

5.4.4. CELL AND ANIMAL-BASED MODEL SYSTEMS

Described herein are cell- and animal-based systems of the present invention which act as models for immune disorders and as models of TH cell subpopulation differentiation, maintenance, and/or effector function. These systems can be used in a variety of applications. For example, such model systems can be used to test compounds identified, e.g., using the in vitro assays described in Section 5.4.1, above, for their ability and/or effectiveness in treating (e.g., ameliorating or modulating symptoms of) immune-related disorders. Thus, the animal- and cell-based models of the invention can be used to identify drugs, pharmaceuticals, therapies and interventions which can be effective in treating immune disorders such as TH cell subpopulation-related disorders. In addition, as described in detail, below, in Section 5.7.1, such animal models can be used to determine the $LD_{50}$ and the $ED_{50}$ in animal subjects, and such data can be used to determine the in vivo efficacy of potential immune disorder treatments.

Animal-Based Systems:

Animal-based model systems of TH cell subpopulation-related disorders can include both non-recombinant animals as well as recombinantly engineered transgenic animals.

Animal models for TH cell subpopulation-related disorders can include, for example, genetic models. For example, such animal models can include *Leishmania* resistance models, experimental allergic encephalomyelitis models and (BALB/c Cr×DBA/2Cr) F1 mice. These latter mice develop a fatal disseminated disease by systemic infection with virulent *Candida albicans* associated with strong TH2-like responses.

Additionally, well known mouse models for asthma can be utilized to study the amelioration of symptoms caused in immune disorders, such as allergy and asthma, that are associated with a strong TH2 or TH2-like response. (See, for example, N. W. Lukacs et al., 1994, *Am. J. Resp. Cell Mol. Biol.* 10:526-532; S. H. Gavett et al. al., 1994, *Am. J. Resp. Cell Mol. Biol.* 10:587-593.) Further, the animal model, murine acquired immunodeficiency syndrome (MAIDS; B. Kanagawa et al., 1993, *Science* 262:240; M. Makino et al., 1990, *J. Imm.* 144:4347) can be used for such studies.

Alternatively, such well known animal models as SCIDhu mice (see for example, H. Kaneshima et al., 1994, *Curr. Opin. Imm.* 6:327-333) which represents an in vivo model of the human hematolymphoid system, can be utilized. Further, the RAG-2-deficient blastocyst complementation technique (J. Chen et al., 1993, *Proc. Natl. Acad. Sci. USA* 90:4528-4532; Y. Shinkai et al., 1992, *Cell* 68:855-867) can be utilized to produce mice containing, for example, humanized lymphocytes and/or which express target gene sequences. Still further, targeting techniques directed specifically to T cells, for example, the technique of Gu et al. (1994, *Science* 265:103-106) can be utilized to produce animals containing transgenes in only T cell populations.

Further, animal models such as the adoptive transfer model described, e.g., in L. Cohn et al., 1997, *J. Exp. Med.* 186: 1737-1747) and described and utilized in Section 6.4, below, can be used. In such an animal system, aeroallergen provocation of TH1 or TH2 recipient mice results in TH effector cell migration to the airways and is associated with an intense neutrophilic (TH1) and eosinophilic (TH2) lung mucosal inflammatory response. The animal model represents an accepted model for asthma.

Animal models exhibiting TH cell subpopulation-related disorder-like symptoms can be engineered by utilizing, for example, target gene sequences such as the 103 gene sequences described, above, in Section 5.1, in conjunction with techniques for producing transgenic animals that are well known to those of skill in the art. For example, target gene sequences can be introduced into, and overexpressed and/or misexpressed in, the genome of the animal of interest, or, if endogenous target gene sequences are present, they can either be overexpressed, misexpressed, or, alternatively, can be disrupted in order to underexpress or inactivate target gene expression. The construction and characterization of exemplary 103 gene transgenic animals is described in Section 6.3, below.

In order to overexpress or misexpress a target gene sequence (e.g., a 103 gene sequence), the coding portion of the target gene sequence can be ligated to a regulatory sequence which is capable of driving high level gene expression or expression in a cell type in which the gene is not normally expressed in the animal and/or cell type of interest. Such regulatory regions will be well known to those of skill in the art, and can be utilized in the absence of undue experimentation.

For underexpression of an endogenous target gene sequence (e.g., of an endogenous 103 gene sequence), such a sequence can be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, squirrels, monkeys, and chimpanzees can be used to generate animal models of TH cell subpopulation-related disorders.

Any technique known in the art can be used to introduce a target gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten et al., 1985, *Proc. Natl. Acad. Sci., USA* 82:6148-6152); gene targeting in embryonic stem cells (Thompson et al., 1989, *Cell* 56:313-321); electroporation of embryos (Lo, 1983, *Mol. Cell. Biol.* 3:1803-1814); and sperm-mediated gene transfer (Lavitrano et al., 1989, *Cell* 57:717-723); etc. For a review of such techniques, see Gordon, 1989, *Intl. Rev. Cytol.* 115:171-229, which is incorporated by reference herein in its entirety.

The present invention provides for transgenic animals that carry the transgene in all their cells, as well as animals which carry the transgene in some, but not all their cells, i.e., mosaic animals. (See, for example, techniques described by Jakobovits, 1994, *Curr. Biol.* 4:761-763.) The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko et al., 1992, *Proc. Natl. Acad. Sci. USA* 89:6232-6236). The regulatory sequences required for such a cell-type specific activation will depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene can also be selectively introduced into a particular cell type, thus inactivating the endogenous gene of interest in only that cell type, by following, for example, the teaching of Gu et al. (Gu et al., 1994, *Science* 265:103-106). The regulatory sequences required for such a cell-type specific inactivation will depend upon the particular cell type of interest, and will be apparent to those of skill in the art.

Once transgenic animals have been generated, the expression of the recombinant target gene and protein can be assayed utilizing standard techniques. Initial screening can be accomplished by Southern blot analysis or PCR techniques to analyze animal tissues and to assay whether integration of the transgene has taken place. The level of mRNA expression of the transgene in the tissues of the transgenic animals can also be assessed using techniques which include but are not limited to Northern blot analysis of tissue samples obtained from the animal, in situ hybridization analysis, and RT-PCR. Samples of target gene-expressing tissue, can also be evaluated immunocytochemically using antibodies specific for the target gene transgene gene product of interest.

103 gene transgenic animals that express 103 gene mRNA or 103 gene transgene peptide (detected immunocytochemically, using antibodies directed against target gene product epitopes) at easily detectable levels can be further evaluated to identify those animals which display characteristic TH cell subpopulation-related disorder-like symptoms, or exhibit characteristic TH cell subpopulation differentiation phenotypes. TH1-like-related disorder symptoms can include, for example, those associated with chronic inflammatory diseases and disorders, such as Crohn's disease, reactive arthritis (including but not limited to Lyme disease), insulin-dependent diabetes, organ-specific autoimmunity, (including but not limited to multiple sclerosis, Hashimoto's thyroiditis and Grave's disease), contact dermatitis, psoriasis, graft rejection, graft versus host disease and sarcoidosis to name a few. TH2-like-related disorder symptoms can include, but are not limited to, those associated with atopic conditions such as asthma and allergy such as allergic rhinitis, gastrointestinal allergies, (including but not limited to food allergies); eosinophilia; conjunctivitis; glomerular nephritis; certain pathogen susceptibilities such as helminthic (e.g., leishmaniasis); and certain viral infections, including HIV, and bacterial infections (for example, tuberculosis and lepromatous leprosy).

Additionally, specific cell types within the transgenic animals can be analyzed and assayed for cellular phenotypes characteristic of TH cell subpopulation-related disorders. Such cellular phenotypes can include, for example, differential cytokine expression characteristic of the TH cell subpopulation of interest. Further, such cellular phenotypes can include an assessment of a particular cell type's fingerprint pattern of expression and its comparison to known fingerprint expression profiles of the particular cell type in animals exhibiting specific TH cell subpopulation-related disorders. Such transgenic animals serve as suitable model systems for TH cell-related disorders.

Once target gene transgenic founder animals are produced (i.e., those animals which express target gene products (e.g., 103 gene proteins) in cells or tissues of interest, and which, preferably, exhibit symptoms of TH cell subpopulation-related disorders), they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of Separate homozygous lines to produce compound heterozygous or homozygous lines; breeding animals to different inbred genetic backgrounds so as to examine effects of modifying alleles on expression of the target gene transgene and the development of TH cell subpopulation-related disorder-like symptoms. One such approach is to cross the target gene transgenic founder animals with a wild type strain to produce an F1 generation that exhibits TH cell subpopulation-related disorder-like symptoms, such as those described above. The F1 generation can then be inbred in order to develop a homozygous line, if it is found that homozygous target gene transgenic animals are viable.

Cell-Based Assays:

Cells that contain and express 103 gene sequences which encode 103 gene protein, and, further, exhibit cellular phenotypes associated with a TH cell subpopulation and/or a TH cell subpopulation-related disorder of interest, can be utilized to identify compounds that exhibit and/or can be tested for an ability to ameliorate TH cell subpopulation-related disorder symptoms. Cellular phenotypes which can indicate an ability to ameliorate TH cell subpopulation-related disorder symptoms can include, for example, an inhibition or potentiation of cytokine or cell surface marker expression associated with the TH cell subpopulation of interest, or, alternatively, an inhibition or potentiation of specific TH cell subpopulations.

Further, the fingerprint pattern of gene expression of cells of interest can be analyzed and compared to the normal, non-TH cell subpopulation-related disorder fingerprint pattern. Those compounds which cause cells exhibiting TH cell subpopulation-related disorder-like cellular phenotypes to produce a fingerprint pattern more closely resembling a normal fingerprint pattern for the cell of interest can be considered candidates for further testing regarding an ability to ameliorate TH cell subpopulation-related disorder symptoms.

Cells which can be utilized for such assays can, for example, include non-recombinant cell lines, such as Dorris, AE7, D10.G4, DAX, D1.1 and CDC25 cell lines. In addition, purified primary naive T cells derived from either transgenic or non-transgenic strains can also be used.

Further, cells which can be used for such assays can also include recombinant, transgenic cell lines. For example, the TH cell subpopulation-related disorder animal models of the invention, discussed, above, in Section 5.7.1, can be used to generate, for example, TH1-like and/or TH2-like cell lines that can be used as cell culture models for the disorder of interest. While primary cultures derived from TH cell subpopulation-related disorder transgenic animals can be utilized, the generation of continuous cell lines is preferred. For examples of techniques which can be used to derive a continuous cell line from the transgenic animals, see, e.g., Small et al., 1985, *Mol. Cell. Biol.* 5:642-648.

Alternatively, cells of a cell type known to be involved in TH cell subpopulation-related disorders can be transfected with sequences capable of increasing or decreasing the amount of 103 gene expression within the cell. For example, 103 gene sequences can be introduced into, and overexpressed in, the genome of the cell of interest, or, if endogenous 103 gene sequences are present, they can either be overexpressed or, alternatively, can be disrupted in order to underexpress or inactivate target gene expression.

In order to overexpress a 103 gene sequence, the coding portion of the 103 gene sequence can be ligated to a regulatory sequence which is capable of driving gene expression in the cell type of interest. Such regulatory regions will be well known to those of skill in the art, and can be utilized in the absence of undue experimentation.

For underexpression of an endogenous 103 gene sequence, such a sequence can be isolated and engineered such that when reintroduced into the genome of the cell type of interest, the endogenous 103 gene alleles will be inactivated. Preferably, the engineered 103 gene sequence is introduced via gene targeting such that the endogenous 103 sequence is disrupted upon integration of the engineered 103 gene sequence into the cell's genome. Gene targeting is discussed above.

Transfection of 103 gene sequence nucleic acid can be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques can be used to demonstrate whether a decrease in endogenous target gene expression and/or in target gene product production is achieved.

Cells to be utilized can, for example, be stimulated or activated as, described e.g., in the Examples presented below.

5.4.5. ASSAYS FOR AMELIORATION OF IMMUNE DISORDER SYMPTOMS AND/OR THE MODULATION OF 103 GENE PRODUCT FUNCTION

Any of the binding compounds, including but not limited to, compounds such as those identified in the foregoing assay systems, can be tested for the ability to ameliorate symptoms of immune disorders, including, for example, any of the TH cell subpopulation-related disorders described herein. Cell-based and animal model-based assays for the identification of compounds exhibiting such an ability to ameliorate immune disorder symptoms are described below. Exemplary embodiments of cell-based and animal-model assays which can be used in the methods and compositions of the present invention are further described in the examples presented in Sections 6.4 and 6.6, below. In particular, an exemplary cell-based assay is presented in Section 6.6. An assay using an exemplary and art recognized animal model for asthma is also described, below, in Section 6.4.

First, cell-based systems such as those described, above, in Section 5.4.4, can be used to identify compounds which can act to ameliorate TH cell subpopulation-related disorder symptoms. For example, such cell systems can be exposed to a compound, suspected of exhibiting an ability to ameliorate the disorder symptoms, at a sufficient concentration and for a time sufficient to elicit such an amelioration in the exposed cells. After exposure, the cells are examined to determine whether one or more of the TH cell subpopulation-related disorder-like cellular phenotypes has been altered to resemble a phenotype more likely to produce a lower incidence or severity of disorder symptoms.

Taking, as a non-limiting example, the TH cell subpopulation-related disorders of allergy and asthma, which are, specifically, TH2-like-related disorders (e.g., the disorders are associated with a strong TH2 or TH2-like immune response), any TH2 or TH2-like cell system can be utilized. Upon exposure to such cell systems, compounds can be assayed for their ability to modulate the TH2-like phenotype of such cells, such that the cells exhibit loss of a TH2-like phenotype. Compounds with such TH2 modulatory capability represent ones which can potentially exhibit the ability to ameliorate allergy and/or asthma-related symptoms in vivo. The Example presented in Section 6.4, below, describes the successful utilization of a 103 gene product/Ig fusion protein, as well as the successful use of a monoclonal antibody directed against the extracellular domain of the 103 gene product to ameliorate symptoms of asthma in an accepted animal model of asthma.

In addition, animal-based systems, such as those described, above, in Section 5.4.4, can be used to identify compounds capable of ameliorating TH cell subpopulation-related disorder-like symptoms. Such animal models can be used as test substrates for the identification of drugs, pharmaceuticals, therapies, and interventions which can be effective in treating such disorders. For example, animal models can be exposed to a compound, suspected of exhibiting an ability to ameliorate TH cell subpopulation-related disorder symptoms, at a sufficient concentration and for a time sufficient to elicit such an amelioration of the symptoms in the exposed animals. The response of the animals to the exposure, and thus the efficacy of the compound in question, can be monitored by assessing the reversal of disorders associated with TH cell subpopulation-related disorders of interest. With regard to intervention, any treatments which reverse any aspect of TH cell subpopulation-related disorder-like symptoms should be considered as candidates for corresponding human TH cell subpopulation-related disorder therapeutic intervention. Dosages of test agents can be determined by deriving dose-response curves, as discussed in Section 5.7, below.

Gene expression patterns can be utilized in conjunction with either cell-based or animal-based systems, to assess the ability of a compound to ameliorate TH cell subpopulation-related disorder-like symptoms. For example, the expression pattern of one or more "fingerprint" genes (including, for example, the expression pattern of the 103 gene) can form part of a fingerprint profile which can be then be used in such an assessment. Fingerprint profiles are described, below, in Section 5.8. Fingerprint profiles can be characterized for known states, either TH cell subpopulation-related disorder states, or normal TH cell differentiative states, within the cell- and/or animal-based model systems.

5.5. COMPOSITIONS AND METHODS FOR TREATMENT OF IMMUNE DISORDERS AND FOR MODULATION OF TH CELL RESPONSIVENESS

Described below are methods and compositions which can be used to ameliorate immune disorder symptoms via, for example, a modulation of the TH cell subpopulation of interest. The methods and compositions described herein can also be used to ameliorate immune disorders symptoms via a modulation of other cell populations, e.g., mast cell populations, that specifically express the 103 gene. Such modulation can be of a positive or negative nature, depending on the specific situation involved, but each modulatory event yields a net result in which symptoms of the immune disorder are ameliorated. Further, described below are methods for the modulation of TH cell responsiveness to antigen.

It is possible that a TH cell subpopulation-related disorder or other immune disorder, can occur as a result of normal 103 gene activity during the course of, for example, exposure to a certain antigen which elicits an immune response that leads to the development of the disorder. For example, the disorders of asthma and allergy are likely candidates of disorders having such a mechanism. Additionally, a disorder can be brought about, at least in part, by an abnormally high level of 103 gene product, or by the presence of a 103 gene product exhibiting an abnormal activity. As such, a technique which elicits a negative modulatory effect, i.e., brings about a reduction in the level and/or activity of 103 gene product, or alternatively, brings about a depletion of the TH cell subpopulation (such as a TH2 cell subpopulation, e.g., via a physical reduction in the number of cells belonging to the TH cell subpopulation), would effect an amelioration of TH cell subpopulation-related disorder symptoms in either of the above scenarios.

Negative modulatory techniques for the reduction of gene expression levels or gene product activity levels, (including 103 gene expression levels or 103 gene product activity levels, either normal or abnormal), and for the reduction in the number of specific TH cell subpopulation cells are discussed in Section 5.6.1, below.

Alternatively, it is possible that a TH cell subpopulation-related disorder or other immune disorders can be brought about, at least in part, by the absence or reduction of the level of 103 gene expression, a reduction in the level of a 103 gene product's activity, or a reduction in the overall number of cells belonging to a specific TH cell subpopulation (e.g., of a TH2 cell subpopulation). As such, a technique which elicits a positive modulatory effect, i.e., brings about an increase in the level of 103 gene expression and/or the activity of such gene products, or, alternatively, a stimulation of the TH cell subpopulation (e.g., via a physical increase in the number of cells belonging to a TH cell subpopulation such as a TH2 cell subpopulation), would effect an amelioration of immune disorder symptoms.

For example, a reduction in the overall number of TH1-like cells relative to TH2-like cells within a HIV-infected individual can correlate with the progression to AIDS (Clerci et al., 1993, *J. Clin. Invest.* 91:759; Clerci. et al., 1993, *Science* 262:1721; Maggi et al., 1994, *Science* 265:244). A treatment capable of increasing the number of TH1-like cells relative to TH2-like cells within an HIV-infected individual may, therefore, serve to prevent or slow the progression to disease.

Positive modulatory techniques for increasing gene expression levels or gene product activity levels, including 103 gene expression levels and 103 gene product activity levels, and for increasing the level of specific TH cell subpopulation cells are discussed, below, in Section 5.6.2.

Among the immune disorders whose symptoms can be ameliorated are TH1 or TH1-like related immune disorders (i.e., immune disorders associated with a strong or inappropriate TH1 or TH1-like immune response) and TH2 or TH2-like related immune disorders (i.e., immune disorders associated with a strong or inappropriate TH2 or TH2-like immune response). Examples of TH1 or TH1-like related disorders include chronic inflammatory diseases and disorders such as Crohn's disease, reactive arthritis including Lyme disease, insulin-dependent diabetes, organ-specific autoimmunity (including multiple sclerosis, Hashimoto's thyroiditis and Grave's disease), contact dermatitis, psoriasis, graft rejection, graft versus host disease and sarcoidosis. Examples of TH2 or TH2-like related disorders include atopic conditions, such as asthma and allergy (including allergic rhinitis), gastrointestinal allergies including food allergies, eosinophilia, conjunctivitis, glomerular nephritis, systemic lupus erythematosus, scleroderma, certain pathogen susceptibilities such as helminthic (e.g., leishmaniasis), certain viral infections, including HIV, and bacterial infections such as tuberculosis and lepromatous leprosy.

The methods described herein can additionally be utilized the modulate the level of responsiveness, for example, responsiveness to antigen, of a TH cell subpopulation. Such methods are important in that many immune disorders involve inappropriate rather than insufficient immune responses. For example, disorders such as atopic, IgE-mediated allergic conditions, including asthma, pathogen susceptibilities and chronic inflammatory disease, involve strong but counterproductive TH2-mediated immune responses. Further, inappropriate TH1-mediated immune responses to self-antigens is central to the development of such disorders as multiple sclerosis, psoriasis, insulin dependent diabetes, Hashimoto's thyroiditis and Crohn's disease.

Methods for modulating TH cell responsiveness can comprise, for example, contacting a compound to a TH cell so that the responsiveness of the T helper cell is modulated relative to the responsiveness of the T helper cell in the absence of the compound. The modulation can increase or decrease the responsiveness of the TH cell. Any of the techniques described, below, in Sections 5.6.1-5.6.3 can be utilized to effect an appropriate modulation of TH cell responsiveness.

The methods described herein can additionally be utilized to modulate the other cell populations, such as mast cell populations, that specifically express the 103 gene product. In particular, many immune disorders, including, the immune disorders described above and, in particular, atopic conditions such as asthma and allergy, are mediated by mast cell populations as well as by other populations of immune cells such as TH1, TH1-like, TH2 or TH2-like subpopulations.

Thus, the methods and compositions described herein can also be used to treat immune disorders, including atopic conditions such as asthma and allergy, by targeting other cell populations (e.g., mast cells) that are involved in such immune disorders, in addition to or even instead of TH cell subpopulations.

The 103 gene is also expressed in human mast cells, as demonstrated in the Example presented in Section 6.5, below. Thus, the above-described compositions (e.g., natural ligands, derivatives of natural ligands and antibodies that specifically bind to the 103 gene product) can also be utilized to modulate the number of mast cells present and/or to modulate the amount of mast cell activity or mast cell cytokine production (e.g., from the degranulation of mast cells). Thus conditions, including atopic conditions such as asthma and allergy, that involve or are mediated by mast cell activity (often in addition to TH2 or TH2-like activity) can be treated by using the methods and compositions of the invention to target mast cells and/or mast cell activity as well as (or instead of) TH2 cells and/or TH2 cell activity.

5.5.1. NEGATIVE MODULATORY TECHNIQUES

As discussed, above, successful treatment of certain immune disorders can be brought about by techniques which serve to inhibit the expression or activity of 103 gene products, or which, alternatively, serve to reduce the overall number of cells belonging to a specific TH cell subpopulation (e.g., a TH2 cell subpopulation).

For example, compounds such as those identified through assays described, above, in Section 5.4, which exhibit negative modulatory activity, can be used in accordance with the invention to ameliorate symptoms of certain immune disorders. As discussed in Section 5.4, above, such molecules can include, but are not limited to peptides (such as, for example, peptides representing soluble extracellular portions of a 103 gene product), phosphopeptides, small organic or inorganic molecules, or antibodies (including, for example, polyclonal, monoclonal, human, humanized, anti-idiotypic, chimeric or single chain antibodies, and FAb, $F(ab')_2$ and FAb expression library fragments, and epitope-binding fragments thereof). In one embodiment, for example, antibodies directed against a 103 gene product, preferably an extracellular or extracellular portion of a 103 gene product, can be utilized. Techniques for the determination of effective doses and administration of such compounds are described, below, in Section 5.7.1.

Antisense and ribozyme molecules which inhibit expression of the 103 gene can also be used in accordance with the invention to reduce the level of 103 gene expression, thus effectively reducing the level of target gene activity. Still further, triple helix molecules can be utilized in reducing the level of 103 gene activity. Such techniques are described hereinbelow.

Techniques for the depletion of specific TH cell subpopulations are discussed, hereinbelow, in Section 5.5.3. Such techniques can take advantage of, for example, novel cell surface markers, including the 103 gene product, which are specific to the TH cell subpopulation to be depleted, and can include in vivo or in vitro targeted destruction, or, alternatively, selective purification away, of the TH cell subpopulation of interest.

As discussed above, the 103 gene represents a TH2-specific gene in that 103 gene expression is found to be absent TH1 cells as well as all other tissues tested. Further, at least one of the proteins produced by the 103 gene is a transmembrane protein. The 103 gene and its products can, therefore, be utilized in the treatment of certain immune disorders such TH2 cell subpopulation-related disorders. For example, a 103 gene product or portions thereof can be utilized, either directly or indirectly, to ameliorate conditions involving inappropriate IgE immune responses, including, but not limited to the symptoms which accompany atopic conditions such as allergy and/or asthma. IgE-type antibodies are produced by stimulated B cells which require, at least in part, IL-4 produced by the TH2 cell subpopulation. Therefore, any treatment, including, for example, the use of a gene 103 product or portion thereof, which reduces the effective concentration of secreted IL-4, e.g., by reducing the number or activity of TH2 cells, can bring about a reduction in the level of circulating IgE, leading, in turn, to the amelioration of the conditions stemming from an inappropriate IgE immune response.

There exist a variety of ways in which the TH2 specific 103 gene products can be used to effect such a reduction in the activity and/or effective concentration of TH2 cells.

For example, natural ligands, derivatives of natural ligands and antibodies which bind to the 103 gene product can be utilized to reduce the number of TH2 cells present by either physically separating such cells away from other cells in a population, thereby deleting the TH2 cell subpopulation, or, alternatively, by targeting the specific destruction of TH2 cells. Such techniques are discussed, below, in Section 5.6.3. Further, such compounds can be used to inhibit the proliferation of TH2 cells.

Additionally, compounds such as 103 gene sequences or gene products can be utilized to reduce the level of TH2 cell activity, cause a reduction in the production of TH2 associated cytokines such as IL-4, IL-5, IL-10 and IL-13, and, ultimately, bring about the amelioration of IgE related disorders.

For example, compounds can be administered which compete with endogenous ligand for the 103 gene product, e.g., by binding to a ligand-binding domain of a 103 gene product. The resulting reduction in the amount of ligand-bound 103 gene transmembrane protein will modulate TH2 cellular activity. Compounds which can be particularly useful for this purpose include, for example, soluble proteins or peptides, such as peptides comprising the extracellular domain, or portions and/or analogs thereof, of the gene 103 product, including, for example, soluble fusion proteins such as Ig-tailed fusion proteins. (For a discussion of the production of Ig-tailed fusion proteins see, for example, U.S. Pat. No. 5,116,964.)

Production of a 103 gene product/Ig fusion is described in Section 6.2, below. Further, use of a 103 gene product/Ig fusion to successfully ameliorate symptoms in an accepted animal model for asthma is described in Section 6.4, below.

Among the compounds which can exhibit the ability to ameliorate TH cell subpopulation-related disorder symptoms are antisense, ribozyme, and triple helix molecules. Such molecules can be designed to reduce or inhibit either wild type, or if appropriate, mutant 103 gene activity. Techniques for the production and use of such molecules are well known to those of skill in the art.

Antisense approaches involve the design of oligonucleotides (either DNA or RNA) that are complementary to 103 gene mRNA. The antisense oligonucleotides will bind to the complementary 103 gene mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. See generally, Wagner, R., 1994, Nature 372:333-335. Thus, oligonucleotides complementary to either the 5'- or 3'-non-translated, non-coding regions of 103 genes could be used in an antisense approach to inhibit translation of endogenous 103 gene mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of 103 gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the 103 RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The antisense molecules should be delivered to cells which express the 103 gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous 103 gene transcripts and thereby prevent translation of the 103 gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review see, for example Rossi, J., 1994, Current Biology 4:469-471). The mechanism of ribozyme action involves sequence specific hybridization of the ribozyme molecule to complementary target RNA, followed by a endonucleolytic cleavage. The composition of ribozyme molecules must include one or more sequences complementary to the 103 gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding 103 gene proteins. Ribozyme molecules designed to catalytically cleave 103 gene mRNA transcripts can also be used to prevent translation of 103 gene mRNA and expression of 103 gene. (See, e.g., PCT International Publication WO90/11364, published Oct. 4, 1990; Sarver et al., 1990, Science 247:1222-1225). While ribozymes that cleave mRNA at site specific recognition sequences can be used to destroy 103 gene mRNAs, the use of hammerhead ribozymes is preferred.

Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591. Preferably the ribozyme is engineered so that the cleavage recognition site is located near the 5' end of the 103 gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO 88/04300 by University Patents Inc.; Been and Cech, 1986, Cell, 47:207-216). The Cech-type ribozymes have an eight base pair active site which hybridizes to a target RNA sequence whereafter cleavage of the target RNA takes place. The invention therefore encompasses those Cech-type ribozymes which target eight base-pair active site sequences that are present in the 103 gene.

As in the antisense approach, the ribozymes can be composed of modified oligonucleotides (e.g. for improved stability, targeting, etc.) and should be delivered to cells which express the 103 gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous 103 gene messages and inhibit translation. Because ribozymes unlike antisense molecules, are catalytic, a lower intracellular concentration is required for efficiency.

In instances wherein the antisense, ribozyme, and/or triple helix molecules described herein are utilized to inhibit mutant gene expression, it is possible that the technique can also efficiently reduces or inhibits the transcription (triple helix) and/or translation (antisense, ribozyme) of mRNA produced by normal 103 gene alleles. Thus, the possibility can arise wherein the concentration of normal target gene product present can be lower than is necessary for a normal phenotype. To ensure that substantially normal levels of target gene activity are maintained in such cases, nucleic acid molecules that encode and express target gene polypeptides exhibiting normal target gene activity can be introduced into cells via gene therapy methods, such as those described in Section 5.6.2 below; that do not contain sequences susceptible to whatever antisense, ribozyme, or triple helix treatments are being utilized. Alternatively, in instances whereby the target gene encodes an extracellular protein, it can be preferable to coadminister normal target gene protein in order to maintain the requisite level of target gene activity.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Endogenous target and/or pathway gene expression can also be reduced by inactivating or "knocking out" the endogenous 103 gene or its promoter using targeted homologous recombination. (e.g., see Smithies et al., 1985, Nature 317: 230-234; Thomas & Capecchi, 1987, Cell 51:503-512; Thompson et al., 1989 Cell 5:313-321; each of which is incorporated by reference herein in its entirety). For example, a mutant, non-functional 103 gene (or a completely unrelated DNA sequence) flanked by DNA homologous to the endogenous 103 gene (either the coding regions or regulatory regions of the 103 gene) can be used, with or without a selectable marker and/or a negative selectable marker, to transfect cells that express the 103 gene in vivo. Insertion of the DNA construct, via targeted homologous recombination, results in inactivation of the 103 gene. Such approaches are particularly suited in the agricultural field where modifications to ES (embryonic stem) cells can be used to generate animal offspring with an inactive 103 gene (e.g., see Thomas & Capecchi 1987 and Thompson 1989, supra). Such techniques can also be utilized to generate T cell subpopulation-related disorder animal models. It should be noted that this approach can be adapted for use in humans provided the recombinant DNA constructs are directly administered or targeted to the required site in vivo using appropriate viral vectors, e.g., herpes virus vectors.

Alternatively, endogenous 103 gene expression can be reduced by targeting deoxyribonucleotide sequences complementary to the regulatory region of the 103 gene (i.e., the 103 gene promoter and/or enhancers) to form triple helical structures that prevent transcription of the 103 gene in target cells in the body. (See generally, Helene, C. 1991, Anticancer Drug Des., 6(6):569-84; Helene, C., et al., 1992, Ann, N.Y. Accad. Sci., 660:27-36; and Maher, L. J., 1992, Bioassays 14(12): 807-15). In yet another embodiment of the invention, the activity of 103 gene can be reduced using a "dominant negative" approach. To this end, constructs which encode defective 103 gene products can be used in gene therapy approaches to diminish the activity of the 103 gene product in appropriate target cells.

5.5.2. POSITIVE MODULATORY TECHNIQUES

As discussed above, successful treatment of certain immune disorders can be brought about by techniques which serve to increase the level of 103 gene expression or to increase the activity of a 103 gene product, or which, or alternatively, serve to effectively increase the overall number of cells belonging to a specific TH cell subpopulation (e.g., a TH2 cell subpopulation).

For example, compounds such as those identified through assays described, above, in Section 5.4, which exhibit positive modulatory activity can be used in accordance with the invention to ameliorate certain TH cell subpopulation-related disorder symptoms. As discussed in Section 5.4, above, such molecules can include, but are not limited to proteins or protein fragments of a 103 gene product, including fragments corresponding to one or more domains of the target gene product (e.g., an extracellular domain, an Ig-like domain, a transmembrane domain, or a cytosolic domain) or portions thereof. Such molecules can also include peptides representing soluble extracellular portions of 103 gene product transmembrane proteins, phosphopeptides, small organic or inorganic molecules, or antibodies (including, for example, polyclonal, monoclonal, human, humanized, anti-idiotypic, chimeric or single chain antibodies, and FAb, F(ab')$_2$ and FAb expression library fragments, and epitope-binding fragments thereof).

For example, a compound, such as a 103 gene protein, can, at a level sufficient to ameliorate immune disorder symptoms, be administered to a patient exhibiting such symptoms. Any of the techniques discussed, below, in Section 5.7, can be utilized for such administration. One of skill in the art will readily know how to determine the concentration of effective, non-toxic doses of the compound, utilizing techniques such as those described, below, in Section 5.7.1.

In another embodiment, fragments or peptides representing a functional domain of a 103 gene product are administered to an individual at sufficient dosages and such that the fragments or peptides may enhance the target gene product's activity in the individual, e.g., by mimicking the function of the target gene product in vivo.

The proteins and peptides which may be used in such methods include synthetic (e.g., recombinant or chemically synthesized) proteins and peptides, as well as naturally occurring proteins and peptides. The proteins and peptides may have both naturally occurring and/or non-naturally occurring amino acid residues (e.g., D-amino acid residues) and/or one or more non-peptide bonds (e.g., imino, ester, hydrazide, semicarbazide, and azo bonds). The proteins or peptides may also contain additional chemical groups (e.g., functional groups) present at the amino and/or carboxy termini, such that, for example, the stability, bioavailability, and/or inhibitory activity of the peptide is enhanced. Exemplary functional groups include hydrophobic groups (e.g., carbobenzoxyl, dansyl, and t-butyloxycarbonyl groups) an acetyl group, a 9-fluorenylmethoxy-carbonyl group, and macromolecular carrier groups (e.g., lipid-fatty acid conjugates, polyethylene glycol, or carbohydrates) including peptide groups. Suitable dosages and formulations for administration of such peptides and proteins are also well known to those of skill in the art, and are described in Section 5.7 above.

In instances wherein the compound to be administered is a peptide compound, DNA sequences encoding the peptide compound can be directly administered to a patient exhibiting immune disorder symptoms, at a concentration sufficient to produce a level of peptide compound sufficient to ameliorate the disorder symptoms. Any of the techniques discussed, below, in Section 5.7, which achieve intracellular administration of compounds, such as, for example, liposome administration, can be utilized for the administration of such DNA molecules. The DNA molecules can be produced, for example, by well known recombinant techniques.

In the case of peptides compounds which act extracellularly, the DNA molecules encoding such peptides can be taken up and expressed by any cell type, so long as a sufficient circulating concentration of peptide results for the elicitation of a reduction in the immune disorder symptoms. In the case of compounds which act intracellularly, the DNA molecules encoding such peptides must be taken up and expressed by the TH cell subpopulation of interest at a sufficient level to bring about the reduction of immune disorders.

Any technique which serves to selectively administer DNA molecules to the TH cell subpopulation of interest is, therefore, preferred, for the DNA molecules encoding intracellularly acting peptides. In the case of asthma, for example, techniques for the selective administration of the molecules to TH cell subpopulations residing within lung tissue are preferred.

In instances wherein the TH cell subpopulation-related disorder involves an aberrant 103 gene, patients can be treated by gene replacement therapy. One or more copies of a normal 103 gene or a portion of the gene that directs the production of a normal 103 gene protein with normal 103 gene function, can be inserted into cells, using vectors which include, but are not limited to adenovirus, adeno-associated virus, and retrovirus vectors, in addition to other particles that introduce DNA into cells, such as liposomes.

Such gene replacement techniques can be accomplished either in vivo or in vitro. As above, for 103 genes encoding extracellular molecules (e.g., a secreted 103 gene product), the cell type expressing the target gene is less important than achieving a sufficient circulating concentration of the extracellular molecule for the amelioration of immune disorders, or to ameliorate one or more symptoms associated with an immune disorder described herein (e.g., asthma). Further, as above, when the gene encodes a gene product which acts intracellularly or as a transmembrane molecule, the gene must be expressed with the TH cell subpopulation cell type of interest. Techniques which select for expression within the cell type of interest are, therefore, preferred for this latter class of target genes. In vivo, such techniques can, for example, include appropriate local administration of target gene sequences.

Additional methods which may be utilized to increase the overall level of 103 gene expression and/or target and/or pathway gene activity include the introduction of appropriate 103 gene-expressing cells, preferably autologous cells, into a patient at positions and in numbers which are sufficient to ameliorate the symptoms of T cell subpopulation related disorders. Such cells may be either recombinant or non-recombinant. Among the cells which can be administered to increase the overall level of 103 gene expression in a patient are normal cells, which express a 103 gene. The cells can be administered at the anatomical site of expression, or as part of a tissue graft located at a different site in the body. Such cell-based gene therapy techniques are well known to those skilled in the art, see, e.g., Anderson et al., U.S. Pat. No. 5,399,349; Mulligan & Wilson, U.S. Pat. No. 5,460,959.

In vitro, target gene sequences can be introduced into autologous cells. These cells expressing the 103 gene sequence can then be reintroduced, preferably by intravenous administration, into the patient such that there results an amelioration of the symptoms of the disorder.

Alternatively, for the amelioration of a TH cell subpopulation-related disorder, TH cells belonging to a specific TH cell subpopulation (e.g., a TH2 cell subpopulation) can be administered to a patient such that the overall number of cells belonging to that TH cell subpopulation relative to other TH cell subpopulation cells is increased. Techniques for such TH cell subpopulation augmentation are described, below, in Section 5.6.3.

5.5.3. NEGATIVE OR POSITIVE MODULATORY TECHNIQUES

Described hereinbelow are modulatory techniques which, depending on the specific application for which they are utilized, can yield either positive or negative responses leading to the amelioration of immune disorders, including TH cell subpopulation-related disorders. Thus, in appropriate instances, the procedures of this Section can be used in conjunction with the negative modulatory techniques described, above, in Section 5.6.1, or, alternatively, in conjunction with the positive regulatory techniques described, above, in Section 5.6.2.

Antibody Techniques:

Antibodies exhibiting modulatory capability can be utilized to ameliorate immune disorders such as TH cell subpopulation-related disorders. Depending on the specific antibody, the modulatory effect can be negative and can, therefore, be utilized as part of the techniques described, above, in Section 5.6.1, or can be positive, and can, therefore, be used in conjunction with the techniques described, above, in Section 5.6.2.

An antibody having negative modulatory capability refers to an antibody which specifically binds to and interferes with the action of a protein. For example, such an antibody could specifically bind the extracellular domain of a transmembrane 103 gene product in a manner which does not activate the 103 gene product but which disrupts the ability of the 103 gene product to bind its natural ligand. Such antibodies can be generated using standard techniques described in Section 5.3, above, against full length wild type or mutant 103 gene proteins, or against peptides corresponding to portions of the 103 gene proteins. The antibodies include but are not limited to polyclonal, monoclonal, FAb fragments, single chain antibodies, chimeric antibodies, and the like.

An antibody having positive modulatory capability refers to an antibody which specifically binds to a protein and, by binding, serves to, either directly or indirectly, activate the function of the protein which it recognizes. For example, an antibody can bind to the extracellular portion of a transmembrane protein, such as a 103 gene protein, in a manner which causes the transmembrane protein to function as though its endogenous ligand was binding, thus activating, for example, a signal transduction pathway. Such antibodies can also be generated using standard techniques described in Section 5.3, above, against full length wild type or mutant 103 gene proteins, or against peptides corresponding to portions of the 103 gene proteins. The antibodies include but are not limited to polyclonal, monoclonal, human, humanized, FAb fragments, single chain antibodies, chimeric antibodies, and the like.

Preferably, the antibodies used in such modulatory techniques specifically recognize and/or bind to the extracellular domain of a 103 gene product and need not be internalized in cells. However, in other, less preferred embodiments the antibodies may target or bind to, e.g., intracellular domains of a 103 gene product and must, therefore, be internalized. In such embodiments, lipofectin or liposomes can be used to deliver the antibody or a fragment of the Fab region which binds to the gene product epitope into cells. Where fragments of the antibody are used, the smallest inhibitory fragment which binds to the protein is preferred. For example, peptides having an amino acid sequence corresponding to the domain of the variable region of the antibody that binds to the protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889-7893).

In more preferred embodiments, where the 103 gene protein to which the antibody is directed is extracellular (e.g., secreted), or is a transmembrane protein, any of the administration techniques described, below in Section 5.7 which are appropriate for peptide administration can be utilized to effectively administer the antibodies to their site of action.

Increasing or Decreasing Specific TH Cell Subpopulation Concentrations:

Techniques described herein can be utilized to either deplete or augment the total number of cells belonging to a given TH cell subpopulation, thus effectively increasing or decreasing the ratio of the TH cell subpopulation of interest to other TH cell subpopulations. Specifically, separation techniques are described which can be used to either deplete or augment the total number of cells present within a TH cell subpopulation, and, further, targeting techniques are described which can be utilized to deplete specific TH cell subpopulations.

Depending on the particular application, changing the number of cells belonging to a TH cell subpopulation can yield either stimulatory or inhibitory responses leading to the amelioration of TH cell subpopulation disorders. Thus, in appropriate instances, the procedures of this Section can be used in conjunction with the inhibitory techniques described, above, in Section 5.6.1 or, alternatively, in conjunction with the stimulatory techniques described, above, in Section 5.6.2.

The separation techniques described herein are based on the presence or absence of specific cell surface markers, preferably transmembrane markers. Such markers can include, but are not limited to, the TH2-specific 103 gene product extracellular domain markers.

In instances wherein the goal of the separation is to increase or augment the number of cells belonging to a specific TH cell subpopulation, the surface markers used can also be surface markers that are present on undifferentiated or partially undifferentiated TH cells. After separation, and purification of such undifferentiated or partially differentiated TH cells, the cells can be cultured in physiological buffer or culture medium and induced to differentiate by culturing in the presence of appropriate factors. For example, IL-4 can be added to induce the TH cells to differentiate into TH2 cells, while the cytokine IL-12 can be added to induce the TH cells to differentiate into TH1 cells. After differentiation, cells can be washed, resuspended in, for example, buffered saline, and reintroduced into a patient via, preferably, intravenous administration.

Separation techniques can be utilized which separate and purify cells, in vitro, from a population of cells, such as hematopoietic cells autologous to the patient being treated. An initial TH cell subpopulation-containing population of cells, such as hematopoietic cells, can be obtained using standard procedures well known to those of skill in the art. Peripheral blood can be utilized as one potential starting source for such techniques, and can, for example, be obtained via venipuncture and collection into heparinized tubes.

Once the starting source of autologous cells is obtained, the T cells, such as TH1 or TH2 cells, can be removed, and thus selectively separated and purified, by various methods which utilize antibodies which bind specific markers present on the T cell population of interest, while absent on other cells within the starting source. These techniques can include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces or magnetic separations using antibody-coated magnetic beads.

Separation via antibodies for specific markers, such as the TH2 specific 103 gene product, can be by negative or positive selection procedures. In negative separation, antibodies are used which are specific for markers present on undesired cells. For example, in the case of immune disorders associated with a strong or inappropriate TH2 or TH2-like immune response, it can be desirable to deplete the number of TH2 cells. In such instances antibodies could be directed to the extracellular domain of the 103 gene product. Cells bound by an antibody to such a cell surface marker can be removed or lysed and the remaining desired mixture retained.

In positive separation, antibodies specific for markers present on the desired cells of interest. For example, in the case of certain immune disorders that are associated with a weak or insufficient TH2 or TH2-like immune response it can be desirable to increase the number of TH2 cells. In such instances antibodies could be directed to the extracellular domain of the 103 gene product. Cells bound by the antibody are separated and retained. It will be understood that positive and negative separations can be used substantially simultaneously or in a sequential manner.

A common technique for antibody based separation is the use of flow cytometry such as by a florescence activated cell sorter (FACS). Typically, separation by flow cytometry is performed as follows. The suspended mixture of cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through a FACS which separates the cells based on different fluorescence characteristics. FACS systems are available in varying levels of performance and ability, including multi-color analysis. The facilitating cell can be identified by a characteristic profile of forward and side scatter which is influenced by size and granularity, as well as by positive and/or negative expression of certain cell surface markers.

Other separation techniques besides flow cytometry can also provide fast separations. One such method is biotin-avidin based separation by affinity chromatography. Typically, such a technique is performed by incubating cells with biotin-coupled antibodies to specific markers, such as, for example, the transmembrane protein encoded by the 103 gene, followed by passage through an avidin column. Biotin-antibody-cell complexes bind to the column via the biotin-avidin interaction, while other cells pass through the column. The specificity of the biotin-avidin system is well suited for rapid positive separation. Multiple passages can ensure separation of a sufficient level of the TH cell subpopulation of interest.

In instances whereby the goal of the separation technique is to deplete the overall number of cells belonging to a TH cell subpopulation, the cells derived from the starting source of cells which has now been effectively depleted of TH cell subpopulation cells can be reintroduced into the patient. Such a depletion of the TH cell subpopulation results in the amelioration of TH cell subpopulation-related disorders associated with the activity or overactivity of the TH cell subpopulation. Reintroduction of the TH cell subpopulation-depleted cells can be accomplished by washing the cells, resuspending in, for example, buffered saline, and intravenously administering the cells into the patient.

If cell viability and recovery are sufficient, TH cell subpopulation-depleted cells can be reintroduced into patients immediately subsequent to separation. Alternatively, TH cell subpopulation-depleted cells can be cultured and expanded ex vivo prior to administration to a patient. Expansion can be accomplished via well known techniques utilizing physiological buffers or culture media in the presence of appropriate expansion factors such as interleukins and other well known growth factors.

In instances whereby the goal of the separation technique is to augment or increase the overall number of cells belonging to a TH cell subpopulation, cells derived from the purified TH cell subpopulation cells can be reintroduced into the patient, thus resulting in the amelioration of TH cell subpopulation-related disorders associated with an under activity of the TH cell subpopulation.

The cells to be reintroduced will be cultured and expanded ex vivo prior to reintroduction. Purified TH cell subpopulation cells can be washed, suspended in, for example, buffered saline, and reintroduced into the patient via intravenous administration.

Cells to be expanded can be cultured, using standard procedures, in the presence of an appropriate expansion agent which induces proliferation of the purified TH cell subpopulation. Such an expansion agent can, for example, be any appropriate cytokine, antigen, or antibody. In the case of TH2 cells, for example, the expansion agent can be IL-4, while for TH1 cells, the expansion agent can, for example, be IL-12.

Prior to being reintroduced into a patient, the purified cells can be modified by, for example, transformation with gene sequences encoding gene products of interest, including, but not limited to, gene sequences encoding any of the 103 gene products described in Section 5.2 above. Such gene products should represent products which enhance the activity of the purified TH cell subpopulation or, alternatively, represent products which repress the activity of one or more of the other TH cell subpopulations. Cell transformation and gene expression procedures are well known to those of skill in the art, and can be as those described, above, in Section 5.2.

Well known targeting methods can, additionally, be utilized in instances wherein the goal is to deplete the number of cells belonging to a specific TH cell subpopulation. Such targeting methods can be in vivo or in vitro, and can involve the introduction of targeting agents into a population of cells such that the targeting agents selectively destroy a specific subset of the cells within the population. In vivo administration techniques which can be followed for such targeting agents are described, below, in Section 5.7.

Targeting agents generally comprise, first, a targeting moiety which, in the current instance, causes the targeting agent to selectively associate with a specific TH cell subpopulation. The targeting agents generally comprise, second, a moiety capable of destroying a cell with which the targeting agent has become associated.

Targeting moieties can include, but are not limited to, antibodies directed to cell surface markers found specifically on the TH cell subpopulation being targeted, or, alternatively, to ligands, such as growth factors, which bind receptor-type molecules found exclusively on the targeted TH cell subpopulation. In the case of TH2 cells, for example, such a targeting moiety can represent an antibody directed against the extracellular portion of the 103 gene product described herein, or can, alternatively, represent a ligand specific for this receptor-type TH2 specific molecule.

Destructive moieties include any moiety capable of inactivating or destroying a cell to which the targeting agent has become bound. For example, a destructive moiety can include, but it is not limited to cytotoxins or radioactive agents. Cytotoxins include, for example, plant-, fungus-, or bacteria-derived toxins, with deglycosylated Ricin A chain toxins being generally preferred due to their potency and lengthy half-lives.

5.6. PHARMACEUTICAL PREPARATIONS AND METHODS OF ADMINISTRATION

The compounds, nucleic acid sequence and TH cell subpopulations described herein can be administered to a patient at therapeutically effective doses to treat or ameliorate symptoms of immune disorders, including TH cell subpopulation related disorders; i.e., immune disorders that are associated with an immune response of a particular TH cell subpopulation. As used herein, a therapeutically effective dose refers to that amount of a compound (or of a TH cell subpopulation) sufficient to result in amelioration of a symptom or symptoms of the immune disorder or, alternatively, to the amount of a nucleic acid sequence sufficient to express a concentration of a gene product which results in amelioration of symptoms of the immune disorders.

5.6.1. EFFECTIVE DOSE

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of a protein or polypeptide (i.e., an effective dose or effective dosage) ranges from about 0.001 to 30 mg/kg of body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide or antibody can include a single treatment or, preferably, can include a series of treatments. In a preferred example, a subject is treated with antibody, protein, or polypeptide in the range of between about 0.1 to 20 mg/kg body weight one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein or polypeptide used for treatment may increase or decrease over the course of a particular treatment. Changes in dosage may also be apparent to one skilled in the art from the results of diagnostic assays as described herein.

5.6.2. FORMULATIONS AND METHODS OF USE

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral, subcutaneous, intraperitoneal, intrapulmonary, intranasal, intralesional, vaginal or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. It is preferred that the TH cell subpopulation cells be introduced into patients via intravenous administration.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Intralesional administration can comprise, for example, perfusing or contacting a graft or organ with a composition prior to transplantation.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

5.6.3. PHARMACEUTICAL PREPARATIONS INCLUDING ANTIBODIES

Antibodies which specifically bind to 103 gene products of the invention and thereby modulate their activity can also be administered to a patient at therapeutically effective doeses to treat or ameliorate immune disorders. For example, Section 6.4, below, demonstrates the use of anti-103 gene product antibodies to reduce symptoms associated with asthma in an art-recognized animal model.

Antibodies of the invention are administered by any suitable means, including those described in Section 5.11.2, above. In addition, antibodies to a 103 gene product of the invention can be suitably administered by pulse infusion, particularly with declining doses of the antibody. Preferably, the dosing is administered by injections, most preferably by intravenous or subcutaneous injections, depending in part on whether the administration is brief or chronic.

The appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody may suitably administered to the patient at one time or, more preferably, over a series of treatments.

As a general proposition, the initial pharmaceutically effective amount of antibody administered parenterally will be in the range of about 0.1 to 20 mg/kg of patient body weight per day, with the typical initial range being 0.3 to 15 mg/kg of patient body weight per day. Where the subsequent dosing is less than 100% of initial dosing, such subsequent dosing is calculated on the basis of daily dosing. Thus, for example, if the dosing regimen consists of daily injections of 2 mg/kg of patient body weight per day for two weeks followed by a biweekly dose of 0.5 mg/kg of patient body weight per day for 99 days, this would amount to a subsequent dose of about 1.8% of the initial dose calculated on a daily basis (i.e., 2/day/100%=0.5/14 days/x %, x=1.8%). Preferably, the subsequent dosing is less than about 50%, more preferably, less than about 25%, still more preferably, less than about 10%, and still more preferably, less than about 5%. Most preferably, the subsequent dosing is less than about 2% of the initial dosing.

Overall, dosage ranges to be administered will, preferably, range from about 1 µg/kg to about 100 mg/kg, 1 µg/kg to about 15 mg/kg, or about 1 µg/kg, to about 2.0 mg/kg body weight.

The preferred scheduling is that the initial dosing is administered no less frequently than daily, and up to an including continuously by infusion. More preferably, depending on the specific disorder or injury, the initial daily dosing is administered for at least about one week, and preferably at least about two weeks. To obtain the most efficacious results, the initial dosing is preferably given as close to the first sign, diagnosis, appearance, or occurrence of the disorder as possible, or, particular in the case of immune disorders, during remission of the disorder.

Subsequent dosing is preferably administered periodically no more about once a week. More preferably, the subsequent dosing is administered no more than once biweekly. Subsequent dosing is typically administered for at least about five weeks, and preferably for at least about 10 weeks, after the initial dosing is terminated.

Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

Antibodies or antibodies conjugated to therapeutic moieties can be administered to an individual alone or in combination with cytotoxic factor(s), chemotherapeutic drug(s), and/or cytokine(s). If the latter, preferably, the antibodies are administered first and the cytotoxic factor(s), chemotherapeutic drug(s) and/or cytokine(s) are administered thereafter within 24 hours. The antibodies and cytotoxic factor(s), chemotherapeutic drug(s) and/or cytokine(s) can be administered by multiple cycles depending upon the clinical response of the patient. Further, the antibodies and cytotoxic factor(s), chemotherapeutic drug(s) and/or cytokine(s) can be administered by the same or separate routes, for example, by intravenous, intranasal or intramuscular administration. Cytotoxic factors include, but are not limited to, TNF-α, TNF-β, IL-1, IFN-γ and IL-2. Chemotherapeutic drugs include, but are not limited to, 5-fluorouracil (5FU), vinblastine, actinomycin D, etoposide, cisplatin, methotrexate and doxorubicin. Cytokines include, but are not limited to, IL-2, IL-3, IL-4, IL-5, IL-6, IL-7, IL-8, IL-9, IL-10 and IL-12.

Exemplary dosing regimens are disclosed in Jardieu, P. M., and Presta, L. G., 1998, WO 98/23761; and in Jardieu, P. M., and Presta, L. G., 1994, WO 94/04188, each of which is incorporated herein, by reference, in its entirety.

5.7. DIAGNOSTIC AND MONITORING TECHNIQUES

A variety of Methods can be employed for the diagnosis of immune disorders, e.g., TH cell subpopulation-related disorders, predisposition to such immune disorders, for monitoring the efficacy of anti-immune disorder compounds during, for example, clinical trials and for monitoring patients undergoing clinical evaluation for the treatment of such disorders. Further, a number of methods can be utilized for the detection of activated immune cells, e.g., activated members of a TH cell subpopulation such as a TH2 or TH2-like cell subpopulation.

Such methods can, for example, utilize reagents such as the 103 gene nucleotide sequences described in Sections 5.1, and antibodies directed against 103 gene peptides, as described, above, in Sections 5.2 (peptides) and 5.3 (antibodies). Specifically, such reagents can be used, for example, for: (1) the detection of the presence of 103 gene expression, 103 gene mutations, the detection of either over- or under-expression of 103 gene mRNA relative to the non-immune disorder state or relative to an unactivated TH cell subpopulation; (2) the detection of aberrant expression (i.e., either an over- or an under-abundance) of 103 gene product relative to the non-immune disorder state or relative to the unactivated TH cell subpopulation state; and (3) the identification of specific TH cell subpopulation cells (including, for example, cells such as TH2 cells involved, e.g. in an atopic conditions such as asthma and allergy) within a mixed population of cells.

The methods described herein can be performed, for example, by utilizing pre-packaged diagnostic kits comprising 103 gene nucleic acid or anti-103 gene antibody reagent described herein, which can be conveniently used, e.g., in clinical settings, to diagnose patients exhibiting TH1- or TH2-related abnormalities.

Any cell type or tissue, preferably TH cells, in which the 103 gene is expressed can be utilized in the diagnostics described below.

Among the methods which can be utilized herein are methods for monitoring the efficacy of compounds in clinical trials for the treatment of immune disorders. Such compounds can, for example, be compounds such as those described, above, in Section 5.6. Such a method comprises detecting, in a patient sample, a gene transcript or gene product, such as a 103 gene transcript or a 103 gene product, which is differentially expressed in a TH cell subpopulation in an immune disorder state relative to its expression in the TH cell subpopulation when the cell subpopulation is in a normal, or non-immune disorder, state.

Any of the nucleic acid detection techniques described hereinbelow, in Section 5.8.1 or any of the peptide detection techniques described hereinbelow, in Section 5.8.2 can be used to detect a 103 gene transcript or gene product which is differentially expressed in the immune disorder TH cell subpopulation relative to its expression in the normal, or non-immune disorder, state.

During clinical trials, for example, the expression of the 103 gene can be determined for the TH cell subpopulation in the presence or absence of the compound being tested. The efficacy of the compound can be followed by comparing the expression data obtained to the corresponding known expression patterns for the TH cell subpopulation in a normal, non-immune disorder state. Compounds exhibiting efficacy are those which alter the 103 gene expression of the immune disorder TH cell subpopulation to more closely resemble that of the normal, non-immune disorder TH cell subpopulation.

The detection of the product or products of genes, such as the 103 gene, that are differentially expressed in a TH cell subpopulation in an immune disorder state relative to their expression in the TH cell subpopulation when the cell subpopulation is in a normal, or non-immune disorder, state can also be used for monitoring the efficacy of potential anti-immune disorder compounds during clinical trials. During clinical trials, for example, the level and/or activity of the products of a 103 gene can be determined for the TH cell subpopulation in the presence or absence of the compound being tested. The efficacy of the compound can be followed by comparing the 103 gene protein level and/or activity data obtained to the corresponding known levels/activities for the TH cell subpopulation in a normal, non-immune disorder state. Compounds exhibiting efficacy are those which alter the 103 gene protein level and/or activity of the immune disorder TH cell subpopulation to more closely resemble that of the normal, non-immune disorder TH cell subpopulation.

Given the TH2-specific nature of the 103 gene, the detection of 103 gene transcripts and/or products can be particularly suitable for monitoring the efficacy of compounds in clinical trials for the treatment of TH2 cell subpopulation-related immune disorders such as, for example, asthma or allergy.

Among the additional methods which can be utilized herein are methods for detecting TH cell responsiveness, for example, responsiveness to antigen, and for detecting activated immune cells, e.g., activated members of TH cell subpopulations. Detection methods such as these are important in that many immune disorders involve inappropriate rather than insufficient immune responses. Such detection methods can be used, for example, to detect a predisposition to an immune disorder.

Methods for detecting TH cell responsiveness and/or activation can comprise, for example, detecting in a TH cell sample a gene transcript or product, such as 103 gene transcript or product, which is differentially expressed in TH cell subpopulation which is in an activated or responsive state (e.g., a state in which the TH cell subpopulation has been exposed to antigen), relative to a TH cell subpopulation which is in an unactivated or nonresponsive state.

Any of the nucleic acid detection techniques described hereinbelow, in Section 5.8.1, or any of the peptide detection techniques described hereinbelow, in Section 5.8.2 can be used to detect such a differentially expressed gene transcript or gene product.

In addition to diagnostic uses, such techniques can also be utilized as part of methods for identifying compounds which alter the cellular expression of one or more of the differentially expressed genes described herein, or as part of methods for identifying compounds which alter the cellular and/or secreted level of product produced by the differentially expressed genes described herein. Such techniques can be used to identify compounds which alter the level of expression of the 103 gene or the level of 103 gene product present in a cell. Such methods can include, for example, contacting a T cell with a compound, measuring the level of 103 gene expression in the cell (or the level of 103 gene product in the cell), then comparing the level obtained to that of a cell not exposed to the compound. The T cells used herein can include, for example, TH0, TH1 or TH2 cells. Such methods can further include stimulating the cells, for example, stimulating the cells prior to contacting the cells with the compound. Among the methods for stimulation are stimulation via anti-CD3 antibody stimulation.

Such methods can be performed such that the cell contacted is presented within a non-human mammal, for example, a mouse. Further, among the non-human mammals which can be utilized as part of these methods are ones which exhibit symptoms of a T cell-related disorder (such as, for example a TH2-related disorder, e.g., asthma), and contacting the cell with the compound can ameliorate symptoms of the disorder.

The TH2-specific nature of the 103 gene can make the detection of its gene transcripts and/or products particularly suitable for detecting activation and/or responsiveness of TH2 cells.

5.7.1. DETECTING 103 GENE NUCLEIC ACIDS

DNA or RNA from the cell type or tissue to be analyzed can easily be isolated using procedures which are well known to those in the art. Diagnostic procedures can also be performed "in situ" directly upon, for example tissue sections (fixed and/or frozen) of patient tissue obtained from biopsies or resections, such that no nucleic acid purification is necessary. Nucleic acid reagents such as those described in Section 5.1 can be used as probes and/or primers for such in situ procedures (see, for example, Nuovo, G. J., 1992, "PCR In Situ Hybridization: Protocols and Applications", Raven Press, NY). Expression of specific cells within a population of cells can also be determined, via, for example, in situ techniques such as those described above, or by standard flow cytometric techniques.

103 gene nucleotide sequences, either RNA or DNA, can, for example, be used in hybridization or amplification assays of biological samples to detect 103 gene structures and expression. Such assays can include, but are not limited to, Southern or Northern analyses, single stranded conformational polymorphism analyses, in situ hybridization assays, and polymerase chain reaction analyses. Such analyses can reveal both quantitative aspects of the expression pattern of the 103 gene, and qualitative aspects of the 103 gene expression and/or gene composition. That is, such techniques can detect not only the presence of 103 gene expression, but can also detect the amount of expression, particularly which specific cells are expressing the 103 gene, and can, further, for example, detect point mutations, insertions, deletions, chromosomal rearrangements, and/or activation or inactivation of 103 gene expression.

Diagnostic methods for the detection of 103 gene-specific nucleic acid molecules can involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule of interest. Preferably, the lengths of these nucleic acid reagents are at least 15 to 30 nucleotides. After incubation, all non-annealed nucleic acids are removed from the nucleic acid:103 gene molecule hybrid. The presence of nucleic acids from the cell type or tissue which have hybridized, if any such molecules exist, is then detected. Using such a detection scheme, the nucleic acid from the tissue or cell type of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled 103 nucleic acid reagents is accomplished using standard techniques well-known to those in the art.

Alternative diagnostic methods for the detection of 103 gene specific nucleic acid molecules can involve their amplification, e.g., by PCR (the experimental embodiment set forth in Mullis, K. B., 1987, U.S. Pat. No. 4,683,202), ligase chain reaction (Barany, F., 1991, Proc. Natl. Acad. Sci. USA 88:189-193), self sustained sequence replication (Guatelli, J. C. et al., 1990, Proc. Natl. Acad. Sci. USA 87:1874-1878), transcriptional amplification system (Kwoh, D.Y et al., 1989, Proc. Natl. Acad. Sci. USA 86:1173-1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA can be isolated include any tissue in which 103 gene sequences are known or suspected to be expressed, including, but not limited to, TH0, TH1 and/or TH2 cell type-containing tissues. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the 103 gene nucleic acid reagents described in Section 5.1. The preferred lengths of such nucleic acid reagents are at least 9-30 nucleotides. For detection of the amplified product, the nucleic acid amplification can be performed using radioactively or non-radioactively labeled nucleotides. Alternatively, enough amplified product can be made such that the product can be visualized by standard ethidium bromide staining or by utilizing any other suitable nucleic acid staining method.

TH1-related disorders can include, for example, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. TH2-related disorders can include, for example, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

Fingerprint patterns can be generated, for example, by utilizing a differential display procedure, as discussed in U.S. patent application Ser. No. 09/324,986 filed on Jun. 2, 1999 and in International Patent Application No. WO 96/27603 published on Aug. 12, 1996 each of which is incorporated herein, by reference, in its entirety. Fingerprint patterns can also be generated, for example, by Northern analysis and/or RT-PCR. Any of the gene sequences described in either of the above-cited patent applications and patent publication can be used as probes and/or RT-PCR primers for the generation and corroboration of such fingerprint patterns.

5.7.2. DETECTING 103 GENE PRODUCTS

Antibodies directed against wild type or mutant 103 gene peptides, which are discussed, above, in Section 5.3, can also be used as TH cell subpopulation-related disorder diagnostics and prognostics, as described, for example, herein. Such diagnostic methods, can be used to detect 103 gene product, abnormalities in the level of 103 gene protein expression, or abnormalities in the structure and/or temporal, tissue, cellular, or subcellular location of fingerprint gene protein. Structural differences can include, for example, differences in the size, electronegativity, or antigenicity of the mutant fingerprint gene protein relative to the normal fingerprint gene protein.

Protein from the tissue or cell type to be analyzed can easily be isolated using techniques which are well known to those of skill in the art. The protein isolation methods employed herein can, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

In one embodiment, aberrant expression of a 103 polypeptide is detected in a subject comprising: (a) contacting a sample of cells, tissue or body fluid from said subject with an antibody or an antigen binding fragment thereof; (b) measuring the level of the 103 polypeptide in said sample, wherein an increase or decrease in the 103 polypeptide level in said sample relative to a standard level of 103 polypeptide indicates aberrant expression of said 103 polypeptide in said subject. This assay may be performed, e.g., to monitor or detect an immune disorder described herein. Preferably, the subject is an animal, more preferably a mammal and most preferably a human. It is also preferred that the antibody is a monoclonal antibody produced by the hyrbridoma clone M15 3F7.3, the hybridoma clone M15 2O3.1, the hybridoma clone M15 10F7.1, the hybridoma clone M15 1B4.1, the hybridoma clone M15 9F11.1, or the hybridoma clone M15 5A16.1. The term "standard level" refers to the level of expression of a 103 polypeptide by cells obtained from a healthy subject or a subject without an immune disorder state, and/or to the level of expression of a 103 polypeptide by a tissue sample or body fluid obtained from a healthy subject or a subject without an immune disorder state. In particular, the term "standard level" can refer to the level of expression of a 103 polypeptide by an unactivated TH cell subpopulation state from a healthy subject. The level of expression of a 103 polypeptide in a sample from a healthy subject or a subject without an immune disorder can be determined concomitantly with the test sample or at an early time.

Preferred diagnostic methods for the detection of wild type or mutant 103 gene peptide molecules can involve, for example, immunoassays wherein 103 gene peptides are detected by their interaction with an anti-fingerprint gene product-specific antibody.

For example, antibodies or fragments of antibodies, such as those described, above, in Section 5.3, useful in the present invention can be used to quantitatively or qualitatively detect the presence of wild type or mutant 103 gene peptides. This can be accomplished, for example, by immunofluorescence techniques employing a fluorescently labeled antibody (see below, this Section,) coupled with light microscopic, flow cytometric, or fluorimetric detection. Such techniques are especially preferred if the 103 gene peptides are expressed on the cell surface, such as, for example, is the case with the transmembrane form of 103 gene product. Thus, the techniques described herein can be used to detect specific cells, within a population of cells, which express the 103 gene product of interest.

The antibodies (or fragments thereof) useful in the present invention can, additionally, be employed histologically, as in immunofluorescence or immunoelectron microscopy, for in situ detection of 103 gene peptides. In situ detection can be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the 103 gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant 103 gene peptides typically comprise incubating a biological sample, such as a biological fluid, a tissue extract, freshly harvested cells, or cells which have been incubated in tissue culture, in the presence of a detectably labeled antibody capable of identifying 103 gene peptides, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant 103 gene product antibody can be determined according to well known methods. Those skilled in the art will be able to determine operative and optimal assay conditions for each determination by employing routine experimentation.

One of the ways in which the 103 gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, ENZYME IMMUNOASSAY, CRC Press, Boca Raton, Fla.; Ishikawa, E. et al., (eds.), 1981, ENZYME IMMUNOASSAY, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect 103 gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}$I, $^{135}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8 KITS

The invention encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention. For example, kits can be used to determine if a subject is suffering from or is at increased risk of immune disorders such as Crohn's disease, reactive arthritis, Lyme disease, insulin-dependent diabetes, multiple sclerosis, Hashimoto's thyroiditis and Grave's disease, contact dermatitis, psoriasis, graft rejection, graft versus host disease, sarcoidosis, asthma and allergies (e.g., allergic rhinitis, gastrointestinal allergies such as food allergies), eosinophilia, conjunctivitis, glomerular nephritis, systemic lupus erythematosus, certain viral infections (e.g., HIV) and bacterial infections (e.g., tuberculosis and lepromatous leprosy).

For antibody-based kits, the kit can comprise, for example: (1) a first antibody (e.g., attached to a solid support) which binds to a 103 polypeptide; and, optionally, (2) a second, different antibody which binds to either the polypeptide or the first antibody and is conjugated to a detectable substance such as horseradish peroxidase, alkaline phosphatase, fluorescein, rhodamine, phycoerythrin, $^{125}$I, $^{131}$I, $^{32}$P, or $^{3}$H (see, e.g., Section 5.3). The kit can also contain a control antibody which does not bind to the 103 polypeptide. Further, the kit can contain a 103 polypeptide as a positive control for the antibodies of the invention. Preferably, the kit comprises the monoclonal antibody produced by clone M15 3F7.3, clone M15 2O3.1, clone M15 10F7.1, clone M15 1B4.1, clone M15 9F11.1, or clone M15 5A16.1. Each component of the kit is usually enclosed within an individual container and all of the various containers are within a single package. The kit may also include instructions for observing whether the tested subject is suffering from or is at risk of developing a disorder associated with aberrant expression of a 103 polypeptide.

For oligonucleotide-based kits, the kit can comprise, for example: (1) an oligonucleotide, e.g., a detectably labeled oligonucleotide, which hybridizes to a nucleic acid sequence encoding a 103 polypeptide or (2) a pair of primers useful for amplifying a nucleic acid molecule encoding a 103 polypeptide. In a preferred embodiment, an oligonucleotide-based kit comprises an oligonucleotide which hybridizes to the complement of a nucleic acid molecule that encodes a polypeptide comprising the amino acid sequence of SEQ ID NO:13. In another preferred embodiment, an oligonucleotide-based kit comprises a pair of primers which amplify a nucleic acid molecule encoding the amino acid sequence of SEQ ID NO:13. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions.

6. EXAMPLES

The following examples are presented as exemplary illustrations of the methods and compositions of the previously described invention and are not limiting of that invention in any way. Specifically, the example presented in Section 6.1 describes the determination that the gene referred to herein as the 103 gene, which is also known as ST2, T1 and Fit-1, is differentially expressed in TH cells. In particular, this example demonstrates that the 103 gene is expressed in TH2 and not in TH1 cells. The example in Section 6.2 describes the quantitative expression of human 103 in primary human cells. The example in Section 6.3 describes the construction and expression of certain exemplary 103 gene IgG1 fusion proteins, and the example in Section 6.4 describes the production of exemplary transgenic animals (transgenic mice) that overexpress the murine 103 gene product. The example presented in Section 6.5 demonstrates, using in vivo data from an art-recognized animal model, that the 103 gene product provides a critical signal to TH2 effector cells and can be utilized as a novel target for the selective suppression of TH2 immune response, e.g., in conditions such as asthma and allergy. Thus, the in vivo data presented in Section 6.5 demonstrates that molecules which target and/or inhibit 103 gene product activity, such as anti-103 antibodies, are useful for treating immune disorders, particularly TH cell subpopulation disorders such as asthma and allergy. The example presented in Section 6.6 shows that the 103 gene is also expressed in mammalian mast cells. The example presented in Section 6.7 describes additional experiments which confirms that the 103 gene product is, not only a useful marker for identifying and detecting TH2 cells, but also play a crucial role in the differentiation and activation of TH2, but not TH1, cells. The example presented in Section 6.8 describes the production of human monoclonal antibodies against a human 103 gene product. Finally, the example presented in Section 6.9 describes the detection of a ligand on mouse spleen cells which specifically binds to a 103 gene product.

Thus, the data presented hereinbelow show that the 103 gene product is an important regulator for a number of key events in both innate and adaptive immunity and that, as such, it is an important target for the therapeutic and diagnostic methods and compositions of the present invention.

6.1. IDENTIFICATION AND CHARACTERIZATION OF A TH2-SPECIFIC GENE

In the Example presented in this Section, a transgenic T cell paradigm was utilized to a identify a gene, referred to herein as the 103 gene, which is differentially expressed in TH2 cells. Specifically, this gene is present in TH2 cells while being completely absent from TH1 cells. The 103 gene, which corresponds to a gene known, alternatively, as ST-2 T1 and Fit-1, does not appear to be expressed in any other assayed cell type or tissue, and is demonstrated herein to encode a marker which is, in vivo, completely TH2-specific. The 103 gene encodes a cell surface protein, the potential significance of which is also discussed herein.

6.1.1. MATERIALS AND METHODS

Transgenic Mice:

Naive CD4+ cells were obtained from the spleens and/or lymph nodes of unprimed transgenic mouse strains harboring a T cell receptor (TCR) recognizing ovalbumin (Murphy et al., 1990, *Science* 250:1720).

Ova-Specific Transgenic T Cells:

Suspensions of ova-specific T cells were co-cultured with stimulatory peptide antigen and antigen presenting cells essentially as described in Murphy et al. (Murphy et al., 1990, *Science* 250:1720). Briefly, 2-4×10$^6$ T cells were incubated with approximately twice as many TA3 antigen presenting cells in the presence of 0.3 µM Ova peptide. TH1 cultures contained approximately 10 ng/ml recombinant mIL-12. Conversely, TH2 cells received IL-4 (1000 u/ml). Cultures were harvested at various time points after initiation of culture. T cells were purified of TA3 cells using anti-CD4 coated magnetic beads (Dynal, Inc.). T cells were pelleted by gentle centrifugation and lysed in the appropriate volume of RNAzol™ (Tel-Test, Friendswood, Tex.).

Tissue Collection and RNA Isolation:

Cells were quick frozen on dry ice. Samples were then homogenized together with a mortar and pestle under liquid nitrogen.

Total cellular RNA was extracted from tissue with either RNAzol™ or RNAzolB™ (Tel-Test, Friendswood, Tex.), according to the manufacturer's instructions. Briefly, the tissue was solubilized in an appropriate amount of RNAzol™ or RNAzolB™, and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically ($A_{260}$).

Differential Display:

Total cellular RNA (10-50 was treated with 20 Units DNase I (Boehringer Mannheim, Germany) in the presence of 40 Units ribonuclease inhibitor (Boehringer Mannheim, Germany). After extraction with phenol/chloroform and ethanol precipitation, the RNA was dissolved in DEPC (diethyl pyrocarbonate)-treated water. RNA (0.4-2 µg) was reverse-transcribed using Superscript reverse transcriptase (GIBCO/BRL). The cDNAs were then amplified by PCR on a Perkin-Elmer 9600 thermal cycler. The reaction mixtures (20 µL) included arbitrary decanucleotides and one of twelve possible $T_{11}$ VN sequences, wherein V represents either dG, dC, or dA, and N represents either dG, dT, dA, or dC. Parameters for the 40 cycle PCR were as follows: Hold 94° C. 2 minutes; Cycle 94° C. 15 seconds, 40° C. 2 minutes; Ramp to 72° C. 30 seconds; Hold 72° C. 5 minutes; Hold 4° C.

Radiolabelled PCR amplification products were analyzed by electrophoresis on 6% denaturing polyacrylamide gels.

Reamplification and Subcloning:

PCR bands of interest were recovered from sequencing gels and reamplified.

Briefly, autoradiograms were aligned with the dried gel, and the region containing the bands of interest was excised with a scalpel. The excised gel fragment was eluted by soaking in 100 µL TE (Tris-EDTA) buffer at approximately 100° C. for 15 minutes. The gel slice was then pelleted by brief centrifugation and the supernatant was transferred to a new microcentrifuge tube. DNA was combined with ethanol in the presence of 100 mM Sodium acetate and 30 µg glycogen (Boehringer Mannheim, Germany) and precipitated on dry ice for approximately 10 minutes. Samples were centrifuged for 10 minutes and pellets were washed with 80% ethanol. Pellets were resuspended in 10 µL distilled water.

5 µL of the eluted DNA were reamplified in a 100 µL reaction containing: standard Cetus Taq polymerase buffer, 20 µM dNTPs, 1 µM of each of the oligonucleotide primers used in the initial generation of the amplified DNA. Cycling conditions used were the same as the initial conditions used to generate the amplified band, as described above. One-half of the amplification reaction was run on a 2% agarose gel and eluted using DE-81 paper (Whatman Paper, Ltd., England) as described in Sambrook et al., supra. Recovered fragments were ligated into the cloning vector pCR™ II (Invitrogen, Inc., San Diego Calif.) and transformed into competent *E. coli* strain DH5α (Gibco/BRL, Gaithersburg, Md.). Colonies were grown on LB-agar plates containing ampicillin (100 µg/mL) and X-gal (40 µg/mL) to permit blue/white selection.

Sequence Analysis:

After subcloning, reamplified cDNA fragments were sequenced on an Applied Biosystems Automated Sequencer (Applied Biosystems, Inc. Seattle, Wash.). Sequence was obtained from four or more independent transformants containing the same insert. The nucleotide sequence shown herein represents either the consensus of the information obtained from the four sequences, or the sequence obtained from a representative clone, as indicated. Such primary sequence data was edited and trimmed of vector sequences and highly repetitive sequences and used to search Genbank databases using the BLAST (Altschul, S. F. et al., 1990, J. Mol. Biol. 215:403-410) program.

Northern Analysis:

RNA samples were electrophoresed in a denaturing agarose gel containing 1-1.5% agarose (SeaKem™ LE, FMC BioProducts, Rockland, Me.) containing 6.3% formaldehyde. Samples containing 5-20 µg of total RNA were mixed with denaturing loading solution (72% deionized formamide and bromophenol blue) and heated to 70° C. for 5 minutes. Samples were placed on ice and immediately loaded onto gels. Gels were run in 1×MOPS buffer (100 mM MOPS, 25 mM sodium acetate, 5 mM EDTA). After electrophoresis, the gels were stained with ethidium bromide and visualized with ultraviolet light.

After completion of electrophoresis, gels were soaked in 50 mM sodium hydroxide with gentle agitation for approximately 30 minutes to lightly cleave RNA. Gels were rinsed twice in water and then neutralized by soaking in 0.1 M Tris-HCl (pH 7.5) for approximately 30 minutes. Gels were briefly equilibrated with 20×SSC (3M sodium chloride, 0.3 M sodium citrate) and then transferred to nylon membranes such as Hybond™, -N, (Amersham, Inc., Arlington Heights, Ill.) or Zeta-Probe (Bio-Rad, Inc., Hercules, Calif.) overnight in 20×SSC. Membranes containing transferred RNA were baked at 80° C. for 2 hours to immobilize the RNA.

DNA fragments to be used as probes were of various sizes and were labeled using a random hexamer labeling technique. Briefly, 25 ng of a purified DNA fragment was used to generate each probe. Fragments were added to a 20 µL random hexanucleotide labeling reaction (Boehringer Mannheim, Inc., Indianapolis, Ind.) containing random hexamers and a mix of the nucleotides dCTP, dGTP, and dTTP (at a final concentration of 25 µM each). The reaction mix was heat-denatured at 100° C. for 10 minutes and then chilled on ice. 5 µL of α-$^{32}$P-dATP (50 µCi; Amersham, Inc., Arlington Heights, Ill.) and Klenow DNA polymerase (2 units; Boehringer Mannheim, Inc., Indianapolis, Ind.) were added. Reactions were incubated at 37° C. for 30 minutes. Following incubation, 30 µL water was added to the labeling reaction and unincorporated nucleotides were removed by passing the reactions through a BioSpin-6™ chromatography column (Bio-Rad, Inc., Hercules, Calif.). Specific incorporation was determined using a scintillation counter. 1-5×10$^6$ cpm were used per ml hybridization mixture.

Nylon membranes containing immobilized RNA were pre-hybridized according to manufacturer's instructions. Radio-labelled probes were heat denatured at 70° C. in 50% deionized formamide for 10 minutes and ten added to the hybridization mixture (containing 50% formamide, 10% dextran sulfate, 0.1% SDS, 100 µg/mL sheared salmon sperm DNA, 5×SSC, 5×Denhardt's solution, 30 mM Tris-HCl (pH 8.5), 50 mM NaPO$_4$ (pH 6.5). Hybridizations were carried out at 42° C. overnight. Nylon membranes were then bathed for 2 minutes in a wash solution of 0.2×SSC and 0.1% SDS at room temperature to remove most of the remaining hybridization solution. The membranes were then bathed twice in fresh 42° C. preheated wash solution for 20 minutes. Filters were covered in plastic wrap and exposed to autoradiographic film to visualize results.

RT-PCR Analysis:

Quantitative RT-PCR was performed as follows. 1-2 µg of total RNA, prepared as described above, was reverse transcribed with oligo dT$_{(12-18)}$ primers and Superscript™ RNAase H$^-$ reverse transcriptase (Gibco-BRL, Gaithersburg, Md.). Briefly, RNA was combined with 1 µL oligo dT (500 µg/mL) in a total volume of 11 µL. The mixture was heated to 70° C. for 10 minutes and chilled on ice. After a brief centrifugation, RNA was reverse transcribed for 1 hour. Aliquots of the first strand cDNA were stored at −20° C. until just prior to use.

Expression levels were determined by PCR amplification of serial dilutions of first strand cDNA. In this procedure, cDNA is serially diluted in water. The dilutions are then batch amplified by PCR using sequence-specific primers. All PCR reactions are amplified under identical conditions. Therefore, the amount of product generated should reflect the amount of sequence template which was initially present. 5-10 fold dilutions of cDNA were used and enough dilutions were used such that the amount of product subsequently produced ranged from clearly visible, by UV illumination of ethidium bromide-stained gels, to below detection levels. The method described herein can distinguish 10-fold differences in expression levels.

Primers were designed for the amplification of the sequenced amplified bands, which were chosen using the program OLIGO (National Biosciences, Plymouth, Minn.). Primer sequences used in this assay were as follows:

```
103 sense primer:
                                    (SEQ ID NO: 14)
    5'-TTGCCATAGAGAGACCTC-3';

band 103 antisense primer:
                                    (SEQ ID NO: 15)
    5'-TGCTGTCCAATTATACAGG-3';

murine gamma actin sense primer:
                                    (SEQ ID NO: 16)
    5'-GAACACGGCATTGTCACTAACT-3';

murine gamma actin antisense primer:
                                    (SEQ ID NO: 17)
    5'-CCTCATAGATGGGCACTGTGT-3'.
```

All quantitative PCR reactions were carried out in a 9600 Perkin-Elmer PCR machine (Perkin-Elmer). Generally, amplification conditions were as follows: 30-40 cycles consisting of a 95° C. denaturation for 30 seconds, 50-60° C. annealing for 30 seconds, and 72° C. extension for 1 minute. Following cycling, reactions were extended for 10 minutes at 72° C.

RNase Protection Assays:

RNAse protection assays were performed according to manufacturer's instructions, using a kit purchased from Ambion, Inc. RNA probes derived from GenBank Accession No. Y07519 were utilized in the RNAse protection assays. These probes were also generated according to manufacturer's instructions, using a kit purchased from Ambion, Inc. The sequence of these RNA probes corresponds to the 5' end of the gene, and includes both coding and 5' untranslated sequences.

Anti CD-3 Stimulation:

T cell clone pardigm searches were conducted using three different clones: D10.G4 (TH2), AE7 (TH1) and D1.1 (TH1). Prior to stimulation, cell cultures were enriched for live cells by centrifugation through a Ficoll gradient. Recovered cells were counted and their viability was examined using trypan blue exclusion. Cells were replated into either T25 or T75 flasks at approximately 5×10$^6$ cells in 5 mLs or 1.5×10$^6$ cells in 10 mLs of culture medium, respectively.

Coating was performed, generally, according to *Current Protocols Immunology*, 1992, Coligan, J. E. et al., John Wiley & Sons, NY, pp 3.12.4-3.12.6. Specifically, prior to plating, the flasks were coated with anti-CD3-ε antibodies (hybridoma supernatant from the 145-C11 hybridoma; Parmingen, Inc., San Diego Calif.). For coating, antibodies were resuspended in PBS at 1-2 µg/mL at a volume sufficient to coat the bottom of the flasks. Coating solution was incubated on the flasks for at least one hour at 37° C.

After incubation, the antibody coating solution was removed by aspiration and cells were immediately added. Flasks were placed in a 37° C. incubator for 6 hours. Cells were harvested by, for example, removal of supernatant from the culture followed by direct lysing of cells by addition of RNAzol™ solution.

6.1.2. RESULTS

A differential display analysis of RNA isolated from TH1 and TH2 cell samples obtained from a transgenic T cell paradigm study. Specifically, TH cells were obtained from transgenic mice harboring a T cell receptor recognizing ovalbumin (Murphy et al., 1990, Science 250:1720) were stimulated three times, and RNA was obtained from TH1 and TH2 cells. Differential display analysis of the RNA samples resulted in the identification of a TH2 differentially expressed band, designated and referred to herein as band 103. The gene corresponding to band 103 is referred to herein as the 103 gene.

103 gene cDNA was isolated, amplified and subcloned, and nucleotide sequence (SEQ ID NO:1) was obtained, as shown in FIG. 1. A database search revealed that the nucleotide sequence of band 103 resulted in an alignment with 98% identity to the mouse form of a gene known, alternatively, as the ST-2, T1 or Fit-1 gene (Klemenz, R. et al., 1989, Proc. Natl. Acad. Sci. USA 86:5708-5712; Tominaga, S., 1989, FEBS Lett. 258:301-301; Werenskiold, A. K. et al., 1989, Mol. Cell. Biol. 9:5207-5214; Werenskiold, A. K., 1992, Eur. J. Biochem. 204:1041-1047; Yanagisawa, K. et al., 1993, FEBS Lett. 318:83-87; Bergers, G. et al., 1994, EMBO J. 13:1176-1188).

The 103 gene encodes, possibly via alternatively spliced transcripts, transmembrane and soluble forms of proteins which belong to the immunoglobulin superfamily. The soluble form of the protein shows a high level of similarity to the extracellular portion of the mouse interleukin-1 receptor type 1 (IL-1R1) and interleukin-1 receptor type 2 (IL-1R2; which lacks a cytoplasmic domain), while the transmembrane portion (termed ST2L) bears a high resemblance to the entire IL-1R1 sequence and to the extracellular IL-1R2 sequences. Further, the 103 gene appears to be tightly linked to the interleukin 1 receptor-type 1 locus (McMahan, C. J. et al., 1991, EMBO J. 10:2821-2832; Tominaga, S. et al., 1991, Biochem. Biophys. Acta. 1090:1-8). Additionally, the human 103 gene homolog has also been reported (Tominaga, S. et al., 1992, Biochem. Biophys. Acta. 1171:215-218). FIG. 2 illustrates the 103 gene transmembrane and soluble forms of protein, and shows their relationship to the IL-1R1 protein sequence.

Figure 12:
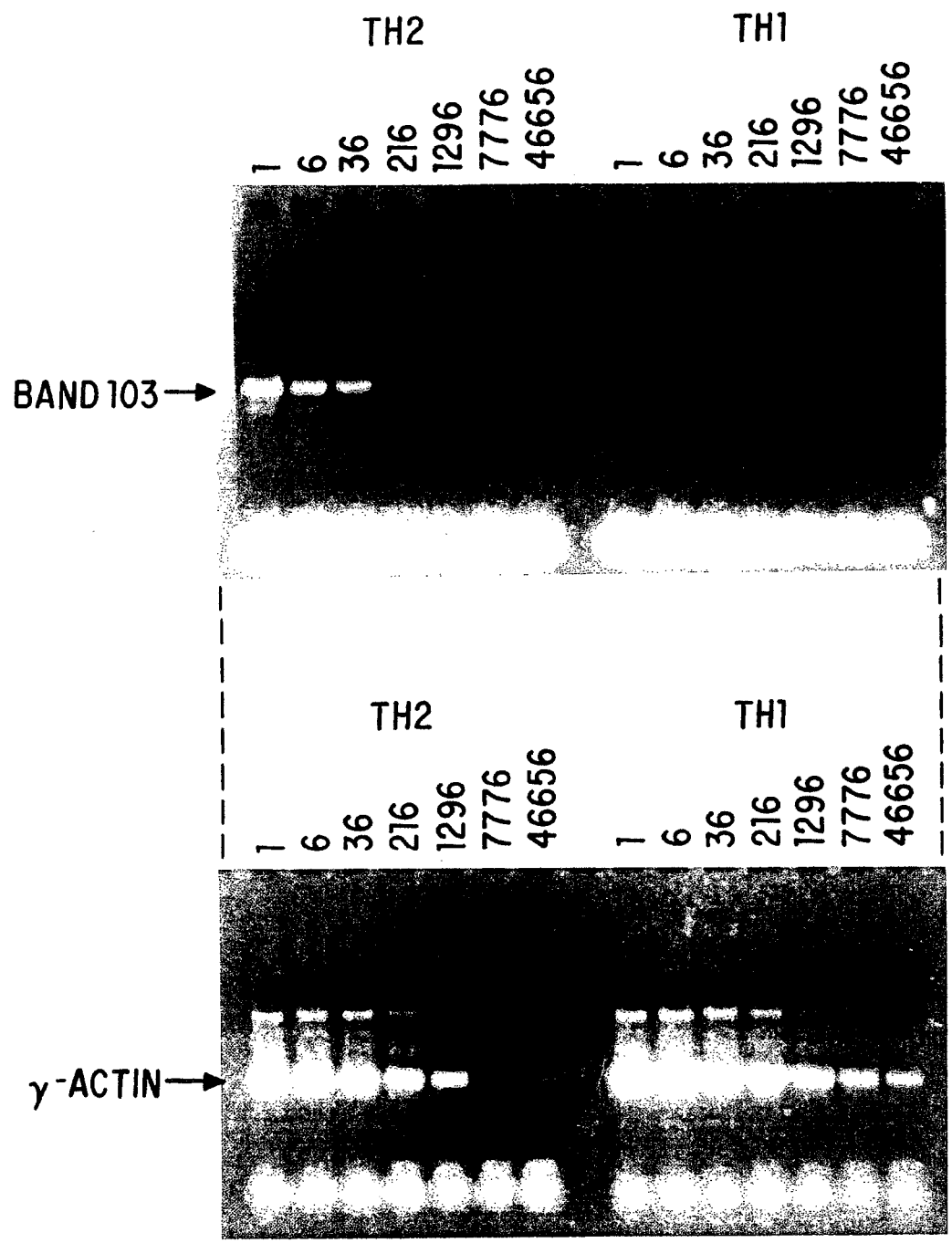

A quantitative RT-PCR analysis (FIG. 12) of RNA obtained from cells of a TH1 and TH2 cells, generated as described above, 24 hours after tertiary antigen stimulation not only confirmed the putative TH2 differential expression of the gene, but, revealed that the expression of the 103 gene appears to be TH2 specific, i.e., the sensitive RT-PCR study detected no 103 gene message in the TH1 RNA sample.

Figure 13:
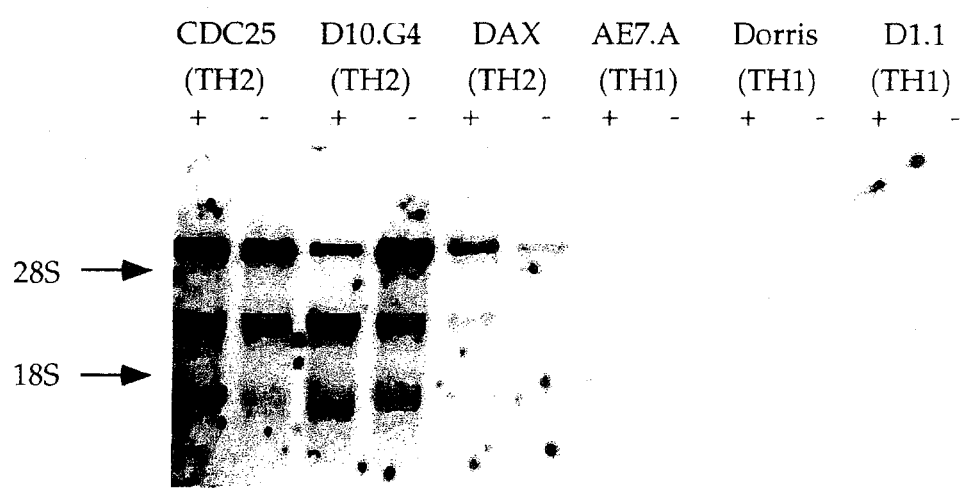

The TH2 specificity of the 103 gene was further confirmed by a Northern analysis of several representative TH cell lines. Specifically, three TH2 clones (CDC25, D10.G4, DAX) and three TH1 clones (AE7.A, Dorris, D1.1) were utilized and RNA samples were isolated from either unstimulated cells or from cells which had been stimulated for 6 hours with plate-bound anti-CD3 antibody. The samples were probed with band 103 sequences, as shown in FIG. 13. While 103 gene RNA is present in RNA obtained from both unstimulated and stimulated cells of each of the TH2 cell lines, 103 gene RNA is completely absent from all of the samples obtained from either stimulated or unstimulated TH1 cells. As the RT-PCR analysis described above first demonstrated, the 103 gene appears to be TH2 specific, with no detectable TH1-derived signal being present.

Figure 14:
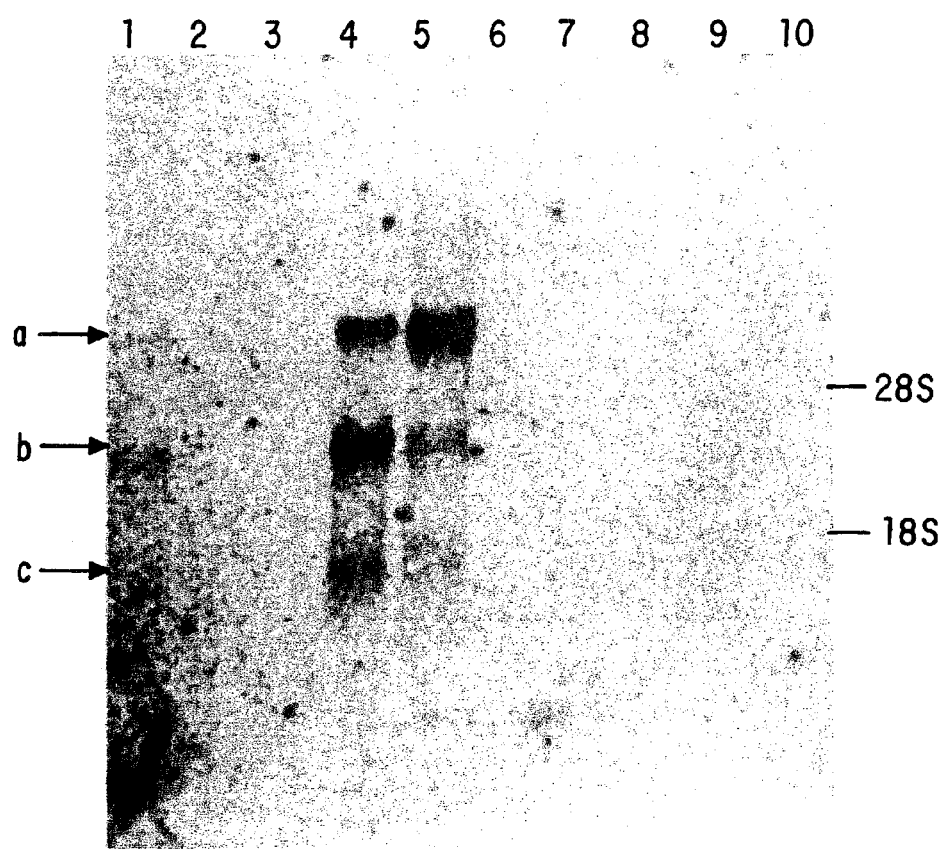

The data presented in FIG. 14 represent an additional Northern analysis in which 103 gene expression was assayed in TH cell clones (lanes 1-5) and in murine tissues (lanes 6-10). In addition to corroborating the expression of 103 gene RNA in both stimulated and unstimulated TH2 cells, the data presented here demonstrate that 103 gene expression appears to be negative in each of the tissues (i.e., brain, heart, lung, spleen, and liver) tested.

Figure 15:
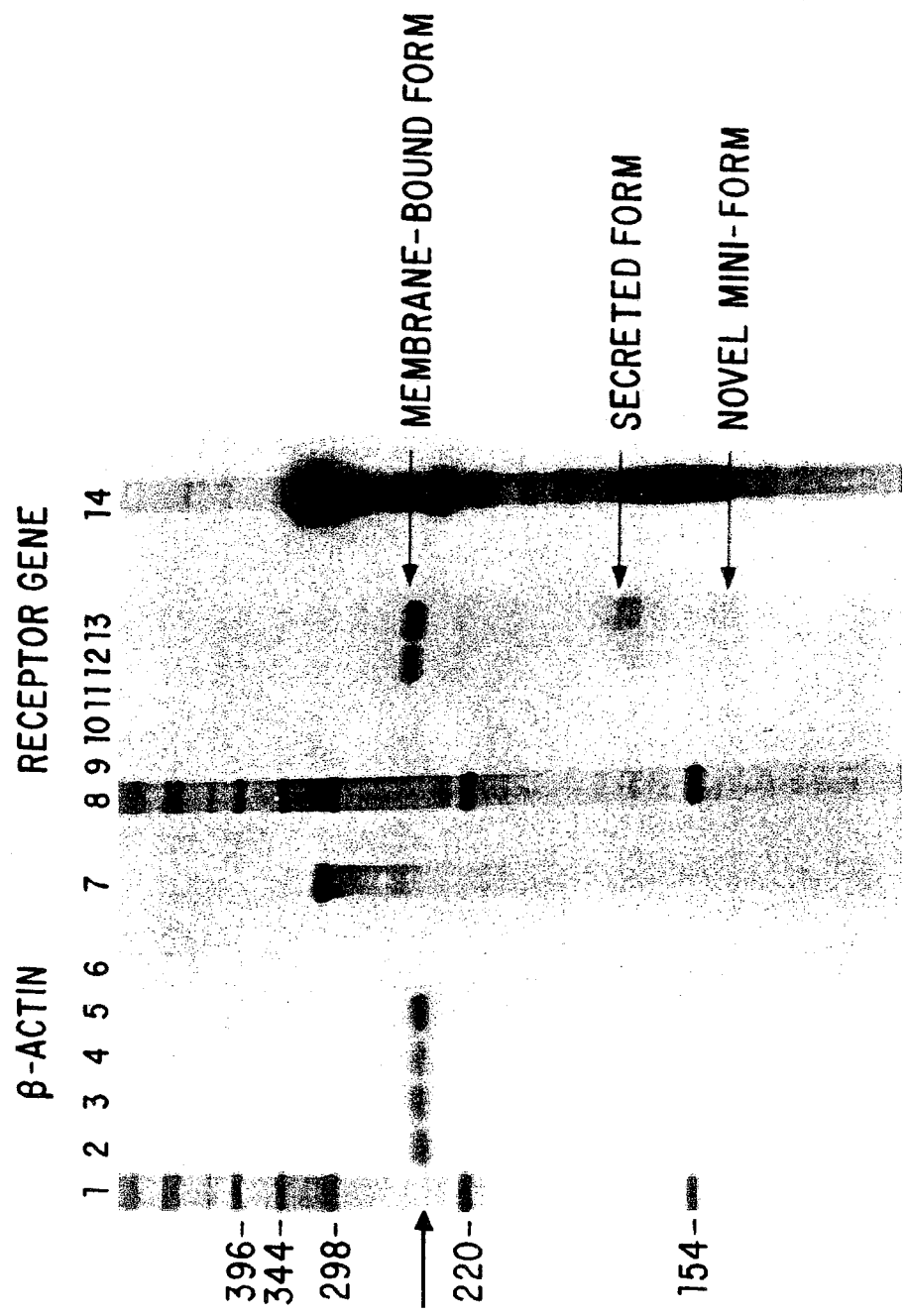

FIG. 15 illustrates an RNAse protection assay which demonstrates two points regarding 103 gene regulation. First, this analysis of TH cell clones confirms the TH2-specific results described, above. Specifically, the results of this study demonstrate by RNase protection, that 103 gene mRNA is absent from the TH1 clone AE7, but is present in the TH2 clone D10.G4.

Second, RNAse protection revealed that alternate forms of 103 gene transcripts are produced upon stimulation of TH2 clones. Specifically, within 6 hours of anti-CD3 stimulation, two additional forms of 103 gene transcript appear in TH2 clones. These additional 103 gene transcript forms represent, one, a transcript encoding a shortened, secreted, soluble form of the band 103 gene product, and, two, a smaller, termed mini, transcript which encodes a yet shorter form of the gene product. Thus, it appears that, while the 103 gene transcript encoding the transmembrane gene product is expressed in both unstimulated and stimulated TH2 cells, the two shorter forms of transcript are expressed in a TH2-specific inducible manner. Further, while the 103 gene transcript encoding the transmembrane product are expressed in both stimulated and unstimulated TH2 cells, the level of this transcript present in stimulated is lower, i.e., is downregulated. Thus, the lower level of transmembrane product and higher level of secreted 103 gene product can act synergistically to dampen some stimulation-induced signal transduction event.

Additionally, it should be noted that the results presented herein represent the first time the mini form of 103 gene transcript, which can encode a shorter version of the soluble form of 103 gene product, has been observed.

To summarize, while 103 gene expression in T helper cell lines had previously been reported (Tominaga, S. et al., 1992, Biochem. Biophys. Acta. 1171:215-218), the TH paradigm/differential display techniques utilized here have demonstrated, for the first time, that the 103 gene encodes a TH2 cell subpopulation-specific surface marker. In fact, the results described in this Example demonstrate that the first identification of any in vivo TH cell subpopulation-specific cellular marker.

Given its status as both a TH2 cell subpopulation-specific marker and cell surface protein, the full length 103 gene product can be utilized in a variety of methods to modulate TH cell subpopulation-related disorders and/or to identify compounds which exhibit such modulatory capability. The truncated forms of the 103 gene products can, additionally, be used as part of these methods. Modulatory methods are described, above, in Section 5.6, while strategies for the identification of modulatory compounds are described, above, in Section 5.4.

6.2. EXPRESSION OF HUMAN 103 GENE PRODUCT

In the Example presented in this Section, primary human cells were analyzed for their quantitative expression of human 103.

6.2.1 MATERIALS AND METHODS

Primary Cells Analyzed:

cDNA was prepared from the following primary cells: resting and phytohemaglutinin (PHA) activated peripheral blood mononuclear cells (PBMC); resting and PHA activated $CD3^+$ cells; $CD4^+$ and $CD8^+$ T cells; resting Th0, Th1 and Th2 cells; Th0, Th1 and Th2 cells stimulated for 1, 6, 24 or 48 hours with anti-CD3 antibody; resting and lipopolysaccharide (LPS) activated $CD19^+$ B cells; $CD14^+$ cells; granulocytes; eosinophils; PBMC stimulated with IL-10 and IL-4; and PBMC stimulated with interferon-γ (IFN-γ) and tumor necrosis factor-α (TNF-α). cDNA was also prepared from two lung biopsies (referred to as biopsy #1 and biopsy #2) obtained from two asthmatic individuals 24 hours after exposure to an antigen (i.e., house dust mites).

RNA Isolation:

Cells were quick frozen on dry ice. Samples were then homogenized together with a mortar and pestle under liquid nitrogen.

Total cellular RNA was extracted from tissue with either RNAzol™ or RNAzolB™ (Tel-Test, Friendswood, Tex.), according to the manufacturer's instructions. Briefly, the tissue was solubilized in an appropriate amount of RNAzol™ or RNAzolB™, and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically ($A_{260}$).

RT-PCR Analysis:

Probes were designed by PrimerExpress software (PE Biosystems) based on the human 103 sequence. The primers and probes for expression analysis of human 103 and β-2 microglobulin were as follows:

```
103 Forward Primer
                                    (SEQ ID NO: 18)
TGTGACGGCGACCAGGT 103 Reverse Primer
                                    (SEQ ID NO: 19)
TCTCTGTTTCCAGTAATCGGAGC 103 TaqMan Probe
                                    (SEQ ID NO: 20)
TTCACGGTCAAGGATGAGCAAGCCTT β-2 microglobulin Forward Primer
                                    (SEQ ID NO: 21)
CACCCCCACTGAAAAAGATGA β-2 microglobulin Reverse Primer
                                    (SEQ ID NO: 22)
CTTAACTATCTTGGGCTGTGACAAAG β-2 microglobulin TaqMan Probe
                                    (SEQ ID NO: 23)
TATGCCTGCCGTGTGAACCACGTG
```

The human 103 sequence probe was labeled using FAM (6-carboxyfluorescein), and the β2-microglobulin reference probe was labeled with a different fluorescent dye, VIC. The differential labeling of the target human 103 sequence and internal reference gene thus enabled measurement in the same well. Forward and reverse primers and the probes for both β2-microglobulin and the target human 103 sequence were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target h16395 sequence. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 103 expression in the various cells relative to β-2 microglobulin expression in the same cells. The threshold cycle (Ct) value is defined as the cycle at which a statistically significant increase in fluorescence is detected. A lower Ct value is indicative of a higher mRNA concentration. The Ct value of the h16395 sequence is normalized by subtracting the Ct value of the β-2 microglobulin gene to obtain a Ct value using the following formula: $Ct=Ct_{h16395}-Ct_{\beta-2\ microglobulin}$. Expression is then calibrated against a cDNA sample showing a comparatively low level of expression of the h16395 sequence. The Ct value for the calibrator sample is then subtracted from Ct for each tissue sample according to the following formula: $Ct=Ct\text{-}_{sample}-Ct\text{-}_{calibrator}$. Relative expression is then calculated using the arithmetic formula given by $2^{-Ct}$. Expression of the target human 103 sequence in each of the tissues tested was then graphically represented as discussed in more detail below.

6.2.2. RESULTS

Figure 16:
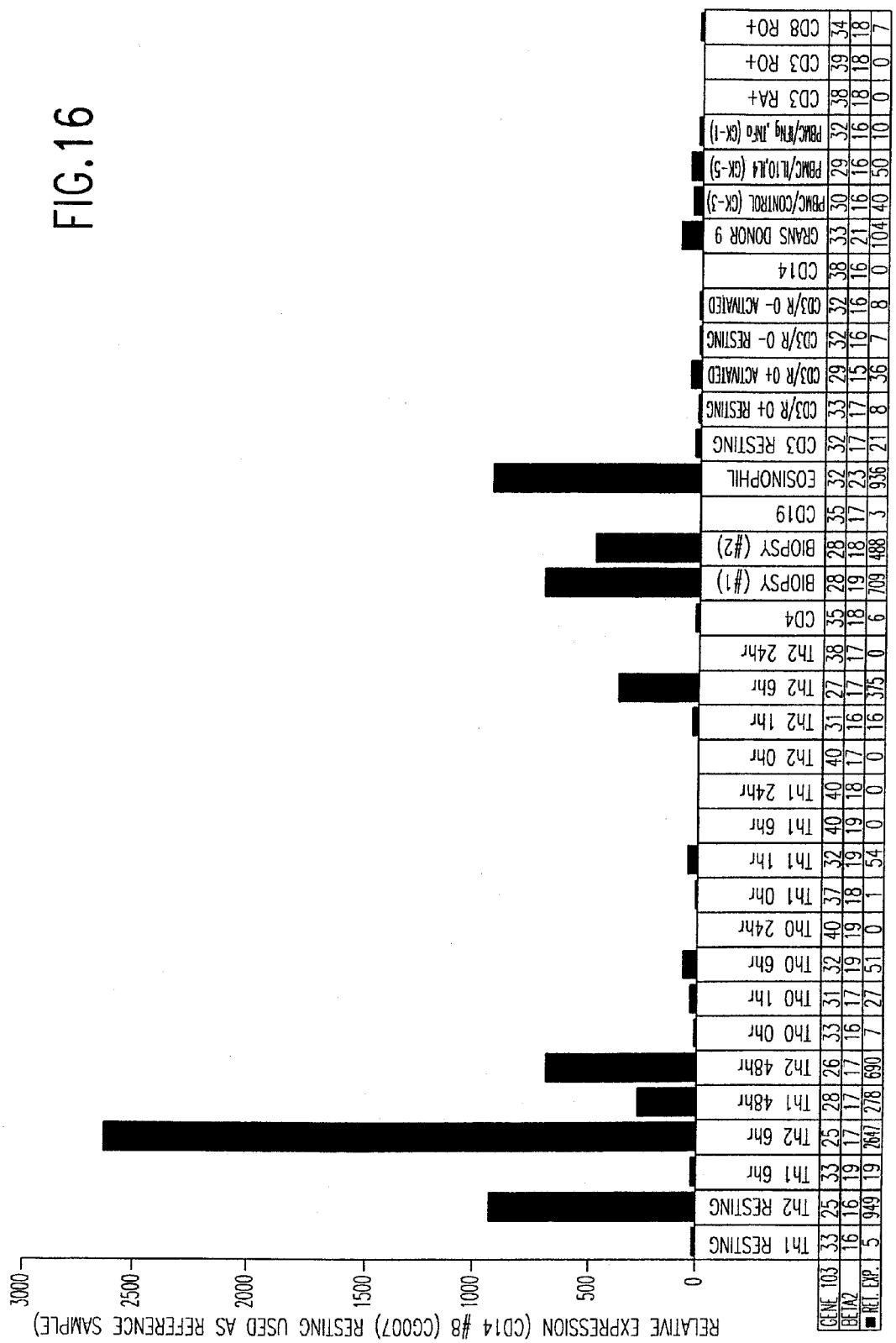
Figure 17A:
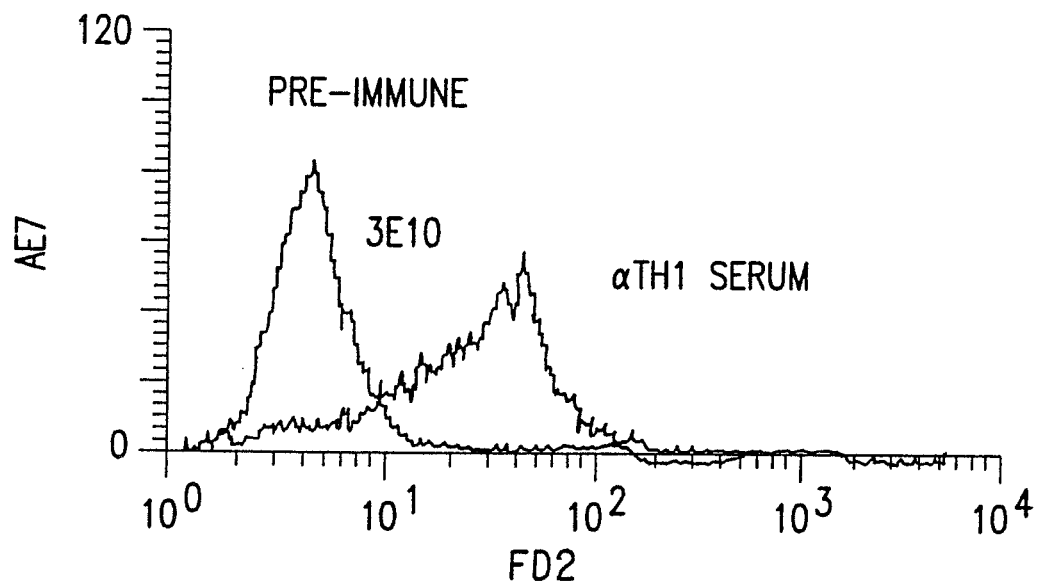
Figure 17B:
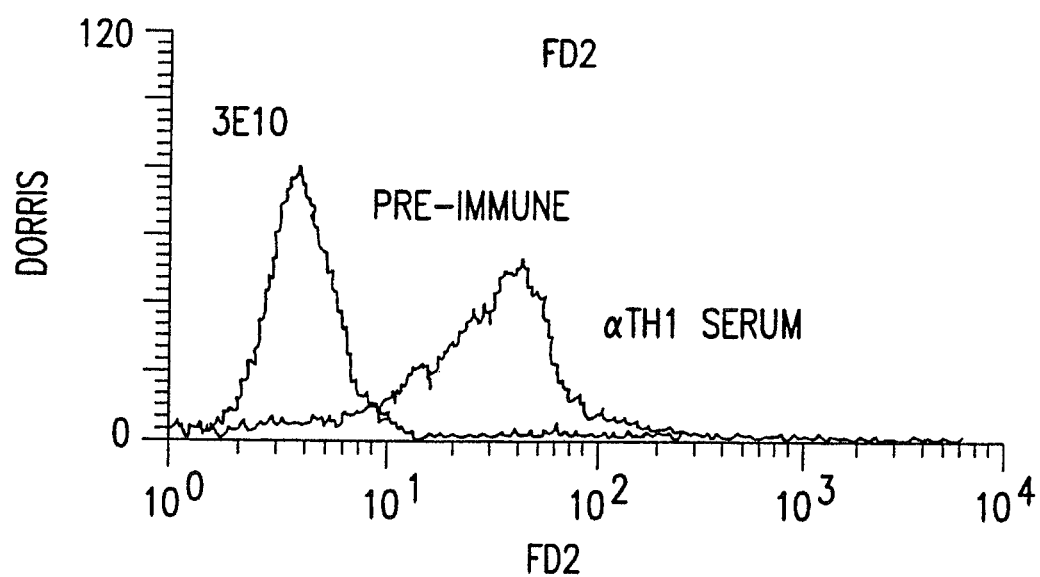
Figure 17C:
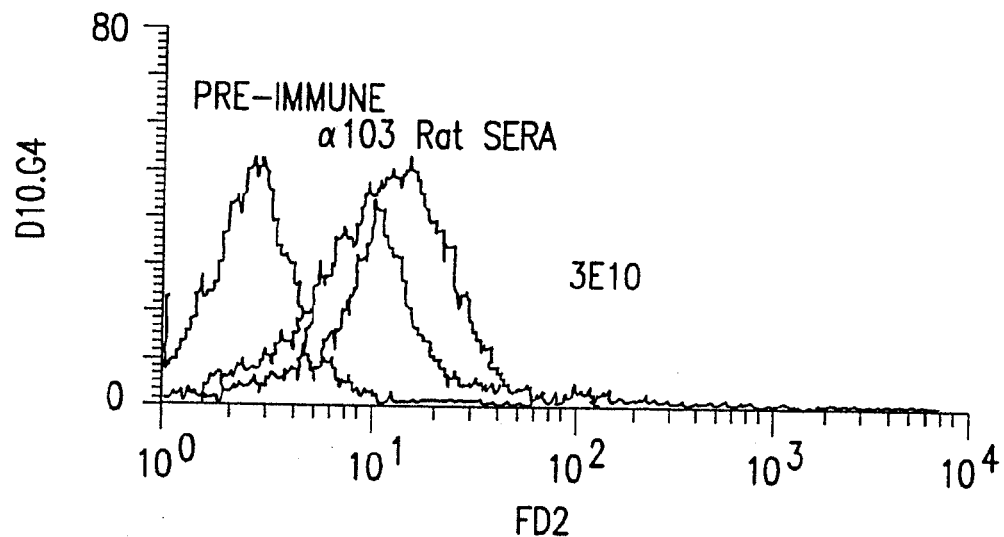
Figure 17D:
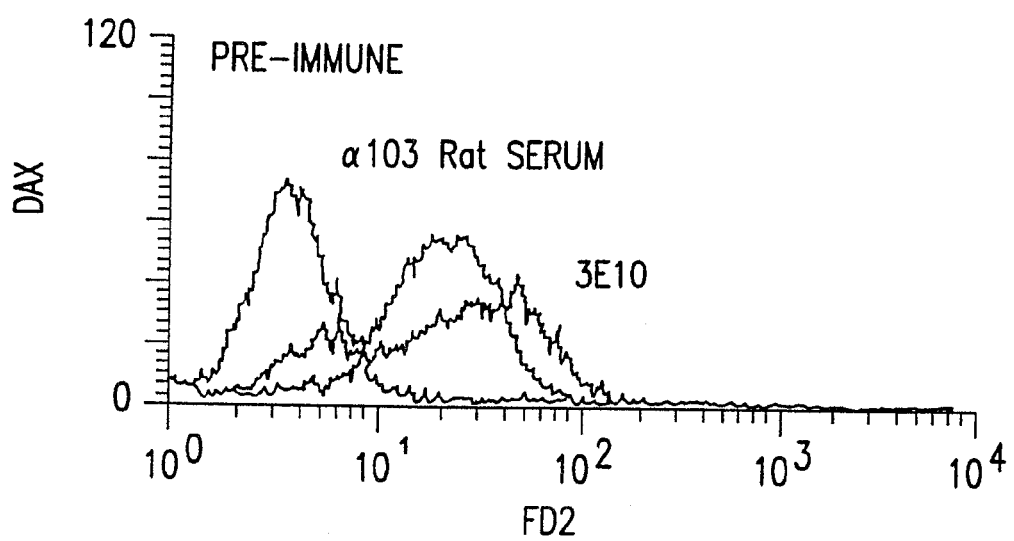
Figure 18A:
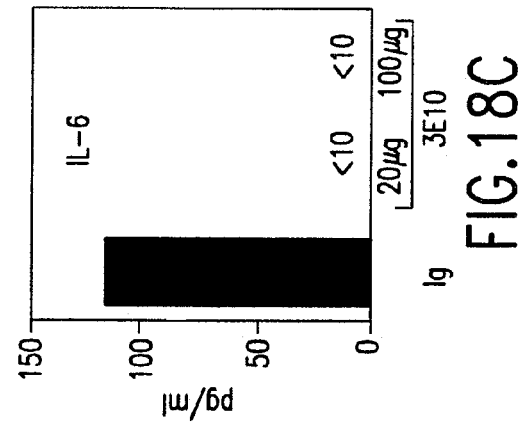
Figure 18B:
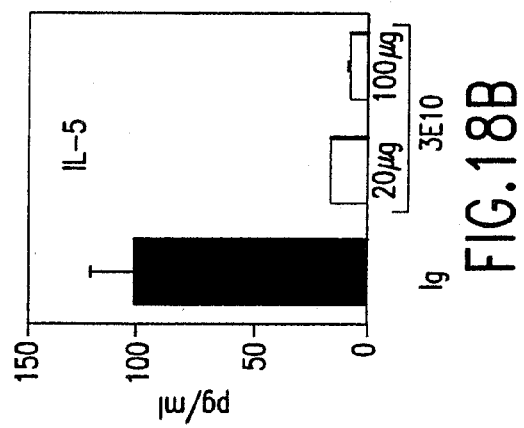
Figure 18C:
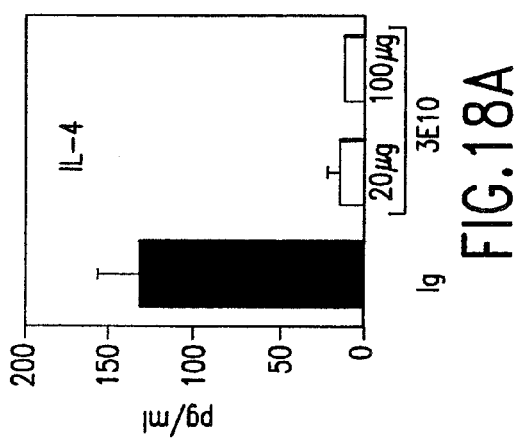
Figure 18D:
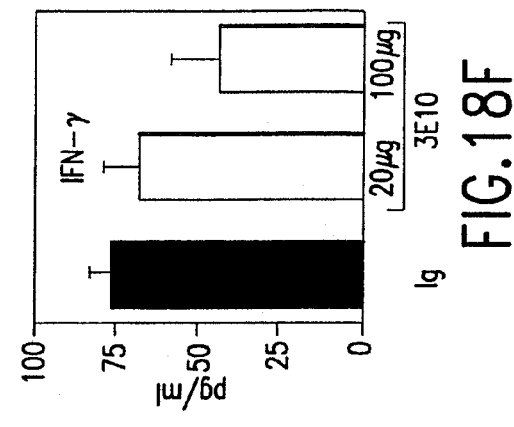
Figure 18E:
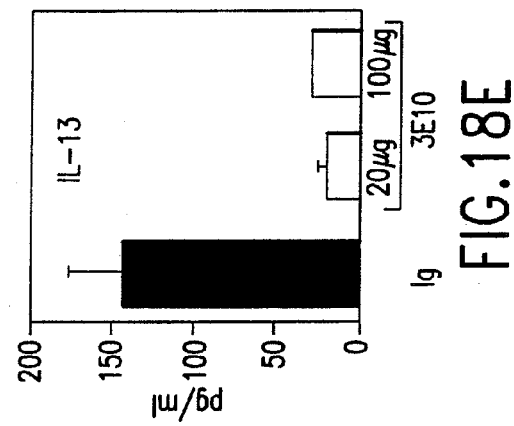
Figure 18F:
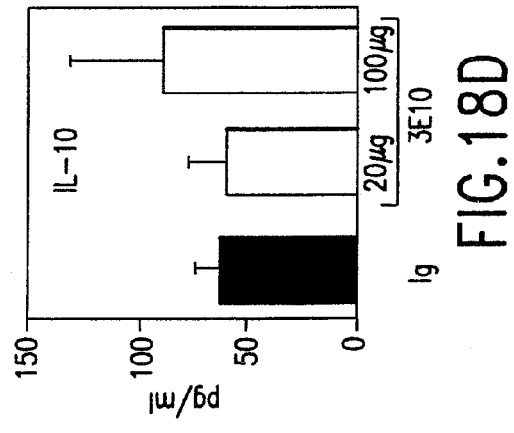

FIG. 16 shows expression of the soluble and transmembrane forms of human 103 as determined in a broad panel of cells as described above, relative to human 103 expression in resting CD14+ cells. The results indicate that expression of human 103 was detectable in resting Th0 cells, Th0 stimulated for 1 and 6 hours with anti-CD3 antibody, Th1 stimulated for 1, 6, and 48 hours with anti-CD3 antibody, TH2 cells, TH2 cells stimulated for 1, 6 and 48 hours with anti-CD3 antibody, eosinophils, granulocytes, resting PBMC, and PBMC stimulated with IL-10 and IL-4. The high expression observed among the hematopoietic cell populations analyzed was seen in resting and stimulated Th2 cells. The pattern of expression indicates that mRNA synthesis of human 103 transiently increases following stimulation with anti-CD3 antibody. The results also indicate that expression of human 103 was detectable in biopsies obtained from the asthmatic individuals exposed to antigen.

6.3. CONSTRUCTION AND EXPRESSION OF 103 GENE IgG1 FUSION PROTEINS

Described in this example is the construction and expression of IgG1 proteins. Specifically, the construction of exemplary murine 103 gene IgG1 fusion proteins is described.

6.3.1. MATERIALS AND METHODS

Generation of the Vector Encoding the Marine 103 Gene-hIgG1 Fusion Protein:

The construction of a vector encoding a soluble Ig-fusion protein (size: approximately 60 kD) containing a murine 103 gene product extracellular domain (but lacking the 103 gene product signal sequence) was constructed as described here. The CD44 portion of the pCD5-CD44-IgG1 vector (described above) was replaced with a nucleotide sequence encoding the 103 gene product extracellular domain. The 103 gene product extracellular domain sequence of the Ig-fusion protein consisted of 103 gene product amino acid residues 27-342 (i.e., the 103 gene product portion ending with amino acid sequence Ile-Val-Ala-Gly-Cys-Ser).

The fragment encoding the 103 gene product extracellular domain was amplified by PCR using synthetic oligonucleotides complementary to the sequences flanking the 103 gene region that would produce the 103 gene product containing amino acid residues 27-341. The oligonucleotides were designed to allow creation of a KpnI site at the 5' end and a BamHI site at the 3' end of each amplified 103 gene fragment to facilitate subsequent insertion into pCD5-CD44-IgG1.

The 5' oligonucleotide was as follows:

(SEQ ID NO: 24)
5'-CCGCGGGTACCAGTAAATCGTCCTGGGGTGG-3'.

The 3' oligonucleotide was as follows (SEQ ID NO: 25)
5'-AAATAAAGGATCCCTACATCCAGCAACTATGTAGTA-3'.

PCR reaction conditions consisted of 15 cycles of 30 seconds at 95° C., 30 seconds at 60° C., and 30 seconds at 72° C., using Vent DNA polymerase (New England Biolabs, Beverly, Mass.) and 103L gene as template.

103 PCR products were digested with KpnI and BamHI, and ligated to KpnI-BamHI sites of CD5-IgG1 vector, thus replacing the CD44 sequences with the 103 gene sequences.

The resulting plasmid, encoding a fusion protein containing CD5-signal sequence, murine 103-extracellular domain and human-IgG1 heavy chain Fc region, was transfected into COS cells using LipofectAMINE™ (GIBCOBRL, MD) following manufacturer's suggestions. 0.18 µg plasmid DNA and 140 µl LipofectAMINE™ were used for transfection of the cells of a 150 mm plate. Twenty-four hours after transfection, medium was replaced with 10% Ultra-low IgG Fetal Bovine Serum (GIBCOBRL, MD)/DMEM (BioWHITTAKER, Maryland), and the transfected cells were allowed to grow for 4-5 days continuously. Supernatants were then harvested, centrifuged to remove nonadherent cells and debris, and stored at −20° C.

For purification, 1 ml of supernatant was precipitated overnight with 1 µl of IPA-300 Immobilized rProteinA (Repligen, Mass.) at 4° C. The next day, beads were collected by centrifugation and washed three times with 10 volumes of PBS. For analysis, the beads were suspended in 20 µl of 2× Laemmli Sample Buffer (BIO-RAD, CA) and boiled at 100° C. for 10 min. The boiled sample was spun briefly and loaded onto a 10% SDS-PAGE gel (JILEinc. CT).

Metabolic Labelling of Recombinant Fusion Protein:

36 hours after transient transfection of COS-7 cultures, cells were rinsed with replacement growth medium [DMEM methionine and cysteine depleted (ICN, Inc., CA)]. After rinsing, 150 µCI/ml medium of a mixture of $^{35}$S-cysteine and $^{35}$S-methionine (Express $^{35}$S$^{35}$S™, Dupont, Mass.) was added to the replacement medium and the cells were cultured overnight.

Analysis of Recombinant Protein by SDS Page:

hIgG1 fusion proteins were generated by LipfectAMINE™ (Gibco, Inc., MD)-mediated transient transfection of COS-7 cells according to manufacturer's suggestion for 200 gene-hIgG1 fusion proteins, 1 ml of day 5 supernatant was mixed with 20 µl of Protein A Trisacryl bead (Pierce, Inc., IL) in the presence of 20 mM HEPES (pH 7.0) overnight at 4° C. with constant agitation. Beads were then washed 3× with PBS prior to the addition to loading buffer. Beads were mixed with either reducing or non-reducing loading buffers (described in, *Molecular Cloning*, Sambrook, Fritsch, and Maniatis, 2nd edition, 1989, with the exception that DTT was replaced with 2.5% β-mercaptoethanol).

6.3.2. RESULTS

The construction and expression of recombinant IgG fusion proteins is described herein. Specifically, an exemplary 103 gene product-IgG1 fusion protein is described. The 103 gene product-IgG1 fusion protein contains a CD5 signal sequence and 103 gene product extracellular domain fused to a human IgG1 heavy chain Fc region.

103 gene-hIgG1 fusion proteins were produced by transient transfection of COS-7 cells, as described in Section 6.3.1, above. Protein A immunoprecipitation of the COS-7 supernatants and their analysis by SDS-PAGE demonstrated, first, that the correct IgG-1 peptide was being produced as part of the fusion (as evidenced by the fusion's protein A immunoprecipitation) and, second, demonstrated substantial expression of the 103 gene-IgG1 fusion protein at a concentration approximately 1 µg/mL of culture supernatant. Further, when the immunoprecipitated supernatants are analyzed and compared under reducing and non-reducing conditions, it is clear that the 103 gene-IgG1 fusion protein undergoes oligomerization, as expected, given the human IgG1 heavy chain peptide sequence present in the fusion protein. Further, the size (i.e., larger than expected from the amino acid sequence alone) and appearance of the fusion proteins as they migrate through the gels (i.e., diffuse, rather than tight bands) indicate that, as expected, the fusion proteins have been glycosylated.

6.4. PRODUCTION AND CHARACTERIZATION OF GENE 103 TRANSGENIC ANIMALS

Described herein is the production and characterization of transgenic mice that over-express murine 103 gene products.

6.4.1. MATERIALS AND METHODS

Construction of 103 Gene Transgenic Clone:

A PCR product of the entire 103 gene sequence was used to replace the IL-10 gene in the pCIL-10 plasmid. The pCIL-10 plasmid was as described in this Section, above. A PCR product of the entire murine long form of the 103 gene (Yanagisawa, K. et al., 1993, FEBS 318:83-87) coding sequence was obtained through 35 cycle-reaction using first-strand cDNA from a mouse TH2-type cell line, D10G4 (ATCC, MD), as template. Total RNA was extracted from the cell line by RNAzole™ (TEL-TEST, Inc., TX). Seven micrograms RNA were used in a 20 µl first-strand cDNA synthesis reaction by Superscript Reverse Transcriptase I (GIBCO BRL, MD) following manufacturer's suggestion. Two microliters of cDNA were used in PCR reaction. The 5'-oligo was:

(SEQ ID NO: 26)
5'-GAACACACTAGTACTATCCTGTGCCATTGCCATAGAGA-3', and the 3'-oligo was:

(SEQ ID NO: 27)
5'-GGAATATTGGGCCCTTGGATCCCAAGTCTGCACACCTGCACT
CC-3', with compatible restriction sites SpeI at 5'-end and BamHI at 3' end, respectively. After heat denaturation at 95° C. for 2 minutes, 3-step cycling was performed at 45 seconds at 95° C., 45 seconds at 65° C. and 60 seconds at 72° C. by Vent™ DNA polymerase (New England Biolabs, Beverly, Mass.). A final step for five minutes, at 72° C., was performed for end-polishing. The PCR product was digested by SpeI and BamHI (New England Biolabs) and ligated into the SpeI-BamHI sites of pBSKIIGH vector, containing the human growth hormone fragment from pCIL-10 subcloned into the BamHI-XhoI site of pBSKII (Stratagene), which was named pBS-103L-GH. The pCIL-10 fragment containing human CD2 enhancer and Pµ promoter was then ligated immediately upstream of the 103L gene of pBS-103L-GH. MaxEfficient *E. coli* DH5α competent cells (GIBCO BRL, MD) were used for transformation following manufacturer's suggestion. The transformants were grown in LB broth containing 0.1 µg/ml ampicillin and DNA were extracted by Qiagene Plasmid Maxi Kit (Qiagene, Calif.). Restriction analysis was performed for confirmation, and the construct was sequenced to eliminate any possible PCR introduced mutations. A plasmid designated pCD2-103L-GH1 was selected for production of transgenic mice.

Production of Transgenic Mice:

C3H/HEJ and FVB/NJ mice were obtained from the Jackson Laboratory (Bar Harbor, Me.). Females aged 3-4 weeks were induced to ovulate by intraperitoneal injection of pregnant mare's serum (PMS) between 10 a.m. to 2 p.m., followed 46 hours later by intraperitoneal injection of human chorionic gonadotropin (hCG). Following hCG administration, the females were housed overnight with males of the same strain. The following morning females were examined for the presence of a copulation plug and embryos were isolated from those females with plugs, essentially as described in *Manipulating the Mouse Embryo* (Hogan et al., eds., Cold Spring Harbor Laboratory Press, 1994).

DNA for embryo microinjection was prepared by digesting of pCD2-103L-GH1 with NotI and XhoI followed by gel electrophoresis. The 9 kb and 10 kb fragments, respectively, were electrophoresed onto an NA-45 membrane (Schleicher and Schuell) by cutting a slit into the gel immediately in front of the desired band, inserting the NA-45 membrane and continuing electrophoresis until the DNA band has been transferred to the membrane. The DNA was eluted from the membrane by incubation with 0.4 ml of 1M NaCl/0.05M arginine-free base at 65-70° C. for several hours in a microfuge tube. The eluted DNA was extracted with phenol/chloroform and chloroform, ethanol precipitated and dissolved in 200 µl of 5 mM Tris, pH 7.5/0.1 mM EDTA. The DNA was then re-precipitated with ethanol and re-dissolved in 40 µl of 10 mM Tris, pH 7.5/0.1 mM EDTA. Prior to microinjection, the DNA was diluted to 1-2 µ/ml in 10 mM Tris, pH 7.5/0.1 mM EDTA.

DNA was microinjected into the male pronuclei of strain C3H/HEJ or FVB/NJ embryos and injected embryos were transferred into the oviducts of pseudopregnant females essentially as described in *Manipulating the Mouse Embryo*. The resulting offspring were analyzed for the presence of transgene sequences by Southern blot hybridization of DNA prepared from tail biopsies.

Southern Blot Analysis of Transgenic Alice:

Approximately ½" piece of tail was clipped and digested in 500 µl proteinase K solution [containing 100 mM Tris HCl, pH 8.0; 5 mM EDTA, pH 8.0; 0.2% SDS; 200 mM NaCl; 100 µg/ml Proteinase K (Boehringer Mannheim, Germany)] at 55° C. overnight. Digests were centrifuged for 15 minutes to remove undigested debris. Supernatants were precipitated with an equal volume of isopropanol at room temperature. Precipitates were centrifuged for 25 minutes and pellets washed in 75% ethanol. Pellets were air dried and resuspended in 100 µl TE; pH 8.0. Restriction digests of tail DNA were performed as follows: 20 µl DNA solution was digested with 80 units BamHI (New England Biolabs) in the presence of 1 mM spermidine overnight at 37° C. Digested samples were analyzed by gel electrophoresis using 0.8% agarose gels. Separated DNA was transferred to Hybond-N+ (Amersham, Inc.) following depurination in 0.25M HCl for 10 minutes followed by 0.5 M NaOH, 1 M NaCl for 30 minutes, and then 2.5M Tris-HCl (pH 7.4), 2.5M NaCl for 30 minutes. Immediately prior to transfer, gels were briefly equilibrated in a 10×SSC transfer buffer. Transfer was carried out overnight in 10×SSC by capillary action. After transfer, the membrane was air dried and UV-crosslinked using a Stratolinker (Stratagene, Inc.). After crosslinking, membranes were rinsed briefly in 2×SSC.

For 103 gene transgenic animals, a $^{32}$P-radiolabelled PCR fragment of the pCD2-103L-GH construct described above was utilized. The PCR fragment was generated using the following primers:

```
5'-oligo:
                                        (SEQ ID NO: 28)
5'-GTA-AAT-CGT-CCT-GGG-GTC-TGG-3';

3'-oligo:
                                        (SEQ ID NO: 29)
5'-CCT-TCT-GAT-AAC-ACA-AGC-ATA-AAT-C-3'.
```

Using these oligonucleotide primers and the pCD2-103L-GH template, PCR reactions conditions were as follows: 20 cycles of 30 seconds at 94° C., 30 seconds at 60° C. and 30 seconds at 72°, using Vent™ DNA polymerase (New England Biolabs, Beverly Mass.). Upon hybridization to mouse genomic digested with EcoRI and SpeI, the resulting probe hybridized to an endogenous 2.4 kb band and a 0.85 kb transgenic-specific band.

6.4.2. RESULTS 103 gene transgenic mice (five FVB founder lines) were produced according to the method described above, in Section 6.4.1. Southern hybridization analysis demonstrated the successful production of 103 gene transgenic founder animals.

6.5. THE 103 GENE PRODUCT EXHIBITS A CRITICAL ROLE IN REGULATING TH2 EFFECTOR CELL RESPONSES

This example presents in vivo data demonstrating that the 103 gene product regulates TH2 effector cell responses. In particular, the example describes generation of a monoclonal antibody, referred to herein as 3E10 mAb, against the 103 gene product. The effect of the monoclonal antibody 3E10 mAb in an in vivo adoptive transfer model of TH1 and TH2 immune responses is also described. Further, the example also describes the effect of a 103 gene product fused to an Ig tail (103/Ig fusion) in the adoptive transfer model.

Specifically, the anti 103 gene product mAb is shown to abrogate, in the in vivo adoptive transfer model, the production of IL-4, IL-5, IL-6 and IL-13, TH2 mediated lung inflammation and the associated airway hyperresponsiveness. The data also demonstrates that the 103/Ig fusion results in a decrease in eosinophil infiltration into and inflammation of lung airways in the model. In contrast, the 103 gene product mAb failed to inhibit TH1-mediated lung pathology and IFN-γ secretion. The results therefore provide in vivo animal data indicating that the 103 gene product provides a critical signal to TH2 effector cells and can be utilized as a novel target for the selective suppression of TH2 immune responses, e.g., in immune disorders such as asthma and allergy. In particular, the data presented herein demonstrates that monoclonal antibodies that specifically bind to a 103 gene product, including the 3E10 mAb disclosed herein, can be used to effectively treat symptoms of immune disorders such as allergy and asthma in vivo.

6.5.1. MATERIALS AND METHODS

CD3/TCR Crosslinking:

Mice expressing the transgene for the DO11.10 αβ-TCR, which recognizes residues 323-339 of chicken ovalbumin (OVA) in association with I-A$^d$ (Murphy, K. M., et al., 1990, Science 250:1720-1723) were utilized. DO11.10 TCR-transgenic CD4$^+$ T cells were cultured in complete RPMI 1640 with OVA$_{323-339}$ (1 μM) and mitomycin C-treated splenocytes. For TH1 phenotype development, recombinant murine Il-12 (10 ng/ml) and neutralizing anti-IL-4 mAb (11B11, 40 μg/ml, R&D Systems) were added and for TH2 development recombinant murine IL-4 (10 ng/ml) and neutralizing polyclonal anti-murine IL-12 (TOSH-2, 3 μg/ml, Endogen, Cambridge, Mass.) were used. Cultures were maintained for 48 hours and 5 days after stimulation, after which time cells were harvested and purified over ficoll. 1×10$^7$ cells were washed and RNA extracted as described below. The remainder of the cells were stimulated on plate bound anti-CD3 in the presence of h IL-2 (Endogen) for 48 hrs.

Anti-103 Monoclonal Antibodies:

Rat monoclonal antibodies (MAbs), including the 3E10 MAb, were generated against the extracellular domain of the mouse 103 gene product. A DNA sequence containing the extracellular domain of 103 gene product was PCR-amplified and cloned into a vector containing the CD5 signal sequence and the human IgG1 constant region. COS cells were transiently transfected using Lipofectamine™ (GIBCO) protocol according to manufacturer's instructions. Cells were cultured in Ultra-Low™ Ig fetal bovine serum (GIBCO) for approximately one week prior to harvest and the recombinant protein was purified by passage over a protein A column.

Lou/M rats were then immunized by subcutaneous injection of 0.5 mg purified recombinant 103 gene product protein. Rats were boosted twice via intraperitoneal injections at 2 week intervals with approximately 300 μg purified protein. Animals were analyzed for reactivity to the fusion protein by FACS and ELISA approximately 10 days after the last boost. Four weeks later, positive reacting animals were boosted once more and sacrificed 3 days later. Splenocytes were fused with SP/2 myeloma cells and resulting clones were screened and selected to be specific for the 103 gene product on the basis of their reactivity against 103 gene product Ig, but not CD44-Ig, and their ability to stain 103 gene product COS transfectants, but not control transfectants. Pre-immune serum from non-immunized Lou/M rats was used as negative-controls.

One of these mAbs was identified and termed 3E10.

Surface Expression of 103 Gene Product on TH2 Clones and TH2 Effector Cells:

The 3E10 mAb was labeled with digoxigenin and the number of 103-positive cells were detected by anti-digoxigenin Fab fragments (Boehringer Mannheim) conjugated to Cy5.

CD4 positive, L-selectin negative cells were isolated using high gradient magnetic cell separation system MACS (Milteny; Biotec, Berg-Gladbach). Expression of 103 was analyzed on a fluorescence-activated cell sorter (FACS)-calibur (Becton-Dickinson) five to seven days after restimulation with OVA peptide under the indicated polarizing conditions.

In Vitro Activation of TH2 Effector Cells:

TH2 effector cells were activated with plate-bound CD3 (1 μg/ml, 2C11) and CD28 (37.51, 4 μg/ml, Pharmingen, San Diego) and 3E110 (20 μg/ml) for 48 hours. IL-4 and IL-5 levels were measured in the supernatant by Elisa.

RNA Isolation:

Total cellular RNA for RT-PCR analysis was extracted from cells using the Rneasy Total RNA kit (Qiagen; Chatsworth, Calif.). Poly A+ RNA (for Northern analysis) was isolated from activated cells using FastTrack mRNA Kit (Invitrogen Corp.; San Diego, Calif.).

Northern Analysis:

1.0 μg RNA were loaded per lane for the Northern blot analysis. The 103 gene probe was a 409 by RsaI fragment from the 103 gene cDNA (position 1252-1661 based on the published sequence for Genbank accession number D13695). IL-4 and beta-actin probes were purchased from Clontech, Inc., Palo Alto, Calif. IFN-γ probe consisted of a 344 bp fragment of murine IFN-γ covering the region from position 532-876 (GenBank accession number M28621). Northern blot analysis was carried out according to standard techniques.

RT-PCR:

First strand cDNA was synthesized from equal amounts of RNA using the Superscript Preamplification System (Life Technologies; Gaithersburg Md.). PCR was performed using 25 ng of first-strand cDNA. The following gene-specific primers were used for PCR amplification:

```
Gene 103:
                                (SEQ ID NO: 30)
5'-ACGGAGGGCAGTAAATC-3',
and (SEQ ID NO: 31)
5'-CAGCCAAGAAGTGAGAGC-3';

IFN-gamma:
                                (SEQ ID NO: 32)
5'-TGTTGCCGGAATCCAGCCTCAG-3',
and (SEQ ID NO: 33)
5'-GTCCCCCACCCCCAGATACAACC-3'.
```

Primers for glyceraldehyde 3-Phosphate Dehydrogenase (G3PDH) and IL-4 were purchased from Clontech Laboratories (Palo Alto, Calif.).

PCR was carried out using the Advantage KlenTaq Polymerase mix (Clontech Laboratories; Palo Alto, Calif.) according to the provided protocol; annealing temperature 56° C. Samples were removed from the PCR reaction beginning after 15 cycles and then after 5-cycle increments. Reactions using the minimum number of cycles to visualize the gene of interest, were loaded onto 1.5% agarose gels for analysis.

TH Recipient Mice:

TH1 and TH2 subsets were generated as described above. Mice were injected with 2×10$^6$ TH2 cells intravenously into recipient BALB/c mice. Twenty four hours later, mice were exposed daily to an aerosol of OVA (50 mg/ml) (Grade V, Sigma, St. Louis) for 20 min for 2 consecutive days. Control mice were either injected with TH2 cells and exposed to an aerosol of PBS or were exposed to OVA in the absence of cell transfer. Mice were sacrificed 24 hrs after the last aeroallergen challenge. One hour prior to allergen exposure, mice were injected with either 20 μg or 100 μg of 3E10 mAb, recombinant 103 gene product-IgG fusion protein, or 100 μg of rat IgG1 (Sigma, St. Louis) as the appropriate isotype control. Twenty fours after the last challenge, the trachea was cannulated and a bronchoalveolar lavage performed with 4×0.3 ml aliquots of PBS (Gonazlo, J. A., et al., 1996, Immunity 4:1-14). Cytokine levels in the lavage fluid were measured by ELISA (PharMingen, San Diego).

Flow Cytometry Analysis of TH Clones:

AE7 (TH1), Dorris (TH1), DAX (TH2) and D10-G4 (TH2) clones were analyzed for the expression of gene 103 protein using fluorescence activated cell sorting (FACS). Cells were stimulated with appropriate antigen and cultured for approximately 3 days prior to analysis. Pre-immune serum was prepared for unimmunized Lou/M rats.

50 μl of 3E10 culture supernatant (or 1 μg purified 3E10 protein) was applied 1×10⁶ cells. After rinsing, cells were contacted with goat anti-rat antibody conjugated with PE (R-phycoerythrin) fluorescent dye. After a final rinse, cell analysis was carried out on a FACS Vantage (Becton Dickenson).

103/Ig Fusion Protein:

The 103/Ig fusion proteins were generated as discussed, above, in the Example presented in Section 6.3.

Cell Preparation and Polarization:

Spleens from DO11.11 OVA αβ TCR mice were removed and CD4+ T cells were purified by negative selection. Cells were plated at a density of 1×10⁶/ml in 75 mm² flasks and stimulated with 10 μg/ml OVA peptide and mitomycin C treated splenocytes at a ratio of 1:1 CD4: APC. Cells were cultured in the presence of IL-4 (20 ng/ml) and anti-IL-12 (3 μg/ml) for TH2 polarization, or IL-12 (20 ng/ml) and anti-IL-4 (40 μg/ml) for TH1 polarization. This procedure was repeated for 3 rounds of polarization. Cells were then harvested, dead cells removed by density centrifugation. TH1 and TH2 cells were then incubated at 1×10⁶/ml for 48 hrs in IL-2 alone (10 ng/ml).

Adoptive Transfer Model:

2×10⁶ cells were injected intravenously via the tail vein into recipient transgenic mice. Twenty four hours later, mice were exposed daily to an aerosol of OVA (50 mg/ml) antigen (Grade V, Sigma, St. Louis) for 20 minutes. Control mice were exposed to an aerosol of PBS alone. Mice were sacrificed on days 3, 5 and 7. In separate experiments, mice received 20 μg/mouse i.v. of either 3E10 mAb or the 103 Ig fusion protein. Control mice were injected with 20 μg of either rat or human Ig as the appropriate isotype control. This procedure was repeated for two consecutive days.

24 hours after the last challenge, mice were anaesthetized with 0.3 ml of 14% urethane i.p. and the trachea cannulated. A bronchoalveolar lavage (BAL) was performed by injecting 0.3 ml of PBS into the lungs. The fluid was then withdrawn and stored on ice. This procedure was repeated a total of 4 times. The cell suspension was then centrifuged (5 mins, 1500 rpm, 4° C.) and the supernatant removed and frozen at −20° C. The cell pellet was then resuspended in 1 ml of PBS and total cell counts were obtained. Cytospin® (Shandon, Inc., preparations were then prepared and stained with Diff-Quik (Baxter Corporation). A total of 200 cells were then counted differentially using standard morphological criteria. Cytokine levels were measured in the BAL fluid by ELISA (Pharmingen, San Diego).

Active Immunization Protocol and IgE Measurement:

Male BALB/c mice (15-20 g) were immunized intraperitoneally with 7.5 μg of OVA and 1.5 mg Al(OH)3 in saline on Day 0 and Day 7. On day 14 and Day 21 the mice were challenged with aerosolized OVA (10 mg/ml) for 1 hours. Control mice were challenged with PBS instead of OVA. One hour prior to each allergen sensitization and challenge, the mice were injected with 100 μg of 3E10 mAb or 100 μg of rat IgG1 (Sigma, St. Louis). Twenty-four hours following the second allergen challenge a BAL was performed and IL-5 levels in the BAL fluid determined. Serum OVA specific IgE was determined by specific ELISA.

Airway Responsiveness:

Airway responsiveness was measured in TH2 recipient mice, 24 hours after the last aerosol challenge by recording respiratory pressure curves by whole body plethysmography (Hamelmann, J. E., 1997, Am. J. Respir. Crit. Care Med. 156:766-775); Buxco®, EMKA Technologies, Paris, France) in response to inhaled methacholine (Aldrich-Chemie, Steinhein, Germany) at a concentration of 2.5 to 25 mg/ml for 1 minute. This method allowed measurements of spontaneous breathing in a non-restrained mouse. Airway responsiveness was expressed in enhanced pause (Penh), a calculated value, which correlates with measurement of airway resistance, impedance and intrapleural pressure in the same mouse. Penh=(Te/TR1)×Pef/Pif (Te=expiration time, Tr=relaxation time, Pef=peak expiratory flow, Pif=peak inspiratory flow) (Hamelmamn, J. E., 1997, Am. J. Respir. Crit. Care Med. 156:766-775).

Lung Histology:

Following the BAL analysis, lungs were inflated with 0.6 ml of a mixture of OCT compound (Tissue-kek®; Miles Inc., Elkhart, Ind.) and 20% sucrose (Sigma, St. Louis, Mich.) at a ratio of 1:1. The lungs were then removed, snap-frozen and 8-10 μm cryosections fixed in methanol at 20° C. for 2.5 minutes. Slides were stained with haematoxylin and eosin (Fluka Chemika, Buchs, Switzerland).

In Situ Hybridization:

Recipient Balb/C mice were injected intervenously with 2×10⁶ TH1 or TH2 cells generated as described above. Twenty-four hours later, mice were exposed to an aerosol of OVA (50 mg/ml; Grade V, Sigma) for 20 minutes for two consecutive days. Mice were sacrificed 24 hours after the last aeroallergen challenge. Lungs were removed and snap frozen for in situ hybridization. A 35-mer antisense oligonucleotide against 3'-UTR 103 gene sequence was synthesized and end-labeled as follows: 100 pmol oligo was incubated for 15 minutes at 37° C. with 10 nmol dATP (Promega), 40 μmol biotin-dUTP, 1× terminal transferase buffer, 5 mM $CoCl_2$, 50 units transferase (Boehringer-Mannheim, Germany). Formalin fixed 5 μm tissue sections were hybridized for 16-18 hours. Control slides were hybridized with probe mix containing 50-fold excess unlabelled oligo. Hybridized probe was detected with a biotinyl tyramide amplification method (Gen-Point, Dako) and visualized by addition of AEC substrate kit (Vector) for five minutes.

6.5.2. RESULTS

RT-PCR analysis performed herein demonstrates that the 103 gene is induced only upon CD3/TCR crosslinking during differentiation of TH0 to TH2, but not TH1 effector cells. The RT-PCR analysis was confirmed by Northern analysis. These data corroborate the results presented in the Example of Section 6.2, above.

To further investigate the expression and role of the 103 gene product in TH cells, a monoclonal antibody (3E10 mAb) directed against the extracellular domain of the 103 gene product was prepared and characterized.

Flow cytometry data is presented in FIG. 17 which demonstrates that the 3E10 mAb recognizes and binds to representative clones of the TH2 cell subpopulation (D10.G4; DAX), but not clones of the TH1 subtype (AE7; Dorris). For these experiments, cells were contacted with 3E10 mAb, preimmune serum (negative control) or a second antiserum (positive control; referred to as "αTH1 serum" for AE7 and Dorris, and "rat α103 serum" for D10.G4 and DAX). In contrast, this mAb failed to recognize resting or activated CD4+ (L-selectin), CD8+, B cells or macrophage cells.

When TH1 cells (AE7, Dorris) were analyzed, the peaks for 3E10 MAb and the negative preimmune serum exhibited the same very low level of staining as the negative control preimmune serum. No detectable 103 gene product is present, therefore, on the surface of the TH1 cells. In contrast, with TH2 cells (D10.G4, DAX), the 3E10 MAb peak shifted significantly to the right, demonstrating the presence of 103 gene product on the TH2 cell surface. It is noted that for each clone analyzed, the positive control peak is shifted well to the right of background levels, as expected.

In addition to the TH2-specific expression pattern observed in established TH clones as discussed above, 3E10 mAb staining and flow cytometry analysis was utilized to successfully demonstrate that 103 expression dramatically increases when freshly isolated TH cells are cultured under conditions that induce TH2 cell polarization, with the expression being dependent on the degree of differentiation of the TH2 phenotype. Such an increase was not observed naive CD4+ (L-selection negative) under TH1 cell polarization conditions (i.e., TH1 effector cells derived from the TH precursor cells).

As shown in FIG. 18, pretreatment of TH2 recipient mice with 3E10 mAb inhibited the secretion of IL-4, IL-5, IL-6 and IL-13 by greater than 90%. In particular, analysis of the cytokine profile in the BAL revealed high levels of IL-4, IL-5, IL-6, IL-10 and IL-13 in TH2 recipient OVA challenged mice (closed bars). There was no detectable TH2 cytokines in the BAL fluid of mice that received TH2 cells and were not exposed to ovalbumin. Pretreatment with 3E10 mAb resulted in a dramatic reduction in IL-4, IL-5, IL-6 and IL-13, but had no effect on IL-10 levels in the BAL (open bars). OVA challenge of TH1 recipient mice resulted in high levels of IFN-γ in the BAL fluid (closed bars) that was not inhibited by 3E10 mAb (open bars).

These data show that the 103 gene is differentially expressed in a TH2-specific manner, thereby corroborating the results presented in the Example of Section 6.1, above. In addition, the data demonstrate the feasibility of using antibodies to separate TH2 subpopulation cells away from other cell types, thereby modulating a TH cell subpopulation by changing the number of cells belonging to one TH cell subpopulation relative to that of another TH cell subpopulation.

An in vivo TH1 and TH2 adoptive transfer model (Cohn, L. et al., 1997, J. Exp. Med. 186:1737-1747) was used to address the role of the 103 gene product in TH cells. In this adoptive transfer animal model, aeroallergen provocation of TH1 or TH2 recipient mice results in TH effector cell migration to the airways and is associated with an intense neutrophilic (TH1) and eosinophilic (TH2) lung mucosal inflammatory response. The model represents an accepted animal model for asthma, a TH2-like disorder. In situ hybridization revealed a marked upregulation of 103 gene mRNA positive cells in lungs from allergen or PBS provoked TH2 recipient mice. In marked contrast there was no detectable 103 gene mRNA expression in lungs obtained from either OVA or PBS provoked TH1 recipient mice.

Figure 19A:
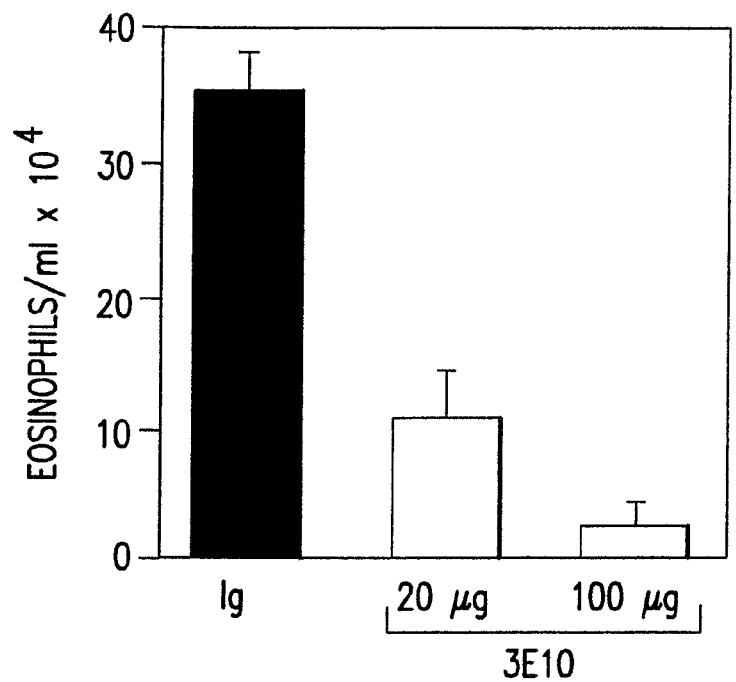
Figure 19B:
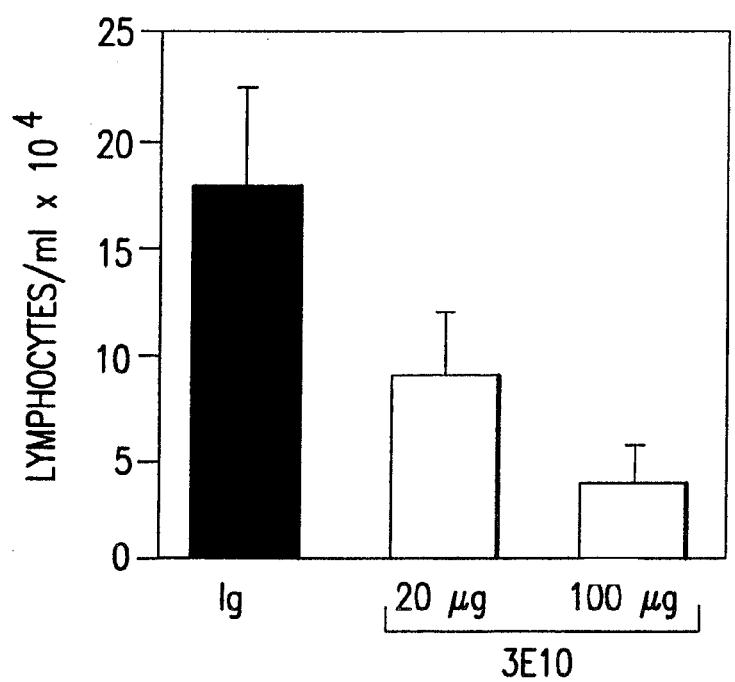

The animal model was used to investigate whether neutralization of the 103 gene product in vivo also abrogated TH2-mediated pathology. Allergen provocation of mice which had received TH2 cells and control rat Ig resulted in infiltration of lymphocytes and eosinophilic inflammation of the airways. In vivo administration of 3E10 mAb markedly suppressed the development of eosinophilic inflammation of the airways. In particular, eosinophilic inflammation was assessed, first, by histological analysis of the airway tissue. Second, an analysis of the cellular composition of the bronchoalveolar lavage fluid (BAL) was performed (FIGS. 19A-B). No significant reduction in the number of antigen specific TH2 cells that migrated into the airway interstitium after allergen challenge was observed.

In marked contrast to the effects on TH2 immune responses, 3E10 mAb treatment did not suppress IFN-γ secretion or neutrophilic lung inflammation induced by allergen challenge of TH1 recipient mice. It is also of interest to note that the anti-103 gene product mAb failed to inhibit IL-10 secretion, a cytokine that has been shown to suppress eosinophil infiltration and prevent IgE mediated mast cell activation.

TH2 mediated lung mucosal eosinophilic inflammation is associated with heightened airway responsiveness to non specific stimuli and is a characteristic feature of bronchial asthma (Ohashi, Y. et al., 1992, Am. Resp. Dis. 145:1469-76). To determine whether the 103 gene product is involved in this physiological consequence of allergen exposure, the degree of airway constriction induced by the methacholine inhalation was assessed using whole body plethysmography.

Figure 20:
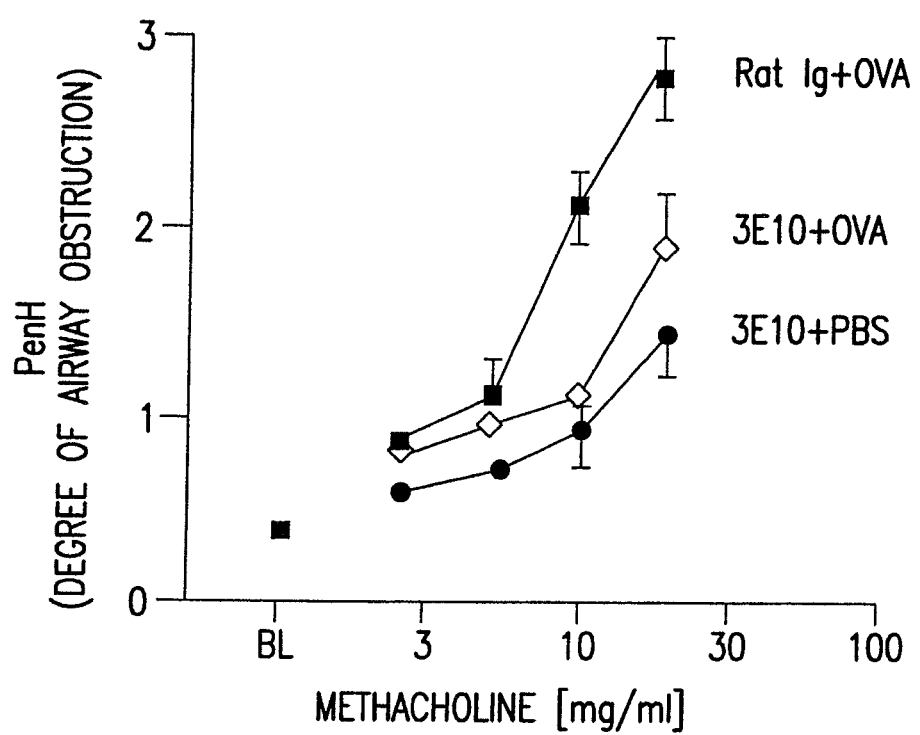

3E10 mAb treatment was, indeed, demonstrated to attenuate allergen induced heightened airway responsiveness. In particular, 3E10 mAb treatment suppressed the development of airway hyperresponsiveness induced by OVA challenge in TH2 recipient mice (FIG. 20). TH effects of treatment with 3E10 mAb were comparable to those previously reported using anti-IL-5 mAbs Wang, L. M., 1992, EMBO 11:4899-4908 and anti-B7-2 mAbs (Tsuyuki, S. et al., 1997, J. Exp. Med. 185:1671-1679).

Figure 21A:
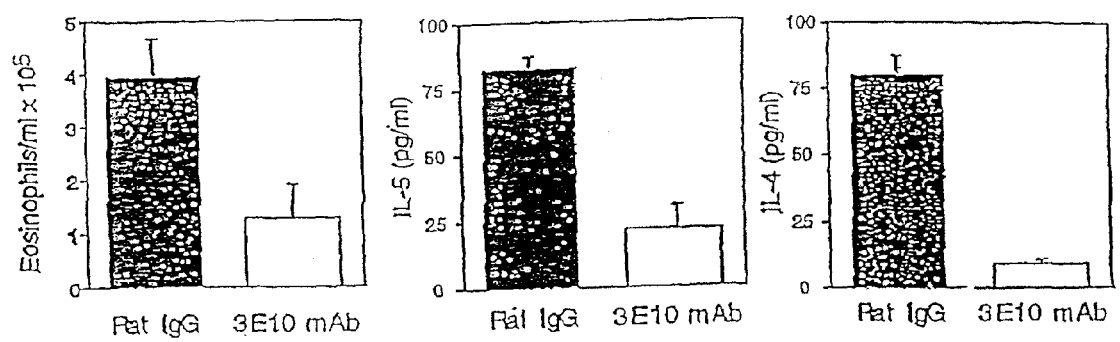
Figure 21B:
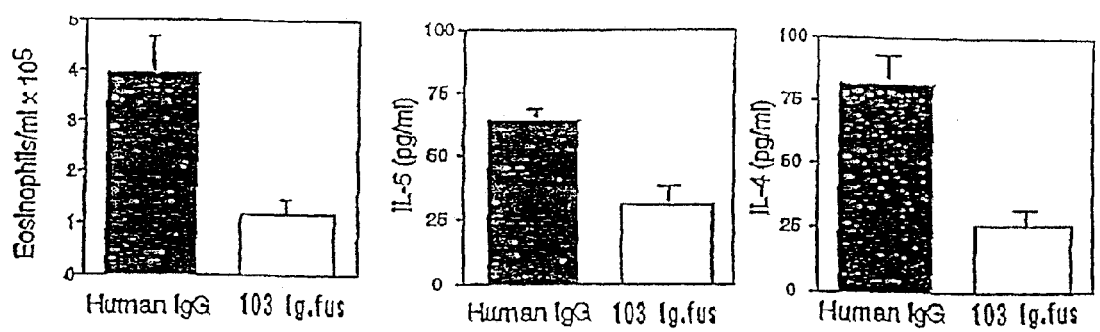

The role played by 103 gene in lung inflammation was also investigated in an active immunization model where mice were injected systemically with antigen and adjuvant prior to two repeated allergen provocations. As summarized in FIGS. 21A-B, administration of either 3E10 mAb or 103/Ig fusion results in a significant reduction in eosinophilic inflammation, as well as a significant reduction in IL-4 and IL-5 cytokine levels in the lung, which represent cytokine hallmarks of activated TH2 cell subpopulations. In addition, 3E10 mAb attenuated the induction of OVA specific IgE in the serum of the active immunization model. Still further, an approximate 60% reduction in airway hyperresponsiveness was observed after repeated aerosol challenge after active immunization.

Further, the level of interferon gamma was measured, which represents a hallmark of TH1 cell subpopulation activation, and an increase in its level was detected. This indicates the presence of a relative increase in TH1 cell subpopulation responses.

In addition, animals were treated with a soluble fusion protein containing the extracellular domain of the 103 gene product fused to an Ig tail (103/Ig fusion). Administration of the 103/Ig fusion results in significant decrease in hallmark symptoms of asthma. As summarized in FIG. 21B, such administration results in animals that exhibit a decrease in eosinophil infiltration into lung airways (this was assessed by both BAL and histological examination). Likewise, administration of the 103/Ig fusion resulted in a 50% attenuation in the degree of eosinophilic inflammation of airways.

Thus, the inhibition of 103 gene function appears to modulate TH cell subpopulations by decreasing the level and/or activity of TH2 cells while bringing about a relative increase in the level and/or activity of TH1 cells.

Figure 22A:
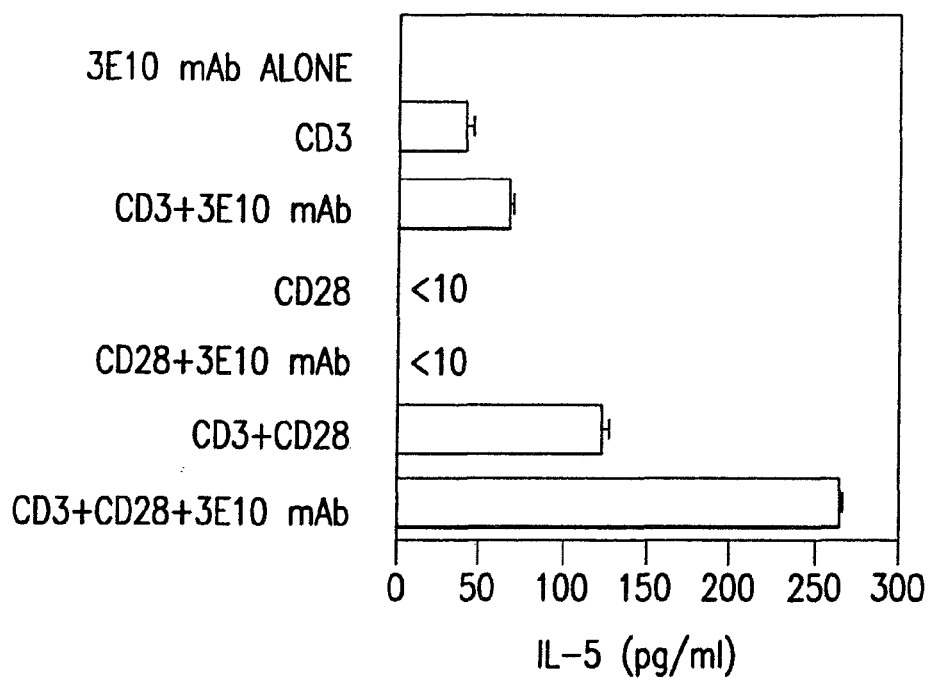
Figure 22B:
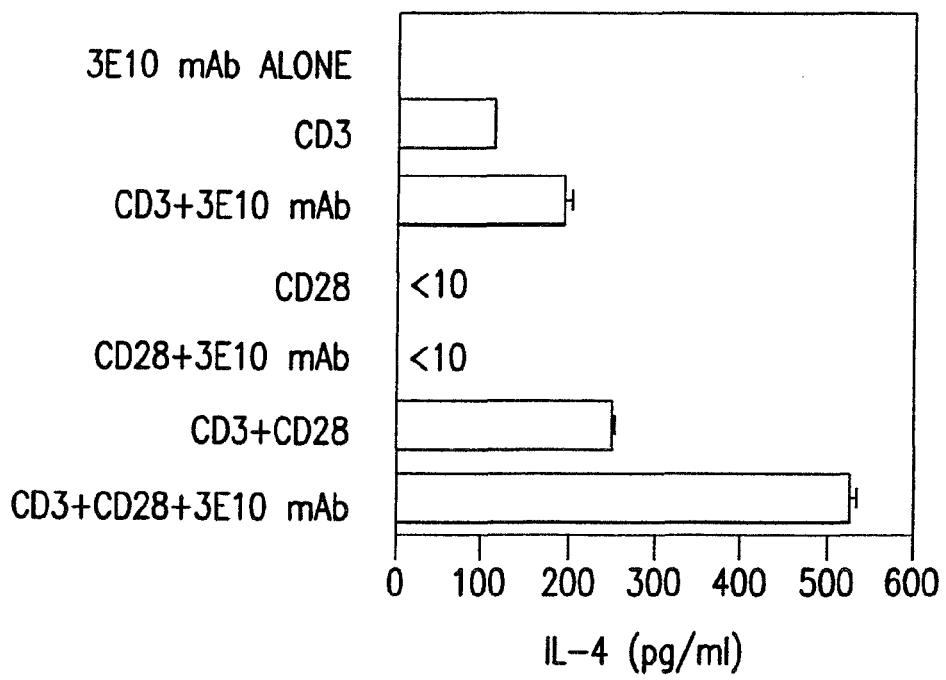

To determine whether signalling through the 103 gene product directly modifies cytokine production, TH2 effector cells were activated with plate bound CD3 and CD28. Under conditions where Fc crosslinking occurred, 3E10 mAb augmented IL-4 and IL-5 secretion in the absence of enhanced proliferation (FIG. 22). In contrast, CD3/CD28 stimulation of TH1 cells in the presence of plate bound 3E10 mAb failed to modify IFN-γ secretion. These results indicate that ligation of the 103 gene product in conjunction with signals delivered through the CD3/CD28 complex together with CD28 mediated co-stimulation provide a novel costimulatory signal specific for TH2 effector cells.

Recently, GATA-3 have been shown to be preferentially expressed in TH2 cells and suggested to play an important role in TH2 differentiation (Zheng, W.-P. & Flavell, R. A., 1997, Cell 89:587-596): Unlike GATA-3, however, the 103 gene product is induced upon CD3/TCR mediated activation and not during TH2 differentiation from TH0 cells. GATA-3 may be involved in TH differentiation, while the 103 gene product may be more involved during activation of TH2 effector cells. Further, the 103 gene promoter in murine mast cells contains a GATA-3 consensus binding sequence (Gachter, T. et al., 1996, J. Biol. Chem. 271:124-129), indicating that GATA-3 may be involved in the TH2 specific expression of the 103 gene.

In summary, these results provide both in vitro characterization of 103 gene expression and the 103 gene product, as well as in vivo animal data indicating that the 103 gene product provides a critical signal to TH2 effector cells and represents a critical regulatory molecule for both cellular and humoral allergic inflammation. These data indicate that the 103 gene and/or gene product can be utilized as a novel target for the selective suppression of TH2 immune responses. For example, the data presented herein demonstrates that monoclonal antibodies that specifically bind to a 103 gene product, including the 3E10 mAb disclosed herein, can be used to effectively treat symptoms of disorders such as allergy and asthma in vivo.

6.6. THE 103 GENE PRODUCT IS EXPRESSED IN HUMAN MAST CELLS

The example provided herein presents data demonstrating that the 103 gene product is expressed in mammalian mast cells. First, Northern analysis showed high levels of 103 gene expression in a human mast cell line. FAC staining of the human mast cell line demonstrated binding of anti-103 monoclonal antibodies, confirming that the 103 gene product is, indeed, expressed in human mast cells. It is noted that these antibodies, the production of which is also described hereinbelow, are specific for human, but not murine, 103 gene products.

6.6.1. MATERIALS AND METHODS

103 Fusion Proteins:

A human 103 IgG1 Fc fusion protein was constructed and utilized to generate monoclonal antibodies directed against the extracellular domain of the human 103 gene product. Specifically, this fusion protein contained, from amino- to carboxy-terminus, a CD5 signal sequence (CD5ss), glycine and threonine amino acid residues (a Kpn1 site), the extracellular domain (i.e., amino acid residues 18 to 323) of the human 103 gene product depicted in FIG. 5B (SEQ ID NO:8) and human IgG1 Fc. The vector encoding this fusion protein was transfected into mammalian 293T cells using LipofectAMINE® (GIBCO BRL, Md.) following the manufacturer's recommended protocol. Supernatants were harvested 3 and 7 days, respectively, after transfection, and fusion protein was purified with a Protein G affinity column (Pierce, Inc., IL.) according to the manufacturer's recommended protocol.

A second Fc fusion protein of the human 103 gene product was constructed, according to the techniques described in Section 6.3 above, to bind ELISA plates for screening. In particular, the fusion protein contained, from amino- to carboxy-terminus, a T075 signal sequence (T075ss; the signal sequence of TANGO 75 in PCT Publication No. WO 99/15663, filed Apr. 1, 1999) plus QR residues, amino acid residues 20-323 of the human 103 gene product (FIG. 5B; SEQ ID NO: 8) plus a linker amino acid sequence (Ala-Ala-Ala-Asp-Pro) and a human IgG1 constant region.

A fusion protein of the mouse 103 gene product was also constructed and utilized that contained, from amino- to carboxy-terminus, a CD5 signal sequence plus GT residues, residues 24 (Thr) to 328 (Pro) of the mouse 103 gene product (FIG. 4B; SEQ ID NO:6), and human IgG1 constant region.

Control fusion proteins were also utilized which contained unrelated proteins, T001, a chemokine (referred to as TANGO 1 in PCT Publication No. WO 97/4224, filed Nov. 13, 1997), or T075, a tumor necrosis family receptor (referred as TANGO 75 in PCT Publication No. WO 99/15663, filed Apr. 1, 1999), fused with a human IgG1 constant region.

The human IgG1 sequence was as described in Aruffo et al., 1990, Cell 61:1303.

Generation of Anti-103 Monoclonal Antibodies:

Monoclonal antibodies were generated in BALB/c mice against the extracellular domain (amino acid residues 18-323) of the human 103 gene product depicted in FIG. 5B (SEQ ID NO: 8) utilizing the above-described human 103 IgG1 Fc fusion protein (see Section 5.6, above) for monoclonal antibody selection and purification. Specifically, BALB/c mice were immunized with the fusion protein according to standard protocols and spleen cells from a mouse that showed positive reactivity to the 103 fusion protein were fused with SP2/0 myeloma cells using standard polyethylene glycol (PEG) techniques (see, e.g., Harlow and Lane, 1988, Antibodies: A Laboratory Manual, Cold Spring Harbor Laboratory Press, Cold Spring Harbor, N.Y.; Current Protocols in Immunology, 1992, Coligan, J. E. et al., Eds., John Wiley & Sons, NY).

The resulting hybridoma cell lines were screened to select clones which secreted antibodies that bound specifically to the human 103 IgG1 Fc fusion protein but not to control Fc fustion by ELISA and Biacore (BIAcore, Inc.; Uppsala, Sweden) as described in Fagerstam et al., 1992, *J. of Chromatography* 597:397-410 and in Kretschmann & Raether, 1968, *Z. Naturforschung Teil. A.* 23:2135. These assays used the above-described plate bound human 103-IgG1 Fc fusion protein and control fusion proteins to select monoclonal antibodies that specifically bound to a human 103 gene product but did not bind to mouse 103-gene product Fc fusion protein or to a control Fc fusion protein.

Six cell lines were selected and cloned using ClonalCell™-HY Medium D (StemCell Technologies, Inc., Vancouver, BC) according to the manufacturer's recommendations and purified from DMEM 3% FCS (Ultra-low IgG, Gibco BRL) supplemented with Penicillin/Streptomycin and L-glutamine. The antibodies were purified by Protein A affinity chromatograph, using standard protocols, and affinities were analyzed by Biacore as described above. The isotypes of the purified monoclonal antibodies were determined using a commercial isotyping kit (Pharmingen, San Diego) following the manufacturer's recommended protocol.

Northern Blots:

Northern procedures performed in the experiments described in this example were performed as described, above, in Section 6.1.

Flow Cytometry Analysis of Mast Cell Lines:

Cells were analyzed for the expression of gene 103 protein using fluorescence activated cells sorting (FACS) according to standard methods described in Section 6.5, above using anti-mouse IgFITC secondary antibodies.

6.6.2. RESULTS

Northern blot analysis of multiple cells lines showed high levels of the 103 gene in a human mast cell line. Expression of the 103 gene product in this cell line was verified using monoclonal antibodies raised against an Fc fusion protein of the human 103 gene product, as described in Subsection 6.5.1, above.

Specifically, six hybridoma cell lines, referred to herein as M15 3F7.3, M15 9F11.1, M15 2O3.1, M15 5A16.1, M15 10F7.1 and M15 1B4.1, were selected, as described in Subsection 6.6.1, above, which produced monoclonal antibodies that bind specifically to the extracellular domain of the human 103 gene product but do not bind to a mouse 103 gene product or to control fusion proteins (i.e., fusion proteins of T001 or T075, see Subsection 6.6.1, above). The isotypes of the monoclonal antibodies produced by these cell lines were determined, and are as follows: M15 3F7.3: IgG1 Kappa; M15 9F11.1: IgG1 Kappa; M15 2O3.1: IgG2a Kappa; M15 5A16.1: IgG1 Kappa; M15 10F7.1: IgG2a Kappa; and M15 1B4.1: IgG2a Kappa. The cell lines were deposited with the American Type Culture Collection (ATCC™) in compliance with the Budapest Treaty on the International Recognition of the Deposit of Microorganisms for the purpose of Patent Procedure (see Section 7, below). Such monoclonal antibodies, as well as hybridoma cell lines which produce such monoclonal antibodies, are considered to be part of the present invention.

FACS staining of the human mast cell line with the six monoclonal antibodies showed positive staining with four of the six antibodies (M15 3F7.3, M15 2O3.1, M15 10F7.1 and M15 1B4.1) compared to isotype controls. The positive FAC staining with these antibodies was also demonstrated to be specifically blocked with an excess of the human 103-IgG1 Fc fusion protein. However, positive FAC staining was not blocked with control Fc fusion proteins.

Interestingly, no positive FACS staining of the human mast cell line was observed with the monoclonal antibodies M15 5A16.1 and M15 9F11.1. These antibodies, therefore, did not recognize the 103 gene product expressed on the human mast cell line, and may recognize a different epitope of the human 103 gene product than do the other four monoclonal antibodies studied.

In summary, these results provide evidence that the 103 gene product is expressed in a human mast cell line. Accordingly, the 103 gene, its gene product, and compositions derived therefrom (e.g., antibodies and other compounds which bind to and/or modulate the expression or activity of the 103 gene or its gene product) may be used not only in the treatment and regulation of immune disorders such as allergy and asthma (i.e., in immune disorders associated with an abnormal or inappropriate TH2 or TH2-like immune response), but may also be used in the treatment and regulation of mast cell related disorders. Such mast cell related disorders include, but are not limited to, atherosclerosis (see, e.g., Metzler and Xu, 1997, Int. Arch. Allergy Immunol. 114: 10-14), myocardial ischemia/reperfusion (see, e.g., Frangogiannis et al., 1998, Circulation 98:699-710), mastocytosis (e.g., cutaneous mastocytosis and systemic mastocytosis), and interstitial cystitis (IC).

6.7. THE 103 GENE PRODUCT PLAYS A CRUCIAL ROLE IN TH2-MEDIATED IMMUNE RESPONSES

The example presented herein substantiates the above-described findings that the 103 gene product is, indeed, a gene product differentially expressed in TH2 cells and plays an important role in TH2 mediated immune responses and can therefore serve as a novel target in the suppression of such responses. Specifically, the data presented herein shows that, not only is the 103 gene product differentially expressed in TH2 and not in TH1 cells, but also that the 103 gene product delivers an important signal instructing naive (i.e., undifferentiated) TH cells to switch to a TH2-like pattern of cytokine production.

6.7.1. MATERIALS AND METHODS

Generation of Fusion Proteins and Monoclonal Antibodies:

A 103 gene IgG1 fusion protein (103-Ig) was prepared according to the methods described in Section 6.3 above. In addition, a DNA sequence referred to as H1 was PCR-amplified and cloned into the identical vector using the same methods. H1 contained the extracellular domain of an Ig superfamily member. The H1-Ig fusion protein failed to bind to either T, B or dendritic cells. Further, H1-Ig was not detectable by PCR analysis in either resting or activated TH1 or TH2 cells. Thus, the H1-Ig fusion protein was used as an control reagent in the below-described experiments.

The anti-103 mAb 3E10 mAB was generated and used as described in Section 6.5, above.

CD3/TCR Crosslinking:

Mice expressing the transgene for the DO11.10 $\alpha\beta$-TCR, which recognizes residues 323-339 of chicken ovalbumin (OVA) in association with I-A$^d$ (Murphy, K. M., et al., 1990, Science 250:1720-1723) were utilized. Naive TCR-transgenic CD4$^+$ T cells were isolated as described by Lohning et al. (1998, Proc. Natl. acad. Sci. U.S.A. 95:6930-6935) and cultured in complete RPMI 1640 with OVA$_{323-339}$ (1 µM) and mitomycin C-treated splenocytes in a ratio of 1:5. For TH1 phenotype development, recombinant murine IL-12 (10 ng/ml) and neutralizing anti-IL-4 mAb (11B11, 40 µg/ml, R&D Systems) were added and for TH2 development recombinant murine IL-4 (10 ng/ml) and neutralizing polyclonal anti-murine IL-12 (TOSH-2, 3 µg/ml, Endogen, Cambridge, Mass.) were used. After 5-7 days cells were washed and restimulated up to 3 times under identical polarizing conditions. Cells were stained after 5-7 days with digoxigenin labeled 3E10 and the number of 103 positive cells detected by anti-digoxigenin Fab fragments (Boehringer Mannheim) conjugated to Phycoerythrin. Expression of 103 gene product was analyzed on a fluorescence-activated cell sorter (FACS)-Calibur (Becton-Dickinson). To determine the cytokine profile at each time point, cells were washed and viable CD4$^+$ cells were isolated over a ficoll gradient and activated in a 96 well (2×10$^5$ per well) plate for 24 hours using platebound CD3 (2C11, 10 µg/mL, Pharmingen, San Diego). IL-4 and IFN-$\gamma$ levels were measured in the supernatant by ELISA (Endogen, Cambridge Mass.).

In Vitro Differentiation of Effector Cells:

CD4$^+$ T cells from DO11.10 $\alpha\beta$-TCR mice were activated as described above in the absence of exogenous cytokines (i.e., in "neutral" conditions) or in the presence of IL-12 or IL-4, together with 103-Ig (100 µg/mL) or human-Ig was the appropriate isotype control Cells were washed and replated in 96 well plates (5×10$^4$ per well) together with 1×10$^5$ splenocytes per well, and restimulated with OVA peptide and cytokines measured 48 hours later. To determine the effect of 103-Ig in effector cells, TH1 and TH2 cells were reactivated with OVA peptide in the presence of either 103-Ig of H1-Ig. In some experiments H1-Ig was used as a second control reagent for the specificity of 103-Ig.

In Vivo Measurement of TH1 or TH2 Immune Responses:

TH1 and TH2 recipient mice were generated as described in Section 6.4 above. However, a second series of experiments were also performed using 103-Ig (100 µg i.v.) or human Ig as the appropriate isotype control. Cytospin preparations were prepared and stained with Giemsa reagent. A total of 200 cells was differentially counted. Lungs were then removed, inflated with 10% neutral buffered formalin, and paraffin-embedded. Four micron sections were stained for cyanide-resistant peroxidase and counterstained with Haematoxylin using standard techniques. Airway inflammation was determined by semiquantitative scoring using an arbitrary system wherein a score of +1 represents one small foci of cells and +5 indicates widespread infiltrates. All scoring was performed by a clinical investigator unaware of the treatment.

Active Immunization Protocol and IgE Measurement:

Mice were immunized and serum OVA specific IgE levels were measured as described in Section 6.4.1, above.

6.7.2. RESULTS

To further investigate the differential expression pattern of the 103 gene, 103 gene expression was determined by flow cytometry on splenocytes, purified naive CD4+ cells ($CD4^+$/CD62L+) and TH2 and TH1 effector cell populations (FIGS. 23A-23D, respectively). Briefly, TH1 phenotype development was stimulated by culturing naive $CD4^+$ T cells in the presence of recombinant murine IL-12 and in neutralizing anti-IL-4 antibody, as described, above, in Section 6.7.1. TH2 phenotype development was stimulated by culturing the naive $CD4^+$ T cells in recombinant murine IL-4 and neutralizing anti-IL-12 antibody. 103 gene expression was determined after primary, secondary, and tertiary restimulation of these cells.

Figure 23A:
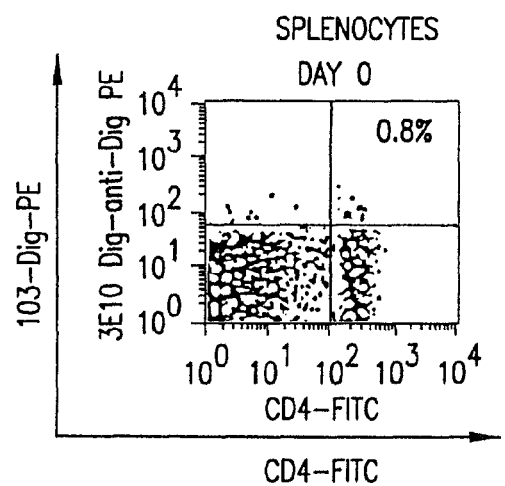
Figure 23B:
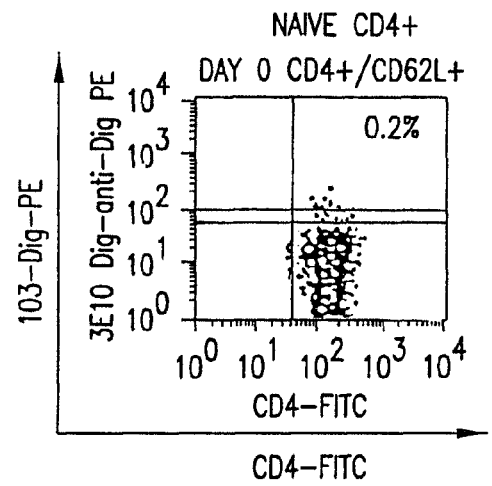
Figure 23C:
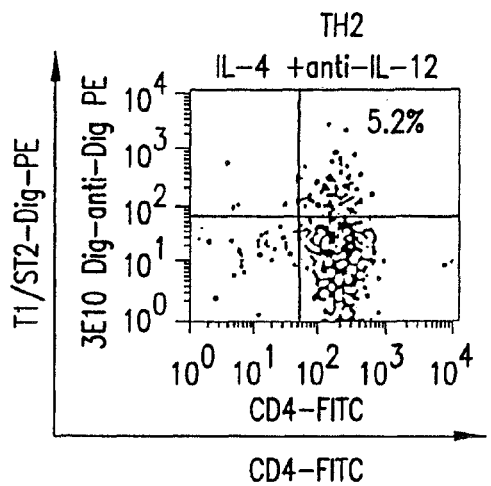
Figure 23D:
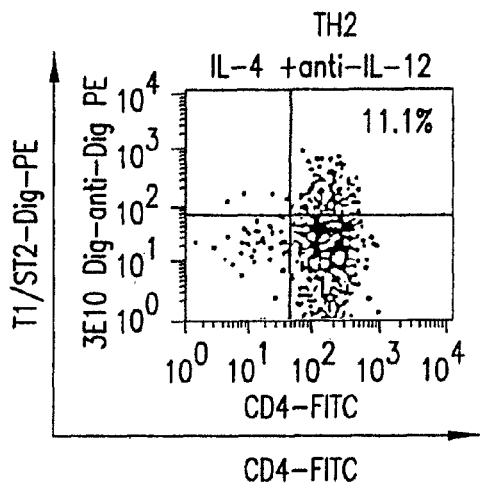
Figure 23E:
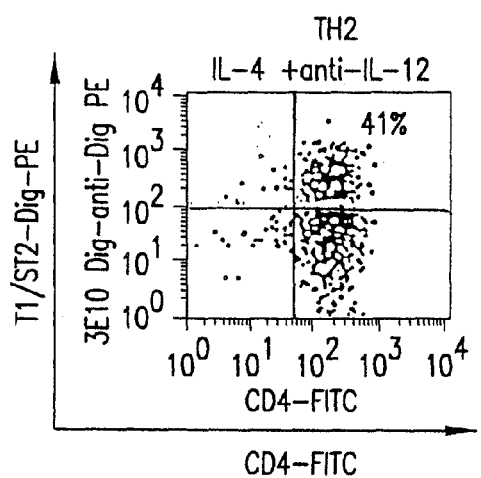
Figure 23F:
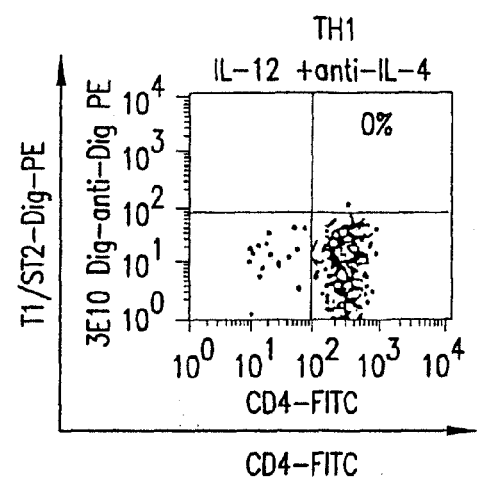
Figure 23G:
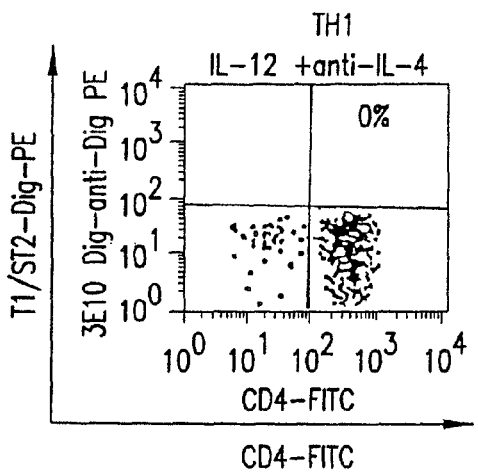
Figure 23H:
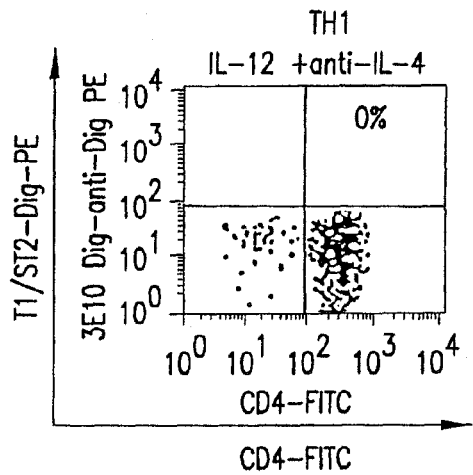
Figure 25A:
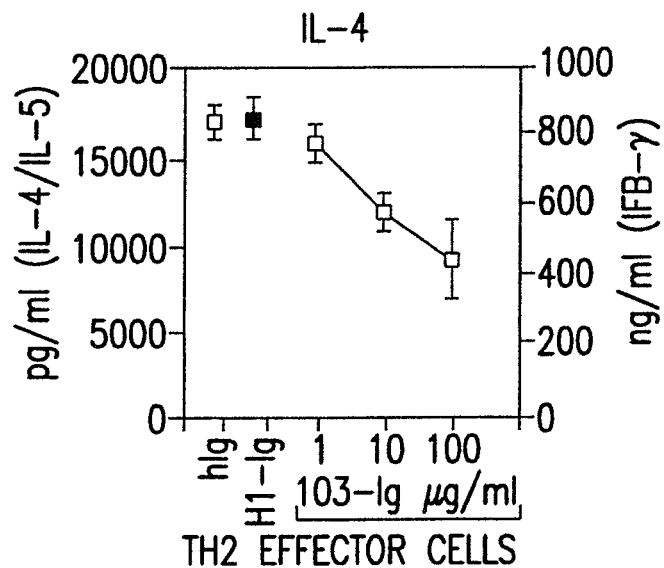
FIG. 25 depicts cytokine (IL-4, IL-5, and IFN-γ) production levels measured in separate TH1 and TH2 effector populations activated with peptide and mitomycin C-treated splenocytes in the presence of either human-Ig (100 μg/mL; open squares) 103-Ig fusion protein (1-100 μg/mL) or a control fusion protein, designated H1-Ig (open squares).
Figure 25B:
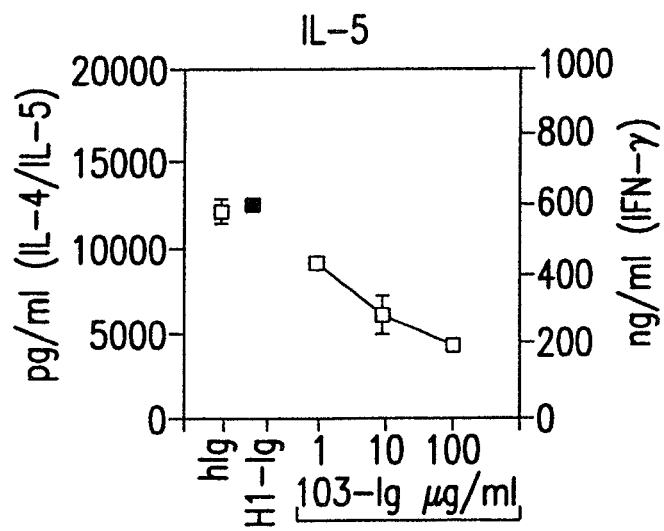
Figure 25C:
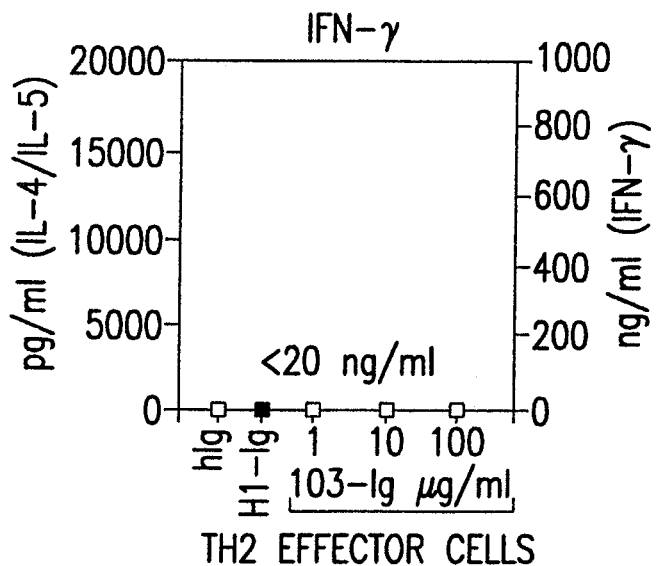
Figure 25D:
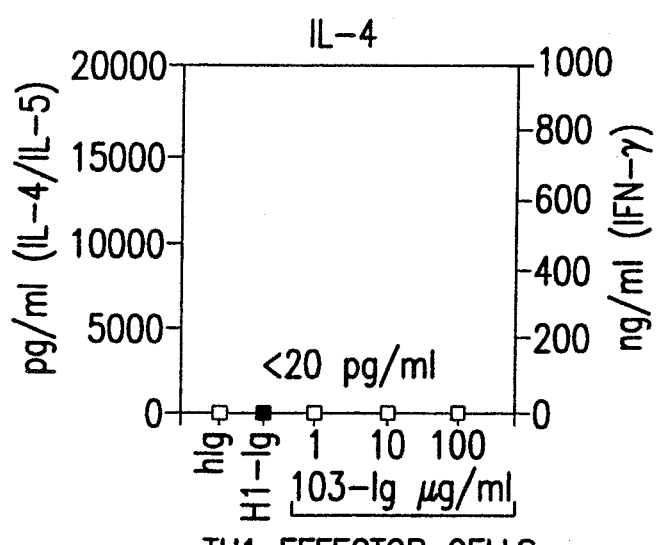
Figure 25E:
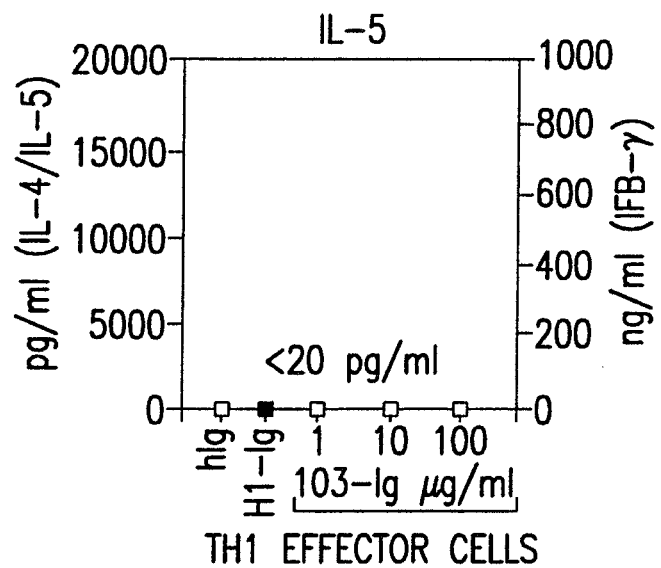
Figure 25F:
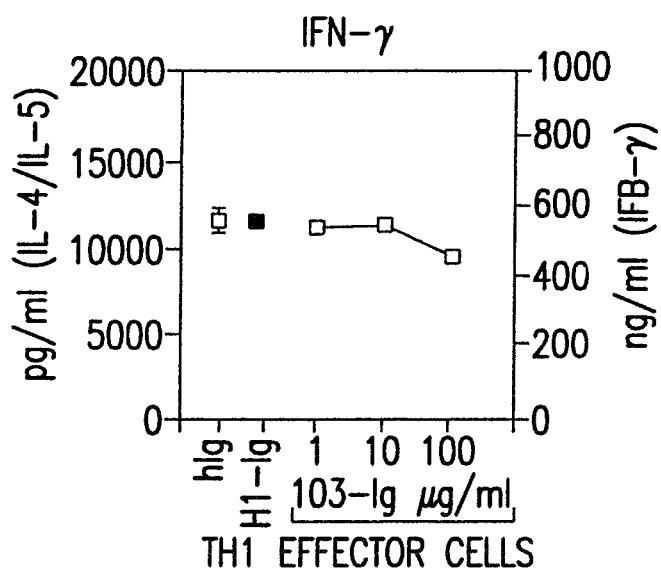

The 3E10 monoclonal antibody failed to detect 103 gene product on naive cells or on TH1 cells, but recognized and bound to 103 gene product on TH2 cells. Further, stimulating naive T cells in TH2 polarizing conditions (i.e., incubating in IL-4 and anti-IL-12) actually increased the percentage of cells expressing the 103 gene product (from 5.2% after primary restimulation to 41% after tertiary restimulation; FIG. 23C). This increase in 103 gene product expression also correlated with an enhanced secretion of IL-4, a cytokine secreted by TH2 and TH2-like cells and associated with TH2 and TH2-like activity. Thus, the results confirm that a majority of cells exhibiting TH2 and/or TH2-like activity also express the 103 gene product. Thus, the data show that the 103 gene product is a useful surface marker for identifying cells exhibiting TH2 or TH2-like activity (e.g., secretion of cytokines such as IL-4 and/or IL-5) both in vivo and in vitro. The 103 gene product can therefore be used, e.g., to modulate numbers of TH2 and/or TH2-like cells present in a population.

Cells were also incubated in the presence of 103-Ig fusion protein to determine the role of the 103 gene product as a signaling molecule. Naive T cells that were not incubated in the presence of exogenous cytokines or in the presence of 103-Ig acquired the capacity to secrete high levels of IL-4 ($\approx$1700 ng/mL) and IL-5 ($\approx$1600 ng/mL), and secreted low levels of IFN-$\gamma$ ($\approx$300 pg/mL). However, when incubated under TH2 polarizing conditions and with 103-Ig, TH2 cytokine production (i.e., IL-4 and IL-5) was reduced while a modest, but reproducible, increase in secretion of the TH1 cytokine IFN-$\gamma$ ($\approx$1500 pg/mL) was observed (FIG. 24, top). In contrast, incubation in the presence of 103-Ig failed to modify IFN-$\gamma$ production in cells incubated under TH1 polarizing conditions (FIG. 24, bottom). Thus, administration of the 103-Ig fusion protein effectively blocks 103-mediated signaling, e.g., by competing with endogenous 103 gene product for its ligand, effectively inhibiting TH2 and/or TH2-like, but not TH1 or TH1-like, activity.

These results are similar to data generated using fusion proteins to inhibit CD28/B7 interactions (Sedar et al., 1994, *J. Exp. Med.* 179:299-304) or B7 deficient antigen presenting cells (Schweitzer and Sharpe, 1998, *J. Immunol.* 161:2762-2771). However, the results also differ from previous findings in that the inhibition of the 103 gene product results in skewing of the immune response from a TH2 to a TH1 phenotype. Further, whereas the absence of CD28 costimulation results in an attenuation of IFN-$\gamma$ and IL-4 secretion when cells are cultured under either TH1 or TH2 polarizing conditions, inhibition of 103 gene signaling selectively inhibits cytokine secretion from TH2 cells without modifying IFN-$\gamma$ secretion from TH1 cells. Thus, the 103 gene product appears to deliver an important signal instruction naive cells to differentiate to TH2 cytokine production.

The requirement of 103 signaling or activation of effector cells was further examined by activating separate TH1 and TH2 effector cell population with a peptide and antigen presenting cells in the presence of different concentrations of the 103-Ig fusion protein. Under these conditions, blockage of 103 signaling reduced cytokine production in TH2 effector cells, but not in TH1 effector cells, in a dose dependent manner (FIG. 25). The specificity of the 103-Ig was verified in identical experiments using the control H1-Ig fusion protein.

The results are in marked contrast to the recent data generated using B7 deficient antigen producing cells (Schweitzer and Sharpe, 1998, *J. Immunol.* 161:2762-2771). Specifically, the previous data demonstrated that cytokine production from TH1 and TH2 effector cells, respectfully, is largely dependent of CD28/B7 mediated costimulation. However, the data presented here suggests that signaling through 103 accounts, at least in part, for CD28/B7 independent activation of TH2 but not TH1 cells.

The contribution of the 103 gene and its gene product to a nascent TH2-dominated response was also investigated in vivo. Briefly, mice were immunized systemically with antigen in adjuvant prior to allergen provocation, as described in Section 6.5 above, and both cellular and humoral responses were evaluated. The results are shown in FIG. 26A-26C. Anti-103 mAb effectively inhibited allergen induced lung eosinophilic inflammation, IL-5 production and the induction of OVA specific IgE, demonstrating 103 gene product is a critical regulatory molecule for both cellular and humoral allergic inflammation in vivo.

The data demonstrate that the 103 gene product is not only a useful marker for identifying and detecting TH2 cells, but also plays a crucial role in the differentiation and activation of TH2, but not TH1, cells. In particular, this conclusion is supported not only by the in vitro data presented in this section, but also by in vivo data presented in both this section and in Section 6.5, above. These data show that inhibition of 103 signaling attenuates TH2 mediated immune responses without affecting TH1 mediated responses. Thus, the 103 gene is apparently an important regulator for a number of key events in both innate and adaptive immunity and, as such, is an important target for the therapeutic and diagnostic methods and compositions described herein.

6.8. GENERATION OF HUMAN ANTIBODIES TO THE HUMAN 103 GENE PRODUCT

The Examples presented in the previous sections (e.g., in Sections 6.5 and 6.6) describe the production of exemplary mouse monoclonal antibodies that specifically bind to a murine and a human 103 gene product, respectively. The Example presented in this Section presents data demonstrating the production of exemplary human antibodies that specifically bind to a human 103 gene product. Such human antibodies are particularly useful in the methods and compositions of the present invention including, in particular, those embodiments of the invention that comprise administering antibodies to a human subject.

6.8.1. MATERIALS AND METHODS

103 Fusion Proteins:

Human 103 IgG1 Fc fusion protein, prepared as described in Section 6.6, above, was used to generate monoclonal antibodies directed against the extracellular domain of the human 103 gene product. A second Fc fusion protein of the human 103 gene product was also constructed to bind to ELISA plates for screening. In particular, this fusion protein was identical to the plate bound human 103 fusion protein described in Section 6.6.1, above, except that the fusion protein contained a leader sequence from the human death receptor (DR6), T075ss, instead of CD5ss, plus amino acid residues QR, amino acid residues 20-323 of the human 103 gene product and a murine IgG1 constant region rather than a human IgG1 constant region.

A third human 103 fusion protein was also constructed for expression on the surface of transfected cells. This fusion protein contained, from amino- to carboxy-terminus, the leader sequence of human death receptor (DR6), amino acid residues 20 to 323 of the human 103 gene product depicted in FIG. 5B (SEQ ID NO:7), a His tag and the C terminal signal sequence from human placental alkaline phosphatase. The vector encoding this fusion protein was transfected into mammalian 293T cells using standard protocols (see, e.g., Section 6.5.1, above). For controls, mammalian 293 T cells were also transfected with a vector that consisted of the human DR6 leader sequence, a His tag and the human placental alkaline phosphatase C terminal signal sequence, but did not contain sequence for a 103 gene product.

Generation of Human Antibodies:

Monoclonal antibodies were generated in xenomice expressing human IgG2 (Abgenix, Inc., 7601 Dumbarton Circle, Fremont, Calif. 94555; B6×129 transgenic produced by microinjection of B6 embryos with 129 ES cells) against the extracellular domain (amino acid residues 18-323) of the human 103 gene product depicted in FIG. 5B (SEQ ID NO:7) utilizing the above-described human 103 IgG1 Fc fusion proteins (see Section 5.6, above) for monoclonal antibody selection and purification. Specifically, five male xeonmice mice were immunized with the fusion protein according to standard protocols and spleen cells from a mouse that showed positive reactivity to the 103 fusion protein were fused with SP2/0 myeloma cells using standard polyethylene glycol (PEG) techniques (see, e.g., Harlow and Lane, 1988, *Antibodies: A Laboratory Manual*, Cold Spring Harbor Laboratory Press, Cold Spring Harbor, N.Y.; *Current Protocols in Immunology*, 1992, Coligan, J. E. et al., Eds., John Wiley & Sons, NY).

The resulting hybridoma cell lines were screened to select clones which secreted antibodies that bound specifically to the human 103 gene product by ELISA and Biacore (BIAcore, Inc.; Uppsala, Sweden) as described in Fagerstam et al., 1992, *J. of Chromatography* 597:397-410 and in Kretschmann & Raether, 1968, *Z. Naturforschung Teil. A.* 23:2135. These assays used the above-described plate bound human 103-mouse IgG1 Fc fusion protein and control fusion proteins containing the same murine IgG1 Fc fusion to select monoclonal antibodies that specifically bound to a human 103 gene product but did not bind to a control Fc fusion protein. Selected cell lines were cloned using ClonalCell™-HY Medium D (StemCell Technologies, Inc., Vancouver, BC) according to the manufacturer's recommendations. Supernatants from the monoclonal cell lines were screened for binding to cells presenting the human 103 gene product on their surface.

6.8.2. RESULTS

Anti-human 103 monoclonal antibodies were generated, as described in Section 6.8.1, above, in xenomice expressing human IgG2. Thus, the antibodies generated by spleen cells isolated from these mice were, in fact, human antibodies against a human 103 gene product.

Supernatants from the hybridoma cell line clones derived from these spleenocytes were screened for binding to the human 103 gene product expressed on the surface of 293T cells transfected with the third human 103 fusion protein described in Section 6.8.1, above. Several clones showed significant binding to these 103 gene expressing cells, indicating binding of monoclonal antibodies to the human 103 gene product antigen expressed on the cell surface. Two clones in particular, referred to herein as MA6 4C7.2 and MA6 10N13.3, showed very strong staining.

Five clones, including the MA6 4C7.2 and MA6 10N13.3 clones described hereinabove, were purified from DMEM 3% FCS (Ultra-low IgG, Gibco BRL) supplemented with Penicillin/Streptomycin and L-glutamine, and the monoclonal antibodies produced by these clones were purified by Protein A affinity chromatography. The binding affinities of these antibodies for the human 103 gene product antigen were evaluated by Biacore (BIAcore, Inc.; Uppsala, Sweden) as described in Fagerstam et al., 1992, *J. of Chromatography* 597:397-410 and in Kretschmann & Raether, 1968, *Z. Naturforschung Teil. A.* 23:2135. The $K_d$ values thus determined ranged from $1.5 \times 10^{-7}$ to $4 \times 10^{-9}$ M.

6.9. IDENTIFICATION OF A 103 GENE PRODUCT LIGAND

This example presents data demonstrating the existence of a previously unknown 103 gene product ligand expressed by mice spleen cells. Specifically, the example describes an assay wherein binding of a 103 gene product to mouse spleen cells is detected. Data is also presented wherein monoclonal antibodies to the human 103 gene product are identified and shown to specifically block binding of the 103 gene product to this novel ligand.

6.9.1. MATERIALS AND METHODS

103 Fusion Proteins:

Fc fusion proteins of the 103 gene product were prepared as described in Section 6.6.1, above.

Monoclonal Antibodies:

Monoclonal antibodies that specifically bind to the extracellular domain of a human 103 gene product were prepared as described in Section 6.6.1, above.

Immunization and Preparation of Tissue Sections:

Approximately 4 month old C57Bl/6 mice were immunized subcutaneously at multiple sites along the back, intraperitoneally, and at the base of the tail with a total volume of approximately 200 µl of a 1:1 emulsion of Freunds complete adjuvant (Sigma, St. Louis, Mich.) and phosphate buffered saline. Spleens were harvested from unimmunized mice and from immunized mice 1, 3, 5 and 14 days after immunization. The harvested spleens were frozen in OCT 4583 embedding medium (Tissue-Tek). Fresh frozen 8 μm sections were prepared, fixed in acetone for 10 minutes, and washed in phosphate buffered saline (PBS) for five minutes. Sections were then blocked for 30 minutes in PBS containing 5% goat serum and 1 mg/ml mIgG (Rockland, Inc.).

103 Binding Assays:

Tissue sections of spleen cells from unimmunized and immunized mice, prepared as described above, were incubated with human 103 gene product-Fc fusion protein or with human IgG1 (10 μg/ml in PBS/1% goat serum) for one hour at room temperature and then washed three times in PBS. Bound Fc-fusion proteins were detected by incubating the sections with alkaline phosphatase-conjugated anti-human IgG1 antibodies (10 μg/ml in PBS/1% goat serum; Jackson Laboratories) for 30 minutes. Following these washes in PBS alkaline phosphatase, activity was visualized with a BCIP/NBT (5-bromo-4-chloro-3-indolylphosphate/nitroblue tetrazolium) substrate kit from Vector Laboratories.

Monoclonal antibodies to the human 103 gene-Fc fusion protein were tested for their ability to block binding of the 103 gene-Fc fusion protein to spleen sections by adding a 60 to 100 fold molar excess of the purified monoclonal antibodies to 10 μg/ml 103 gene-Fc fusion protein in PBS/1° A goat serum and incubating the tissue sections with the mixture as described above.

6.9.2. RESULTS

Spleen sections from unimmunized mice and immunized mice were screened with purified human 103 gene-Fc fusion protein, as described in Section 6.8.1, above, for binding sites that specifically bind to the 103 gene product. Immunization dependent binding of the fusion protein was observed to scattered cells in the red pulp of spleens. However, no binding of hIgG1, which was used as a control protein, was observed to any of the spleens analyzed. These binding experiments were repeated with two other groups of mice and were found to be repeatable. The results were further confirmed using murine 103-human IgG1-Fc fusion protein and with murine 103-alkaline phosphatase fusion proteins (prepared as described in Section 6.3.1, above). Immunization dependent binding of the murine 103-alkaline phosphatase fusion protein to scattered cells in the T cell zones of the white pulp of the spleens was further detected.

Binding of the murine 103 gene-alkaline phosphatase fusion protein to spleen cells was blocked by incubating in the presence of a 100 fold excess of murine 103 gene-human IgG1-Fc fusion protein. However, binding of the murine 103-gene alkaline phosphatase fusion protein was not blocked when incubated in the presence of control murine IgG1 (anti-TNP). These results demonstrate that immunization leads to the regulation of binding sites for the 103 gene product on a subpopulation of cells in the spleen and/or the migration of cells in the spleen which have binding sites to the 103 gene product.

To further characterize the above-described binding of the 103 gene product to its ligand in spleen cells, five anti-human 103 monoclonal antibodies, prepared as described in Section 6.6.1, above, were tested for their ability to block this binding. The monoclonal antibodies tested included the monoclonal antibodies M15 1B4.1, M15 A16.1, M15 9F11.1, and M15 3F7.3, which are described in Section 6.6.2, above, and also the monoclonal antibody produced by the hybridoma cell line referred to as M15 10F7.1, which produces a monoclonal antibody of the isotype IgG2a Kappa. Incubation with a 100 fold excess of M15 10F7.1, M15 1B4.1 or M15 5A16.1 monoclonal antibody completely abolished binding of the 103 gene-Fc fusion protein to spleens cells from immunized mice prepared 3, 5 or 14 days post immunization. Incubation with a 70 fold excess of M15 9F11.1 or with a 60 fold excess of M15 3F7.3 monoclonal antibody only partially blocked the 103 gene-Fc fusion protein binding to these spleen cells. As controls, the 103 gene-Fc fusion protein was also incubated with two irrelevant isotype-matched monoclonal antibodies: anti-TNP, an IgG2a isotype; and anti-hT075, an IgG1 isotype. Incubation with these control antibodies did not block binding of the 103 gene-Fc fusion protein to spleen cells. Thus, binding of the 103 gene product to its ligand in spleen cells can be effectively blocked, e.g., by administering antibodies that compete with the 103 gene product for its ligand.

7. MICROORGANISM DEPOSITS AND REFERENCES CITED

The murine hybridomas listed below were deposited with the American Type Culture Collection (ATCC™), 10801 University Blvd., Manassas, Va. 20110, under the provisions of the Budapest Treaty on the International Recognition of the Deposit of Microorganisms for the Purposes of Patent Procedure, and compliance with the criteria set forth in 37 C.F.R. §1.801-1.809 regarding availability and permanency of deposits. The murine hybridomas were produced as described above in Section 6.6.1. The deposits were made on the date indicated and assigned the indicated accession number:

| Microorganism Deposit | ATCC ™ No. | Date of Deposit |
| --- | --- | --- |
| M15 3F7.3 | PTA-593 | Aug. 24, 1999 |
| M15 9F11.1 | PTA-590 | Aug. 24, 1999 |
| M15 2O3.1 | PTA-591 | Aug. 24, 1999 |
| M15 5A16.1 | PTA-587 | Aug. 24, 1999 |
| M15 10F7.1 | PTA-592 | Aug. 24, 1999 |
| M15 1B4.1 | PTA-588 | Aug. 24, 1999 |

All publications, patents and patent applications cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for treating asthma in a mammalian subject, comprising administering to the subject a pharmaceutical composition comprising a monoclonal antibody produced by:
   (a) hybridoma clone M15 3F7.3 (ATCC™ No. PTA-593);
   (b) hybridoma clone M15 203.1 (ATCC™ No. PTA-591);
   (c) hybridoma clone M15 10F7.1 (ATCC™ No. PTA-592);
   (d) hybridoma clone M15 1B4.1 (ATCC™ No. PTA-588);
   (e) hybridoma clone M15 9F11.1 (ATCC™ No. PTA-590); or
   (f) hybridoma clone M15 5A16.1 (ATCC™ No. PTA-587); or an antigen binding fragment thereof, and a pharmaceutically acceptable carrier.

2. A method for treating allergy in a mammalian subject, comprising administering to the subject a pharmaceutical composition comprising a monoclonal antibody produced by:
   (a) hybridoma clone M15 3F7.3 (ATCC™ No. PTA-593);
   (b) hybridoma clone M15 203.1 (ATCC™ No. PTA-591);
   (c) hybridoma clone M15 10F7.1 (ATCC™ No. PTA-592);
   (d) hybridoma clone M15 1B4.1 (ATCC™ No. PTA-588);
   (e) hybridoma clone M15 9F11.1 (ATCC™ No. PTA-590); or
   (f) hybridoma clone M15 5A16.1 (ATCC™ No. PTA-587); or an antigen binding fragment thereof, and a pharmaceutically acceptable carrier.

3. A method for treating an IgE-mediated immune disorder in a mammalian subject, comprising administering to the subject a pharmaceutical composition comprising a monoclonal antibody produced by:
   (a) hybridoma clone M15 3F7.3 (ATCC™ No. PTA-593);
   (b) hybridoma clone M15 203.1 (ATCC™ No. PTA-591);
   (c) hybridoma clone M15 10F7.1 (ATCC™ No. PTA-592);
   (d) hybridoma clone M15 1B4.1 (ATCC™ No. PTA-588);
   (e) hybridoma clone M15 9F11.1 (ATCC™ No. PTA-590); or
   (f) hybridoma clone M15 5A16.1 (ATCC™ No. PTA-587); or an antigen binding fragment thereof, and a pharmaceutically acceptable carrier.

* * * * *

SEQUENCE LISTING

<160> NUMBER OF SEQ ID NOS: 34

<210> SEQ ID NO 1
<211> LENGTH: 255
<212> TYPE: DNA
<213> ORGANISM: Homo sapiens

<400> SEQUENCE: 1

| | | | | |
|---|---|---|---|---|
| ttagcgccat tgccatagag agacctcagc catcaatcac tagcacatga ttgacagaca | | | | 60 |
| gagaatggga ctttgggctt tggcaattct gacacttccc atgtatttga cagttacgga | | | | 120 |
| gggcagtaaa tcgtcctggg gtctggaaaa tgaggcttta attgtgagat gcccccaaag | | | | 180 |
| aggacgctcg acttatcctg tggaatggta ttactcagat acaaatgaaa gtattcctac | | | | 240 |
| ccaaaaaaaa aaaaa | | | | 255 |

<210> SEQ ID NO 2
<211> LENGTH: 1011
<212> TYPE: DNA
<213> ORGANISM: Mus musculus

<400> SEQUENCE: 2

| | |
|---|---|
| atgattgaca gacagagaat gggactttgg gctttggcaa ttctgacact tcccatgtat | 60 |
| ttgacagtta cggagggcag taaatcgtcc tggggtctgg aaaatgaggc tttaattgtg | 120 |
| agatgccccc aaagaggacg ctcgacttat cctgtggaat ggtattactc agatacaaat | 180 |
| gaaagtattc ctactcaaaa aagaaatcgg atctttgtct caagagatcg tctgaagttt | 240 |
| ctaccagcca gagtcgaaga ctctgggatt tatgcttgtg ttatcagaag ccccaacttg | 300 |
| aataagactg gatacttgaa tgtcaccata cataaaaagc cgccaagctg caatatccct | 360 |
| gattatttga tgtactcgac agtacgtgga tcagataaaa atttcaagat aagctgtcca | 420 |
| acaattgacc tgtataattg gacagcacct gttcagtggt ttaagaactg caaagctctc | 480 |
| caagagccaa ggttcagggc acacaggtcc tacttgttca ttgacaacgt gactcatgat | 540 |
| gatgaaggtg actacacttg tcaattcaca cacgcggaga atggaaccaa ctacatcgtg | 600 |
| acggccacca gatcattcac agttgaagaa aaaggctttt ctatgtttcc agtaattaca | 660 |
| aatcctccat acaaccacac aatggaagtg aaataggaa aaccagcaag tattgcctgt | 720 |
| tcagcttgct ttggcaaagg ctctcacttc ttggctgatg tcctgtggca gattaacaaa | 780 |
| acagtagttg gaaattttgg tgaagcaaga attcaagaag aggaaggtcg aaatgaaagt | 840 |
| tccagcaatg acatggattg tttaacctca gtgttaagga taactggtgt gacagaaaag | 900 |
| gacctgtccc tggaatatga ctgtctggcc ctgaaccttc atggcatgat aaggcacacc | 960 |
| ataaggctga aaggaaaca accaagtaag gagtgtccct cacacattgc t | 1011 |

<210> SEQ ID NO 3
<211> LENGTH: 4989
<212> TYPE: DNA
<213> ORGANISM: Mus musculus

<400> SEQUENCE: 3

| | |
|---|---|
| tgccattgcc atagagagac ctcagccatc aatcactagc acatgattga cagacagaga | 60 |
| atgggacttt gggctttggc aattctgaca cttcccatgt atttgacagt tacggagggc | 120 |
| agtaaatcgt cctggggtct ggaaaatgag gctttaattg tgagatgccc caaagagga | 180 |
| cgctcgactt atcctgtgga atggtattac tcagatacaa atgaaagtat tcctactcaa | 240 |

```
aaaagaaatc ggatctttgt ctcaagagat cgtctgaagt ttctaccagc cagagtggaa      300
gactctggga tttatgcttg tgttatcaga agccccaact tgaataagac tggatacttg      360
aatgtcacca tacataaaaa gccgccaagc tgcaatatcc ctgattattt gatgtactcg      420
acagtacgtg gatcagataa aaatttcaag ataacgtgtc caacaattga cctgtataat      480
tggacagcac ctgttcagtg gtttaagaac tgcaaagctc tccaagagcc aaggttcagg      540
gcacacaggt cctacttgtt cattgacaac gtgactcatg atgatgaagg tgactacact      600
tgtcaattca cacgcggga gaatggaacc aactacatcg tgacggccac cagatcattc      660
acagttgaag aaaaaggctt ttctatgttt ccagtaatta caaatcctcc atacaaccac      720
acaatggaag tggaaatagg aaaaccagca agtattgcct gttcagcttg ctttggcaaa      780
ggctctcact tcttggctga tgtcctgtgg cagattaaca aaacagtagt tggaaatttt      840
ggtgaagcaa gaattcaaga agaggaaggt cgaaatgaaa gttccagcaa tgacatggat      900
tgtttaacct cagtgttaag gataactggt gtgacagaaa aggacctgtc cctggaatat      960
gactgtctgg ccctgaacct tcatggcatg ataaggcaca ccataaggct gagaaggaaa     1020
caaccaattg atcaccgaag catctactac atagttgctg gatgtagttt attgctaatg     1080
tttatcaatg tcttggtgat agtcttaaaa gtgttctgga ttgaggttgc tctgttctgg     1140
agagatatag tgcaccctta caaaacccgg aacgatggca agctctacga tgcgtacatc     1200
atttaccctc gggtcttccg gggcagcgcg gcgggaaccc actctgtgga gtactttgtt     1260
caccacactc tgcccgacgt tcttgaaaat aaatgtggct acaaattgtg catttatggg     1320
agagacctgt tacctgggca agatgcagcc accgtggtgg aaagcagtat ccagaatagc     1380
agaagacagg tgtttgttct ggcccctcac atgatgcaca gcaaggaatt tgcctacgag     1440
caggagattg ctctgcacag cgccctcatc cagaacaact ccaaggtgat tcttattgaa     1500
atggagcctc tgggtgaggc aagccgacta caggttgggg acctgcaaga ttctctccag     1560
catcttgtga aaattcaggg gaccatcaag tggagggaag atcatgtggc cgacaagcag     1620
tctctaagtt ccaaattctg gaagcatgtg aggtaccaaa tgccagtgcc agaaagagcc     1680
tccaagacgg catctgttgc ggctccgttg agtggcaagg catgcttaga cctgaaacac     1740
ttttgagttg agagctgcgg agtcccagca gtaggcaccg gagtgcaggt gtgcagactt     1800
gaaatgccaa gggtggggc cccaagtctc agctaaagag caactctagt ttattttcct     1860
ggttatggta ggagccaccc atcgtttgtt tccggtttcc ttttcctact tcactcttgt     1920
ggcacaagat caaccctgag cttttccctt ttcttttatt tctcttttg ttccttcttt     1980 taaaagcttt ttaaaattga ttatcttatt tatctacctt tcaaaggtta tccccttcc     2040 cggtgccccc tctacaaatc cccatcctgc ttccctcctc cctgcttcta tgagggtgcc     2100
cccccacctg cccatccact ccagccttac aggccttgtg ttcccctatg ctgggcatc     2160 gagcctccat aagacctccc ctctcattca tcaattatct acattctgaa tatcaagccg     2220
acacttttgt ttttgttttt gatttttga acagggtttt ctctgtgtag ccctggctgt     2280
cttgaaactc acattgtaga ccaggctggc ctcgaactca gaaatcagcc tgcctctgcc     2340 tcccgagtg ctgggattaa aggcgtgcgc caccacgccg ggctaagcct acactttcag     2400
aataaagttc tgattcacct caaagagcag tctcattccc agaggcagag agccggaaag     2460
agcctccaat gtgcttgtcc aggcagagct gaccttattt gcttaccagt cacaggtaaa     2520
caaagcgttt ctccgtgttg cctcttgtag acatccctgt aatagattag aagggaatg     2580 agccgtccta ctgaccagtt tgtgaattgt ggtagaaaaa gcgttgacgt tgttaaata     2640
```

-continued

```
cttgttagca atgtaaacct cattcctaac acaccagaat ttcttacttt ttattcgtca    2700
attaccgagt tttgtcaagt cagtattaac agatttggtc gaataccta  cccaaattgc    2760 cattacagtc gagcatgttt tcagttctaa atgccttta  tatatttttt attcttctta    2820
gaaatacttc ctcactttaa aagtaatgta aagatgtgtt agaaaacata aggtgtaaga    2880
gaaagtatga taaaatataa aaaataatag aaaggaaagg aaatataatg aaaatcataa    2940
ctcttaagat taattttggt aggtctgtat tttaaaatat aattaaattt tataccgata    3000
acttttatag ctgagattgt acactacaga ctaggcagct tttcctattt accaccataa    3060
tgaaaactgg tggctgattt ctttaacatt cacagaagtt ccaaatgtct cattttagac    3120
tgtgctgcag actatggctg aagcagccag aatgagaaac aggtctgcca tgtcacatcg    3180
ggacattttc ctacttactg aaatgtatct gtcactgtgc gacagctaac ttttgtgata    3240
ctcctatgaa atgtgtaggg aatttggaca gaacagaatc aatctatagt cagaggtcct    3300
ctggacagtc ttttccagga gcacacacag accgtgaggt cctaggcacc caggaaacgg    3360
atccagagcc caggcaagtg tcttacaggt accttgaatt ttgccaatag atatgagccc    3420
tgccttagct gagttgctca gtcggtgatg ggactccagg ctgaggtgac aatgaacaca    3480
gaatttggga gactcttgaa aggagggaa  tgttgaactc acggtcaaca tatgaggctg    3540
cagagaagcc gtatgcagaa gtgtgtgtag aggatctaga gtagcccgtt tctctgggga    3600
cagtgtgctc ttagtctgta cccttaggct gggttgccag gtaaacatt  gctagtgttc    3660 agttcaaagg ctgaagcttg agctgagggt gatgaggaat tcaaacttcc cctcgcatgc    3720
atccaccctg tggttgcctg gtttgctaag tccacctgct ctgctgtagt agaaggtttt    3780
gatcttctgc agcttcatct acttcttagt gagttgccaa aactgaccac tgaaaagcat    3840
gctgtgtaca taactgtctc atgtcccaga acgtgcaatc aggaggaagt cctcactccc    3900
gataacggaa tccttgctct gtggctgtga ggacgtccct tagcaacctc agatagtaat    3960
ttttcttagg ttgatggaa  catagtaacg tgctggattc tttgctaact gaaaatagaa    4020
gtattcggat ttcagaaaga actggataaa tattaatgtt ggtgattatg aaatctcatt    4080
gtgagccgtg tgagtttgag tgtgtattcc atgattgtgc tgaatgaaga cctctaaaaa    4140
tgaaattctc tccaatctca tccctgggaa tagttgcttc ctcatgcctg ctgctccatc    4200
catgaaaaat gactaaagag aattattatt tgttcccgag attcttctga taagtctaaa    4260
ctatttgcat gtaattgagc tgggcagcat ggcacacttg ggaggcagag gcaggtggat    4320
ctctgtgagt ttgaggccag cctgctctac agagttagtt ccaggacacc agagctacaa    4380
aaagaaaacc tgtcctaaca acaacagcaa cagctgcagc agcaacaaca acaacaaaga    4440 aaagaagag  gaggaggagg aaaggaaaga aggaagaagg aagaagaaag ggaagaaata    4500
atagattttt ctgtaatgaa cacacatatg ctttgatgct tttgctaaac tcaaaatatt    4560
agttttattt tactgttttg aaaggttcaa agcatgatcc atgtaaaaat gtcttctgtg    4620
gggctttctc ccatttctac ttttgttccc ctcatttctt caaagtgctt gtccaggcag    4680
agctgacctt atttgcttac cagttacagg taaacaaagc gtttcctcgt gttgcctctt    4740
gtagccatct ctgtattaga ttaggaaggg aaggagccgt cctactgtcc agtttgtgag    4800
ttctggtaga aagagtgttg aagtttgtta aatgcttgtt ttccatgtat caaaatgtta    4860 tgccttttcct atttattatt gtatgacaaa ttattttca  ctgggcaaaa ataattgtgc    4920
cattgactcc ttgtgtgttt tcttcatgtg tgtttgaaga gttctagctt attaaaaaaa    4980
aaaatctag                                                            4989
```

<210> SEQ ID NO 4
<211> LENGTH: 2058
<212> TYPE: DNA
<213> ORGANISM: Homo sapiens

<400> SEQUENCE: 4

```
aaagagaggc tggctgttgt atttagtaaa gctataaagc tgtaagagaa attggctttc      60
tgagttgtga aactgtgggc agaaagttga ggaagaaaga actcaagtac aacccaatga     120
ggttgagata taggctactc ttcccaactc agtcttgaag agtatcacca actgcctcat     180
gtgtggtgac cttcactgtc gtatgccagt gactcatctg gagtaatctc aacaacgagt     240
taccaatact tgctcttgat tgataaacag aatggggttt tggatcttag caattctcac     300
aattctcatg tattccacag cagcaaagtt tagtaaacaa tcatgggcc tggaaaatga      360
ggctttaatt gtaagatgtc ctagacaagg aaaacctagt tacaccgtgg attggtatta     420
ctcacaaaca aacaaaagta ttcccactca ggaaagaaat cgtgtgtttg cctcaggcca     480
acttctgaag tttctaccag ctgaagttgc tgattctggt atttatacct gtattgtcag     540
aagtcccaca ttcaatagga ctggatatgc gaatgtcacc atatataaaa aacaatcaga     600
ttgcaatgtt ccagattatt tgatgtattc aacagtatct ggatcagaaa aaaattccaa     660
aatttattgt cctaccattg acctctacaa ctggacagca cctcttgagt ggtttaagaa     720
ttgtcaggct cttcaaggat caaggtacag ggcgcacaag tcattttggg tcattgataa     780
tgtgatgact gaggacgcag gtgattacac ctgtaaattt atacacaatg aaaatggagc     840
caattatagt gtgacggcga ccaggtcctt cacggtcaag gatgagcaag cttttctct     900
gtttccagta atcggagccc ctgcacaaaa tgaaataaag gaagtggaaa ttggaaaaaa     960
cgcaaaccta acttgctctg cttgtttttgg aaaaggcact cagttcttgg ctgccgtcct    1020
gtggcagctt aatggaacaa aaattacaga ctttggtgaa ccaagaattc aacaagagga    1080
agggcaaaat caaagtttca gcaatgggct ggcttgtcta cacatggttt taagaatagc    1140
tgacgtgaag gaagaggatt tattgctgca gtacgactgt ctggccctga atttgcatgg    1200
cttgagaagg cacaccgtaa gactaagtag gaaaaatcca attgatcatc atagcatcta    1260
ctgcataatt gcagtatgta gtgtattttt aatgctaatc aatgtcctgg ttatcatcct    1320
aaaaatgttc tggattgagg ccactctgct ctggagagac atagctaaac ttacaagac     1380
taggaatgat ggaaagctct atgatgctta tgttgtctac ccacggaact acaaatccag    1440
tacagatggg gccagtcgtg tagagcactt tgttcaccag attctgcctg atgttcttga    1500
aaataaatgt ggctatacct tatgcattta tgggagagat atgctacctg gagaagatgt    1560
agtcactgca gtgaaaccca catacgaaa gagcaggcgg cacattttca tcctgacccc     1620
tcagatcact cacaataagg agtttgccta cgagcaggag gttgccctgc actgtgccct    1680
catccagaac gacgccaagg tgatacttat tgagatggag gctctgagcg agctggacat    1740
gctgcaggct gaggcgcttc aggactccct ccagcatctt atgaaagtac agggaccat     1800
caagtggagg gaggaccaca ttgccaataa aggtccctg aattccaaat tctgaaagca     1860
cgtgaggtac caaatgcctg tgccaagcaa aattcccaga aaggcctcta gtttgactcc    1920
cttggctgcc cagaagcaat agtgcctgct gtgatgtgca aagggatctg ggtttgaagc    1980
tttcctgact tctcctagct ggcttatgcc cctgcactga agtgtgagga gcgggaatat    2040
taaagggatt caggccac                                                  2058
```

<210> SEQ ID NO 5

<211> LENGTH: 1357
<212> TYPE: DNA
<213> ORGANISM: Homo sapiens

<400> SEQUENCE: 5

| | | | | | |
|---|---|---|---|---|---|
| atctcaacaa | cgagttacca | atacttgctc | ttgattgata | aacagaatgg | ggttttggat | 60 |
| cttagcaatt | ctcacaattc | tcatgtattc | cacagcagca | aagtttagta | acaatcatg | 120 |
| gggcctggaa | aatgaggctt | taattgtaag | atgtcctaga | caaggaaaac | ctagttacac | 180 |
| cgtggattgg | tattactcac | aaacaaacaa | agtattccc | actcaggaaa | gaaatcgtgt | 240 |
| gtttgcctca | ggccaacttc | tgaagtttct | accagctgaa | gttgctgatt | ctggtattta | 300 |
| tacctgtatt | gtcagaagtc | ccacattcaa | taggactgga | tatgcgaatg | tcaccatata | 360 |
| taaaaaacaa | tcagattgca | atgttccaga | ttatttgatg | tattcaacag | tatctggatc | 420 |
| agaaaaaaat | tccaaaattt | attgtcctac | cattgacctc | tacaactgga | cagcacctct | 480 |
| tgagtggttt | aagaattgtc | aggctcttca | aggatcaagg | tacagggcgc | acaagtcatt | 540 |
| tttggtcatt | gataatgtga | tgactgagga | cgcaggtgat | tacacctgta | aatttataca | 600 |
| caatgaaaat | ggagccaatt | atagtgtgac | ggcgaccagg | tccttcacgg | tcaaggatga | 660 |
| gcaaggcttt | tctctgtttc | cagtaatcgg | agcccctgca | caaaatgaaa | taaaggaagt | 720 |
| ggaaattgga | aaaacgcaa | acctaacttg | ctctgcttgt | tttggaaaag | gcactcagtt | 780 |
| cttggctgcc | gtcctgtggc | agcttaatgg | aacaaaaatt | acagactttg | gtgaaccaag | 840 |
| aattcaacaa | gaggaagggc | aaaatcaaag | tttcagcaat | gggctggctt | gtctagacat | 900 |
| ggttttaaga | atagctgacg | tgaaggaaga | ggatttattg | ctgcagtacg | actgtctggc | 960 |
| cctgaatttg | catggcttga | gaaggcacac | cgtaagacta | agtaggaaaa | atccaagtaa | 1020 |
| ggagtgtttc | tgagactttg | atcacctgaa | ctttctctag | caagtgtaag | cagaatggag | 1080 |
| tgtggttcca | agagatccat | caagacaatg | ggaatggcct | gtgccataaa | atgtgcttct | 1140 |
| cttcttcggg | atgttgtttg | ctgtctgatc | tttgtagact | gttcctgttt | gctgggagct | 1200 |
| tctctgctgc | ttaaattgtt | cgtcctcccc | cactccctcc | tatcgttggt | ttgtctagaa | 1260 |
| cactcagctg | cttctttggt | catccttgtt | ttctaacttt | atgaactccc | tctgtgtcac | 1320 |
| tgtatgtgaa | aggaaatgca | ccaacaaccg | aaaactg | | | 1357 |

<210> SEQ ID NO 6
<211> LENGTH: 337
<212> TYPE: PRT
<213> ORGANISM: Mus musculus

<400> SEQUENCE: 6

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

```
Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
        195                 200                 205

Glu Glu Lys Gly Phe Ser Met Phe Pro Val Ile Thr Asn Pro Pro Tyr
    210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
            260                 265                 270

Glu Glu Glu Gly Arg Asn Glu Ser Ser Asn Asp Met Asp Cys Leu
    275                 280                 285

Thr Ser Val Leu Arg Ile Thr Gly Val Thr Glu Lys Asp Leu Ser Leu
290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ser Lys Glu Cys Pro Ser His Ile
                325                 330                 335

Ala

<210> SEQ ID NO 7
<211> LENGTH: 567
<212> TYPE: PRT
<213> ORGANISM: Mus musculus

<400> SEQUENCE: 7

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140
```

-continued

```
Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
            165                 170                 175

Val Thr His Asp Asp Glu Gly Asp Tyr Thr Cys Gln Phe Thr His Ala
        180                 185                 190

Glu Asn Gly Thr Asn Tyr Ile Val Thr Ala Thr Arg Ser Phe Thr Val
    195                 200                 205

Glu Glu Lys Gly Phe Ser Met Phe Pro Val Ile Thr Asn Pro Pro Tyr
210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
            245                 250                 255

Gln Ile Asn Lys Thr Val Val Gly Asn Phe Gly Glu Ala Arg Ile Gln
        260                 265                 270

Glu Glu Glu Gly Arg Asn Glu Ser Ser Asn Asp Met Asp Cys Leu
    275                 280                 285

Thr Ser Val Leu Arg Ile Thr Gly Val Thr Glu Lys Asp Leu Ser Leu
290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ile Asp His Arg Ser Ile Tyr Tyr
            325                 330                 335

Ile Val Ala Gly Cys Ser Leu Leu Leu Met Phe Ile Asn Val Leu Val
        340                 345                 350

Ile Val Leu Lys Val Phe Trp Ile Glu Val Ala Leu Phe Trp Arg Asp
    355                 360                 365

Ile Val Thr Pro Tyr Lys Thr Arg Asn Asp Gly Lys Leu Tyr Asp Ala
370                 375                 380

Tyr Ile Ile Tyr Pro Arg Val Phe Arg Gly Ser Ala Ala Gly Thr His
385                 390                 395                 400

Ser Val Glu Tyr Phe Val His Thr Leu Pro Asp Val Leu Glu Asn
            405                 410                 415

Lys Cys Gly Tyr Lys Leu Cys Ile Tyr Gly Arg Asp Leu Leu Pro Gly
        420                 425                 430

Gln Asp Ala Ala Thr Val Val Glu Ser Ser Ile Gln Asn Ser Arg Arg
    435                 440                 445

Gln Val Phe Val Leu Ala Pro His Met Met His Ser Lys Glu Phe Ala
450                 455                 460

Tyr Glu Gln Glu Ile Ala Leu His Ser Ala Leu Ile Gln Asn Asn Ser
465                 470                 475                 480

Lys Val Ile Leu Ile Glu Met Glu Pro Leu Gly Glu Ala Ser Arg Leu
            485                 490                 495

Gln Val Gly Asp Leu Gln Asp Ser Leu Gln His Leu Val Lys Ile Gln
        500                 505                 510

Gly Thr Ile Lys Trp Arg Glu Asp His Val Ala Asp Lys Gln Ser Leu
    515                 520                 525

Ser Ser Lys Phe Trp Lys His Val Arg Tyr Gln Met Pro Val Pro Glu
530                 535                 540

Arg Ala Ser Lys Thr Ala Ser Val Ala Ala Pro Leu Ser Gly Lys Ala
545                 550                 555                 560

Cys Leu Asp Leu Lys His Phe
            565
```

<210> SEQ ID NO 8
<211> LENGTH: 556
<212> TYPE: PRT
<213> ORGANISM: Homo sapiens

<400> SEQUENCE: 8

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
        355                 360                 365

Lys Thr Arg Asn Asp Gly Lys Leu Tyr Asp Ala Tyr Val Val Tyr Pro
370                 375                 380

-continued

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
            405                 410                 415

Leu Cys Ile Tyr Gly Arg Asp Met Leu Pro Gly Glu Asp Val Val Thr
        420                 425                 430

Ala Val Glu Thr Asn Ile Arg Lys Ser Arg Arg His Ile Phe Ile Leu
    435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
    530                 535                 540

Ala Ser Ser Leu Thr Pro Leu Ala Ala Gln Lys Gln
545                 550                 555

<210> SEQ ID NO 9
<211> LENGTH: 328
<212> TYPE: PRT
<213> ORGANISM: Homo sapiens

<400> SEQUENCE: 9

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 10
<211> LENGTH: 1680
<212> TYPE: DNA
<213> ORGANISM: Homo sapiens

<400> SEQUENCE: 10
cttagctccg tcactgactc caagttcatc ccctctgtct ttcagtttgg ttgagatata    60
ggctactctt cccaactcag tcttgaagag tatcaccaac tgcctcatgt gtggtgacct   120
tcactgttgt atgccagtga ctcatctgga gtaatctcaa caacgagtta ccaatacttg   180
ctcttgattg ataaacagaa tggggttttg gatcttagca attctcacaa ttctcatgta   240
ttccacagca gcaaagttta gtaaacaatc atggggcctg gaaaatgagg ctttaattgt   300
aagatgtcct agacaaggaa aacctagtta caccgtggat tggtattact cacaaacaaa   360
caaaagtatt cccactcagg aaagaaatcg tgtgtttgcc tcaggccgac ttctgaagtt   420
tctaccagct gaagttgctg attctggtat ttatacctgt attgtcagaa gtcccacatt   480
caataggact ggatatgcga atgtcaccat atataaaaaa caatcagatt gcaatgttcc   540
agattatttg atgtattcaa cagtatctgg atcagaaaaa aattccaaaa tttattgtcc   600
taccattgac tctacaact tggacagcacc tcttgagtgg tttaagaatt gtcaggctct   660
tcaaggatca aggtacaggg cgcacaagtc attttttggtc attgataatg tgatgactga   720
ggacgcaggt gattacacct gtaaatttat acacaatgaa aatggagcca attatagtgt   780
gacggcgacc aggtccttca cggtcaaggt ttggtgtcag agtttctgca aattaaaaaa   840
gagcttaatc tttagtaata ctcattggat tcaaagtcta atgagaggct tgtgatggt    900
atactatggt gtacataaat gttgtcgagt ggttttaat ctttgtttgc aatactttca    960
acatcatcaa tggccttgaa tgagcaaggc ttttctctgt tccagtaat cggagcccct   1020
gcacaaaatg aaataaagga agtggaaatt ggaaaaaacg caaacctaac ttgctctgct  1080
tgttttggaa aaggcactca gttccttggct gccgtcctgt ggcagcttaa tggaacaaaa  1140
attacagact tggtgaacc aagaattcaa caagaggaag gcaaaatca agtttcagc    1200
aatgggctgg cttgtctaga catggtttta agaatagctg acgtgaagga agaggattta  1260
ttgctgcagt acgactgtct ggccctgaat ttgcatggct tgagaaggca caccgtaaga  1320
ctaagtagga aaaatccaag taaggagtgt ttctgagact ttgatcacct gaactttctc  1380
tagcaagtgt aagcagaatg gagtgtggtt ccaagagatc catcaagaca atgggaatgg  1440

| cctgtgccat aaaatgtgct tctcttcttc gggatgttgt ttgctgtctg atctttgtag | 1500 |
|---|---|
| actgttcctg tttgctggga gcttctctgc tgcttaaatt gttcgtcctc ccccactccc | 1560 |
| tcctatcgtt ggtttgtcta gaacactcag ctgcttcttt ggtcatcctt gttttctaac | 1620 |
| tttatgaact ccctctgtgt cactgtatgt gaaaggaaat gcaccaacaa ccgaaaactg | 1680 |

<210> SEQ ID NO 11
<211> LENGTH: 259
<212> TYPE: PRT
<213> ORGANISM: Homo sapiens

<400> SEQUENCE: 11

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Arg Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Val Trp Cys Gln Ser
        195                 200                 205

Phe Cys Lys Leu Lys Lys Ser Leu Ile Phe Ser Asn Thr His Trp Ile
    210                 215                 220

Gln Ser Leu Met Arg Gly Phe Val Met Val Tyr Tyr Gly Val His Lys
225                 230                 235                 240

Cys Cys Arg Val Val Phe Asn Leu Cys Leu Gln Tyr Phe Gln His His
                245                 250                 255

Gln Trp Pro

<210> SEQ ID NO 12
<211> LENGTH: 1210
<212> TYPE: DNA
<213> ORGANISM: Homo sapiens
<220> FEATURE:
<221> NAME/KEY: CDS
<222> LOCATION: (84)...(557)

<400> SEQUENCE: 12
gtcgacccac gcgtccgccc acgcgtccgc tggagtaatc tcaacaacga gttaccaata          60

-continued

```
cttgctcttg attgataaac aga atg ggg ttt tgg atc tta gca att ctc aca    113
                         Met Gly Phe Trp Ile Leu Ala Ile Leu Thr
                          1               5                    10 att ctc atg tat tcc aca gca gca aag ttt agt aaa caa tca tgg ggc      161
Ile Leu Met Tyr Ser Thr Ala Ala Lys Phe Ser Lys Gln Ser Trp Gly
             15                  20                  25 ctg gaa aat gag gct tta att gta aga tgt cct aga caa gga aaa cct      209
Leu Glu Asn Glu Ala Leu Ile Val Arg Cys Pro Arg Gln Gly Lys Pro
             30                  35                  40 agt tac acc gtg gat tgg tat tac tca caa aca aac aaa agt att ccc      257
Ser Tyr Thr Val Asp Trp Tyr Tyr Ser Gln Thr Asn Lys Ser Ile Pro
         45                  50                  55 act cag gaa aga aat cgt gtg ttt gcc tca ggc caa ctt ctg aag ttt      305
Thr Gln Glu Arg Asn Arg Val Phe Ala Ser Gly Gln Leu Leu Lys Phe
     60                  65                  70 cta cca gct gca gtt gct gat tct ggt att tat acc tgt att gtc aga      353
Leu Pro Ala Ala Val Ala Asp Ser Gly Ile Tyr Thr Cys Ile Val Arg
 75                  80                  85                  90 agt ccc aca ttc aat agg act gga tat gcg aat gtc acc ata tat aaa      401
Ser Pro Thr Phe Asn Arg Thr Gly Tyr Ala Asn Val Thr Ile Tyr Lys
                 95                 100                 105 aaa caa tca gat tgc aat gtt cca gat tat ttg atg tat tca aca gta      449
Lys Gln Ser Asp Cys Asn Val Pro Asp Tyr Leu Met Tyr Ser Thr Val
             110                 115                 120 tct gga tca gaa aaa aat tcc aaa att tat tgt cct acc att gac ctc      497
Ser Gly Ser Glu Lys Asn Ser Lys Ile Tyr Cys Pro Thr Ile Asp Leu
         125                 130                 135 tac aac tgg aca gca cct ctt gag tgg ttt aag atg agc aag gct ttt      545
Tyr Asn Trp Thr Ala Pro Leu Glu Trp Phe Lys Met Ser Lys Ala Phe
     140                 145                 150 ctc tgt ttc cag taatcggagc ccctgcacaa atgaaataa aggaagtgga           597
Leu Cys Phe Gln
155 aattggcact cagttcttgg ctgccgtcct gtggcagctt aatggaacaa aaattacaga    657 ctttggtgaa ccaagaattc aacaagagga agggcaaaat caaagtttca gcaatgggct    717 ggcttgtcta gacatggttt taagaatagc tgacgtgaag gaagaggatt tattgctgca    777 gtacgactgt ctggccctga atttgcatgg cttgagaagg cacaccgtaa gactaagtag    837 gaaaaatcca gtaaggagt gtttctgaga ctttgatcac ctgaactttc tctagcaagt     897 gtaagcagaa tggagtgtgg ttccaagaga tccatcaaga caatgggaat ggcctgtgcc    957 ataaaatgtg cttctcttct tcgggatgtt gtttgctgtc tgatctttgt agactgttcc    1017 tgtttgctgg gagcttctct gctgcttaaa ttgttcgtcc tcccccactc cctcctatcg    1077 ttggtttgtc tagaacactc agctgcttct tggtcatcc ttgttttcta actttatgaa     1137 ctccctctgt gtcactgtat gtgaaaggaa atgcaccaac aaccgtaaaa aaaaaaaaa     1197 aagggcggcc gct                                                      1210
```

<210> SEQ ID NO 13
<211> LENGTH: 158
<212> TYPE: PRT
<213> ORGANISM: Homo sapiens

<400> SEQUENCE: 13

```
Met Gly Phe Trp Ile Leu Ala Ile Leu Thr Ile Leu Met Tyr Ser Thr
 1               5                  10                  15

Ala Ala Lys Phe Ser Lys Gln Ser Trp Gly Leu Glu Asn Glu Ala Leu
             20                  25                  30
```

-continued

```
Ile Val Arg Cys Pro Arg Gln Gly Lys Pro Ser Tyr Thr Val Asp Trp
     35                  40                  45

Tyr Tyr Ser Gln Thr Asn Lys Ser Ile Pro Thr Gln Glu Arg Asn Arg
         50                  55                  60

Val Phe Ala Ser Gly Gln Leu Leu Lys Phe Leu Pro Ala Ala Val Ala
 65                  70                  75                  80

Asp Ser Gly Ile Tyr Thr Cys Ile Val Arg Ser Pro Thr Phe Asn Arg
                 85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
                115                 120                 125

Ser Lys Ile Tyr Cys Pro Thr Ile Asp Leu Tyr Asn Trp Thr Ala Pro
130                 135                 140

Leu Glu Trp Phe Lys Met Ser Lys Ala Phe Leu Cys Phe Gln
145                 150                 155

<210> SEQ ID NO 14
<211> LENGTH: 18
<212> TYPE: DNA
<213> ORGANISM: Artificial Sequence
<220> FEATURE:
<223> OTHER INFORMATION: sense primer

<400> SEQUENCE: 14
ttgccataga gagacctc                                                 18

<210> SEQ ID NO 15
<211> LENGTH: 19
<212> TYPE: DNA
<213> ORGANISM: Artificial Sequence
<220> FEATURE:
<223> OTHER INFORMATION: antisense primer

<400> SEQUENCE: 15
tgctgtccaa ttatacagg                                                19

<210> SEQ ID NO 16
<211> LENGTH: 22
<212> TYPE: DNA
<213> ORGANISM: Artificial Sequence
<220> FEATURE:
<223> OTHER INFORMATION: sense primer

<400> SEQUENCE: 16
gaacacggca ttgtcactaa ct                                            22

<210> SEQ ID NO 17
<211> LENGTH: 21
<212> TYPE: DNA
<213> ORGANISM: Artificial Sequence
<220> FEATURE:
<223> OTHER INFORMATION: antisense primer

<400> SEQUENCE: 17
cctcatagat gggcactgtg t                                             21

<210> SEQ ID NO 18
<211> LENGTH: 17
<212> TYPE: DNA
<213> ORGANISM: Artificial Sequence
<220> FEATURE:
<223> OTHER INFORMATION: forward primer
```

```
<400> SEQUENCE: 18
tgtgacggcg accaggt                                              17

<210> SEQ ID NO 19
<211> LENGTH: 23
<212> TYPE: DNA
<213> ORGANISM: Artificial Sequence
<220> FEATURE:
<223> OTHER INFORMATION: reverse primer

<400> SEQUENCE: 19
tctctgtttc cagtaatcgg agc                                       23

<210> SEQ ID NO 20
<211> LENGTH: 26
<212> TYPE: DNA
<213> ORGANISM: Artificial Sequence
<220> FEATURE:
<223> OTHER INFORMATION: TaqMan probe

<400> SEQUENCE: 20
ttcacggtca aggatgagca agcctt                                    26

<210> SEQ ID NO 21
<211> LENGTH: 21
<212> TYPE: DNA
<213> ORGANISM: Artificial Sequence
<220> FEATURE:
<223> OTHER INFORMATION: forward primer

<400> SEQUENCE: 21
cacccccact gaaaaagatg a                                         21

<210> SEQ ID NO 22
<211> LENGTH: 26
<212> TYPE: DNA
<213> ORGANISM: Artificial Sequence
<220> FEATURE:
<223> OTHER INFORMATION: reverse primer

<400> SEQUENCE: 22
cttaactatc ttgggctgtg acaaag                                    26

<210> SEQ ID NO 23
<211> LENGTH: 24
<212> TYPE: DNA
<213> ORGANISM: Artificial Sequence
<220> FEATURE:
<223> OTHER INFORMATION: TaqMan probe

<400> SEQUENCE: 23
tatgcctgcc gtgtgaacca cgtg                                      24

<210> SEQ ID NO 24
<211> LENGTH: 31
<212> TYPE: DNA
<213> ORGANISM: Artificial Sequence
<220> FEATURE:
<223> OTHER INFORMATION: 5' oligonucleotide

<400> SEQUENCE: 24
ccgcgggtac cagtaaatcg tcctggggtg g                              31

<210> SEQ ID NO 25
<211> LENGTH: 36
<212> TYPE: DNA
```

```
<213> ORGANISM: Artificial Sequence
<220> FEATURE:
<223> OTHER INFORMATION: 3' oligonucleotide

<400> SEQUENCE: 25
aaataaagga tccctacatc cagcaactat gtagta                           36

<210> SEQ ID NO 26
<211> LENGTH: 38
<212> TYPE: DNA
<213> ORGANISM: Artificial Sequence
<220> FEATURE:
<223> OTHER INFORMATION: 5' oligonucleotide

<400> SEQUENCE: 26
gaacacacta gtactatcct gtgccattgc catagaga                         38

<210> SEQ ID NO 27
<211> LENGTH: 44
<212> TYPE: DNA
<213> ORGANISM: Artificial Sequence
<220> FEATURE:
<223> OTHER INFORMATION: 3' oligonucleotide

<400> SEQUENCE: 27
ggaatattgg gcccttggat cccaagtctg cacacctgca ctcc                  44

<210> SEQ ID NO 28
<211> LENGTH: 21
<212> TYPE: DNA
<213> ORGANISM: Artificial Sequence
<220> FEATURE:
<223> OTHER INFORMATION: 5' oligonucleotide

<400> SEQUENCE: 28
gtaaatcgtc ctggggtctg g                                           21

<210> SEQ ID NO 29
<211> LENGTH: 25
<212> TYPE: DNA
<213> ORGANISM: Artificial Sequence
<220> FEATURE:
<223> OTHER INFORMATION: 3' oligonucleotide

<400> SEQUENCE: 29
ccttctgata acacaagcat aaatc                                       25

<210> SEQ ID NO 30
<211> LENGTH: 17
<212> TYPE: DNA
<213> ORGANISM: Artificial Sequence
<220> FEATURE:
<223> OTHER INFORMATION: primer

<400> SEQUENCE: 30
acggagggca gtaaatc                                                17

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
cagccaagaa gtgagagc                                               18
```

```
<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
tgttgccgga atccagcctc ag                                    22

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
gtcccccacc cccagataca acc                                   23

<210> SEQ ID NO 34
<211> LENGTH: 5
<212> TYPE: PRT
<213> ORGANISM: Artificial Sequence
<220> FEATURE:
<223> OTHER INFORMATION: linker

<400> SEQUENCE: 34

Ala Ala Ala Asp Pro
1               5
```